(12) United States Patent
Krezel et al.

(10) Patent No.: US 12,029,715 B2
(45) Date of Patent: Jul. 9, 2024

(54) PRECURSOR COMPOUNDS FOR PROVIDING RETINOIDS OF THE VITAMIN A5 PATHWAY AND USES THEREOF

(71) Applicants: UNIVERSITY OF DEBRECEN, Debrecen (HU); UNIVERSIDADE DE VIGO, Vigo Pontevedra (ES); UNIVERSITÉ DE STRASBOURG, Strasbourg (FR)

(72) Inventors: Wojciech Krezel, Strasbourg (FR); Ralph Rühl, Debrecen (HU); Angel R. De Lera, Vigo Pontevedra (ES)

(73) Assignees: University of Debrecen, Debrecen (HU); Universidade de Vigo, Vigo Pontevedra (ES); Université de Strasbourg, Strasbourg Cedex (FR)

( * ) Notice: Subject to any disclaimer, the term of this patent is extended or adjusted under 35 U.S.C. 154(b) by 0 days.

(21) Appl. No.: 16/102,137

(22) Filed: Aug. 13, 2018

(65) Prior Publication Data
US 2019/0054056 A1 Feb. 21, 2019

Related U.S. Application Data

(63) Continuation-in-part of application No. 15/572,549, filed as application No. PCT/IB2016/052639 on May 9, 2016, now abandoned, application No. 16/102,137, filed on Aug. 13, 2018 is a continuation-in-part of application No. PCT/HU2017/050047, filed on Nov. 17, 2017.

(60) Provisional application No. 62/158,634, filed on May 8, 2015.

(30) Foreign Application Priority Data

Nov. 17, 2016 (HU) .................................. P1600629
May 5, 2017 (HU) .................................. P1700196

(51) Int. Cl.
*A61K 31/215* (2006.01)
*A61P 25/24* (2006.01)

(52) U.S. Cl.
CPC ............ *A61K 31/215* (2013.01); *A61P 25/24* (2018.01)

(58) Field of Classification Search
CPC .............................. A61K 31/215; A61P 25/24
USPC ......................................................... 514/529
See application file for complete search history.

(56) References Cited

U.S. PATENT DOCUMENTS

| | | | |
|---|---|---|---|
| 5,508,456 A | 4/1996 | Boehm | |
| 6,320,074 B1 | 11/2001 | Boehm et al. | |
| 7,348,359 B2 | 3/2008 | Gardinier et al. | |
| 7,566,795 B2 | 7/2009 | Boaz et al. | |
| 2008/0249042 A1* | 10/2008 | Moise | A61P 37/02 514/44 R |
| 2012/0178806 A1 | 7/2012 | Boch | |
| 2016/0296478 A1 | 10/2016 | Cadden | |
| 2019/0367451 A1 | 12/2019 | Gazit et al. | |

FOREIGN PATENT DOCUMENTS

| | | | |
|---|---|---|---|
| WO | 94/10140 A1 | 5/1994 | |
| WO | 95/32946 A1 | 12/1995 | |
| WO | 2013/134867 A1 | 9/2013 | |
| WO | WO-2013134867 A1 * | 9/2013 | ............. A61K 31/11 |

OTHER PUBLICATIONS

Moise et al. (The Journal of Biological Chemistry, vol. 280, No. 30, Issue of Jul. 29, pp. 27815-27825, 2006, 892).*
AD-prevention, 2022,https://www.alz.org/alzheimers-dementia/research_progress/prevention.*
AD-treatment, 2022, https://www.alzheimers.org.uk/about-dementia/treatments/drugs/drug-treatments-alzheimers-disease.*
Schizophrenia-prevention, 2022, https://www.webmd.com/schizophrenia/features/is-it-possible-to-prevent-schizophrenia.*
Schizophrenia-treatment, 2022,https://www.mayoclinic.org/diseases-conditions/schizophrenia/diagnosis-treatment/drc-20354449.*
Allenby et al.: "Retinoic acid receptors and retinoid X receptors: Interactions with endogenous retinoic acids", Proc Natl Acad Sci USA, 1993, vol. 90(1), pp. 30-34.
Altucci L et al.: " RAR and RXR modulation in cancer and metabolic disease", Nat Rev Drug Discov, 2007, vol. 6, pp. 793-810.
De Lera et al.: "An Endogenous Mammalian Retinoid X Receptor Ligand, At Last!", ChemMedChem, 2016, vol. 11, pp. 1027-1037.
Desvergne: "RXR: From Partnership to Leadership in Metabolic Regulations", Vitamins and Hormones, 2007, vol. 75, pp. 1-32.
Evans et al.: "Nuclear Receptors, RXR and the Big Bang", Cell, 2014, vol. 157, pp. 255-266.
Harari et al.: "A 9-cis beta-Carotene-Enriched Diet Inhibits Atherogenesis and Fatty Liver Formation in LDL Receptor Knockout Mice", J. Nutr., 2008, vol. 138, pp. 1923-1930.
Heyman et al.: "9-cis retinoic acid is a high affinity ligand for the retinoid X receptor", Cell, 1992, vol. 68, pp. 397-406, Abstract only.
Huang et al.: "Retinoid X receptor gamma signaling accelerates CNS remyelination", Nat Neurosci, 2011, vol. 14, pp. 45-53.
Kane et al.: "Quantification of endogenous retinoic acid in limited biological samples by LC/MS/MS", Biochem J, 2005, vol. 388, pp. 363-369.
Kastner et al.: "Genetic evidence that the retinoid signal is transduced by heterodimeric RXR/RAR functional units during mouse development", Development, 1997, vol. 124. pp. 313-326.

(Continued)

*Primary Examiner* — Sun Jae Yoo
(74) *Attorney, Agent, or Firm* — Jason D. Voight

(57) ABSTRACT

The invention relates to the field of retinoid X receptor (RXR) signaling and a novel vitamin A pathway called Vitamin A5 pathway. Compounds which are useful to provide (R)-9-cis-13,14-dihydroretinoic acid, an endogenous RXR ligand, are claimed as well as their uses and method for preparation thereof. The compounds of the invention are useful for pharmaceutical and nutritional uses.

17 Claims, 31 Drawing Sheets

(56) References Cited

OTHER PUBLICATIONS

Kastner et al.: "Vitamin A deficiency and mutations of RXRalpha, RXRbeta and RARalpha lead to early differentiation of embryonic ventricular cardiomyocytes", Development, 1997, vol. 124, pp. 4749-4758.

Kedishvili: "Enzymology of retinoic acid biosynthesis and degradation", Journal of Lipid Research, 2013, vol. 54, pp. 1744-1760.

Krezel et al.: "RXR gamma null mice are apparently normal and compound RXR alpha +/-/RXR beta -/-/RXR gamma -/- mutant mice are viable", Proc Natl Acad Sci USA, 1996, vol. 93, pp. 9010-9014.

Krzyosiak et al.: "Retinoid X Receptor Gamma Control of Affective Behaviors Involves Dopaminergic Signaling in Mice", Neuron, 2010, vol. 66, pp. 908-920.

Lerner et al.: "The Retinoid X Receptor Agonist Bexarotene Relieves Positive Symptoms of Schizophrenia: A 6-Week, Randomized, Double-Blind, Placebo-Controlled Multicenter Trial", J Clin Psychiatry, 2013, vol. 74, pp. 1224-1232, Abstract only.

Moise et al.: "Metabolism and Transactivation Activity of 13,14-Dihydroretinoic Acid", J Biol Chem, 2005, vol. 280, pp. 27815-27825.

Rühl et al.: "Method to determine 4-oxo-retinoic acids, retinoic acids and retinol in serum and cell extracts by liquid chromatography/diode-array detection atmospheric pressure chemical ionisation tandem mass spectrometry", Rapid Commun Mass Spectrom, 2006, vol. 20, pp. 2497-2504.

Rühl et al.: "9-cis-13, 14-Dihydroretinoic Acid Is an Endogenous Retinoid Acting as RXR Ligand in Mice", PLOS Genetics, 2015, vol. 11(6):e1005213, pp. 1-16.

Shirley et al.: "Oxidative and Reductive Metabolism of 9-C/S-Retinoic Acid in the Rat Identification of 13,14-Dihydro-9-cis-retinoic Acid and Its Taurine Conjugate", Drug Metabolism and Disposition, 1996, vol. 24(3), pp. 293-302.

Stefan: "Chiral Retinoid Derivatives: Synthesis and Structural Elucidation of a New Vitamin A Metabolite", Dissertation, 2006, Fakultät für Lebenswissenschaften der Technischen Universität Carolo-Wilhelmina zu Braunschweig.

Wietrzych: "Working memory deficits in retinoid X receptor gamma-deficient mice", Learn Mem, 2005, vol. 12, pp. 318-326.

Wietrzych-Schindler et al.: "Retinoid X Receptor Gamma Is Implicated in Docosahexaenoic Acid Modulation of Despair Behaviors and Working Memory in Mice", Biol Psychiatry, 2011, vol. 69, pp. 788-794.

Yamada et al.: "Retinoid X receptor ligands: a patent review (2007-2013)", Expert Opin. Ther. Patents, 2014, vol. 24, pp. 443-452.

ACS (American Chemical Society), RN : 959369-28-9, 2007.

Gaziano et al.: "Discrimination in absorption or transport of β-carotene isomers after oral supplementation with either all-trans- or 9-cis-β-carotene", The American Journal of Clinical Nutrition, 1995, vol. 61, pp. 1248-1252.

Ben-Amotz et al.: "Bioavailability of a natural isomer mixture compared with synthetic all-trans β-carotene in human serum", The American Journal of Clinical Nutrition, 1996, vol. 63, pp. 729-734.

Harari et al.: "Supplementation with 9-cis β-carotene-rich alga Dunaliella improves hyperglycemia and adipose issue inflammation in diabetic mice", Journal of Applied Phycology, 2013, vol. 25, pp. 687-693.

Yeum et al.: "Human plasma carotenoid response to the ingstion of controlled diets high in fruits and vegetables", The American Journal of Clinical Nutrition, 1996, vol. 64, pp. 594-602.

* cited by examiner

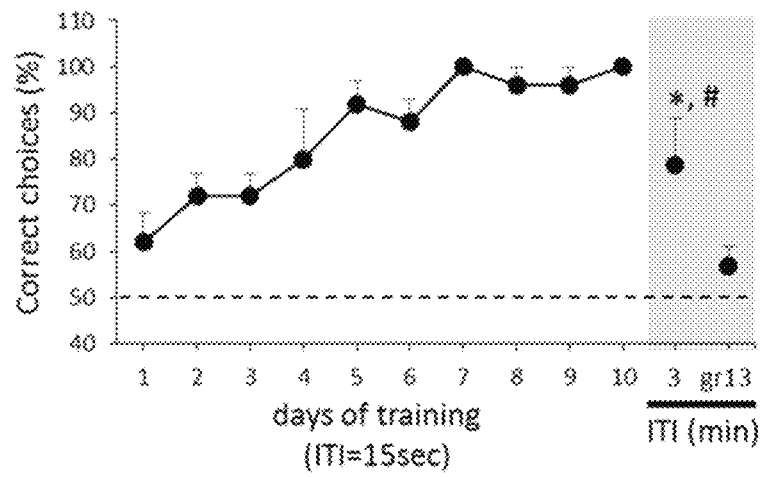
FIG. 1A
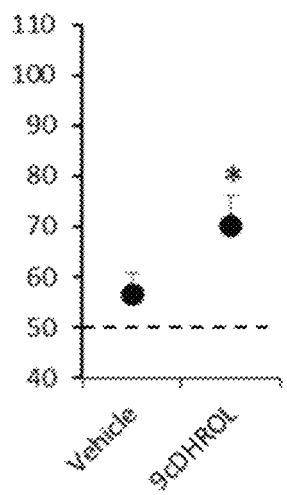
FIG. 1B
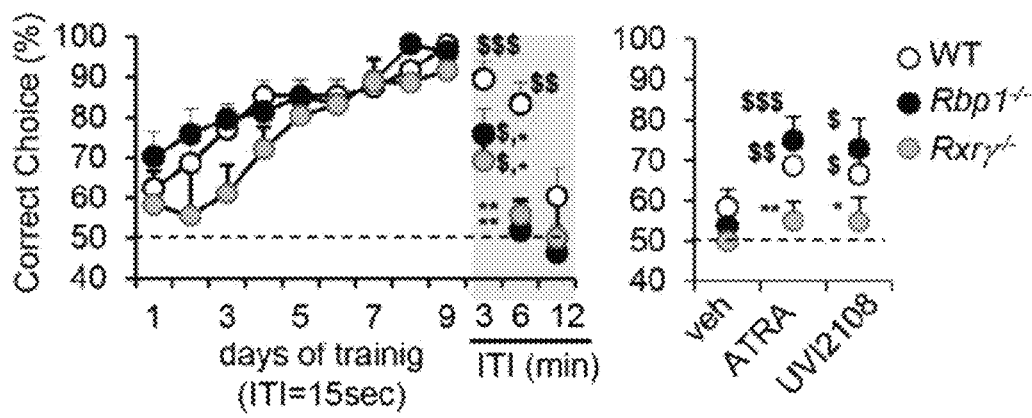
FIG. 1C
FIG. 1D

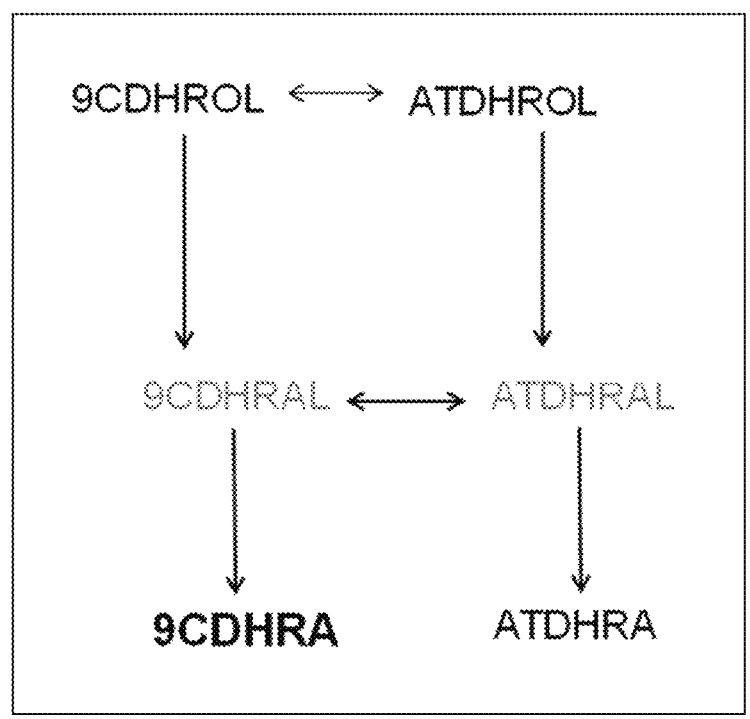
FIG. 7 PUTATIVE METABOLIC VITAMIN A5 PATHWAY

PRECURSOR COMPOUNDS FOR PROVIDING RETINOIDS OF THE VITAMIN A5 PATHWAY AND USES THEREOF

The application is a continuation in part (CIP) of U.S. Ser. No. 15/572,549 (national phase of PCT/IB2016/052639 and filed on May 9, 2016) claiming priority from U.S. provisional patent application U.S. 62/158,634 (filed on May 8, 2015) and a continuation in part (CIP) of PCT/HU2017/050047 (filed on Nov. 17, 2017) and claiming priority from Hungarian patent applications HU P1600629 filed on Nov. 17, 2016 and HU P1700196 filed on May 5, 2017, each of which is incorporated herein by reference.

FIELD OF THE INVENTION

Retinoid X receptors (RXRs) are ligand-activated transcription factors controlling a variety of physiological processes. The invention relates to the field of retinoid X receptor (RXR) signaling and a novel vitamin A pathway recognized by the present inventors and called herein Vitamin A5 pathway.

Preferably, the invention relates to a novel retinoic acid, (R)-9-cis-13,14-dihydroretinoic acid (9CDHRA) and its precursors, including dietary precursors, their stereoselective synthesis and to pharmaceutical compositions containing the same as well as medical and dietary uses thereof.

Compounds which are useful to provide (R)-9-cis-13,14-dihydroretinoic acid an endogenous RXR ligand are claimed as well as their uses and method for preparation thereof. The compounds of the invention are useful for pharmaceutical and nutritional uses.

More particularly, precursors of 9CDHRA are among others 9-cis-13,14-dihydroretinol (9CDHROL, vitamin A5) and 9-cis-13,14-dihydro-β,β-carotene (9CDHBC, pro-vitamin A5), which are respectively novel types of retinoid and carotenoid RXR ligand precursors. It has been surprisingly found herein that such precursors might be directly or indirectly metabolized to 9CDHRA. The invention also relates to preventive/pharmaceutical usage of those compounds and in particular in treatment of depressive-like behaviors in chronic stress animal model of depression and other various diseases where RXR-mediated signaling is affected or was proposed as therapeutic target. Such diseases include neurodegenerative and metabolic diseases, skin- and immunological dysfunctions (including inflammation) as well as cardiovascular diseases and life-style applications like memory enhancing effects.

BACKGROUND ART

Vitamin A, in parallel with vitamins C and D, was among the first group of compounds that were associated to deficiency symptoms. This active lipid was later named "vitamin A". In 1931 Karrer et al. identified this fat-soluble nutrient derivative in cod liver oil (Karrer et al., 1931a; Karrer et al., 1931b). Paul Karrer, who elucidated the structure of retinol (i.e. vitamin A1), was awarded the Nobel Prize in Chemistry, for basic vitamin A research in 1937. In parallel, Edisbury et al. (Edisbury et al., 1937) and Gilliam et al. (Gillam et al., 1938) found in 1937-38 a food factor mainly present in marine fish. They used the term vitamin A2 to name this second category of vitamin A, as it displays different absorption spectra than retinol due to the presence of an additional double bound at the ring C3-C4 positions.

In the 1980's the molecular action of vitamin A was further expanded mainly by the groups of Pierre Chambon and Ronald Evans through the identification of all-trans-retinoic acid (ATRA) as the bioactive mediator of a large array of vitamin A effects. They identified ATRA as a nutrient derived lipid hormone and thereby the association of ATRA with RAR (retinoic acid receptors) for mediating transcriptional activity (Giguere et al., 1987) and the RARs themselves as new members of the nuclear hormone receptor superfamily (Petkovich et al., 1987). Besides RARs, also the retinoid-X receptors (RXRs) (Kliewer et al., 1992; Leid et al., 1992; Mangelsdorf et al., 1990; Evans 2014) identified as mediators of important function and were established as the obligatory heterodimer-binding partner for a large variety of nuclear hormone receptors. In 1992, 9-cis-retinoic acid, 9CRA, was identified as the putative "endogenous" ligand for the RXRs (Heyman et al., 1992; Levin et al., 1992). In parallel the vitamin A2 derivative all-trans-3,4-didehydroretinoic acid (ATDDRA; Vitamin A2-acid) was identified endogenously in humans (Vahlquist et al., 1982) and later shown to display similar activity as ATRA in activating RAR-mediated gene transcription (Torma et al., 1994). However, 9CRA, although a potent RXR ligand, has only been rigorously identified in vivo only after high pharmacological (toxicological) relevant retinoid administration or after artificial nutritional interventions with food that is rich in vitamin A (Arnhold et al., 1996; Schmidt et al., 2002; Ulven et al., 2001). In addition "vitamin A" derivatives were found in invertebrates, namely 3-hydroxyretinal ("Vitamin A3") in arthropods and 4-hydroxyretinal ("Vitamin A4") in some crustaceans (Babino et al., 2016).

Retinol (Vitamin A1) is an essential micronutrient, thus its complete absence is not compatible with life as it controls many vital developmental processes. It plays an essential role in normal, heart, brain, bone and tooth development, reproduction, and the health of skin and mucous membranes (the mucus-secreting layer that lines body regions such as the respiratory tract). Vitamin A also acts in the body as an antioxidant, a protective chemical that may reduce the risk of certain cancers. If these antioxidant effects are mediated in physiological or nutritional relevant levels is highly questionable. At the aldehyde oxidation level, derivatives 11-cis-retinal and all-trans-retinal are ligands for the membrane protein opsin, which forms rhodopsin complexes used by the body for vision, particularly night vision.

As to medical uses of these compounds, all-trans-retinoic acid (ATRA, also called Tretinoin®) is the active agent in several medicinal formulations and is used, among others, in cosmetic and topical applications against e.g. acne and in acute promyelocytic leukemia.

Isomer 9-cis-retinoic acid (9CRA) is also used as a medicament under the name of Alitretinoin®. The oral formulation of 9CRA (Alitretinoin®) is marketed under the trade name Toctino®.

The primary indication for Isotretinoin® (the active agent being 13-cis-retinoic acid) is the treatment of severe cystic acne vulgaris, and is also indicated for the treatment of skin lesions in AIDS-related Kaposi's sarcoma.

Under the trade name Toctino® the compound has been granted prescription rights in the UK for oral use in chronic hand eczema; guidance suggests, however, to prescribe it in severe cases only.

Thus, somewhat contrary to the multiple role of retinoids only a few of them are used as medicaments in a relatively few specific diseases.

All these variants present in medicaments are present in the acid form and comprise a C13=C14 double bond.

The Palczewski group reported the endogenous presence of 13,14-dihydroretinoids, wherein the C13=C14 double bond is hydrogenated, and identified all-trans-13,14-dihydroretinoic acid (ATDHRA) as a low affinity ligand for RARs and a weaker activator than ATRA of RAR-controlled genes in cell-based assays (Moise et al., 2004; Moise et al., 2005, Moise et al., 2009).

Besides RARs, a further class of receptors, retinoid X receptors (RXRs) forming heterodimers with RARs play an important role in nuclear receptor signaling [Mangelsdorf and Evans, 1995]. As mentioned above 9-cis-retinoic acid (9CRA) is a potent activator of RXRs, mediators of important function and obligatory heterodimer-binding partners for a large variety of nuclear hormone receptors.

Nuclear hormone receptors sense such molecular signals and accordingly regulate gene expression, thus functioning as ligand controlled transcription factors. RXRs occupy a central place in nuclear receptor signaling as obligatory heterodimerization partners for several of those receptors. RXR ligands can regulate activity of some heterodimers including for example LXR-RXR or PPAR-RXR, collectively called permissive heterodimers in opposition to nonpermissive heterodimers, like RAR-RXR, which cannot be activated by RXR ligands alone (Perez E et al. 2012; Shulman A I et al., 2004).

Ligand-dependent modulations might be particularly relevant for control of various physiological events and their pathology. In particular, a number of synthetic RXR agonists are currently in clinical development for the treatment of cancer and metabolic diseases (Altucci L et al., 2007). WO2013/134867 describes a method of improving visual function in a subject by administration of a synthetic retinal. Recent studies also showed that memory functions are affected by RXR specific ligands (Wietrzych-Schindler M et al., 2011), suggesting their utility for the treatment of some neuropsychiatric or neurodegenerative disorders (Wietrzych-Schindler M et al., 2011, Huang J K et al. 2011, Lerner V et al., 2008).

In contrast to development and use of synthetic RXR ligands, no endogenous RXR ligand has been conclusively demonstrated by previous studies. Among the potential RXR ligands, 9-cis-retinoic acid (9CRA) (Allenby G et al., 1993), an isomer of all-trans-retinoic acid (ATRA), was either undetectable (Kane M A, et al., 2005, Rühl R. 2006) or was not present in sufficient concentrations (Arnold S L et al. 2012) to enable RXR-mediated signaling in mammalian organisms.

Besides 9CRA a second class of derivatives that have been found to activate RXR-mediated signaling are various fatty acids like phytanic acid (PHYA), docosahexaenoic acid (DHA) and oleic acid (de Urquiza et al., 2000; Goldstein et al., 2003; Kitareewan et al., 1996). Several findings indicate, however, that the endogenous levels of these derivatives are too low to bind RXR and elicit transcriptional activation.

As a summary, vitamin A research has thus far established fundamental principles for connecting diet with vitamin A and activation of lipid hormone receptors to control their signaling in ligand dependent manner in various (patho)-physiological conditions. Unfortunately, the endogenous presence and nutritional relevance of the RXR ligand and especially the status of 9CRA in that regard has proven highly controversial.

The present inventors have identified 9-cis-13,14-dihydroretinoic acid (9CDHRA) as the first endogenous and physiologically relevant retinoid which acts as RXR ligand in mammals and demonstrated its usefulness in model experiments thereby identifying an independent new vitamin A pathway (Vitamin A5).

Inventors have also prepared pure enantiomers of 9-cis-13,14-dihydroretinoic acid (9CDHRA) with a novel synthesis method.

The present inventors have detected the endogenous presence of 9-cis-13,14-dihydroretinoic acid (9CDHRA) in some organs (liver, serum, brain) of mice through a combined LC-MS-MS and UV analytical set-up and comparison with synthetic standard samples. In fact, 9CDHRA was found to display biological activities similar to those of synthetic RXR agonists and coordinated the transcriptional activities of several nuclear receptor-signaling pathways, possibly through the corresponding permissive heterodimers. Among others it was shown that reduced bioavailability of 9CDHRA in mice carrying null mutation for cellular retinol binding protein 1 (Rbp1) leads to depressive-like behaviors, whereas pharmacological treatment with 9CDHRA restores normal behavior in these animals.

Thus, the present inventors have in fact identified a novel lipid hormone in the mammalian organism. In absolute terms, the levels of this compound was analysed to be in very low concentrations in the nano molar range. Usually lipid hormones and other hormones are present in such low levels and can not be extracted or extracts or body fluids can not be used for therapeutic or nutritional relevant applications.

Therefore importantly a de novo synthesis was established to apply these derivatives in therapeutic, cosmetic and nutritional relevant applications. These lipid hormones, even if present endogenously, are just usable comparable in many cased as artificially synthesized derivatives to the human or mammalian organism.

The present compounds which may occur in the animal body are present in a spatial and temporal regulated pattern within the organism and are usually present in low systemic levels and higher enriched in special compartments. Thus, the compounds of the invention so that they may be effective in a pharmaceutical or nutraceutal composition, must be synthetic.

Thus, a series of compounds including, among others, 9-cis-13,14-dihydroretinol (9CDHROL) have been synthesized, which act as precursors of the actual endogenous RXR ligand, 9CDHRA.

The present inventors have also synthesized further physiological as well as nutritional precursors of 9CDHRA. The major potential precursors are esters of 9-cis-13,14-dihydroretinol (9CDH-retinyl ester, 9CDHROL-ES) and 9-cis-13,14-dihydroretinoic acid esters (9CDH-retinoyl ester, 9CDHRA-ES) in addition to novel carotenoids as pro-vitamin A5 precursors like 9-cis-13,14-dihydro-β,β-carotene (9CDHBC) as well as its precursor 9-cis-β,β-carotene (9CBC).

The inventors provided evidence that these precursors produce an unexpectedly high increase of 9CDHRA in the brain (e.g. preferential as to the liver), and are useful vectors to target brain signaling related to RXR-mediated signalling and related deficiencies.

Moreover, further work characterized this ligand and determined its multiple roles in biological systems.

These findings render the compounds of the invention useful both in medicaments and in nutraceuticals.

BRIEF DESCRIPTION OF THE INVENTION

The invention relates to a compound of general formula (I)

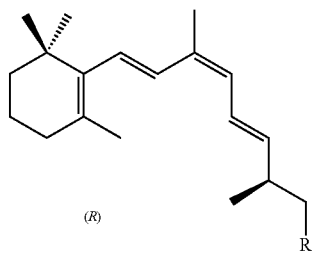

(I)

wherein R is selected from COOR₁ and CH₂OR₂ and a group of general formula (A) wherein R₁ is H or is a group which is removed by hydrolysis in a mammalian tissue or organ to result in (R)-9-cis-13,14-dihydroretinoic acid and a biologically acceptable tolerable compound and/or R₂ is H or an acyl group C(O)R₃ wherein —C(O)R₃ is a group which is removed by hydrolysis in a mammalian tissue or organ to result in (R)-9-cis-13,14-dihydroretinol and a biologically acceptable tolerable compound, and/or R is a group of general formula (A)

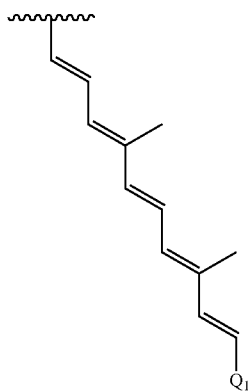

(A)

wherein Q₁ is a substituted or unsubstituted C₆₋₁₀ alkenyl or cycloalkenyl group, preferably a substituted or unsubstituted trimethylcycloalkenyl or more preferably a substituted or unsubstituted 2,6,6-trimethylcyclohexenyl, even more preferably unsubstituted 2,6,6-trimethylcyclohex-1-en-1-yl or 2,6,6-trimethylcyclohex-2-en-1-yl. If the trimethylcyclohexenyl, e.g. 2,6,6-trimethylcyclohexenyl, group is substituted it is preferably hydroxyl-substituted or oxo-substituted, preferably oxo-substituted;

wherein said compound is converted into 9-cis-13,14-dihydroretinol in mammalian tissue or organ or cells, once administered.

In particular, the compound is a synthetic compound.

Highly preferably the group of general formula (A) is a group of formula (a)

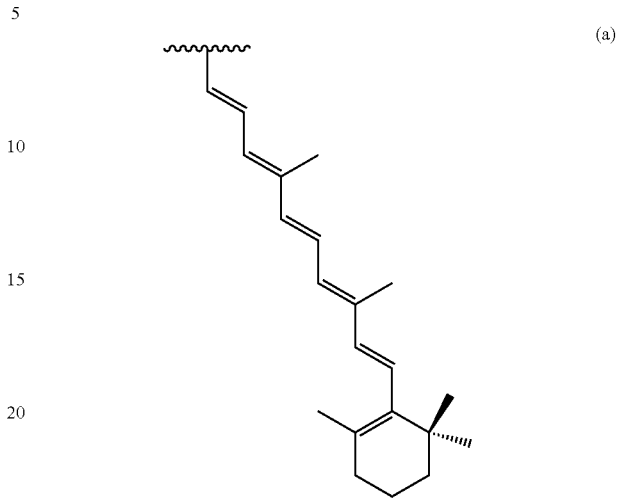

(a)

wherein said compound is a (R)-9-cis-13,14-dihydro-β,β-carotene (9CDHBC).

Preferably, said compound is present in a composition for providing 9-cis-13,14-dihydroretinoic acid (9CDHRA) as an RXR ligand or for activation of RXR signaling, preferably in a subject suffering from or endangered by impairment of RXR-mediated signaling or from mild to severe Vitamin A5 deficiency, said composition comprising an (R)-9-cis-13,14-dihydroretinoid compound of general formula (I), said compound being converted into (R)-9-cis-13,14-dihydroretinoic acid in mammalian tissue or organ or cells, and at least one pharmaceutically or nutraceutically acceptable excipient for stabilizing the (R)-9-cis-13,14-dihydroretinoid compound, i.e. a stabilizer, preferably an antioxidant and/or for solubilizing or emulsifying the (R)-9-cis-13,14-dihydroretinoid compound, i.e. a solubilizer or an emulsifier, and/or said composition being formulated to protect said compound against light.

In particular, the compound is a synthetic compound. In particular, the compound is present in the composition in an effective amount. In a particular case the composition comprises the compound in a concentrated form. In a particular case the composition comprising a synthetic compound is not a natural extract or a composition comprising a compound isolated from nature. Preferably the compound or any composition comprising it is enriched in this enantiomer (normally indicated as (R)) or preferably enantiopure, as defined herein.

Said compound is converted into (R)-9-cis-13,14-dihydroretinoic acid in a mammalian tissue or organ or cells, once administered. Mammalian tissue or organ or cells is understood herein as at least one or at least one type of tissue or organ or cell culture or population of cells or multiple tissue or organ or cell culture or population of cells including the case when different steps of the conversion take place in different tissue or organ or cell types.

Preferably said compound is for use in therapy in a mammalian subject, preferably in a human subject. Preferably said compound is for use in therapy of a disease wherein a retinoid X receptor mediated signaling related disease is treated.

Optionally, in particular wherein the invention relates to the compounds themselves $R_1$ is different from ethyl in particular in cases defined above.

The absolute configuration of the compound is indicated in the formula. Preferably the compound or any composition comprising it is enriched in the R enantiomer (normally indicated as (R) meaning R configuration) or preferably enantiopure, as defined herein.

The invention also relates to a compound of general formula (I)

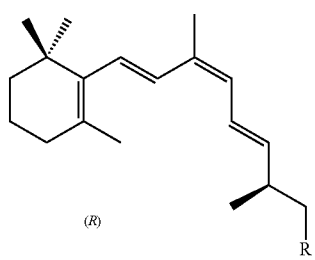

(I)

wherein R is selected from $COOR_1$ and $CH_2OR_2$ and a group of formula (A), wherein $R_1$ is a $C_{1-25}$ alkyl or a $C_{2-25}$ alkenyl and/or $R_2$ is H or an acyl group $C(O)R_3$ wherein $R_3$ is a $C_{1-25}$ alkyl or a $C_{2-25}$ alkenyl and/or R is a group of general formula A

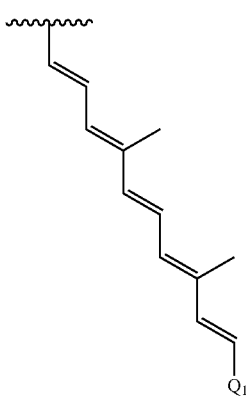

(A)

wherein $Q_1$ is a substituted or unsubstituted trimethylcycloalkenyl group forming a tetraterpenoid derivative compound of general formula A, or more preferably $Q_1$ is a substituted or unsubstituted 2,6,6-trimethylcyclohexenyl, even more preferably unsubstituted 2,6,6-trimethylcyclohex-1-en-1-yl or 2,6,6-trimethylcyclohex-2-en-1-yl. If the trimethylcyclohexenyl, e.g. 2,6,6-trimethylcyclohexenyl group, is substituted it is preferably hydroxyl-substituted or oxo-substituted, preferably oxo-substituted;

wherein said compound is converted into 9-cis-13,14-dihydroretinol in mammalian tissue or organ or cells, once administered.

Highly preferably the group of general formula A is a group of formula a

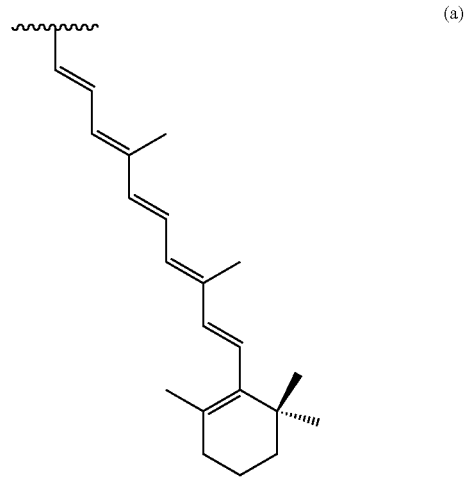

(a)

wherein said compound is a 9-cis-13,14-dihydro-β,β-carotene (9CDHBC).

Said compound is capable of converting into (R)-9-cis-13,14-dihydroretinoic acid in a mammalian tissue or organ, once administered.

In a preferred embodiment in the compound of the invention of general formula I $R_1$ or $R_2$ is as defined above or the compound is a 9-cis-carotenoid compound which is a 9-cis-13,14-dihydro-β,β-carotene derivative or a 9-cis-13,14-dihydro-β,β-carotene, preferably 9-cis-13,14-dihydro-β,β-carotene, as a precursor compound, wherein said compound is converted into (R)-9-cis-13,14-dihydroretinoic acid in a mammalian tissue or organ or cells, once administered.

Preferred options for the length of alkyl or alkenyl chain in case of $R_1$ or $R_2$ are as defined herein.

Preferably said compound is for use in therapy, as defined herein, in a mammalian, preferably in a human subject.

Optionally, in particular wherein the invention relates to the compounds themselves $R_1$ is different from ethyl. The "invention relates to the compounds themselves" means that the compounds are claimed as products and are not limited by a medical or diagnostic use or purpose carried out on human or animal body. Moreover, it means that the compound is not claimed as a part of a use or a method in a use or method claim.

The enantiomeric configuration of the compound is indicated in the formula. Preferably the compound or any composition comprising it is enriched in this enantiomer (normally indicated as (R)) or preferably enantiopure, as defined herein.

In a first aspect the compound is a compound of general formula (III)

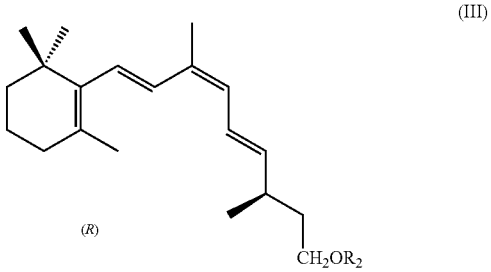

(III)

wherein $R_2$ is H or an acyl group $C(O)R_3$ wherein $R_3$ is selected from a $C_{1-25}$ alkyl or a $C_{1-23}$ alkyl, preferably a $C_{1-8}$ alkyl or a $C_{1-6}$ alkyl and a $C_{9-23}$ alkyl, more preferably $R_3$ is selected from a $C_{1-4}$ alkyl and a $C_{11-21}$ alkyl and a $C_{2-25}$ alkenyl, preferably $R_3$ is selected from a $C_{2-8}$ alkenyl or $C_{2-6}$ alkenyl and a $C_{2-23}$ alkenyl, more preferably $R_3$ is a $C_{13-23}$ alkenyl.

In a preferred embodiment $R_3$ is a $C_{1-s}$ alkyl, preferably a $C_{1-6}$ alkyl, more preferably a $C_{1-4}$ alkyl.

In a preferred embodiment $R_3$ is a $C_{9-23}$ alkyl, preferably a $C_{11-21}$ alkyl, more preferably a $C_{13-19}$ alkyl. In a preferred embodiment $R_3$ is $C_{2-8}$ alkenyl, preferably $C_{2-6}$ alkenyl, more preferably $C_{2-4}$ alkenyl.

In a preferred embodiment $R_3$ is $C_{9-25}$ alkenyl, preferably a $C_{11-23}$ alkenyl, more preferably a $C_{13-23}$ alkenyl.

In an embodiment $R_2$ is H and the compound is (R)-9-cis-13,14-dihydroretinol.

In a further embodiment $R_2$ is an acyl group $C(O)R_3$ and $R_3$ is a compound as defined above and $R_3$ is a group which is removed by hydrolysis of the ester in a mammalian tissue or organ to result in the corresponding alcohol (R)-9-cis-13,14-dihydroretinol. Thus, the ester is converted to an alcohol and a biologically tolerable and/or acceptable compound. Said alcohol compound is converted into (R)-9-cis-13,14-dihydroretinoic acid in a mammalian tissue or organ, once administered. This means that the compound has this capability, i.e. "is" also means "being capable of" depending on whether the compound is actually administered.

Preferably said compound is for use in therapy in a mammalian subject, preferably in a human subject.

The absolute configuration of the compound is indicated in the formula. Preferably the compound or any composition comprising it is enriched in this enantiomer (normally indicated as (R)) or preferably enantiopure, as defined herein.

In a preferred embodiment of this aspect of the invention said compound is of general formula (IV)

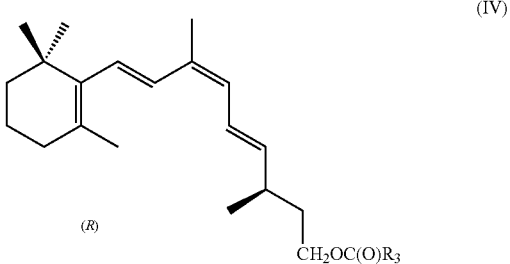

(IV)

wherein $R_3$ is as defined for general formula (III) or $R_3$ is selected from a $C_{1-4}$ alkyl, preferably methyl, ethyl, propyl or isopropyl, a $C_{11-21}$ alkyl, preferably $C_{13-19}$ alkyl and a $C_{11-23}$ alkenyl.

Preferably alkenyl is a polyunsaturated $C_{13-23}$ alkenyl.

In a preferred embodiment said compound being converted into (R)-9-cis-13,14-dihydroretinol in a mammalian tissue or organ, once administered.

More preferably the mammalian tissue is a nervous tissue or the tissue or organ is that of the central nervous system or of the peripheral nervous system. The mammalian cells are preferably nerve cells (neurocytes), preferably or in particular oligodendrocytes and Schwann cells.

In a further preferred embodiment the mammalian tissue is blood. In a further preferred embodiment the mammalian tissue is liver.

In a further aspect of the invention said compound is of general formula (II)

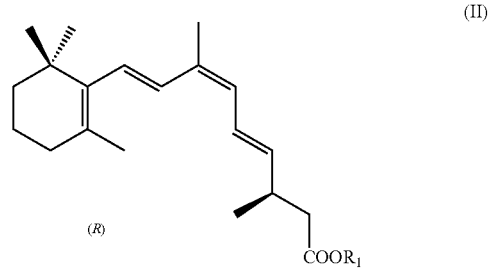

(II)

wherein $R_1$ is selected from

H and a $C_{1-25}$ alkyl or $C_{1-23}$ alkyl, preferably a $C_{1-6}$ alkyl and a $C_{9-23}$ alkyl, more preferably $R_1$ is selected from a $C_{1-4}$ alkyl and a $C_{11-21}$ alkyl; and a $C_{2-25}$ alkenyl or $C_{2-24}$ alkenyl, preferably $R_1$ is selected from a $C_{2-6}$ alkenyl and a $C_{9-23}$ alkenyl, more preferably $R_1$ is a $C_{13-23}$ alkenyl.

Optionally, in particular wherein the invention relates to the compounds themselves $R_1$ is different from ethyl. Optionally, in another embodiment $R_1$ is ethyl.

The absolute configuration of the compound is indicated in the formula. Preferably the compound or any composition comprising it is enriched in this enantiomer (normally indicated as (R)) or preferably enantiopure, as defined herein.

In a preferred embodiment $R_1$ is selected from a $C_{1-8}$ alkyl and a $C_{9-23}$ alkyl, more preferably $R_1$ is selected from a $C_{1-4}$ alkyl and a $C_{11-21}$ alkyl and a $C_{2-25}$ alkenyl or $C_{2-24}$ alkenyl, preferably a $C_{2-6}$ alkenyl and a $C_{9-23}$ alkenyl, more preferably a $C_{13-23}$ alkenyl.

In a preferred embodiment $R_1$ is a $C_{1-8}$ alkyl, preferably a $C_{1-6}$ alkyl, more preferably a $C_{1-4}$ alkyl.

In a preferred embodiment $R_1$ is $C_{2-8}$ alkenyl preferably $C_{2-6}$ alkenyl more preferably $C_{2-4}$ alkenyl.

In a preferred embodiment $R_1$ is selected from methyl, ethyl, propyl or isopropyl optionally methyl, propyl or isopropyl.

In a further aspect the invention also relates to a compound of general formula (V)

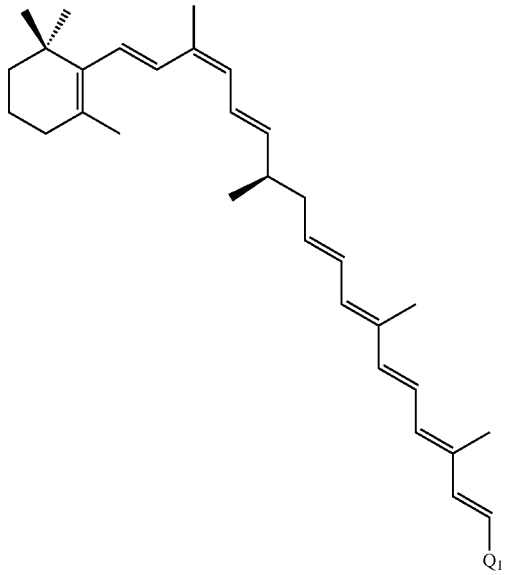

wherein $Q_1$ is a substituted or unsubstituted $C_{6-10}$ alkenyl or cycloalkenyl group, preferably a substituted or unsubstituted trimethylcycloalkenyl or more preferably a substituted or unsubstituted 2,6,6-trimethylcyclohexenyl, even more preferably unsubstituted 2,6,6-trimethylcyclohex-1-en-1-yl or 2,6,6-trimethylcyclohex-2-en-1-yl. If the trimethylcyclohexenyl, e.g. 2,6,6-trimethylcyclohexenyl group, is substituted it is preferably hydroxyl-substituted or oxo-substituted, preferably oxo-substituted;

wherein said compound is converted into 9-cis-13,14-dihydroretinol in mammalian tissue or organ or cells, once administered.

Highly preferably the group of general formula (A) is a group of formula (a)

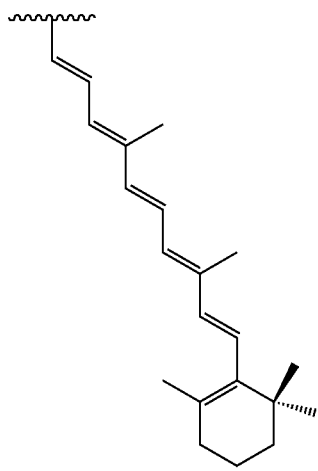

In a preferred embodiment the invention also relates to a 9-cis-carotenoid compound, preferably a 9-cis-13,14-dihydrocarotenoid, which is a 9-cis-13,14-dihydro-β,β-carotene or a 9-cis-13,14-dihydro-β,α-carotene, or a derivative thereof, meaning that it is present in the form of 9-cis-13,14-dihydro-β,β-carotene or of 9-cis-13,14-dihydro-β,α-carotene, respectively, in a living system, or preferably a 9-cis-13,14-dihydro-β,β-carotene, as a precursor compound, wherein said compound is converted into (R)-9-cis-13,14-dihydroretinoic acid in a mammalian tissue or organ or cells, once administered. In particular the 9-cis-carotenoid compound is a biologically acceptable tolerable compound.

The present invention concerns, in a further aspect, the compound of formula (II), in particular formula (IIR) and formula (IIS) and to a method for preparing same. The invention also relates to pharmaceutical compositions comprising the compounds according to the invention in a pharmaceutically acceptable carrier.

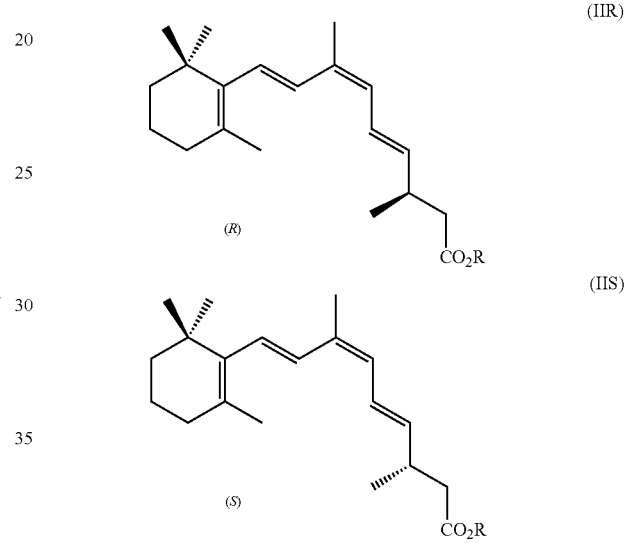

Highly preferably, the invention relates to an enantiopure (R)-9-cis-13,14-dihydroretinoic acid or a solvate, solid form or salt thereof.

Compositions

The present invention relates to, in another aspect, a pharmaceutical composition containing enantiopure 9-cis-13,14-dihydroretinoic acid (9CDHRA). The invention also relates to a pharmaceutical composition comprising the compounds according to the invention in a pharmaceutically acceptable carrier. The invention also describes a pharmaceutical composition for use in a therapeutic method, in particular for the treatment of a psychiatric disorder or disease.

In a further aspect the invention relates to a dietary supplement or a neutraceutical or a functional food; or relates to pharmaceutical composition comprising an enantiopure (R)-9-cis-13,14-dihydroretinoic acid, solvate, solid form or salt thereof, in a pharmaceutically acceptable carrier. Preferably said compound is obtainable or obtained according to the invention.

The embodiments when present compositions comprise synthetic compounds are different from a case of an endogenous substance present in nature and which can be used as an extract or as a product from nature containing this substance in significant levels.

In a further aspect the invention relates to a pharmaceutical composition comprising the compound as defined above for a compound of general formula (I) said composition also comprising one or more pharmaceutically acceptable carriers, e.g. additive(s) and/or excipient(s).

In a further aspect the invention relates to a pharmaceutical composition comprising the compound as defined above for a compound of general formula (II) said composition also comprising one or more pharmaceutically acceptable carriers, e.g. additive(s) and/or excipient(s).

In a further aspect the invention relates to a pharmaceutical composition comprising the compound as defined above for a compound of general formula (III) said composition also comprising one or more pharmaceutically acceptable carriers, e.g. additive(s) and/or excipient(s).

Preferably, the invention relates to a pharmaceutical composition comprising the compound as defined above for a compound of general formula (IV) said composition also comprising one or more pharmaceutically acceptable carriers, e.g. additive(s) and/or excipient(s).

Preferably, the invention relates to a pharmaceutical composition comprising the compound as defined above for the 9-cis-carotenoid and/or a compound of general formula (V), in particular a 9-cis-13,14-dihydro-β,β-carotene as a precursor compound said composition also comprising one or more pharmaceutically acceptable carriers, e.g. additive(s) and/or excipient(s).

The invention also relates to a nutraceutical composition comprising the compound as defined above for a compound of general formula (II) or for a compound of general formula (III) or preferably for a compound of general formula (IV), or of general formula (V) or the 9-cis-carotenoid compound, preferably 9-cis-13,14-dihydro-β,β-carotene as a precursor compound said composition also comprising one or more nutraceutically acceptable additive(s) and/or excipient(s). Preferably, said composition being a dietary supplement, a functional food, a medical food or a food with a health claim. Preferably said nutraceutical composition comprises said compound in an amount or concentration higher than it is present in the natural food matrix and/or comprises additional amount of the compound, preferably additional isolated or artificially prepared compound.

Compositions comprise, besides the active agent at least one excipient or carrier.

The carrier or excipient may be a stabilizer or a solubilizer.

Pharmaceutical carriers in liquid formulae can be sterile liquids, such as water and oils, including those of petroleum, animal, vegetable or synthetic origin.

Where necessary, the composition can also include a solubilizing agent.

The composition, if desired, can also contain wetting or emulsifying agents, like lipids.

Preferably, the stabilizer is an antioxidant.

In liquid formulations preferably an oil is used. Preferably the composition is to be stored in a vial which protects against light, in particular ultraviolet light. In a preferred embodiment a solvent and an oil is applied together.

Solid forms preferably also comprise an emulsifier and/or solubilizer. Preferably the active agents in solid forms also comprise a protection from light, e.g. a coating.

Food concentrate or food extract added to a composition of the invention may also be considered as a stabilizer and/or emulsifier.

Alkaline pH is preferred.

Liquid forms are typically protected from light by the packaging.

Preferably, daily dosages may vary from about 1 mg or 5 mg to about 70 mg, or to about 80 mg or to about 100 mg. Typically the dosages are calculated for 9CDHRA or 9CDRHOL. Precursors are considered in amounts equivalent to these doses, e.g. in doses providing an equivalent amount or effect.

In an embodiment the composition comprises a synthetic compound in an amount which provides at least 5%, 10%, 20%, 30%, 40%, 50%, 60%, 70% or 80% of the daily dose for a subject, preferably of a recommended daily dose, preferably the dosages are calculated for 9CDHRA or 9CDRHOL.

Synthesis Methods

The invention also relates to a novel chemical synthesis of 9-cis-13,14-dihydroretinol and ester forms thereof via alkyl 9-cis-13,14-dihydroretinoate. The method comprises i) reduction of alkyl 9-cis-13,14-dihydroretinoate into 9-cis-13,14-dihydroretinol and optionally ii) alkylation of 9-cis-13,14-dihydroretinol into the corresponding ester form. The esters are exemplified herein below.

In a preferred embodiment reduction is carried out by a hydride catalyst, like diisobutylaluminium hydride (DIBAL-H) reduction in an organic solvent, preferably a small heterocycle like THF.

Esterifications of alcohols are preferably carried out by alkylic anhydride reagents. Preferably a basic nitrogen containing single ring heterocycle, like pyridine and/or derivatives, is applied. In a highly preferred embodiment the reaction is carried out in the presence of dimethylaminopyridine (DMAP).

Preferred organic solvent applied are e.g. $CH_2Cl_2$, chloroform, $CCl_4$ etc.

Other esters of 9-cis-13,14-dihydroretinoic acid and 9-cis-13,14-dihydroretinol (such as palmitate and others) can be easily prepared using the same sequence.

In a further embodiment the invention also relates to a novel chemical synthesis of a compound of general formula (5) as defined above, preferably a 9-cis-carotenoid compound which is a 9-cis-13,14-dihydro-β-carotene derivative preferably a 9-cis-13,14-dihydro-β,β-carotene, said method comprising conversion of a compound of general formula (III)

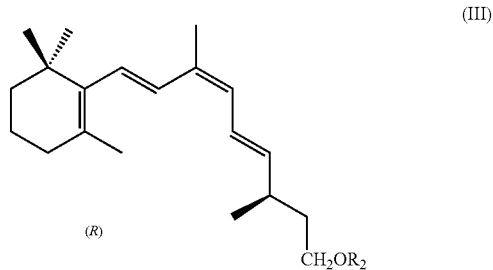

wherein $R_2$ is H or an OH-protecting group;
into the corresponding aldehyde of formula (VI) as an intermediate

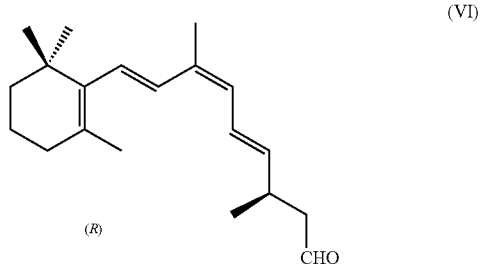

reacting said aldehyde intermediate with Wittig-reagent compound (VII)

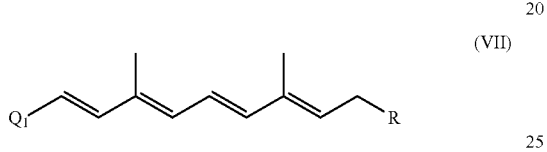

wherein $Q_1$ is a substituted or unsubstituted $C_{6-10}$ alkenyl or cycloalkenyl group, preferably a substituted or unsubstituted trimethylcycloalkenyl or more preferably a substituted or unsubstituted 2,6,6-trimethylcyclohexenyl, even more preferably unsubstituted 2,6,6-trimethylcyclohex-1-en-1-yl or 2,6,6-trimethylcyclohex-2-en-1-yl. If the trimethylcyclohexenyl group, e.g. 2,6,6-trimethylcyclohexenyl, is substituted it is preferably hydroxyl-substituted or oxo-substituted, preferably oxo-substituted;
and R is a group forming a phosphorous ylide, preferably a phosphonium salt, preferably a triphenylphosphonium salt, to give the desired compound according to formula (V).

In a preferred embodiment 9-cis-13,14-dihydro-β,β-carotene is prepared wherein general formula (VII) is a compound of general formula (VIII)

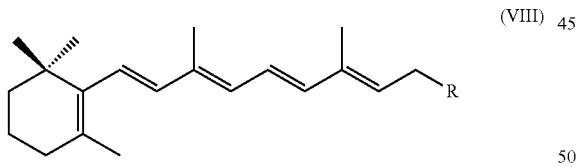

R is a group forming a phosphorous ylide, preferably a phosphonium group, preferably a triphenylphosphonium group, to give 9-cis-13,14-dihydro-β,β-carotene.

In a further aspect the invention also relates to a use of a compound as defined above for a compound of general formula (III) or preferably for a compound of general formula (IV) or for a compound of general formula (V) or the 9-cis-carotenoid or the particular options as a food ingredient or food supplement. Preferably, the food ingredient is ingredient of a functional food or a medical food.

In an embodiment of the invention the compound as defined above for a compound of general formula (III) or preferably for a compound of general formula (IV) or a compound of general formula (V) or the 9-cis-carotenoid or the particular options is for use in therapy in a mammalian subject.

In a preferred embodiment the compound is in the form of a pharmaceutical composition.

In a further preferred embodiment the compound is in the form of a nutraceutical composition, which requires an authorization to be marketed for the indication as provided herein.

The invention also relates to a method for the preparation of a compound selected from the group consisting of R or S enantiomer of 9-cis-13,14-dihydroretinoic acid ((R)-9CDHRA or (S)-9CDHRA) or esters thereof according to general formula II [(IIR) and/or (IIS)], a solvate and, if appropriate, a salt thereof, said method comprising

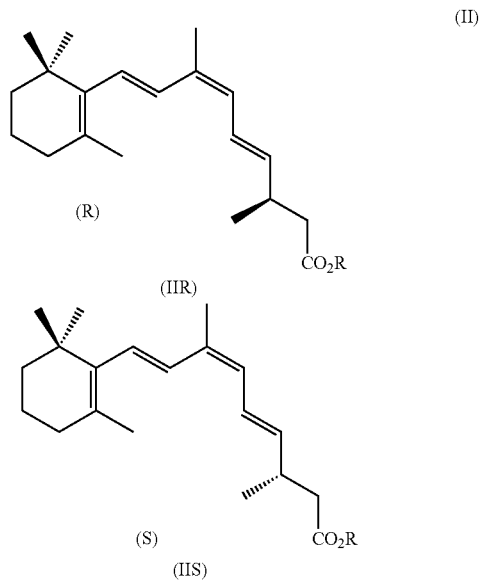

wherein in said formula R is selected from H or ethyl;
providing the respective (9Z,11E) geometric isomer of the (R) or (S) enantiomer (preferably enantiopure) trienyliodide of formula 24 [(R) and/or (S)]

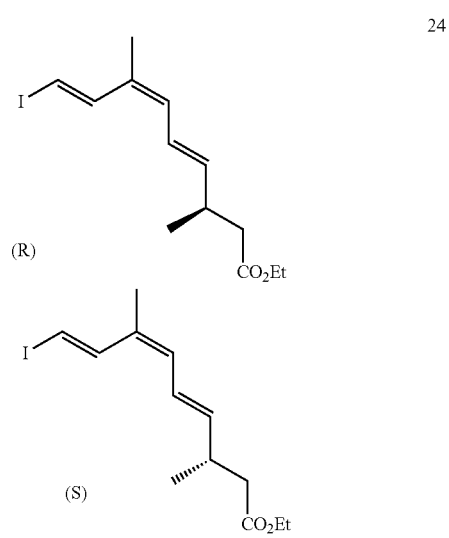

reacting, respectively, said (R)- or (S)-enantiomer (preferably) enantiopure trienyliodide of formula 24 with boronic acid of formula 25 by Suzuki coupling to obtain said compound as ethyl (R)- or (S)-9-cis-13,14-dihydroretinoate of general formula (II);

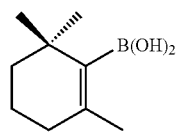

25 optionally saponifying said ethyl (R)- or (S)-9-cis-13,14-dihydroretinoate to obtain said compound as (R)- or (S)-9-cis-13,14-dihydroretinoic acid, respectively; and optionally forming said compound into a solvate or, if appropriate, salt thereof.

Preferably, the (R)- or (S)-enantiomer, preferably enantiopure, trienyliodide of formula 24 is prepared from the enantiopure stannane of formula 23 [(R)-23 and/or (S)-23]

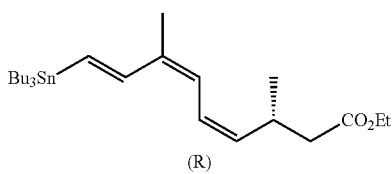

23

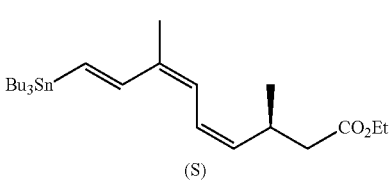

with a solution of iodine in solvent, preferably CH$_2$Cl$_2$, via Sn-1 exchange and iodine-promoted isomerization of the (9Z,11Z)-diene to the desired (9Z,11E) geometric isomer.

Preferably, said method further comprises the steps of (a) transforming the stannyldienol of formula 19

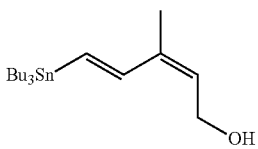

19 by Mitsunobu reaction with the corresponding thiol into benzothiazolyl allyl sulfide having formula 20

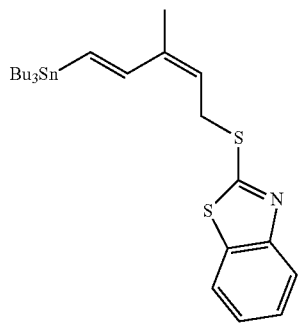

20

(b) oxidizing the benzothiazolyl allyl sulfide having formula 20 to the corresponding sulfone having Formula 21

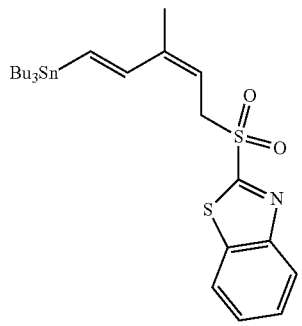

21 with hydrogen and a peroxymolybdate (e.g. (NH$_4$)$_6$Mo$_7$O$_{24}$·4H$_2$O) reagent, preferably at −10° C.;

(c) reacting the sulfone having formula 21 with (preferably enantiopure) (R)- or (S)-aldehyde 22 [(R)-22 and/or (S)-22], (preferably 1.7 equivalents thereof), respectively,

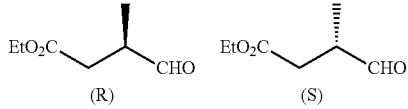

22 in the presence of base, preferably excess of base or slight excess of base, by Julia-Kocienski olefination, to obtain the stannane of Formula 23 [(R)-23 and/or (S)-23].

In a preferred embodiment all steps of the methods as defined above are carried out.

Preferably the compound of the invention is obtained as an enantiopure or enantiomerically pure compound.

Highly preferably, in the method of the invention, an (R) enantiomer of 9-cis-13,14-dihydroretinoic acid, a solvate and/or a salt thereof is prepared, wherein formula (II) is

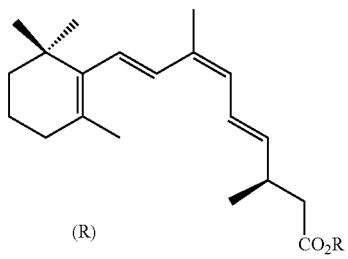

IIR wherein in said formula R is H;
the compound of formula 13 is

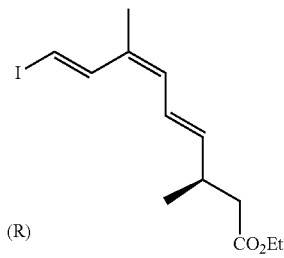

(R)-24 wherein the stannane of formula 23 is of (R) configuration

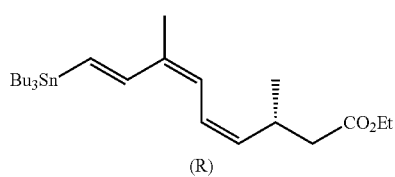

23

Preferably the sulfone having formula 21 is reacted with enantiopure aldehyde R of formula 22, respectively,

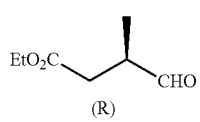

22 in the presence of base, to obtain the stannane of formula 23.

In a preferred embodiment, when an (R) enantiomer of 9-cis-13,14-dihydroretinoic acid, a solvate and/or a salt thereof is prepared, all steps of the methods as defined above are carried out.

Preferably the sulfone having formula 21 is reacted with 1.7 equivalents of enantiopure (R)- or (S)-aldehyde 22. Preferably the compound of the invention is obtained as an enantiopure or enantiomerically pure compound.

Compositions and Medical Uses

In a further aspect the invention relates to a dietary supplement or a nutraceutical or a functional food; or relates to pharmaceutical composition comprising an enantiopure (R)-9-cis-13,14-dihydroretinoic acid, solvate, solid form or salt thereof, in a pharmaceutically acceptable carrier. Preferably said compound is obtainable or obtained according to the invention.

In a highly preferred embodiment the invention relates to an enantiopure (R)-9-cis-13,14-dihydroretinoic acid for use in the treatment and/or prevention and/or reduction the risk of memory impairment or for use in enhancing memory performance.

In a highly preferred embodiment the invention relates to an enantiopure (R)-9-cis-13,14-dihydroretinoic acid for use in the treatment and/or prevention and/or reduction the risk of working memory impairment or for use in enhancing working memory performance.

In a highly preferred embodiment the invention relates to an enantiopure (R)-9-cis-13,14-dihydroretinoic acid for use in the treatment and/or prevention and/or reduction the risk of impaired cognitive functions or impaired learning.

In a highly preferred embodiment the invention relates to an enantiopure (R)-9-cis-13,14-dihydroretinoic acid for use in the treatment of depression.

The invention also relates to a functional food or a dietary supplement comprising one or more enantiomerically pure compound(s) according to the invention.

In a further aspect the invention relates to a pharmaceutical composition comprising the compound as defined above for general compound (2) said composition also comprising one or more pharmaceutically acceptable carriers, e.g. additive(s) and/or excipient(s).

The invention also relates to a nutraceutical composition comprising the compound as defined above for general compound (2) said composition also comprising one or more nutraceutically acceptable additive(s) and/or excipient(s). Preferably, said composition being a dietary supplement, a functional food, a medical food or a food with a health claim.

In a further aspect the invention also relates to a use of a compound as defined above for general compound (2) as a food ingredient. Preferably, the food ingredient is ingredient of a functional food or a medical food.

In an embodiment of the invention the compound as defined above for general compound (2) is for use in therapy in a mammalian subject.

In a preferred embodiment the compound is in the form of a pharmaceutical composition.

In a further preferred embodiment the compound is in the form of a nutraceutical composition, which requires an authorization to be marketed for the indication as provided herein.

In a preferred embodiment the compound or the pharmaceutical composition or the nutraceutical composition is for use in the treatment and/or prevention and/or reduction the risk of an RXR-signaling mediated dysfunction.

In a preferred embodiment the compound or the pharmaceutical composition or the nutraceutical composition is for activation of or improving or increasing the activation of RXR signaling in a subject.

The invention also relates to a method for the activation of RXR-mediated signaling in a subject suffering from or endangered by impairment of RXR-mediated signaling or from mild to severe Vitamin A5 deficiency In a preferred embodiment the compound or the pharmaceutical composition or the nutraceutical composition is for use in the treatment and/or prevention and/or reduction the risk of a disease related to or due to impaired retinoid X receptor-mediated signaling. Said disease preferably can be treated or prevented or alleviated by a selective retinoid X receptor ligand.

In a preferred embodiment the compound or the pharmaceutical composition or the nutraceutical composition is for use in the treatment and/or prevention and/or reduction the risk of a disease selected from central nervous system related diseases and peripheral nervous system related diseases.

In a preferred embodiment the compound or the pharmaceutical composition or the nutraceutical composition is for use in the treatment and/or prevention and/or reduction the risk of mental diseases.

In a preferred embodiment the compound or the pharmaceutical composition or the nutraceutical composition is for use in the treatment and/or prevention and/or reduction the risk of memory impairment or for use in enhancing memory performance, wherein preferably said memory is working memory.

In a preferred embodiment the compound or the pharmaceutical composition or the nutraceutical composition is for use in the treatment and/or prevention and/or reduction the risk of impaired cognitive functions or impaired learning.

In a preferred embodiment the compound or the pharmaceutical composition or the nutraceutical composition is for use in the treatment and/or prevention and/or reduction the risk of depression.

In a preferred embodiment the compound or the pharmaceutical composition or the nutraceutical composition is for use in the treatment and/or prevention and/or reduction the risk of a neurodegenerative disorder.

In a preferred embodiment the compound or the pharmaceutical composition or the nutraceutical composition is for use in the treatment and/or prevention and/or reduction the risk of a neurodegenerative disorder selected from Alzheimer's disease, Parkinson's disease, Mild Cognitive Impairment (MCI), Parkinson's disease with MCI, Huntington's disease, Dementia with Lewy bodies (DLB), Amyotrophic lateral sclerosis (ALS), and other neurodegenerative related dementias due to changes in the brain caused by ageing, disease or trauma; or spinal cord injury and ataxias, disseminated sclerosis and multiple sclerosis or other neurological conditions, preferably from Alzheimer's disease and Parkinson's disease.

In the above medical indication embodiments the compound is preferably selected from compounds as defined above for general compound (II), (III) or (IV). In the above medical indication embodiments the compound is preferably selected from compounds as defined above for general compound (III) or preferably (IV).

The invention also relates to the use of any of the above compounds in the preparation of a pharmaceutical preparation or a medicament as defined herein or above.

The invention also relates to the use of any of the above compounds in the preparation of a nutraceutical preparation, preferably a medical food or a food with a health claim as defined herein or above.

The invention also relates to a method for treatment of a disease as defined above wherein a compound of the invention or a pharmaceutical composition of the invention or a nutraceutical composition is administered to a mammalian subject preferably a human in need thereof in an effective dose. In a preferred embodiment administration is regular, e.g. daily administration.

The invention also relates to a method for maintaining or improving health of a subject, said method comprising administration of any of the compounds as defined herein preferably as a food ingredient, a dietary supplement, e.g. as a vitamin or precursor thereof or as a nutraceutical ingredient. In a preferred embodiment the invention relates to a method for maintaining or improving health to prevent a condition as defined herein. In an embodiment said method is for maintenance of normal vision, maintenance of normal skin and mucous membranes, and maintenance of normal hair.

More preferably the invention relates to a method for maintaining or improving health of a subject by administration of a compound as defined herein, wherein said method is for maintenance of normal brain function or maintenance of mental health or maintenance of mental performance or maintenance normal psychological function or cognitive function or for contribution of the functioning of the nervous system. In an embodiment these uses are defined in a health claim. The health claim can be for example a qualified health claim or an authorized health claim.

The invention also relates to a method for maintaining or improving a healthy condition of a subject as defined above wherein a compound of the invention or a nutraceutical composition of the invention is administered to a mammalian subject preferably a human in need thereof as a part of a diet. In a preferred embodiment administration is regular, e.g. daily administration.

It is mentioned herein that non-selective precursors cannot be used for the treatment and prevention of RXR-mediated signaling dysfunctions according to the invention, as explained herein in connection with RXR and RAR receptors.

The invention also relates to a method for using a compound according to any of general formulae (III), (IV) and/or (V) as defined above as a dietary supplement as a vitamin A5 (9CDHROL) or precursor thereof. In a particular embodiment the precursor is 9CDHBC. In a further particular embodiment the precursor is selected from 9CDHROL-esters.

The invention also relates to a method for using a compound according to any of general formulae (III), (IV) and/or (V) as defined above as a dietary supplement as a 9CDHRA precursor, and RXR-ligand. In a particular embodiment the 9CDHRA precursor is selected from 9CDHBC, 9CDHROL, 9CDHROL-esters (9CDHROL-ES) and 9CDHRA-esters (9CDHRA-ES).

Preferably the precursors are administered in an intravenous, topical or oral route. The precursors can be administered systemically or locally.

These precursors can be given for selective metabolic conversion to 9CDHRA, the endogenous RXR-ligand for enabling RXR-mediated signaling.

In a particular embodiment the invention relates to a method for using of 9CDHBC to prevent, treat or ameliorate any condition as defined above. In a preferred embodiment the condition is selected from the group consisting of: (a) affective abnormalities in stress associated disorders including (but not limited to) psychiatric disorders such as depression, schizophrenia (b) memory deficits associated with dementia, and in particular Alzheimer-disease.

In a particular embodiment 9CDHBC is used for memory improvement.

The invention also relates to the use of 9CDHBC in the preparation of a pharmaceutical preparation or a medicament as defined herein or above; or in the preparation of a nutraceutical preparation, preferably a medical food or a food with a health claim as defined herein or above.

In a particular embodiment the invention relates to a method for using 9CDHROL or any ester thereof as defined herein to prevent, treat or ameliorate any condition as defined above. In a preferred embodiment the condition is selected from the group consisting of: (a) affective abnormalities in stress associated disorders including (but not limited to) psychiatric disorders such as depression, schizophrenia (b) memory deficits associated with dementia, and in particular Alzheimer-disease.

In a particular embodiment 9CDHROL or any ester thereof is used for memory improvement.

In a particular embodiment the invention relates to a method for using of 9CBC as a carotenoid precursor of 9CDHBC. In particular the invention relates to a method for using 9CBC as a pro-vitamin A5. Said method comprises administering 9CBC, or a food extract or a nutraceutical comprising 9CBC, to a subject as described above. In a preferred embodiment a food extract containing 9CBC in an increased or additional amount is used. Preferably the food extract comprises 9CBC in a higher concentration than the natural form or the form present in nature. Food extract may be or may include an algal extract.

In a further aspect the invention relates to methods for using food extract or algal extract comprising high amount of 9CBC. In these compositions the 9CBC may be of natural origin.

In a particular embodiment the invention relates to a method for using of 9CBC as a food supplement to increase the level of 9CDHBC in the human body in a non-therapeutic application.

In a particular embodiment the invention relates to a method for using a food extract or an algal extract containing 9CBC
- for the prevention or treatment of a retinoid X receptor (RXR)-mediated signaling related and/or dependent disease by providing 9-cis-13,14-dihydroretinoic acid (9CDHRA) as an RXR ligand in a subject or
- for providing 9-cis-13,14-dihydroretinoic acid (9CDHRA) as an RXR ligand in a subject suffering from or endangered by impairment of RXR-mediated signaling, or
- for the prevention or treatment of (mild to severe) vitamin A5 deficiency, said method comprising the administration of 9CBC or the food extract to a mammalian subject suffering from or being endangered by a retinoid X receptor-mediated signaling related and/or dependent disease, The invention also relates to a method for improving the health of a mammalian subject according to claim 17 wherein a 9-cis-carotenoid compound is administered to said mammalian subject,
- which is a 9-cis-13,14-dihydro-β,β-carotene or a 9-cis-13,14-dihydro-β,α-carotene, more preferably a 9-cis-13,14-dihydro-β,β-carotene wherein said compound is converted into (R)-9-cis-13,14-dihydroretinoic acid in the mammalian tissue or organ or cells, once administered to the subject;
- or wherein said compound is a 9-cis-carotenoid which is a 9-cis-β,β-carotene (9CBC) or a 9-cis-β,α-carotene, said compound being converted into a 9-cis-13,14-dihydro-β,β-carotene or a 9-cis-13,14-dihydro-β,α-carotene, once administered to the subject.

The invention also relates to a method for using any of the above compounds in the preparation of a pharmaceutical preparation or a medicament as defined herein or above.

The invention also relates to a method for using any of the above compounds in the preparation of a nutraceutical preparation, preferably a medical food or a food with a health claim as defined herein or above.

The invention also relates to a method for treatment of a disease as defined above wherein a compound of the invention or a pharmaceutical composition of the invention or a nutraceutical composition is administered to a mammalian subject preferably a human in need thereof in an effective dose. In a preferred embodiment administration is regular, e.g. daily administration.

The invention also relates to a method for using any of the compounds as defined herein for maintaining or improving health, preferably as a food ingredient, a dietary supplement, e.g. as a vitamin or precursor thereof or as a nutraceutical ingredient. In a preferred embodiment the invention relates to a method for maintaining or improving health to prevent a condition as defined herein. In an embodiment said method is for maintenance of normal vision, maintenance of normal skin and mucous membranes, and maintenance of normal hair.

More preferably the use of any of the compounds as defined herein for maintaining or improving health is for maintenance or improvement of normal brain function or maintenance of mental health or maintenance or improvement of mental performance or maintenance or improvement normal psychological function or cognitive function or for contribution of the functioning of the nervous system. In an embodiment these uses are defined in a health claim.

The invention also relates to a method for maintaining or improving a healthy condition of a subject as defined above wherein a compound of the invention or a nutraceutical composition of the invention is administered to a mammalian subject preferably a human in need thereof as a part of a diet. In a preferred embodiment administration is regular, e.g. daily administration.

It is mentioned herein that non-selective precursors cannot be used for the treatment and prevention of RXR-mediated signaling mediated dysfunctions according to the invention, as explained herein in connection with RXR and RAR receptors.

BRIEF DESCRIPTION OF THE FIGURES

FIG. 1A An increasing learning curve for wild type C57BL6N male mice (n=5) illustrates acquisition of the working memory task. Memory performance scored for increased inter-trial intervals (ITI) is shown in grey field and corresponds to ITI of 3 min and a mean ITI at which mice displayed memory deficit and which for the whole group attained mean value of 13 min (indicated as gr13).

FIG. 1B Correct choices 7-9 h. after treatment with 9CDHROL and vehicle when tested at mean ITI of 13 min. 9CDHROL, but not vehicle treatment improved working memory performance 7-9 hrs after treatment when tested at mean ITI of 13 min. Statistical differences identified with one or two group t-test were indicated respectively as: *, $p<0.05$ when compared to 50% performance at chance level and #, $p<0.05$, for comparison with the performance on the last day of acquisition phase (day 10).

FIG. 1C Learning curve for Rbp1−/− (n=8) and Rxrγ−/− (n=7) mice.

Rbp1−/− (n=8) and Rxrγ−/− (n=7) mice acquired working memory DNMTP task similarly to WT (n=8) mice ($F[8,160]=14$, $p<0.001$; ANOVA on repeated measures) when trained with 15 sec inter-trial intervals (ITI), but showed forgetting when tested at 3, and 6 min ITIs, which was more rapid than 12 or 18 min in WT mice (indicated in the graph as 12 min ITI).

FIG. 1D RXR agonists improved working memory performance in Rbp1−/− mice tested at 6 min ITI or WT mice at 12 or 18 min ITIs, but was inactive in Rxrγ−/− mice at ITI of 6 min. Statistical differences identified with PLSD Fischer test were indicated as: *, $p<0.05$; **, $p<0.01$ as compared to WT controls in respective groups; \$, $p<0.05$; \$\$, $p<0.01$; \$\$\$, $p<0.001$ in comparison with 50% of chance level.

Figure 2A:
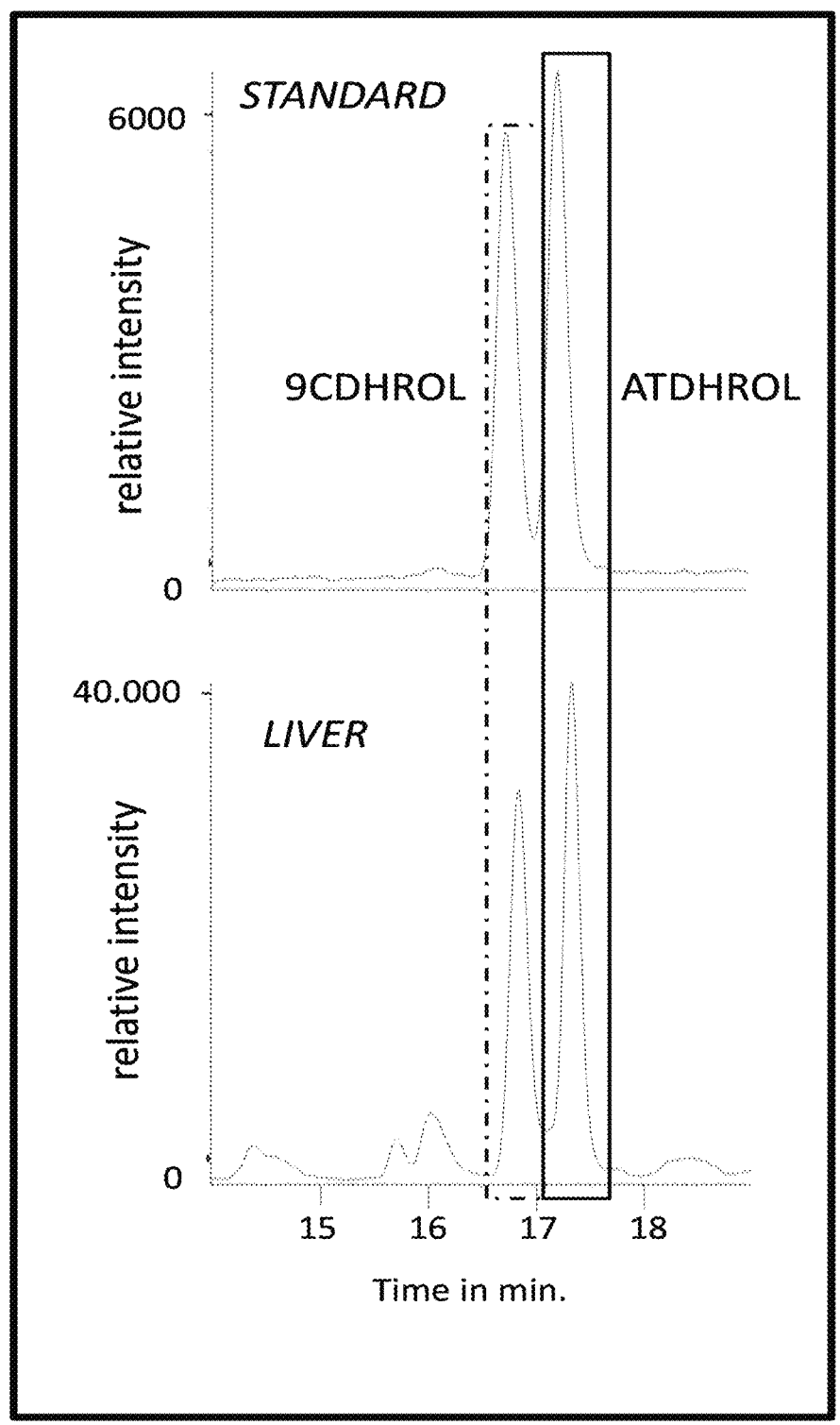

FIG. 2:

FIG. 2A 9CDHROL standard mixture (top chromatogram) and endogenous levels in the liver of mice after vehicle treatment (bottom chromatogram).

Figure 2B:
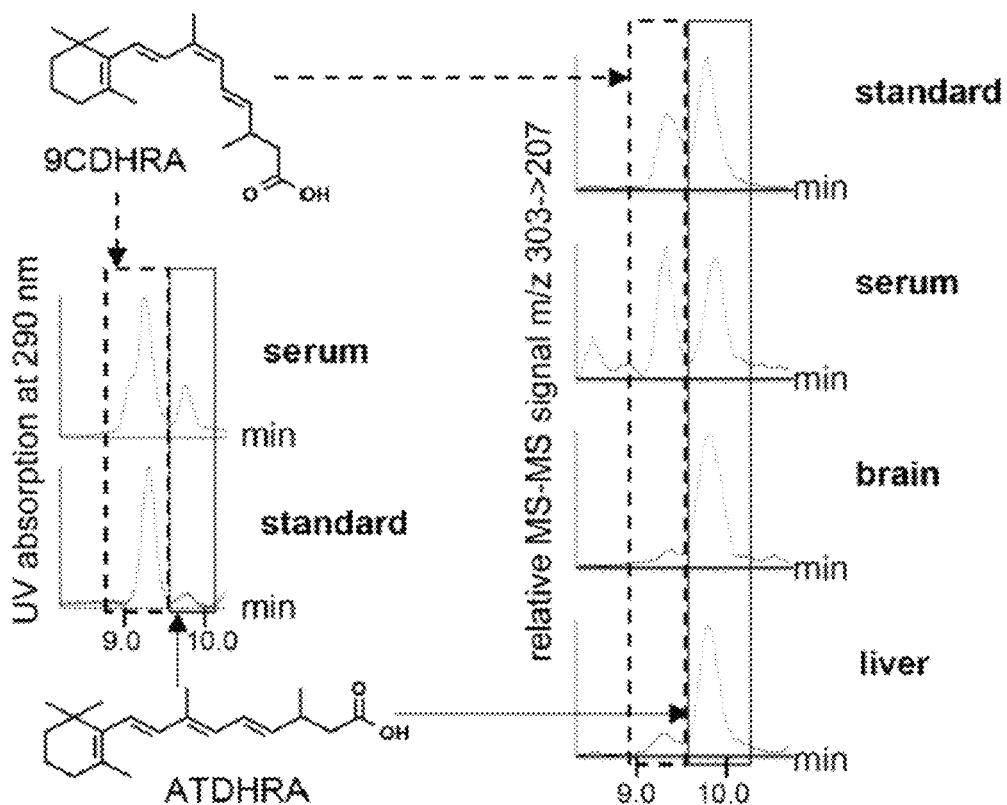

FIG. 2B 9-cis-13,14-dihydroretinoic acid (9CDHRA) is present in mouse serum (n=7) and liver (n=7) samples as determined by co-elution with a mixture of 9CDHRA and all-trans-13,14-dihydroretinoic acid (ATDHRA) standard solution and confirmed by MS-MS (303→207 m/z) and DAD (290 nm) detection.

Figure 2C:
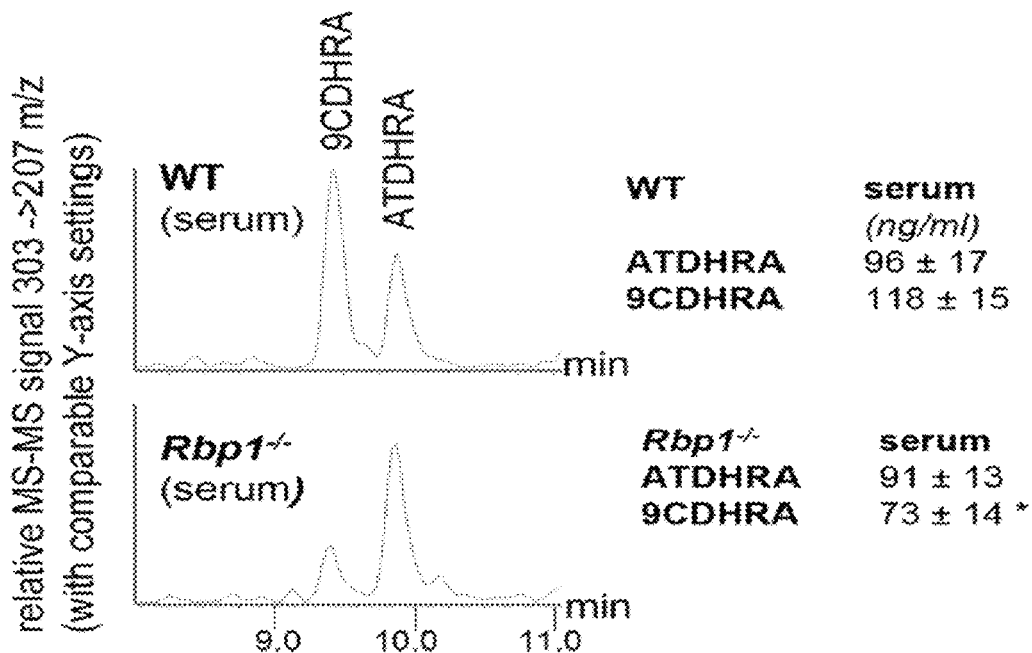

FIG. 2C Significant reduction of 9CDHRA, but not ATDHRA levels in serum brain and liver of Rbp1−/− animals (n=8) as compared to WT mice (n=8). All the error bars represent S.E.M.

FIG. 3:

9CDHRA binds and transactivates RXR in vitro, and displays RXR agonist-like activities in vivo.

Figure 3A:
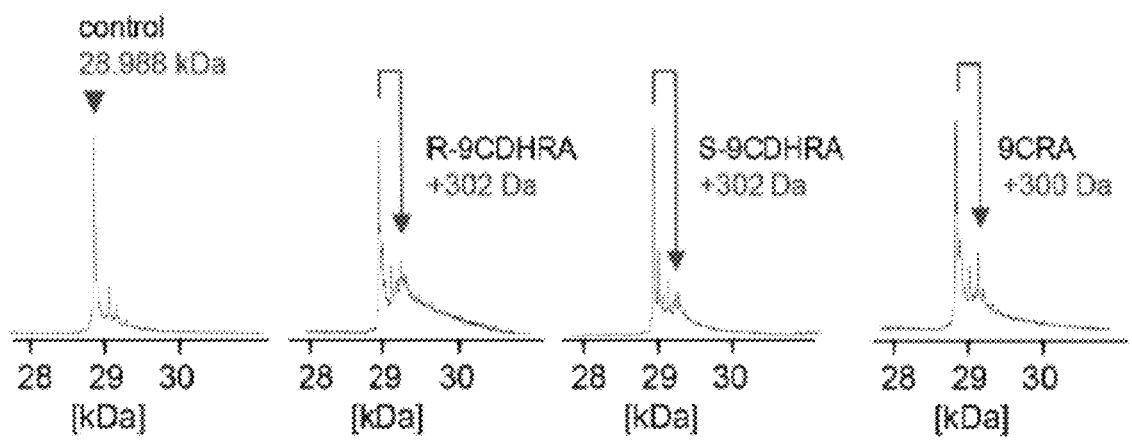

FIG. 3A ESI mass spectra of hRXRα LBD protein after incubation with a 5-fold molar excess of 9CRA, (R)-9CDHRA and (S)-9CDHRA.

Figure 3B:
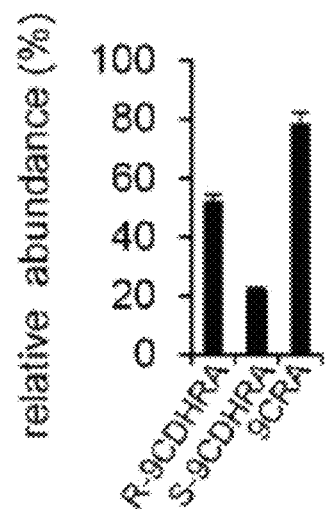

FIG. 3B Distribution plot of the percentage of bound for hRXRα.

Figure 3C:
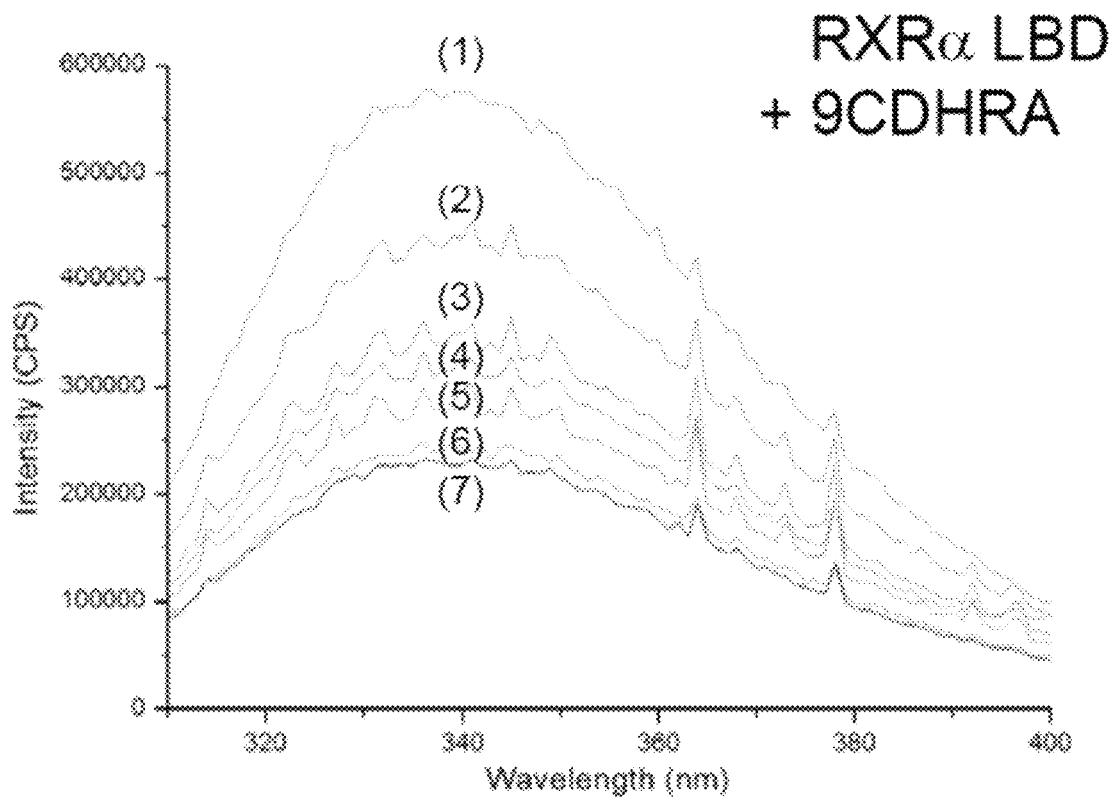
Figure 3D:
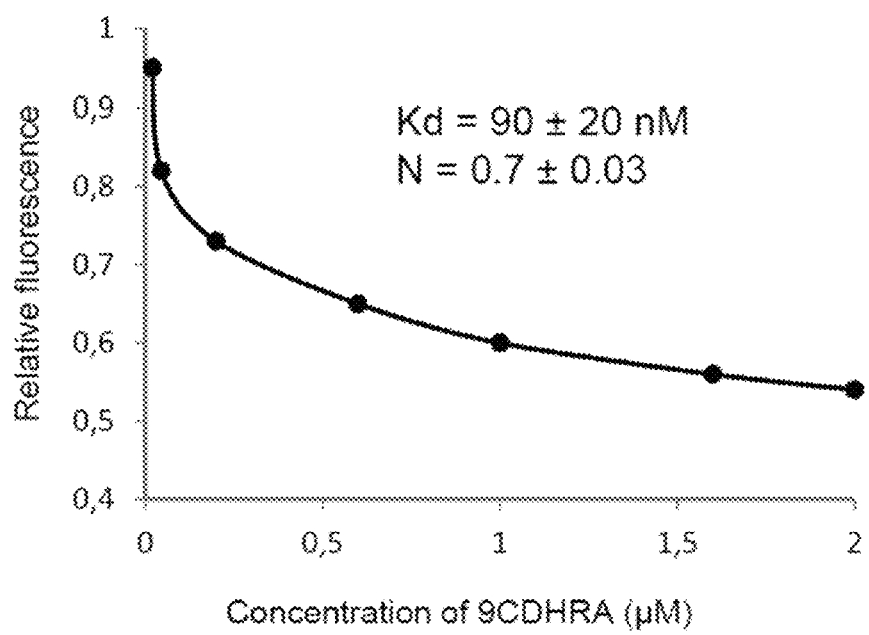

FIGS. 3C-3D Fluorescence quenching assay.

FIG. 3C An example of fluorescence emission spectra for the binding of increasing amounts of 9CDHRA to RXRα LBD (1.25 µM). Curves 1-7 correspond to concentration of 0, 0.2, 0.45, 0.6, 1, 1.6, 1.2 µM of 9CDHRA;

FIG. 3D Titration curve for 9CDHRA was used to calculate the Kd value of 90±20 nM as previously described (Chen et al., 1994). N corresponds to number of binding sites.

FIGS. 3E-3J Binding of 9CDHRA (R and S enantiomers) to RAR LBD isotypes in non-denaturing ESI-MS assays and in silico, and crystallography analyses of 9CDHRA binding to RXR.

Figures 1, 3E:
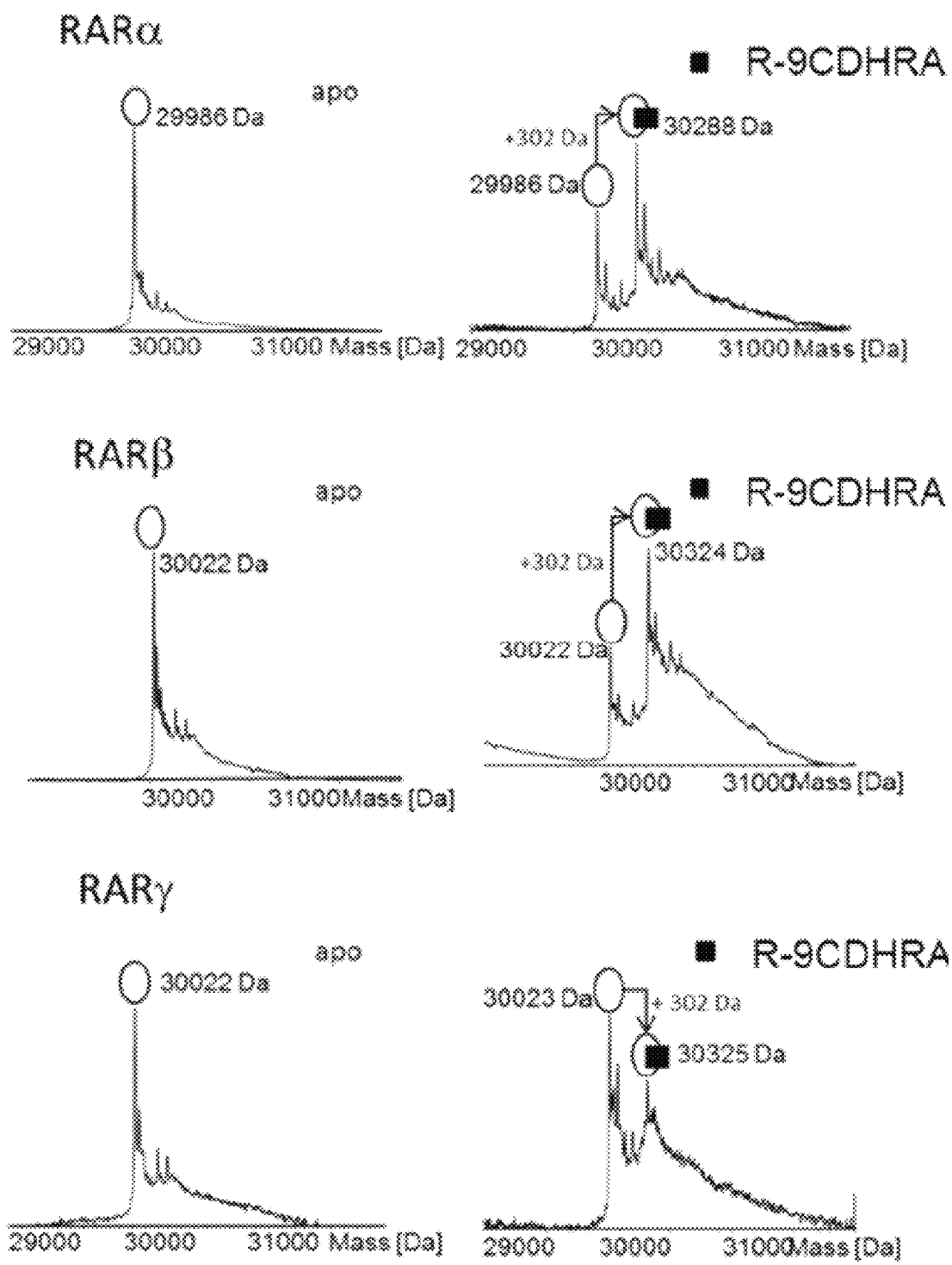
FIG. 1: 9CDHROL treatment improves working memory performance in Delayed Non-Match to Place Task (DNMTP).
Figures 2, 3E:
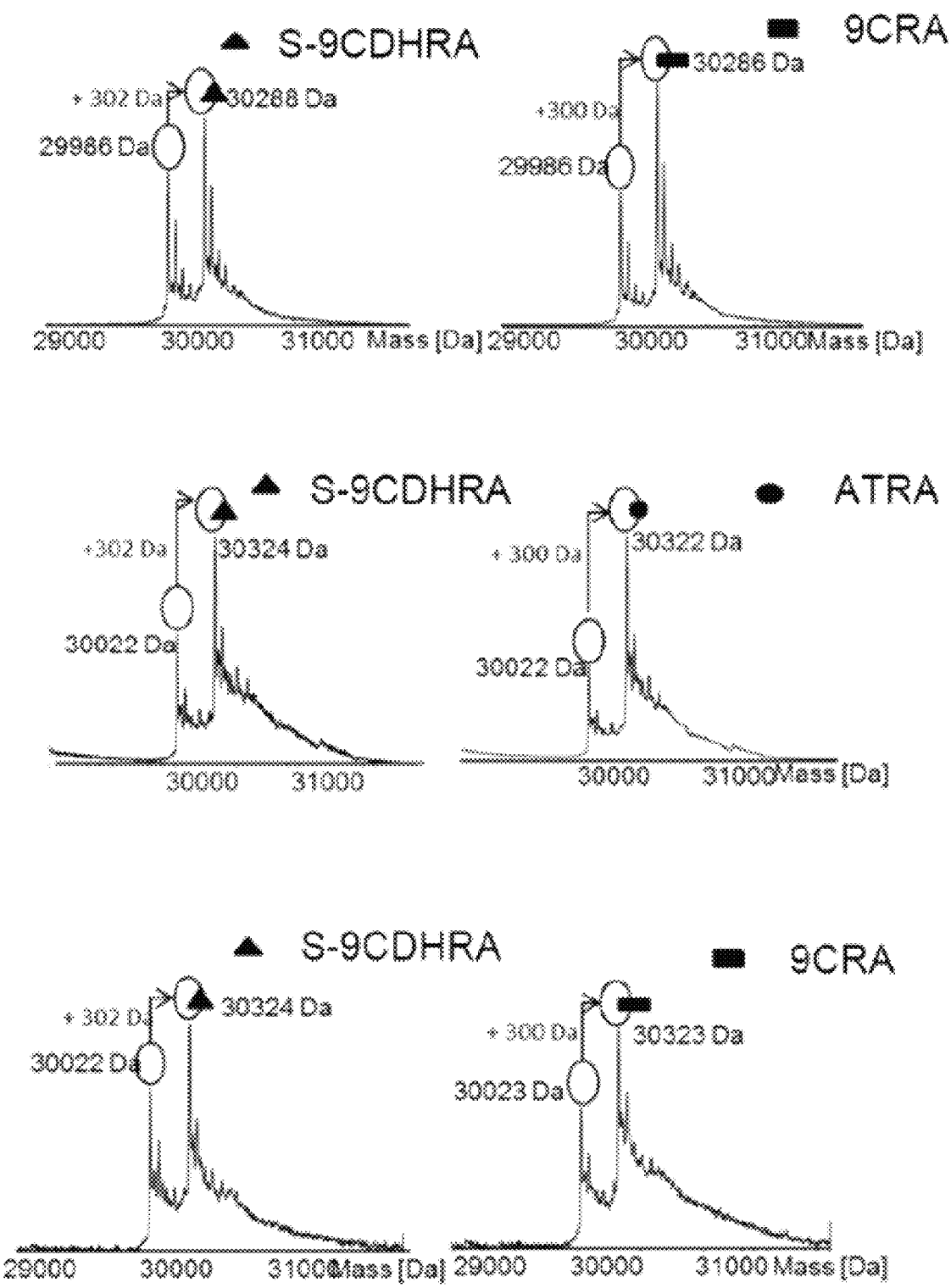
Figure 3F:
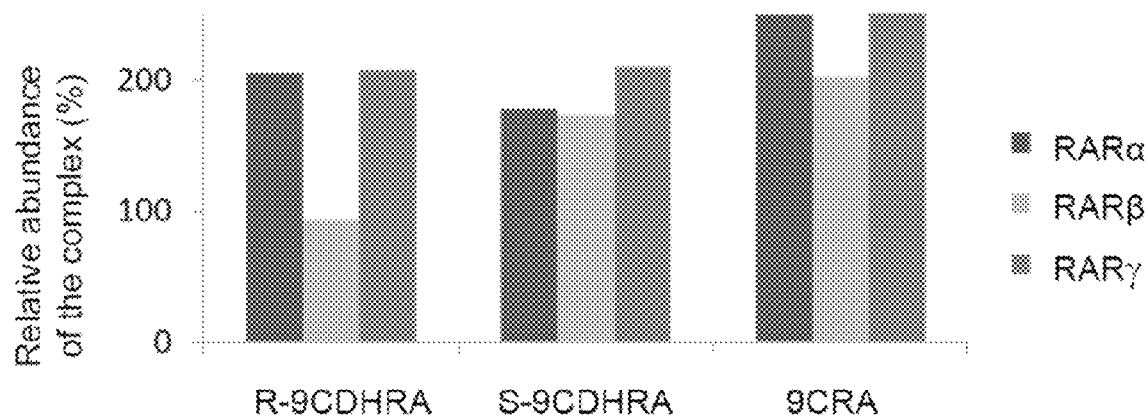

FIGS. 3E-1 and 3E-2 ESI mass spectra of hRARα (top), hRARβ (middle) and hRARγ (bottom) LBDs protein after incubation with a 5-fold molar excess of ligands;

FIG. 3F Distribution plot of the relative proportion of percent of bound/free protein for hRAR isotypes for R and S enantiomers of 9CDHRA and 9CRA.

Figure 3G:
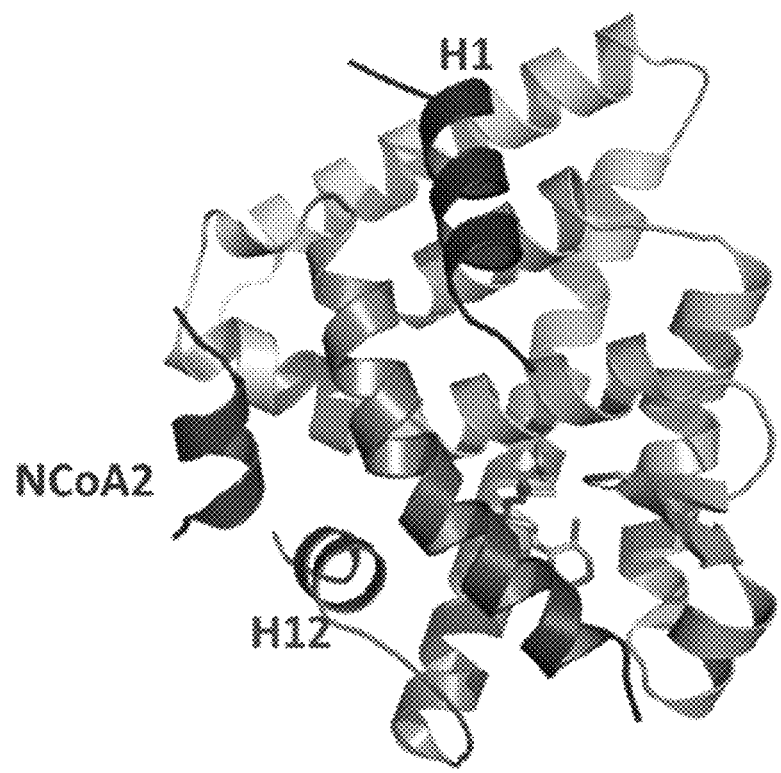

FIG. 3G Overall crystal structure of the RXRα LBD in complex with (R)-9CDHRA.

Figure 3H:
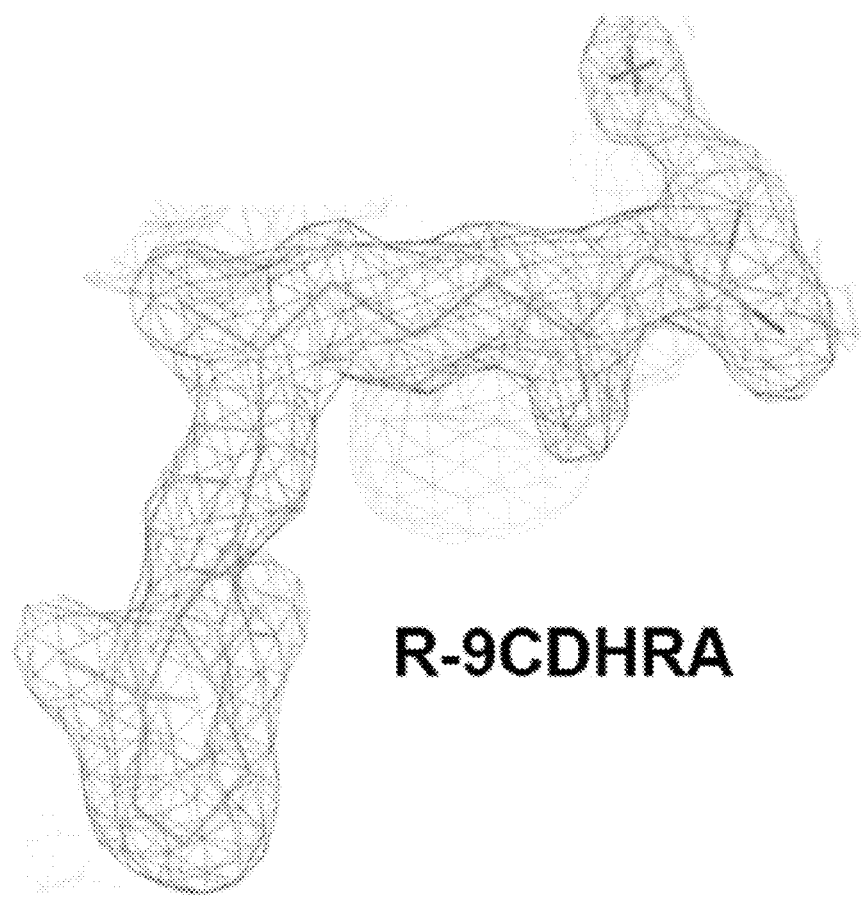

FIG. 3H Experimental 2Fo-Fc electron density map of (R)-9CDHRA ligand contoured at 1 sigma.

Figure 3I:
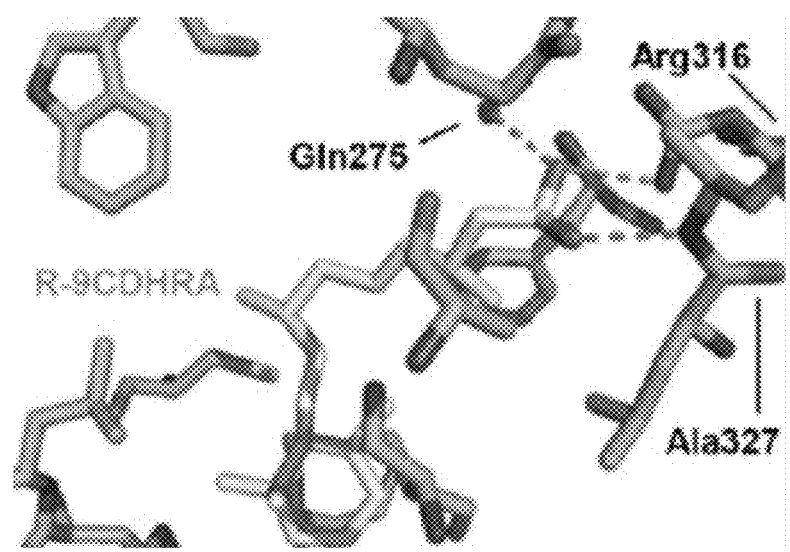

FIG. 3I Close-up view showing the ligand-binding pocket (LBP) of RXRα bound to (R)-9CDHRA (in grey). Dashed lines indicate hydrogen bonds.

Figure 3J:
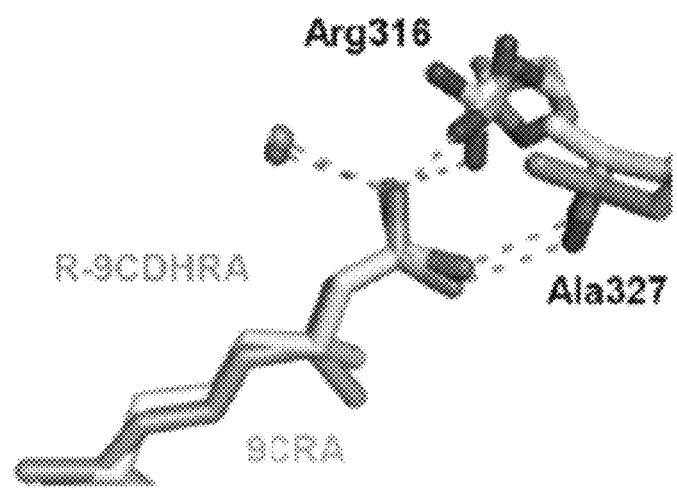

FIG. 3J Superposition of the RXRα ligand-binding pocket bound by (R)-9CDHRA (grey) and 9CRA (cyan, PDB code 1XDK).

Figure 3K:
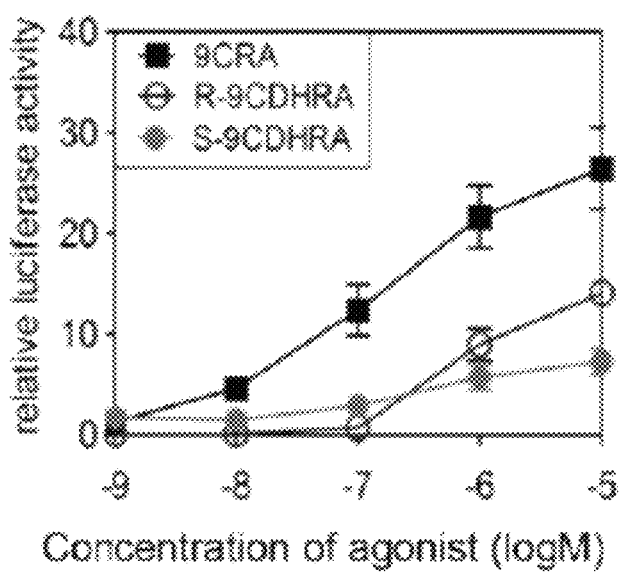
Figure 3L:
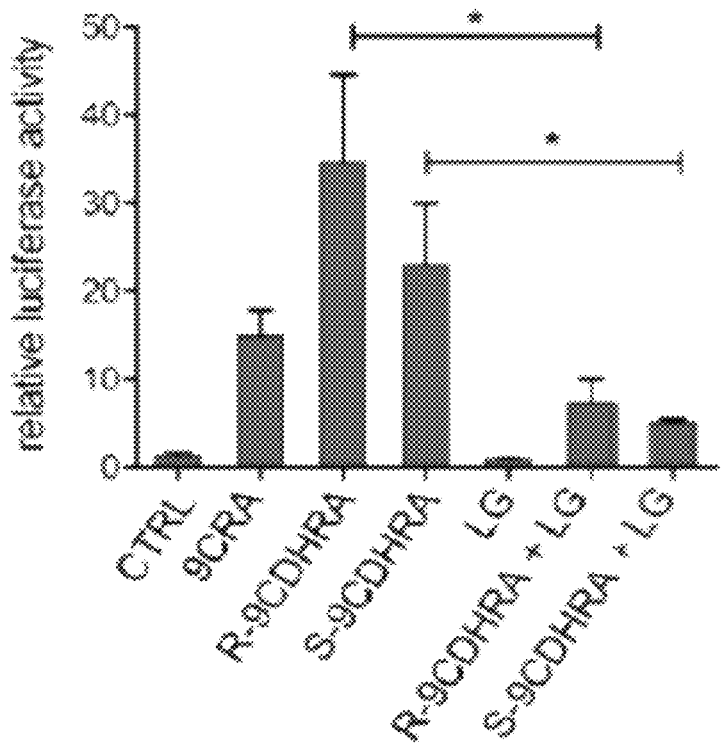
Figure 3M:
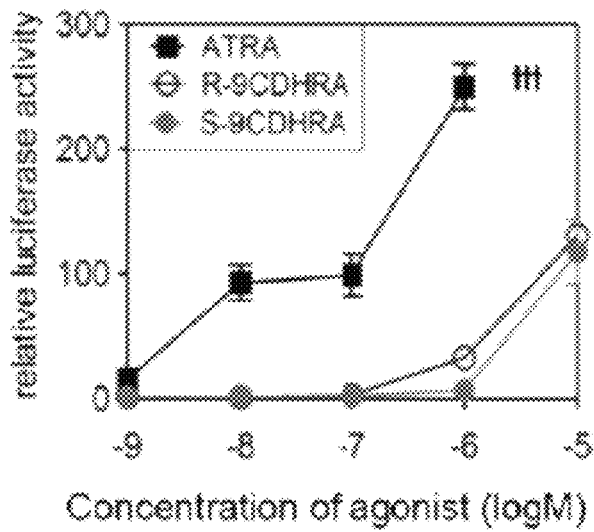

FIGS. 3K-3M Transcriptional activation and signaling measurements

FIG. 3K Transcriptional activation of RXRα by (R)-9CDHRA and (S)-9CDHRA in comparison to 9CRA ($10^{-5}$-$10^{-9}$M) in RXR-reporter COS1 cells.

FIG. 3L RXR-antagonist LG101208 (LG) diminishes 9CDHRA induced RXR-mediated signaling.

FIG. 3M Transcriptional activation of RAR-RXR heterodimers by (R)- and (S)-9CDHRA in comparison to ATRA in RAR-RXR-reporter COS1 cells.

FIG. 4: Molecular evidence for 9CDHRA selective activation of RXRs.

Figure 4A:
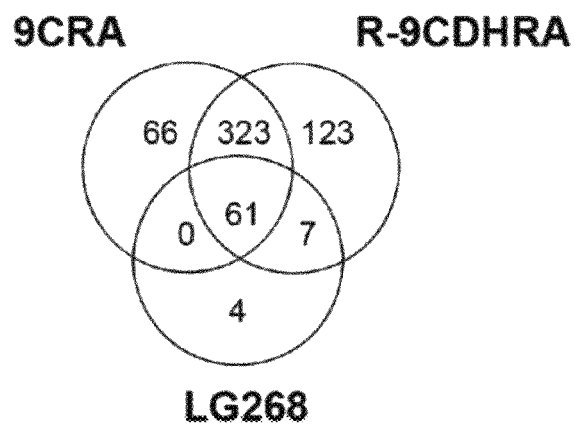

FIG. 4A Significant overlap between global transcriptional changes induced by (R)-9CDHRA ($10^{-5}$M), 9CRA ($10^{-6}$ M) or a synthetic RXR agonist (LG268; $10^{-7}$ M) revealed by DNA microarray analyses in differentiating monocyte-derived human dendritic cells.

Figure 4B:
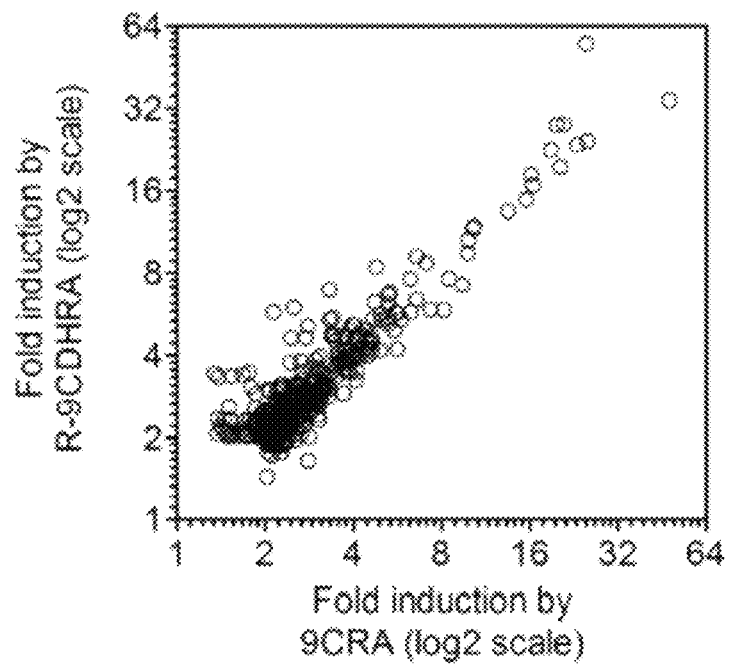

FIG. 4B Scatter plot comparison of fold-changes for transcripts altered by 9CRA and (R)-9CDHRA treatments.

Figure 4C:
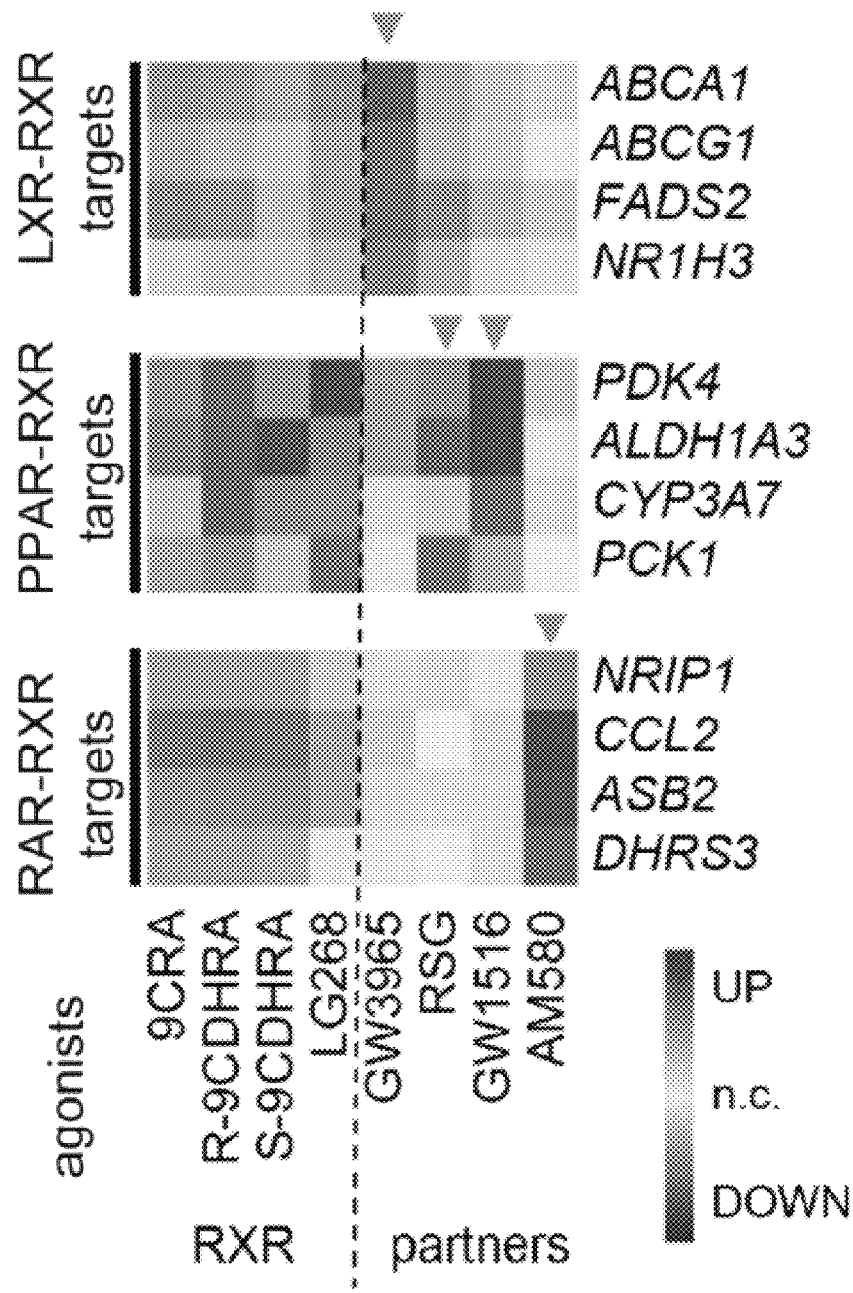

FIG. 4C (S)- and (R)-9CDHRA, similarly to 9CRA and/or LG268 (see "RXR" columns), induced the expression of genes (see rows) identified previously as direct transcriptional targets of LXR-RXR, PPAR-RXR and RAR-RXR. Corresponding transcripts were also induced by agonists of respective RXR-heterodimer partners (see "partners" column and arrowheads): GW3965 (LXRα/β; $10^{-6}$M), RSG (PPARγ; $10^{-6}$M), GW1516 (PPARδ; $10^{-6}$M) and AM580 (RAR; $10^{-7}$M).

Figure 5A:
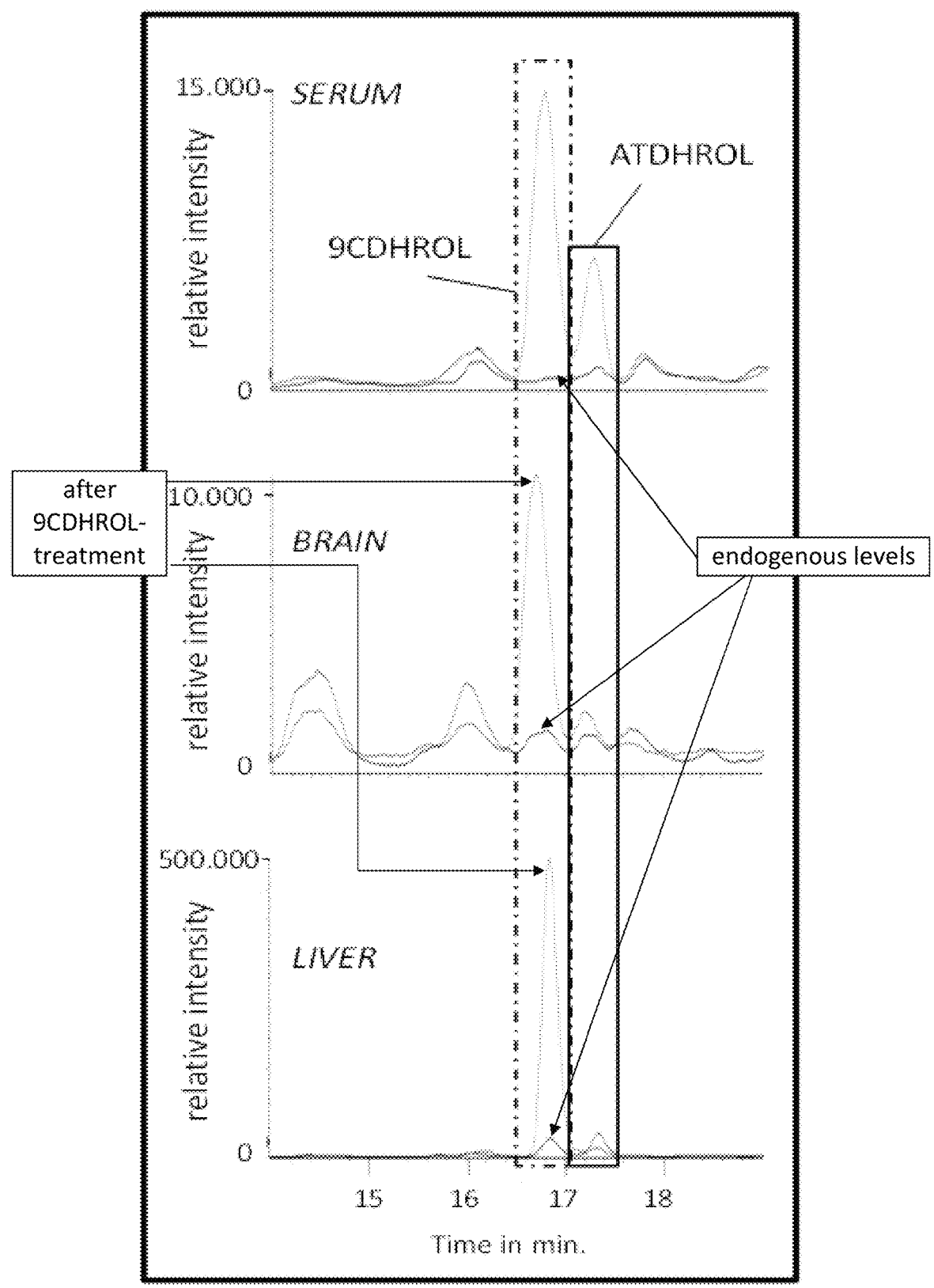

FIG. 5:

FIG. 5A 9CDHROL in mice after vehicle treatment representing endogenous levels (blue or dark grey and additionally marked "endogenous level") and after 9CDHROL-treatment (red or light grey and additionally marked with "after 9CDHROL treatment") in mice.

Figure 5B:
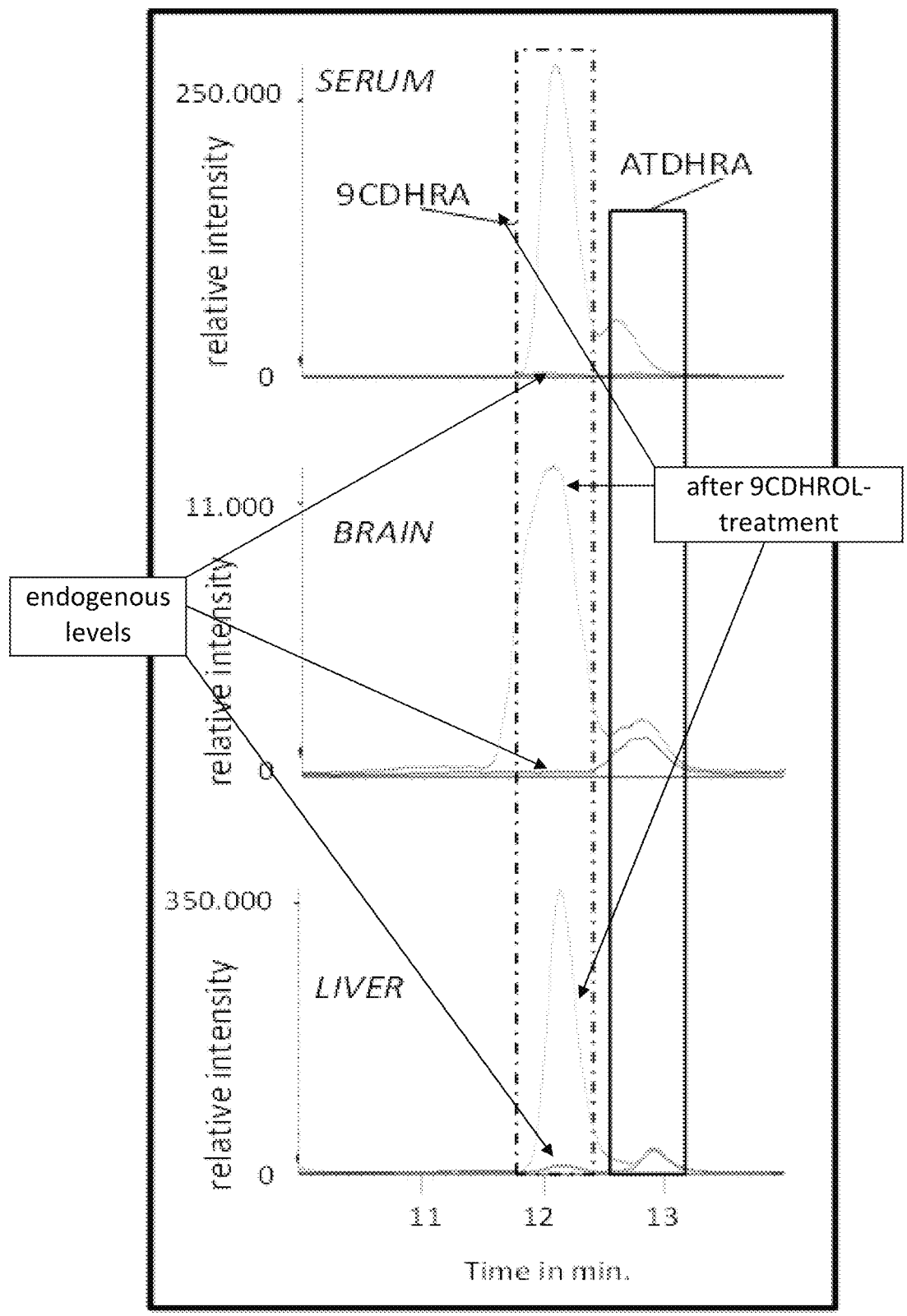

FIG. 5B Levels of 9CDHRA after vehicle treatment representing endogenous levels (blue or dark grey and marker "endogenous levels") and after 9CDHROL-treatments (red or light grey and marked "after 9CDHROL treatment") in mice.

Figure 6:
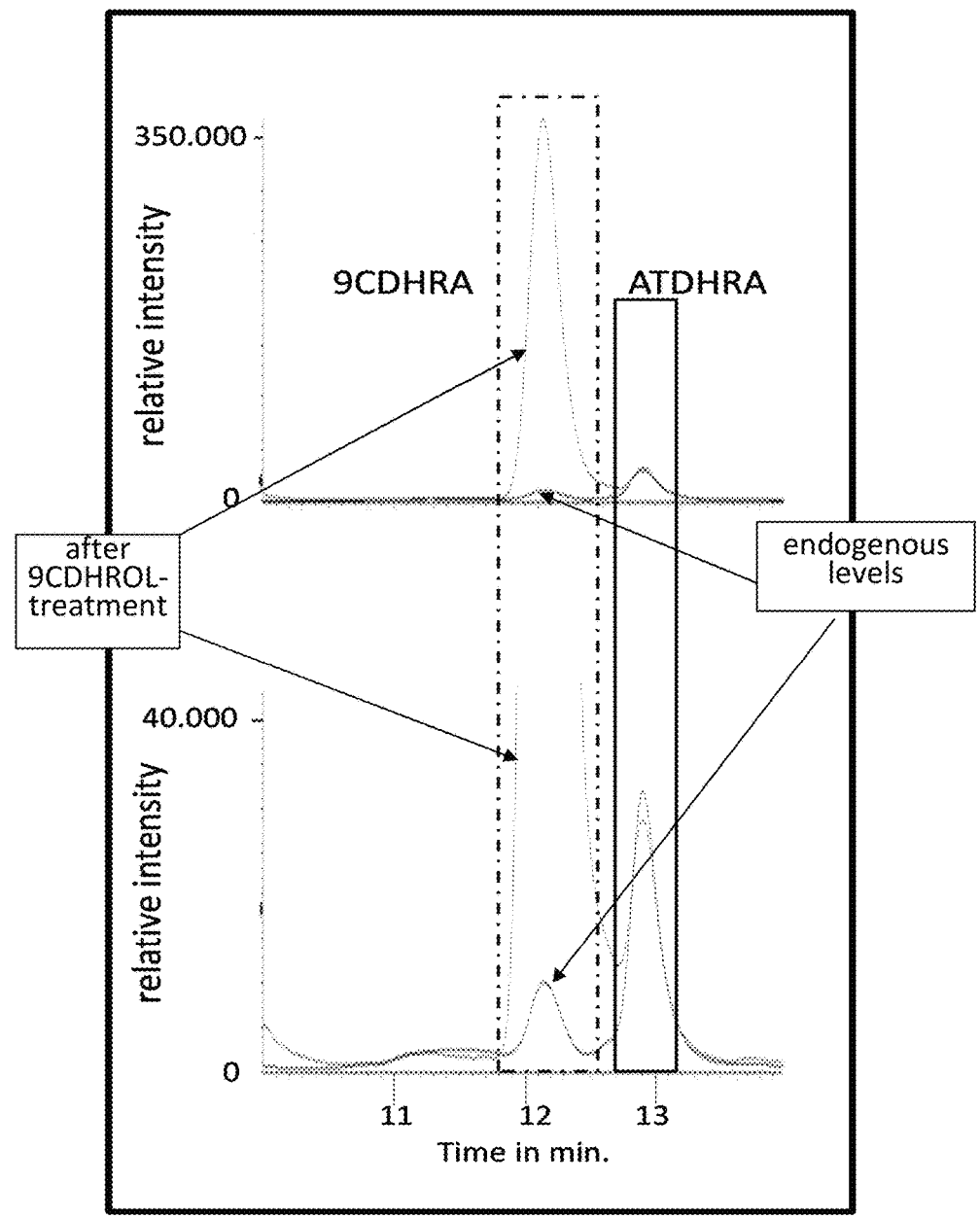

FIG. 6:

FIG. 6 Levels of 9CDHRA after vehicle treatment representing endogenous levels (blue or dark grey and marked endogenous levels"), and after 9CDHROL-treatment (red or light grey and marked "after 9CDHROL treatment") in mouse liver. Top figure: Normal range (set on maximum); bottom figure: extended range for the maximum range of endogenous retinoids.

FIG. 7:

FIG. 7 Summary of putative nutritional precursors of the new vitamin A5 cluster precursors. Retinoids not yet identified as endogenous retinoids are marked with blue letters. Abbreviations: 9-cis-13,14-dihydro-retinol (9CDHROL), 9-cis-13,14-dihydroretinal (9CDHRAL) and 9-cis-13,14-dihydroretinoic acid (9CDHRA), all-trans-13,14-dihydroretinal (ATDHRAL), all-trans-13,14-dihydroretinol (ATDHROL) and all-trans-13,14-dihydroretinoic acid (ATDHRA).

FIG. 8: Compromised RXR signaling in Rbp1−/− mice.

Figures 8A, 8B:
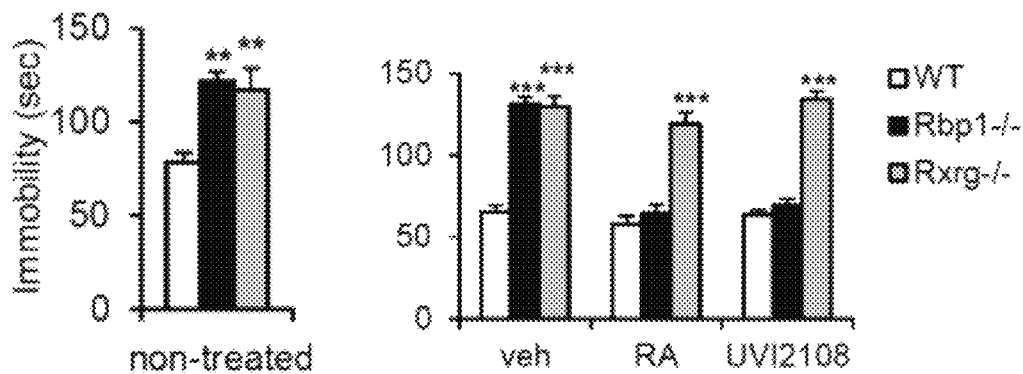

FIG. 8A Rbp1−/− (n=14) and Rxrγ−/− (n=11) mice display increased despair behaviour in the forced swim test as compared to WT mice (n=20).

Figure 8C:
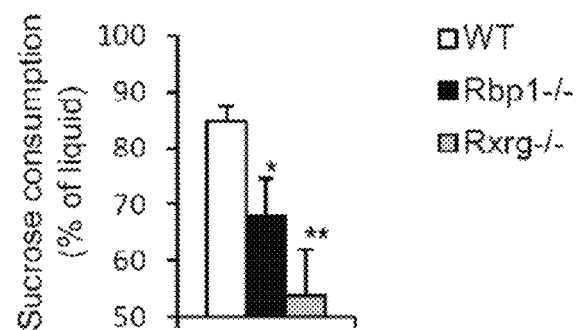

FIG. 8B All-trans retinoic acid (RA), similarly to a synthetic RXR agonist, UVI2108 (known also as BMS649) reduced significantly immobility time of Rbp1−/− mice in the forced swim test FIG. 8C preference for 0.8% sucrose solution was significantly reduced in RBP1−/− (n=19) but not in RXRγ−/− (n=11) mice as comparable with WT mice (n=22).

Figure 8D:
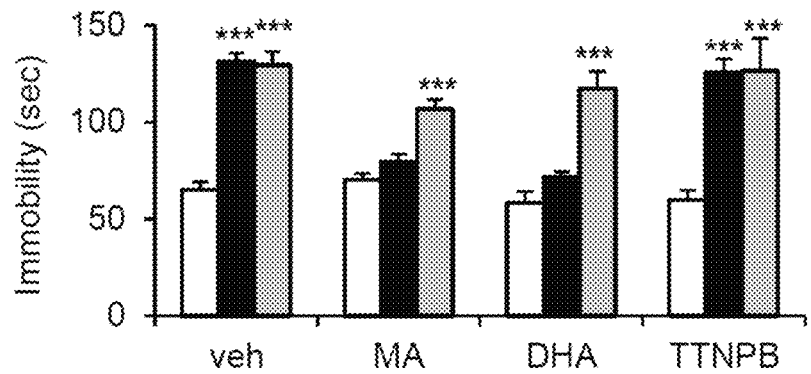

FIG. 8D increased immobility in the forced swim task can be normalised in Rbp1−/− mice using methoprene acid (MA), docosahexaenoic acid (DHA) but not TTNPB (n=10-19/group).

Figure 8E:
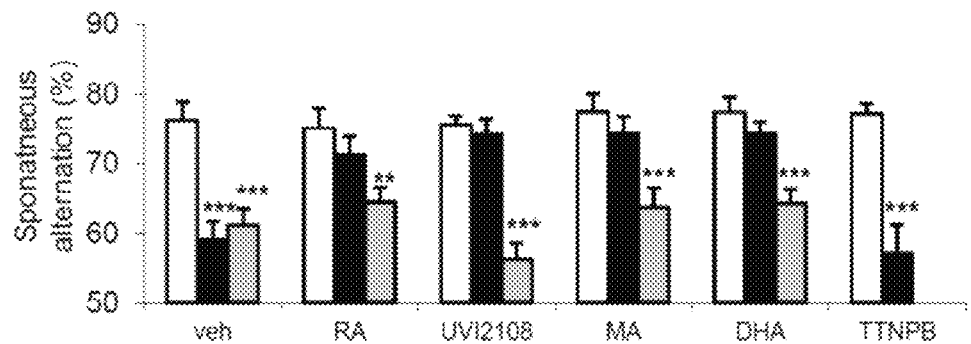

FIG. 8E Working memory deficits observed in the spontaneous alternation task in the Y-maze could be normalised in Rbp1−/− mice, but not in Rxrγ−/− mice using all-trans retinoic acid (ATRA; 5 mg/kg), UVI2108 (1 mg/kg), MA (5 mg/kg), DHA (1 mg/kg), but not TTNPB (5 mg/kg) (n=8-15/group). All compounds were applied 5-6 hours prior to testing and all mice were tested only one time in this task. Statistical differences revealed by PLSD Fisher test results were indicated: , $p<0.01$; *, $p<0.001$ as compared to WT animals in respective group.

FIG. 9.

Figure 9A:
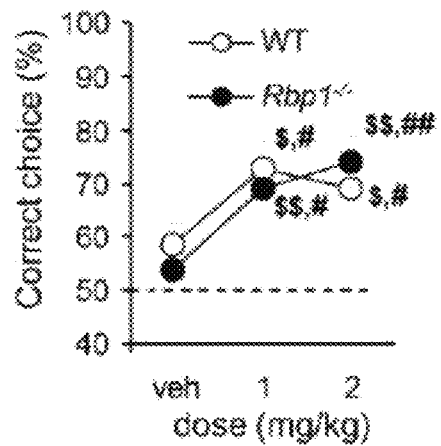

FIG. 9A Increasing doses of (R)-9CDHRA reversed working memory deficits in Rbp1−/− mice and showed pro-mnemonic activity in WT mice (n=8/group) in DNMTP task when tested at minimal ITI, at which mice performed at chance level (50%) and which was 6 min for the Rbp1−/− or 12 min for WT mice. ttt: ATRA at concentration 10-5 M was cytotoxic.*, $p<0.05$. #, $p<0.05$; ##, $p<0.01$ as compared to vehicle treatment in the same group; $, $p<0.05$; $$, $p<0.01$; one group student t-test for comparison with performance at chance level of 50%. All the error bars represent S.E.M.

Figure 9B:
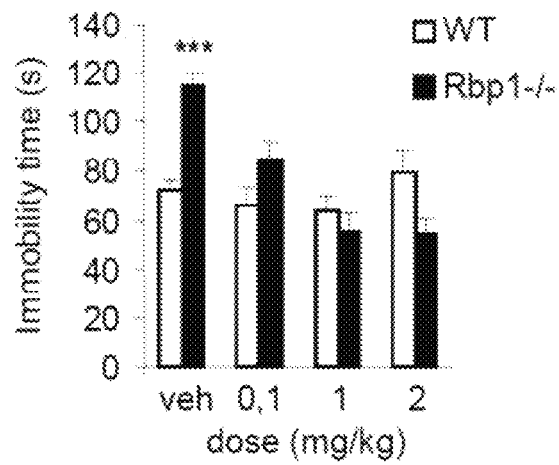

FIG. 9B (R)-9CDHRA displays RXR agonist-like activities in vivo. Reverse of behavioral deficits after treatments with UVI2108 and (R)-9CDHRA.

Increasing doses of (R)-9CDHRA (0.1, 1, 2 mg/kg) reduce despair behavior in Rbp1−/− mice in the forced swim test (n=26 for vehicle groups and n=6-8 for each remaining group); Statistical differences revealed by PLSD Fisher test were indicated as: ***, $p<0.001$ for comparison with vehicle treated WT controls in respective group. All the error bars represent S.E.M.

FIG. 10: (R)-9CDHRA displays antidepressant effects in chronic social defeat stress model.

Figure 10A:
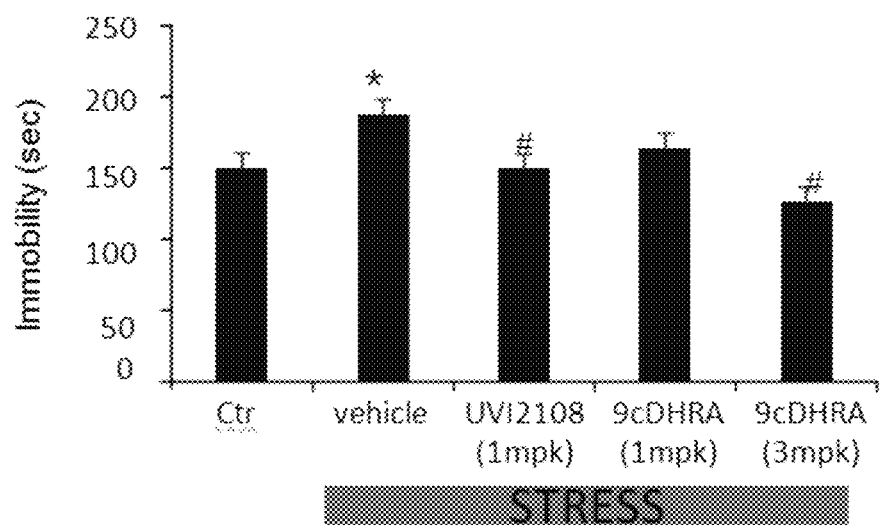

FIG. 10A Social defeat stress significantly increased immobility time in the forced swim test in mice receiving (vehicle; n=12) as compared to non-stressed control (ctr; n=17) mice. 9CDHRA (9cDHRA) treatments decreased such immobility in stressed mice in a dose dependently manner (n=8 for 1 mg/kg (mpk) and n=6 for 3 mg/kg of 9CDHRA) and to a similar extent as synthetic RXR agonists UVI2108 (n=12).

Figure 10B:
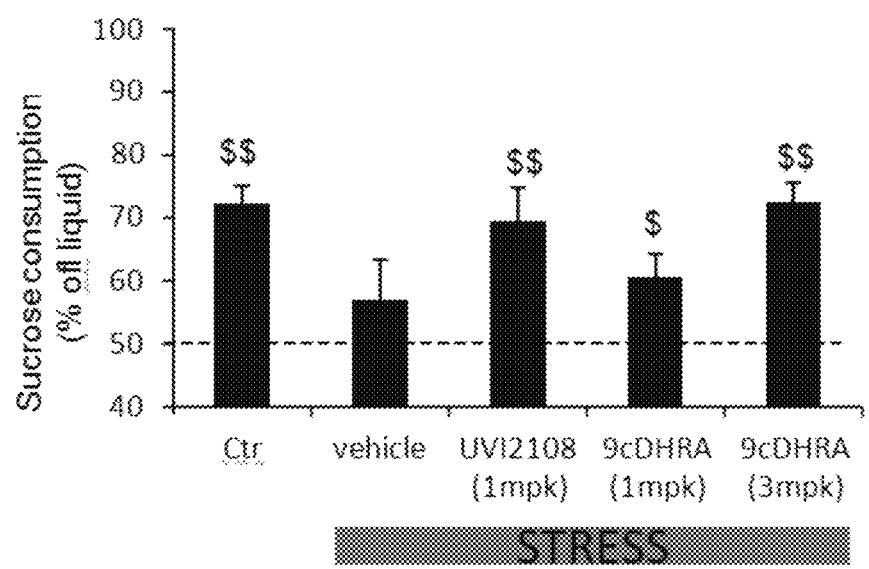

FIG. 10B Sucrose preference deficit induced by social defeat stress in vehicle treated mice (n=12) as compared to non-stressed control (ctr; n=17) mice. 9CDHRA (9cDHRA) treatments decreased such immobility in stressed mice in a dose dependently manner (n=8 for 1 mg/kg (mpk) and n=6 for 3 mg/kg of 9CDHRA) and to a similar extent as synthetic RXR agonists UVI2108 (n=12). Social stress was prevented by UVI2108 or by 9CDHRA treatments. Statistical differences revealed by PLSD Fisher test were indicated as: *, $p<0.05$ when compared to control mice; #, $p<0.05$ as compared to vehicle treated stressed mice; $$, $p<0.01$, $, $p<0.05$ as compared to absence of sucrose preference corresponding to the value of 50% of sucrose consumption. All the error bars represent S.E.M.

FIG. 11

Figures 11A, 11B:
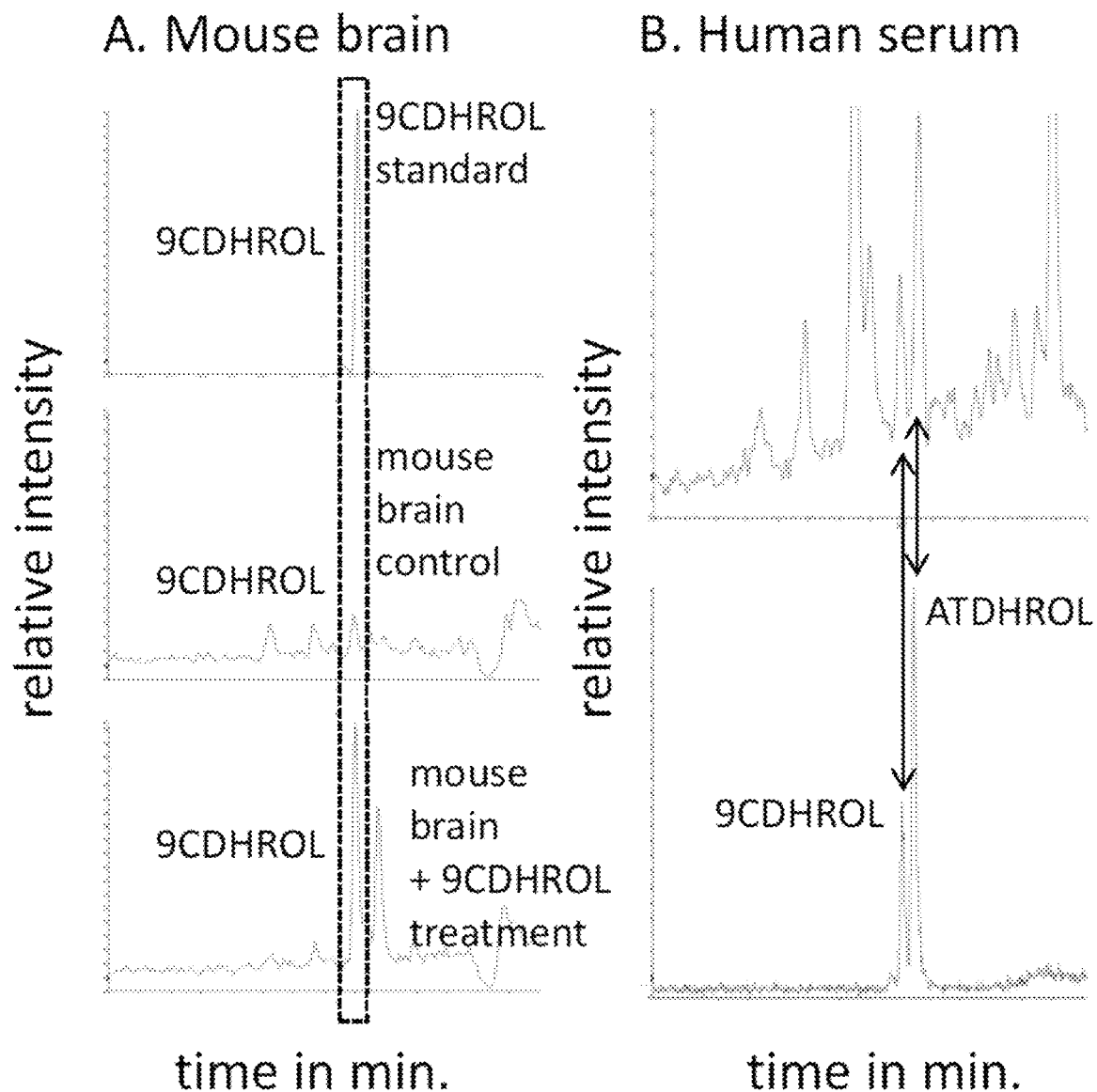

FIG. 11A 9CDHROL standard mixture (top chromatogram) and endogenous levels in mouse brain (middle chromatogram) and after 9CDHROL-treatment (bottom chromatogram), both y-axis scales of the brain samples were identical, while the y-axis of the standard are not similar and was fit on the maximum high of the relevant peaks.

FIG. 11B 9CDHROL in human serum (top chromatogram) and 9CDHROL standard mixture including ATDHROL (bottom chromatogram), both y-axis scales are not similar and were fit on the maximum high of the relevant peaks.

Figures 11C, 11D:
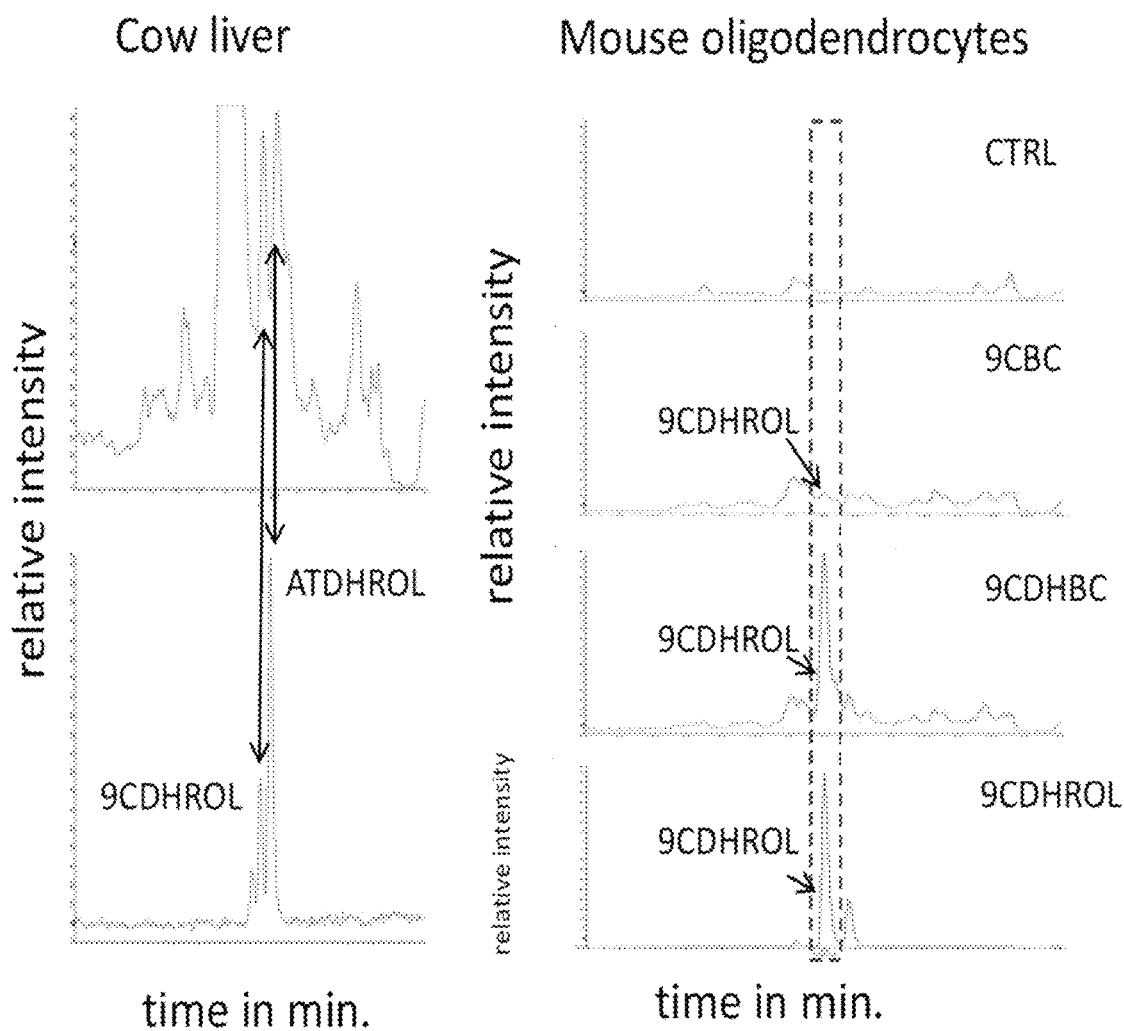

FIG. 11C 9CDHROL in human food chain/cow liver (top chromatogram) and 9CDHROL standard mixture including ATDHROL (bottom chromatogram), both y-axis scales are not similar and were fit on the maximum high of the relevant peaks.

FIG. 11D Conversion of 9CDHBC and 9CBC to 9CDHROL in mouse oligodendrocyte cell line in vitro after CTRL, 9CBC, 9CDHBC and 9CDHROL administration. Y-axis scales of the top three chromatograms are similar and were fit on the maximum high of the relevant peaks, while the bottom chromatogram has a much larger scale.

Figure 11E:
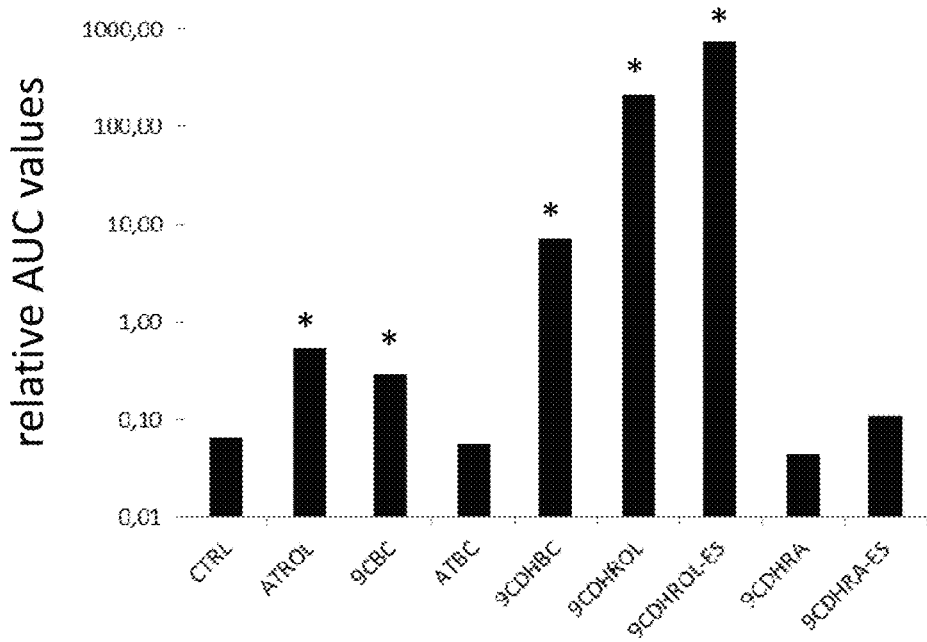

FIG. 11E 9CDHROL levels including standard deviation in human culture oligodendrocytes after control treatment using ethanol (CTRL), ATROL treatment (ATROL), 9CBC treatment (9CBC), ATBC treatment (ATBC), 9CDHBC treatment (9CDHBC), 9CDHROL treatment (9CDHROL), 9CDHROL-ester treatment (9CDHROL-ES), 9CDHRA treatment (9CDHRA) or 9CDHRA-ester treatment (9CDHRA-ES), each with $10^{-6}$M treatment and n=3.

Figure 11F:
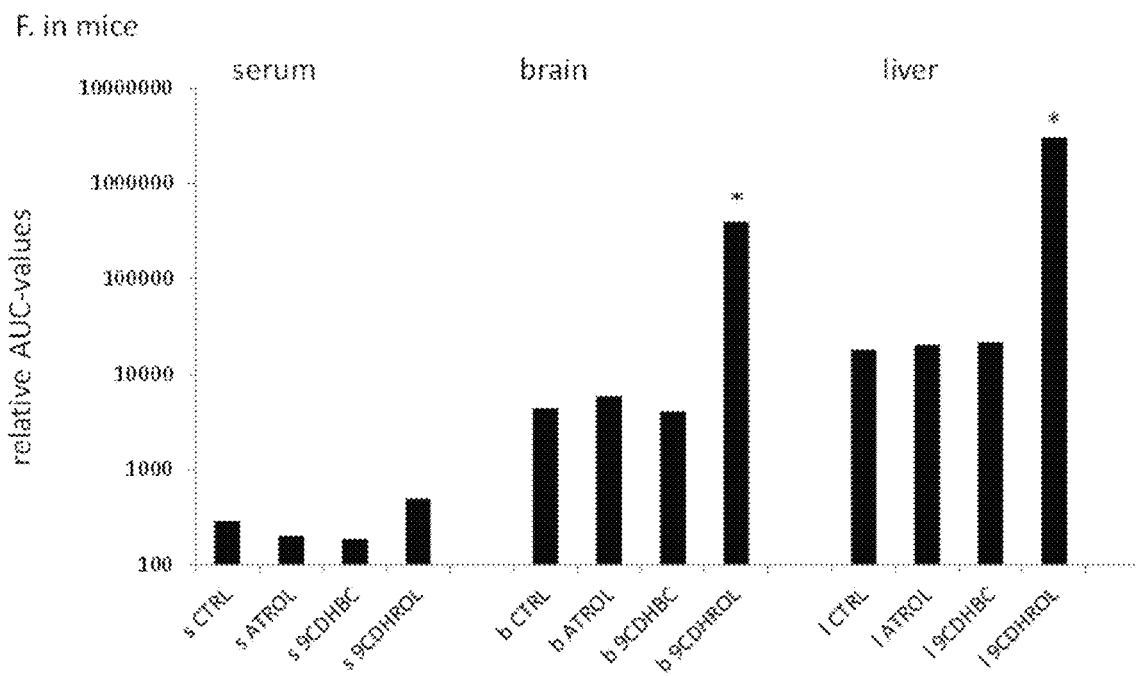

FIG. 11F 9CDHROL levels including standard error mean in mouse organs (s—serum, b—brain, l—liver) after control treatment (CTRL), ATROL treatment (ATROL), 9CDHBC treatment (9CDHBC) or 9CDHROL treatment (9CDHROL) each applied as an oral gavage of 40 mg/kg. Statistical significance in figures E and F is marked with a star over the bar, when $p<0.05$.

Figure 11G:
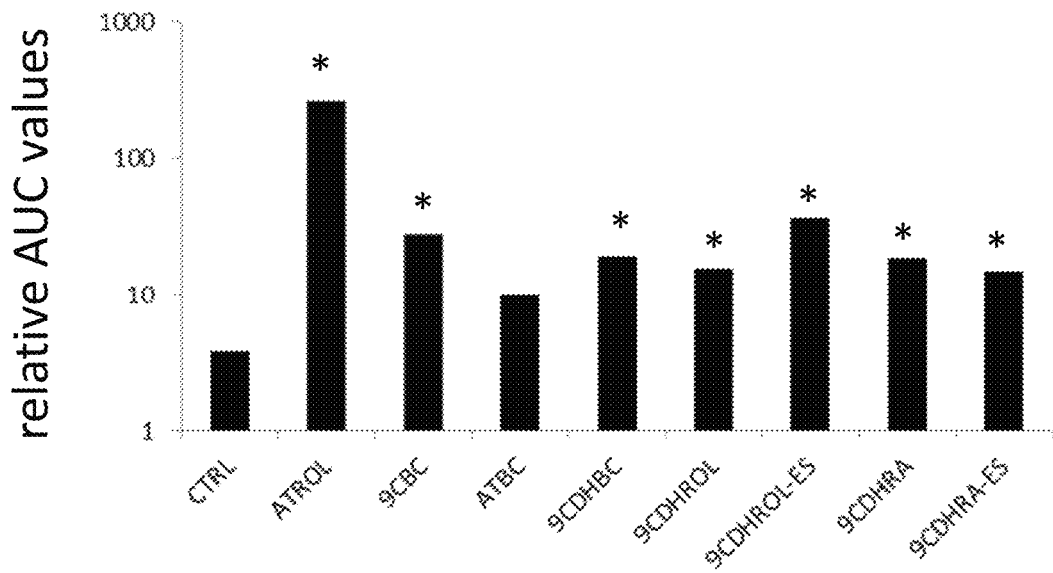

FIG. 11G ATROL levels including standard deviation in human culture oligodendrocytes after control treatment using ethanol (CTRL), ATROL treatment (ATROL), 9CBC treatment (9CBC), ATBC treatment (ATBC), 9CDHBC treatment (9CDHBC), 9CDHROL treatment (9CDHROL), 9CDHROL-ester treatment (9CDHROL-ES), 9CDHRA treatments (9CDHRA) or 9CDHRA-ester treatment (9CDHRA-ES), each with $10^{-6}$M treatment and n=3.

Figure 11H:
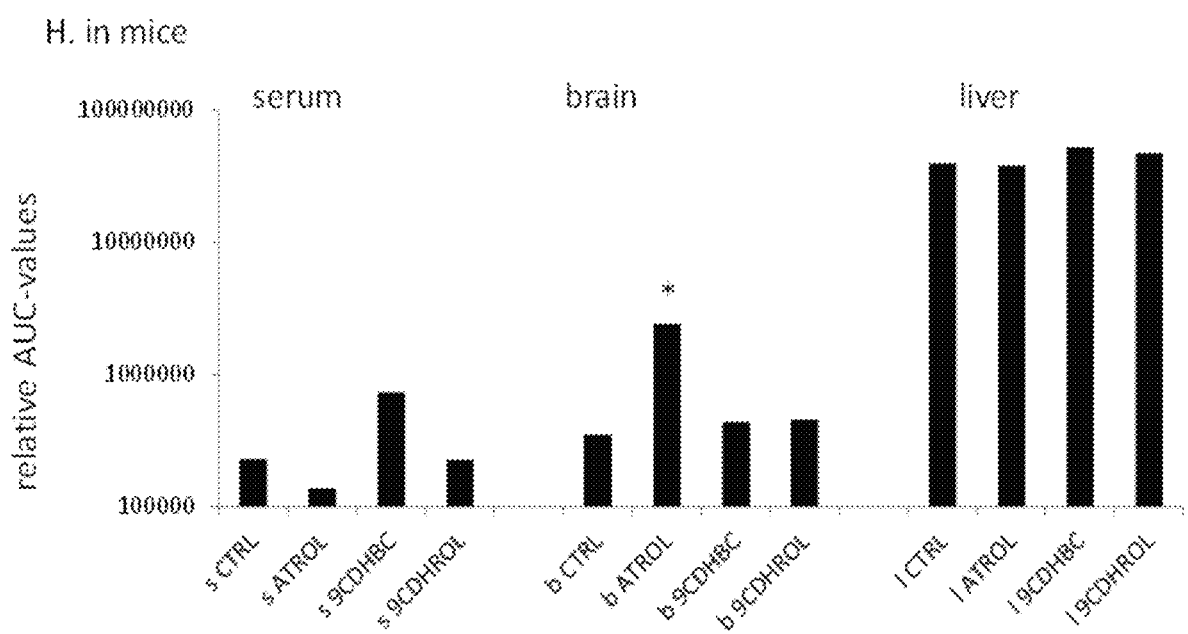

FIG. 11H ATROL levels including standard error mean in mouse organs (s—serum, b—brain, l—liver) after control treatment (CTRL), ATROL treatment (ATROL), 9CDHBC treatment (9CDHBC) or 9CDHROL treatment (9CDHROL) each applied as an oral gavage of 40 mg/kg. Statistical significance in figures E to H is marked with a star over the bar, when $p<0.05$.

Figure 12:
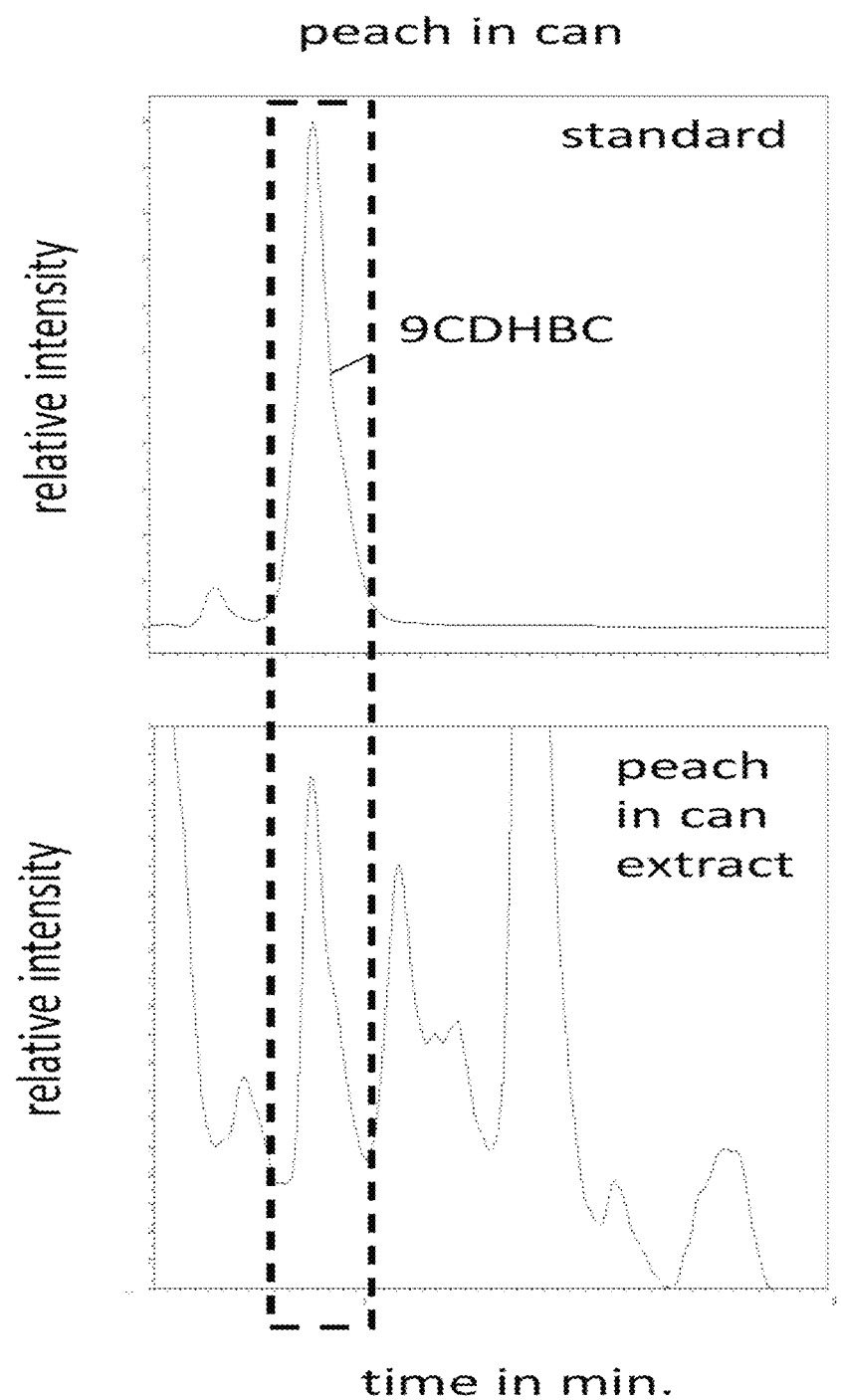

FIG. 12:

FIG. 12 9CDHBC in the human food chain, standard 9CDHBC eluting at 25.0 min (upper figure) and extracted peach from a can (bottom figure) with a peak co-eluting at 25.0 min and comparable UV/VIS spectra (data not shown).

FIG. 13:

FIG. 13 Intra-conversion of carotenoids: A. Conversion of administered 9CBC to 9CDHBC in mouse oligodendrocytes cell line in vitro. Peak with a retention time of 25.1 min is present after 9CDHBC treatment as well in lower levels after 9CBC treatment. B. No conversion of ATBC to either 9CBC or 9CDHBC in oligodendrocytes human cell line in vitro. ATBC is eluting at 27.2 min (detectable at 411 nm, while having a UV $\lambda_{max}$ of 450 nm) and present in very high levels after ATBC-treatment (second figure from the top at the right panel). 9CBC is present as a major shoulder peak after 9CBC-treatments while non-detectable after CTRL or alternative treatments.

Figure 14A:
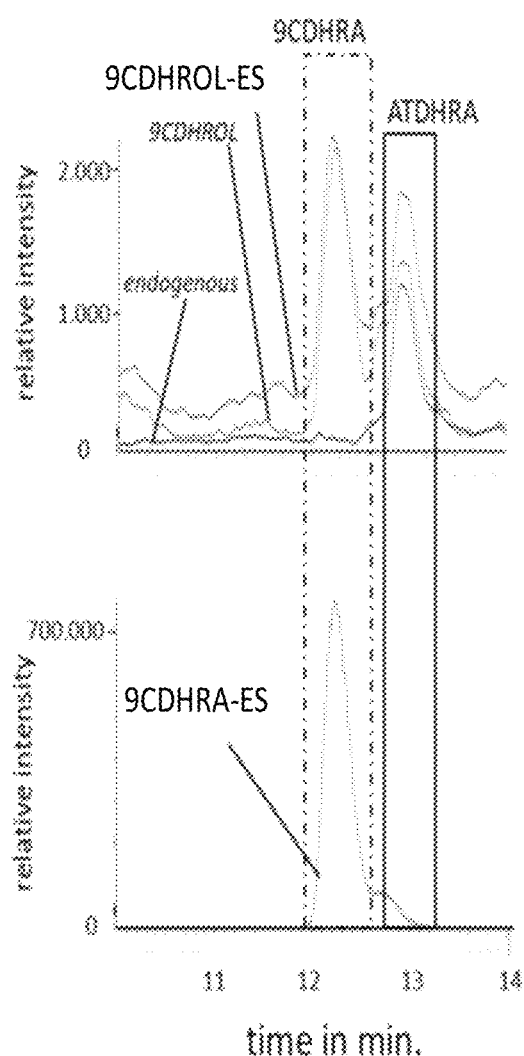

FIG. 14:

FIG. 14A Conversion of 9CDHROL, 9CDHROL-ester (9CDHROL-ES) and 9CDHRA-ester (9CDHRA-ES) to 9CDHRA in mouse oligodendrocytes cell line in vitro. A slightly different retention time of the derivatives was observed due to a different HPLC-system and extraction procedure used as explained in the materials and methods section, under "retinoid gradient".

Figure 14B:
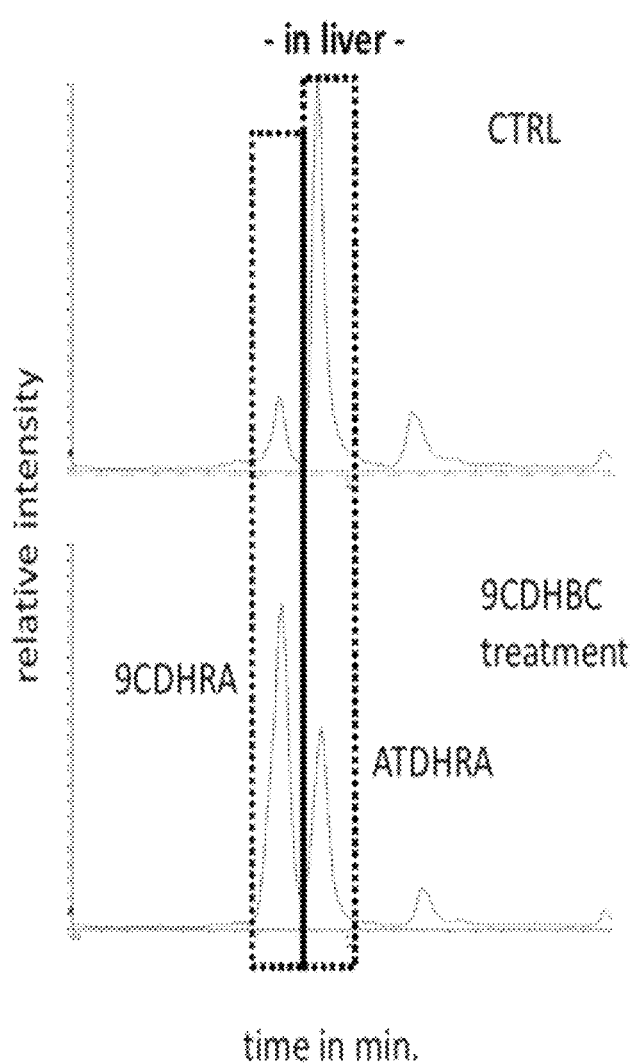

FIG. 14B Conversion of 9CDHBC to 9CDHRA: 9CDHRA (and ATDHRA as peak eluting after 9CDHRA) standard level after control-treatment (CTRL, endogenous value, top chromatogram) and after 9CDHBC-supplementation (bottom chromatograms) in mouse liver using the same y-axis scale dimension.

Figure 14C:
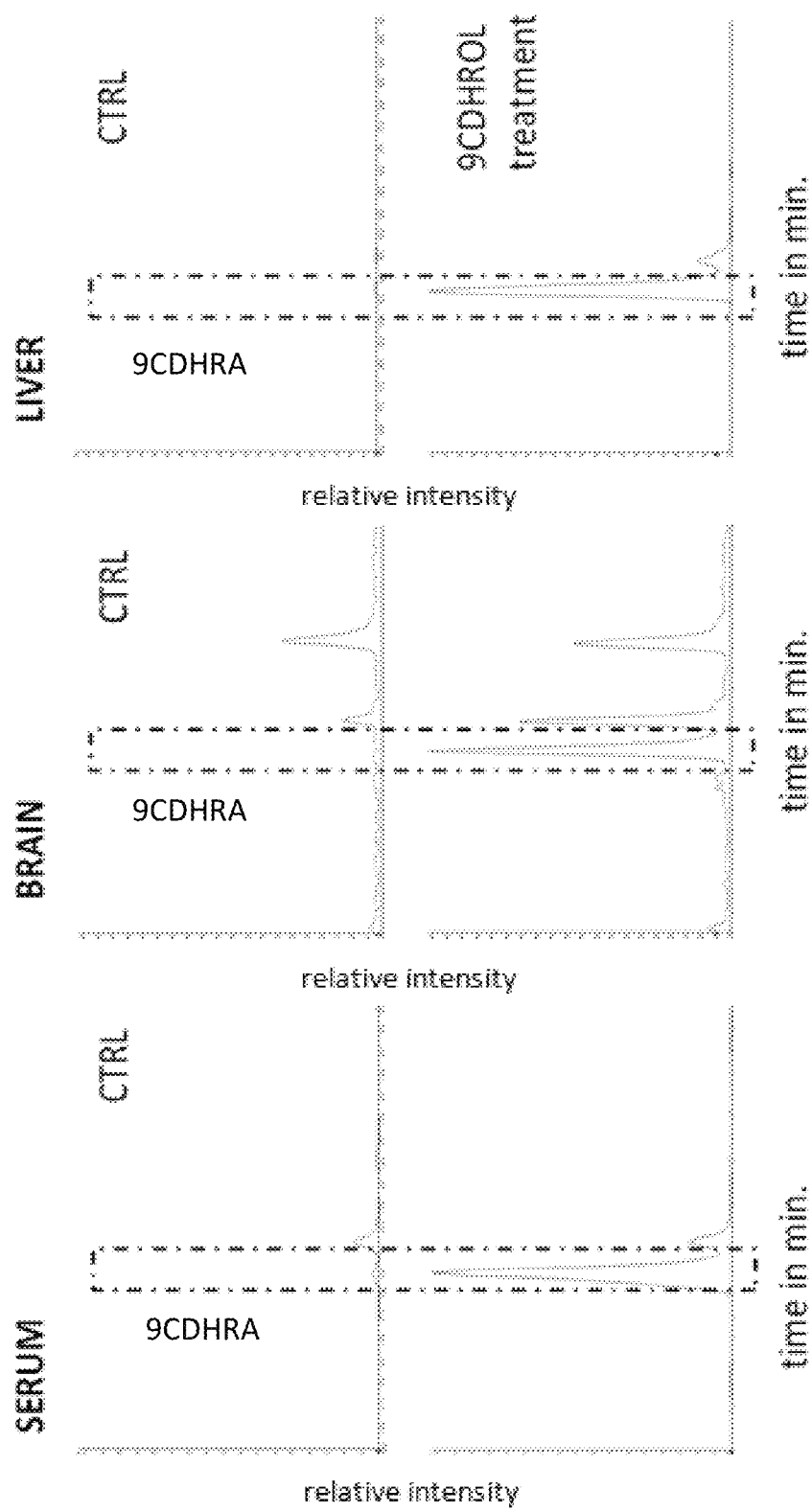

FIG. 14C Conversion of 9CDHROL to 9CDHRA: 9CDHRA standard levels (including also ATDHRA as a later eluting peak) in serum, brain and liver after control-treatment (CTRL, endogenous level, top chromatograms) and after 9CDHROL-supplementation (bottom chromatograms) in mice using the same y-axis scale dimension per relevant organ (serum, brain, liver).

Figure 14D:
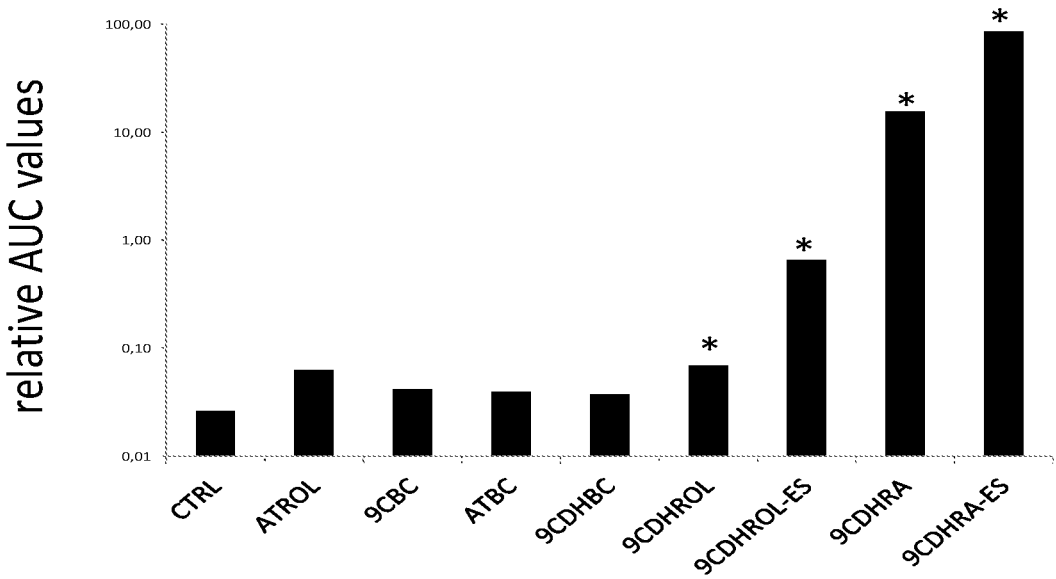

FIG. 14D 9CDHRA levels including standard deviation in human culture oligodendrocytes after control treatment using ethanol (CTRL), ATROL treatment (ATROL), 9CBC treatment (9CBC), ATBC treatment (ATBC), 9CDHBC treatment (9CDHBC), 9CDHROL treatment (9CDHROL), 9CDHR-ester treatment (9CDHROL-ES), 9CDHRA treatment (9CDHRA) or 9CDHRA-ester treatment (9CDHRA-ES), each with $10^{-6}$M treatment and n=3.

Figure 14E:
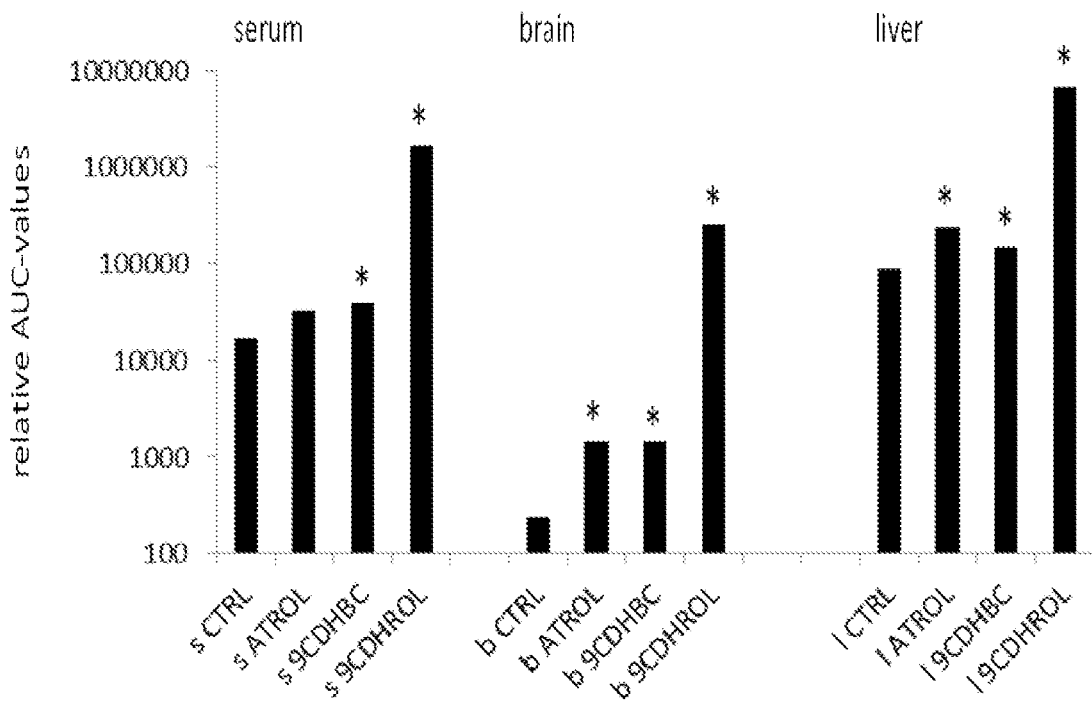

FIG. 14E 9CDHRA levels including standard deviation in mouse organs (s—serum, b—brain, l—liver) after control treatment (CTRL), ATROL treatment (ATROL), 9CDHBC treatment (9CDHBC) or 9CDHROL treatment (9CDHROL) each applied as an oral gavage of 40 mg/kg. Statistical significance in figures B and E is marked with a star over the bar, when p<0.05.

FIG. 15: Antidepressant activities of 9CDHROL (9cDHROL) and 9CDHBC (9cDHBC) in chronic social defeat stress model.

Figure 15A:
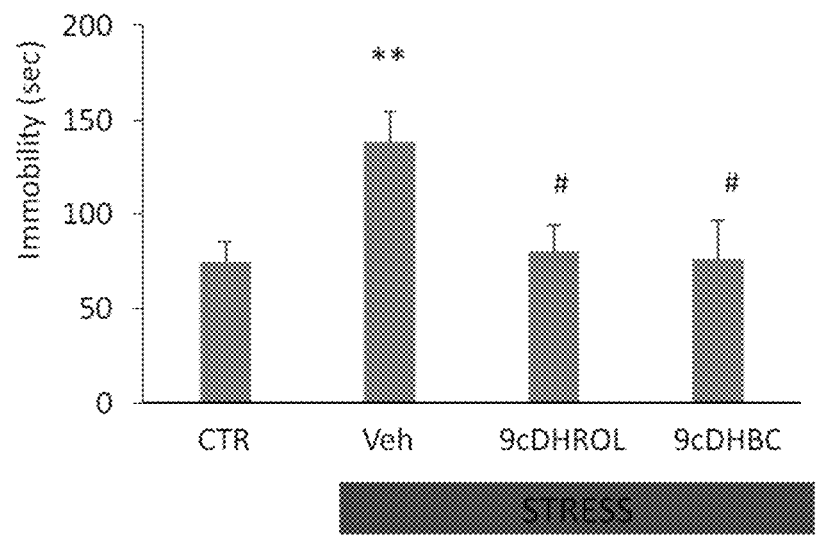

FIG. 15A Social defeat stress significantly increased immobility time in the forced swim test in mice receiving (veh; n=6) as compared to non-stressed control (CTR; n=6) mice. 9CDHROL treatment (n=5) decreased such immobility in stressed mice similarly to 9CDHBC (n=4).

Figure 15B:
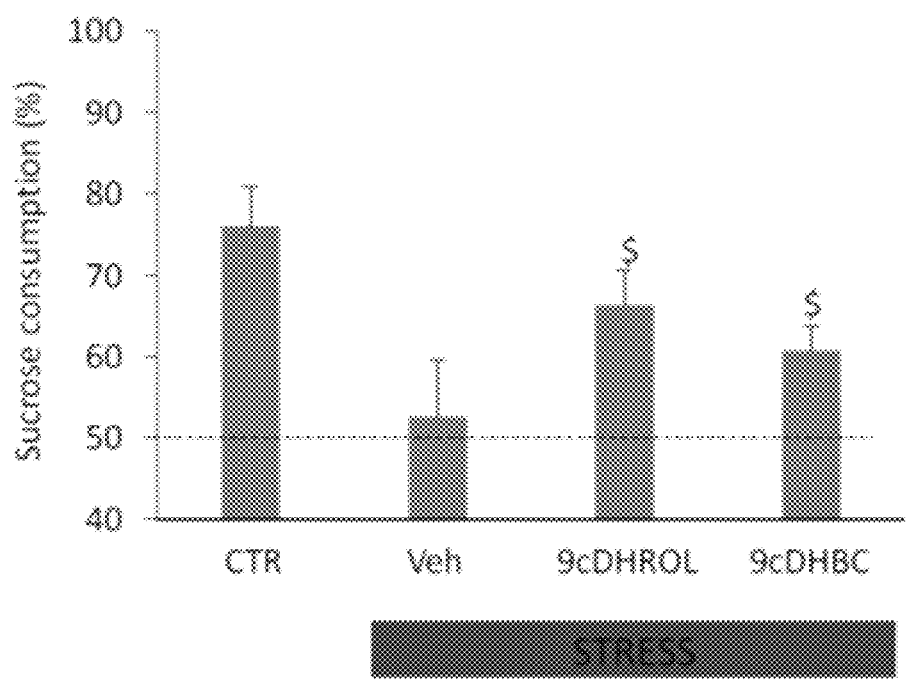

FIG. 15B Sucrose preference deficit induced by social defeat stress was prevented by 9CDHROL or 9CDHBC treatments. Statistical differences revealed by student t-test were indicated as: **, p<0.01 when compared to control mice; #, p<0.05 as compared to vehicle treated stressed mice; $, p<0.05 as compared to the value of 50% of sucrose consumption corresponding to absence of sucrose preference. All the error bars represent S.E.M.

Figure 16:
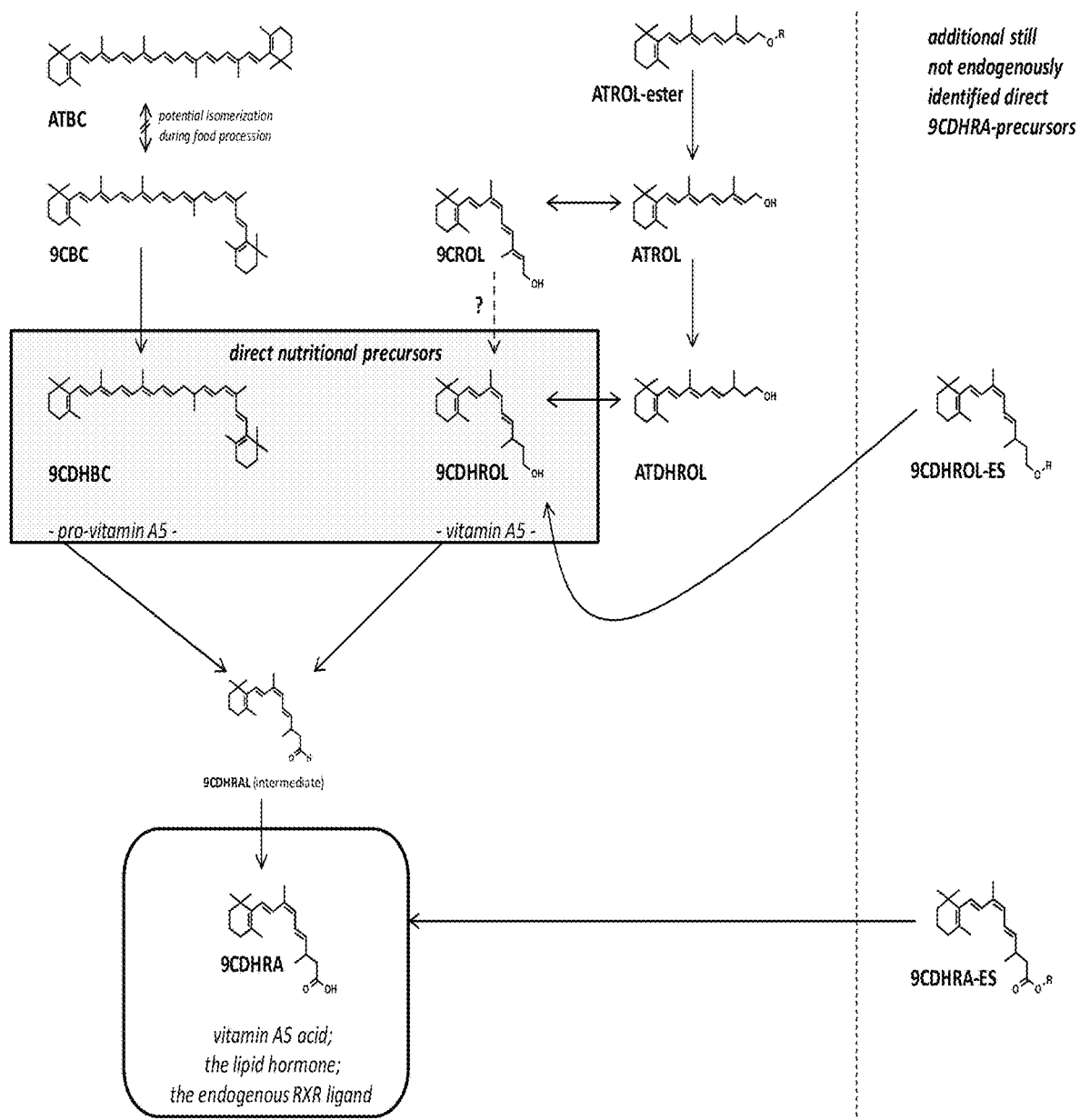

FIG. 16:

FIG. 16 Metabolic pathway including structural formula starting from nutritionally-derived retinoids

DEFINITIONS

It is to be understood that this invention is not limited to the specific examples and embodiments provided herein and alternatives, which are within the skills of a person skilled in the art, are to be included. It is also to be understood that the terminology used herein is for the purpose of describing particular embodiments only, and is not intended to be limiting.

As used in this specification and the appended claims, the singular forms "a", "an" and "the" include plural references unless the context clearly dictates otherwise.

Typically the compounds according to the invention relate to enantiomers (pure enantiomers or mixture provided that they are obtainable by the method of the invention), hydrates and solvates of same, solid forms of same, as well as mixtures of said forms.

An "enantiomer" is either one of a pair of optical isomer compounds that are different compound and are mirror images of each other.

"Enantiomer" is preferably understood herein as a compound of the invention as obtainable by an enantioselective method preferably an enantioselective preparation method, highly preferably as an enantiopure or enantiomerically pure compound. "Enantiopure" or "enantiomerically pure" is a compound wherein the molecules have (to the extent obtainable by the method of the invention) the same chirality. Preferably enantiopure or enantiomerically pure means optically pure, more preferably having at least 90%, preferably at least 95%, more preferably at least 98% or 99% optical purity. Highly preferably the molecules of the "enantiopure" or "enantiomerically pure" have the same chirality within limits of detection.

"Alkyl" refers to herein a straight or branched hydrocarbon chain radical, which is saturated, consisting solely of carbon and hydrogen atoms, having up to 25 (preferably 23 or 21 or 19) carbon atoms. In certain embodiments an alkyl may comprise 1 to 25 carbon atoms (referred to as $C_{1-25}$ alkyl), or preferably it can be a $C_{13-25}$ alkyl, a $C_{13-23}$ alkyl a $C_{13-21}$ alkyl, a $C_{13-19}$ alkyl or a $C_{13-17}$ alkyl; alternatively, it can be a short chain alkyl, e.g. a $C_{1-3}$ alkyl, a $C_{1-4}$ alkyl, a $C_{1-5}$ alkyl, a $C_{1-6}$ alkyl, a $C_{1-7}$ alkyl or a $C_{1-8}$ alkyl; still alternatively in some embodiment it can be a $C_{8-17}$ alkyl, a $C_{5-15}$ alkyl or a $C_{8-13}$ alkyl. The alkyl is attached to the rest of the molecule by a single covalent bond. The alkyl is preferably a non-branched, straight hydrocarbon chain. Alternatively it may comprise a branched hydrocarbon chain, however, the branched side chains are typically methyl, ethyl or propyl groups, preferably methyl or ethyl groups. The alkyl chain may be optionally substituted by one or more of the following substituents: halo (including —F, Br, Cl or I), cyano, nitro, oxo, $C_{1-3}$ alkoxyl or hydroxyl. Preferably the alkyl is unsubstituted.

"Alkenyl" refers to herein a straight or branched hydrocarbon chain radical consisting solely of carbon and hydrogen atoms, which is unsaturated, i.e. containing at least one double bond (i.e. C=C), having at least 2 and up to 25 (preferably 23 or 21 or 19) carbon atoms. In certain embodiments an alkyl may comprise 2 to 25 carbon atoms (referred to as $C_{2-25}$ alkyl); mutatis mutandis the chain length can be the same as with alkyls, however the shortest chain comprises at least 2 carbon atoms. In respect of branching and substitution the same applies as in case of alkyl chain.

The esters of (R)-9-cis-13,14-dihydroretinol of the present invention may be fatty acid esters. Here, the term "fatty acid" refers to a carboxylic acid having a long aliphatic (non-aromatic) chain which can be saturated (alkyl) or unsaturated (alkenyl). Preferably the alkyl chains in fatty acids used in the invention are open chain compounds, which are either straight or branched. Typically, fatty acid alkyl chains contain at least 11 and at most 25, preferably 23, 22 or 21 carbons.

The compounds of the invention have pharmaceutical (medicinal) and nutritional uses as well.

A "pharmaceutical composition" relates to a composition for use in treatment of human or animal body to restore or maintain health, said composition comprising an (one or more) active agent and one or more additional substance useful as carrier. The term "carrier" refers to a diluent, adjuvant, filler, excipient, stabilizer, or vehicle with which the agent is formulated for administration.

"Nutraceutical" refers to a foodstuff that provides health benefits in addition to its basic nutritional value. A nutraceutical has a physiological benefit or provide protection against physiological disorder or discomfort. A nutraceutical composition comprises a composition of the invention and at least an additional substance, e.g. a nutraceutical carrier or a food component.

The term "dietary supplement" refers to a nutraceutical e.g. a nutraceutical composition intended to provide nutrients that may otherwise not be consumed in sufficient quantities.

"Functional food" is also a nutraceutical e.g. a nutraceutical composition and refers to any modified food or food ingredient that may provide a benefit or provide protection against physiological disorder or discomfort; beyond the traditional nutrients it contains.

A "health claim" defines a health benefit for a nutraceutical and is subject to regulatory approval (analogous to an indication in case of a medicament) in accordance with a national or equivalent law. A "health claim" is to be as food labels and in food marketing.

The word "comprising" as used herein means contain i.e. is allows the presence of other entities or members. The term may be limited to "consisting essentially of" meaning comprising the listed essential components or ingredients and optionally other non-essential components or ingredients; or to "consisting of" which means that any additional component is excluded.

"Therapy" may include prevention and/or treatment.

"Preventing" or "prevention" of the development of a disease or condition refers to at least the reduction of likelihood of the risk of or susceptibility to acquiring a disease or disorder, or preferably causing at least one of the clinical symptoms of the disease or disorder not to develop in a patient that may be exposed to or predisposed to the disease but does not yet experience or display symptoms of the disease.

"Treating" or "treatment" of any disease or disorder refers, in some embodiments, to amelioration of at least one disease, disorder or condition or preferably reducing the development of the disease or disorder or at least one of the clinical symptoms thereof. In certain embodiments "treating" or "treatment" refers to ameliorating at least one physical parameter of the disease. In certain embodiments "treating" or "treatment" refers to inhibiting the disease or disorder or condition, either physically or physiologically. In certain embodiments, "treating" or "treatment" refers to preventing or delaying the onset of the disease or disorder.

Specifically in case of diseases of the central or peripheral nervous system treatment and in particular in case of degenerative disorders or in case of mental disorders, as appropriate, may include slowing in the rate of degeneration or decline; making the degeneration less debilitating; improving a subject's physical or mental well-being; improving or preserving memory and/or cognitive functions; restoring and/or improving alertness and ability to concentrate or, in some situations, preventing the onset of dementia.

Thus, the terms "prevention" and "treatment" may overlap as follows from the above definition as far as and when the latter includes preventing or delaying the onset of the disease or disorder.

A subject is any animal subject or a human subject, in particular a vertebrate subject, more particularly a warm-blooded subject or a mammalian subject.

A "mammalian subject" as used herein may be any mammal, preferably a laboratory animal, a pet, a livestock animal or a domestic animal. A mammalian subject may be, as example, a rodent, a primate, an ape or a human. Preferably mammals are any vertebrates within the class Mammalia having neocortex (a region of the brain), hair and mammary glands.

The compounds and the pharmaceutical compositions according to the invention may be used in a therapeutic method.

The compounds and the pharmaceutical compositions according to the invention are use in a therapeutic method for the treatment of disease involving retinoic acid receptors (RAR) and retinoid X receptors (RXR). Preferably the disease involves retinoid X receptors and the ligand of the invention is selective thereto. Such disease may be a disease due to impairment of RXR signaling.

The compounds and the pharmaceutical compositions according to the invention are used in a therapeutic method, in particular for the treatment of a mental disorder/disease.

The term "central nervous system related diseases" are diseases or disorders affecting the central nervous system (CNS) i.e. either the brain or the spinal cord, resulting in neurological or mental disorders, preferably linked to RXR-mediated signaling in complex with RAR or other nuclear receptors. Causes of CNS diseases may be e.g. trauma, infections, degeneration, autoimmune disorders, structural defects, tumors, and stroke. Here we focus on neurodegenerative diseases, mood disorders, schizophrenia, and autism.

The term "peripheral nervous system related diseases" are diseases affecting the peripheral nervous system, which are preferably linked to RXR-mediated signaling in complex with RAR or other nuclear receptors. However the ligand of the invention is preferably selective to RXR.

The term "mental disorder" include among others obsessive-compulsive disorder, post-traumatic stress disorder, anxiety, panic attacks, schizophrenia, schizoaffective disorders, depression, mania, manic-depression (bipolar disorder), apathy, delirium, phobias, amnesia, eating disorders (e.g., bulimia, anorexia), and the like. In one embodiment, the mental disorders include obsessive-compulsive disorder, post-traumatic stress disorder, panic attacks, schizophrenia, schizoaffective disorders, depression, mania, manic-depression (bipolar disorder), apathy, delirium, phobias, amnesia, and eating disorders (e.g., bulimia, anorexia). In another embodiment, the psychiatric disorders include obsessive-compulsive disorder, schizophrenia, schizoaffective disorders, depression, mania, manic-depression (bipolar disorder), apathy, delirium, and phobias. In another embodiment, the psychiatric disorders include obsessive-compulsive disorder, schizophrenia, schizoaffective disorders, depression, mania, and manic-depression (bipolar disorder). Preferably or in particular the term "psychiatric disorder" as used herein refer to and will be understood by the skilled person as "mental disorders" as described in sections F06-F50 of WHO International Statistical Classification of Diseases and Related Health Problems $10^{th}$ Revision. In an embodiment neurodegenerative disorders are excluded from the scope of mental disorders or mental disorders.

"Working memory or synonym short-term memory" characterizes the acquisition, storage, retention and recall of the information for a short interval of time spanning from some minutes to several hours, optionally days and used to modify behavior of the subject.

"Memory loss" refers to a reduction in the ability to acquire, store, retain and/or recall information including past experiences, knowledge and thoughts.

The term "depression" or "depressive disorder" or "mood disorder" refers to a medical field that can be understood by the skilled practitioner. A "mood disorder" refers to disruption of feeling tone or emotional state experienced by an individual for an extensive period of time. Mood disorders include major depression disorder (i.e., unipolar disorder), mania, dysphoria, bipolar disorder, dysthymia, cyclothymia and many others. See, e.g., Diagnostic and Statistical Manual of Mental Disorders, Fourth Edition, (DSM IV). A "Major depression disorder," "major depressive disorder," or "unipolar disorder" refers to a mood disorder involving any of the following symptoms: persistent sad, anxious, or "empty" mood; feelings of hopelessness or pessimism; feelings of guilt, worthlessness, or helplessness; loss of interest or pleasure in hobbies and activities that were once enjoyed, including sex; decreased energy, fatigue, being "slowed down"; difficulty concentrating, remembering, or making decisions; insomnia, early-morning awakening, or oversleeping; appetite and/or weight loss or overeating and weight gain; thoughts of death or suicide or suicide attempts; restlessness or irritability; or persistent physical symptoms that do not respond to treatment, such as headaches, digestive disorders, and chronic pain. Various subtypes of depression are described in, e.g., DSM IV.

The term "neurodegenerative disease or disorder" as used herein refers to a disease or disorder characterized by progressive nervous system dysfunction or by progressive loss of structure or function of neural tissue, preferably of neurons, including death of neurons. The "neurodegenerative disease or disorder" is preferably selected from the group consisting of Parkinson's disease, Alzheimer's disease, Huntington's disease, frontotemporal lobar degeneration associated with protein TDP-43 (FTLD-TDP, Dementia with Lewy bodies (DLB), vascular dementia, Amyotrophic lateral sclerosis (ALS), Mild Cognitive Impairment (MCI), Parkinson's disease with MCI, and other neurodegenerative related dementias due to changes in the brain caused by ageing, disease or trauma; or spinal cord injury and ataxias, disseminated sclerosis and multiple sclerosis, or other neurological conditions. In an embodiment glaucoma is also a neurodegenerative disease.

The compounds and the pharmaceutical compositions according to the invention are used in a therapeutic method, in particular for the treatment of Alzheimer disease.

The term "Alzheimer's disease" refers to the most common form of dementia, which is well recognized clinically. Memory loss also plays an important part in this disease.

In a particularly preferred embodiment in the solutions of the invention comprising is to be understood as consisting essentially of or particularly highly preferably consisting of.

DETAILED DESCRIPTION OF THE INVENTION

Vitamin A is a substance that can fully reverse vitamin A deficiency syndrome (IUPAC-IUB, 1982; Moore, 1929; Rühl, 2007). Vitamin A1, used herein as a term applied to the retinol, retinyl esters and retinal, and pro-vitamin A derivatives like β,β-carotene, α,β-carotene and β-cryptoxanthin and comparable vitamin A2 derivatives (3,4-didehydroretinoids and the carotenoid anhydrolutein), which mainly occur in avian and fish species (Cama et al., 1952; Moise et al., 2007), belong to this category. The human relevance of visual pigments from the vitamin A3 and A4 cluster, which thus far have not been linked to vertebrates may also be considered critically (Babino et al., 2016).

In adult animals RXR-heterodimers, mainly RXR-VDR, RXR-PPAR, RXR-FXR and RXR-LXR heterodimers along with RXR-RAR, regulate homeostatic lipid metabolism and inflammation (reviewed in (Chawla et al., 2001; Desvergne, 2007; Evans and Mangelsdorf, 2014; Mangelsdorf and Evans, 1995; Mangelsdorf et al., 1995; Shulman and Mangelsdorf, 2005)). Changes in this receptor-mediated signaling result in severe metabolic and immunological diseases (reviewed in (Szanto et al., 2004a) and (Desvergne, 2007)). Several of these physiological effects are dependent on RXR-mediated processes like inflammatory response and lipid signaling and they are thereby linked to various pathophysiological effects identified in adult vitamin A-deficient animals (Nunez et al., 2010; Stephensen et al., 2007; Wan et al., 2003).

An endogenous RXR ligand serves as the major switch to enable RXR-heterodimer-mediated signaling in the mammalian organism. Various effects observed in vitamin A-deficient animals were comparable to effects found in RXR-KO animals (Kastner et al., 1997a; Kastner et al., 1997b). The present inventors believe that, besides nonnuclear hormone receptor-mediated effects in vision, RAR- and especially RXR-mediated pathways are the major pathways for vitamin A-activity and that these are dependent on endogenous RAR and/or RXR ligands.

It is widely accepted that ATRA is the endogenous relevant RAR ligand but other ligands have also been described (Moise et al., 2005; Rühl et al., 2015). 9-cis-Retinoids can be converted to all-trans-retinoids and serve as additional precursors for the endogenous RAR-ligand ATRA.

Shirley M A et al. in 1996 (Shirley M A et al. 1996) have found that in rats 9-cis-RA is reduced to 9-cis-13,14-dihydro-RA and the latter is conjugated with taurine to form a novel metabolite, considered this, nevertheless, as an initial step leading to beta-oxidation.

Although RXRs occupy central position in signaling of several nuclear hormone receptors acting as their heterodimerisation partner, endogenous ligand(s) of RXRs, its metabolic pathway and physiological functions were not conclusively determined. In order to search for endogenous retinoids that may act as RXR ligand(s), the inventors first employed behavioral and pharmacological analyses sensitive to RXR signaling as a tool to identify animal models with reduced RXR signaling. In particular, inventors focused on spatial working memory previously reported as dependent on RXR and not RAR functions, including ligand-dependent RXR activities [Wietrzych-Schindler M. 2011].

It has been found that Rbp1$^{-/-}$ displayed a phenotype suggestive of reduced RXR signaling, which could not be attributed to the reduced levels of RXR expression or of 9CRA, the potential endogenous RXR ligand which we and others failed to detect [Ulven et al., 2001; Kane et al, 2005; Rühl, 2006] in wild type animals.

In the result of a set of experiments, the conclusion of which is summarized below, the present inventors have identified 9CDHRA, a novel endogenous retinoid, as an endogenous RXR ligand.

The inventors report herein that RBP1 modulates animal behavior by control of the availability of an RXR ligand. Accordingly, mice carrying null mutation of RBP1 display working memory deficits, the hallmark of deficient signaling through RXRγ, a functionally predominant RXR in the control of working memory in adult mice [Wietrzych-Schindler M. 2011; Krzyzosiak A et al, 2010]. Reduced expression of RXRγ or other RXRs (data not shown) do not account for these changes, suggesting compromised availability of RXR ligand. This unique model enabled to search for the endogenous RXR ligand(s). As the initial analyses failed to detect 9CRA in wild type and Rbp1$^{-/-}$ mice, inventors turned their attention to dihydroretinoids proposed recently as a novel group of bioactive, endogenous retinoids

[Moise A R et al., 2008]. Using HPLC-MS-MS conditions specific for detection of dihydroretinoic acids, including 13,14-dihydroretinoic acids, and aided by organic synthesis inventors detected the presence of ATDHRA and 9CDHRA in mouse serum, liver and brain in WT mice and Rbp1$^{-/-}$ mice. Serum and liver concentration of 9CDHRA were particularly high, ranging from 4 to $7 \times 10^{-7}$M, and much lower in whole-brain extracts in WT animals. The quantities measured were considered sufficient to maintain RXR-dependent activities. Nevertheless they were significantly reduced in all corresponding samples of Rbp1$^{-/-}$ mice.

In fact, 9CDHRA was found to display biological activities similar to those of former synthetic RXR agonists and coordinated the transcriptional activities of several nuclear receptor-signaling pathways, possibly through the corresponding permissive heterodimers (Rühl et al., 2015).

Reduced serum availability of 9CDHRA in Rbp1$^{-/-}$ mice may result from reduced synthesis of 9CDHRA in the liver, the main site of RBP1 expression [Ghyselinck N B. et al. 1999]. Because levels of ATDHRA were comparable in the serum, liver and brain of WT and Rbp1$^{-/-}$ mice, reduced levels of 9CDHRA in Rbp1$^{-/-}$ mice indicate that RBP1 plays an important role specifically in generation of different forms of 9-cis-retinoids as previously suggested [Kane et al., 2005]. Thus, 9CDHRA, similarly to ATRA and 1,25-dihydroxyvitamin D3 could act in endocrine and paracrine manner as a lipid hormone of nutritional origin being distributed in the serum but also synthetized locally in specific organs [Rühl et al., 2008]. In consequence, reduced systemic levels of 9CDHRA may synergize with local reduction of its synthesis in specific brain areas of Rbp1$^{-/-}$ mice leading to compromised RXR activities and mnemonic deficits. In favor of this hypothesis, systemic administration of (R)-9CDHRA, a 9CDHRA enantiomer obtained by stereoselective chemical synthesis, normalized working memory deficits in Rbp1$^{-/-}$ mice. That such effects are mediated by RXRs may be suggested by absence of promnemonic effects of 9CDHRA and other RXR ligands in mice carrying null mutation of RXRγ, a functionally predominant RXR in the control of these brain functions [Wietrzych-Schindler M et al. 2011].

Direct evidence of 9CDHRA binding to RXRs is provided by electrospray ionisation mass spectrometry (ESI-MS) performed in non-denaturing conditions using purified RXR LBD and fluorescence quenching assay. In particular, (R)-9CDHRA binds RXR LBD with affinity close to that of 9CRA as indicated by respective Kd values of 90±20 nM for 9CDHRA and 20±10 nM for 9CRA. Such data are supported by the crystal structure of the complex of (R)-9CDHRA with RXR LBD, in which (R)-9CDHRA adopts the canonical active agonist conformation and the carboxylate interacts with Arg316. Importantly, the (R)-9CDHRA enantiomer efficiently induces RXR transcriptional activity in reporter cell assays at physiologically relevant concentrations below $10^{-6}$M, which can be prevented by coadministration of RXR pan-antagonist LG101208. Although (S)-9CDHRA displays lower affinity to bind RXR LBD in ESI-MS, most probably due to the inverse configuration at the C20-carbon atom, it is also active in transactivation of RXR in vitro with threshold concentration between $10^{-7}$ and $10^{-6}$ M.

Further relevance of 9CDHRA for the activation of RXRs in vitro was indicated by the regulation of transcriptional targets of LXR-RXR or PPAR-RXR permissive heterodimers, which are known to be sensitive to pharmacological activation of RXR as well as its nuclear receptor partners. Such activation was demonstrated in human dendritic cells cultured in vitro, a well-established model for analyses of RXR signaling [Altucci L. et al. 2007; Szeles L. et al. 2010]. Importantly, almost all (68 out of 72) transcripts regulated by LG268 (RXR-specific agonist) were also regulated by 9CDHRA. Such a result obtained in a course of transcriptomics study was very similar to the data obtained for 9CRA, which controlled 61 out 72 LG268 transcriptional targets, indicating the extremely high capacity of 9CDHRA and 9CRA to control RXR transcriptional targets. Such genes correspond most probably to permissive heterodimers, and indirect targets of ligated RXR and their regulation provide evidence that 9CDHRA can control RXR signaling also in human cells. High degree of overlap between transcriptional activities of 9CRA and 9CDHRA, which goes beyond the activation of RXR-specific transcripts, reflects their capacity to bind and transactivate also RARs. That 9CRA and 9CDHRA act as a mixed RXR and RAR agonists is supported by about 80% overlap in transcriptional changes induced by (R)-9CDHRA (or (S)-9CDHRA) and 9CRA.

Whereas 13,14-dihydroretinol was detected by Moise and colleagues [Moise A R et al. 2004] as a hepatic retinol saturase (RETSAT) metabolite in the mammalian organism, other dihydroretinoids or their precursors were also identified in other vertebrates [Moise A R et al. 2007] and also non-vertebrates [Foster J M 1993]. All-trans-13,14-dihydroretinol saturase has also been described by Moise and colleagues (WO2006/029398). Besides RETSATmediated retinol metabolism as the major potential pathway for endogenous 9CDHRA synthesis, also apocarotenoids and carotenoids may serve as substrates for hydrogenation via RETSAT or other saturases, followed by the synthesis of dihydroretinoic acids [Gouranton E et al.].

This metabolic pathway may be phylogenetically ancient, as RXR orthologs from several non-vertebrate species including mollusk [Foster J M. et al. 1993], primitive chordate like amphioxus [Tocchini-Valentini G D et al. 2009] and some primitive insects like Tribolium [Iwema T et al. 2007] or Locusta migratoria [Nowickyj S M et al., 2009; Palli S R et al., 2005] have also a potential to bind RXR ligands. In addition, Locusta migratoria ultraspiracle (a fly RXR orthologue), displayed higher affinity to bind 9CRA than human RXR [Palli S R et al., 2005], raising the possibility that 9CDHRA could also activate the USP pathway and be an ancestral RXR ligand.

Considering these data in view of the findings of the present invention discussed below the inventors have concluded that, it in addition to the active ligands originating from vitamin A1 and vitamin A2, 9CDHRA and its nutritional precursors represent a novel distinct pathway of vitamin A metabolism and signaling, which evolved specifically to control RXR activity and thus which is to be called the vitamin A5 pathway.

In summary, the inventors characterized 9CDHRA as the first endogenous and physiologically relevant retinoid that acts as RXR ligand in mammals and thus may be used in conditions wherein the RXR signaling is impaired.

Further work has been required to characterize this ligand and to determine its presumably multiple roles in biological systems (de Lera et al., 2016). Retinoid X receptor (RXR) is involved in the regulation of various physiological relevant pathways in the brain, lipid metabolism, inflammation, differentiation, proliferation and cell cycle. The RXR-mediated signaling has been reported to be dysregulated in various diseases ranging from neurological dysfunctions, cardiovascular diseases and skin/immune-related diseases where an RXR-signaling related dysregulation of lipid homeostasis and inflammation are involved. The inventors have further identified the endogenous RXR ligand, 9CDHRA, as a signaling lipid molecule possibly related to the dysfunctions of RXR due to reduced levels of the ligand.

Thereby a new vitamin A pathway called vitamin 5 pathway has been identified.

The present invention also relates to physiological as well as nutritional precursors of 9CDHRA. The major precursor is claimed to be 9-cis-13,14-dihydroretinol (9CDHROL), i.e. vitamin A5 and its esters, 9-cis-13,14-dihydroretinyl esters (9CDHROL-esters, 9CDHROL-ES) as well as 9-cis-13,14-dihydroretinoic acid esters (9CDHRA-esters, 9CDHRA-ES). In addition to these molecules novel carotenoids as pro-vitamin A5 precursors like 9-cis-13,14-dihydro-$\beta,\beta$-carotene (9CDHBC) have been identified. Obtained data support also a possibility that further upstream precursors of 9CDHBC may exist and may include 9-cis-3,3-carotene (9CBC).

The aim of the present study was to find and synthesize by organic chemical synthesis these additional derivatives and test representative examples of these precursors in animal models for depression in mouse models.

In the set of experiments described in the Examples the present inventors have developed a new chemical synthesis of 9-cis-13,14-dihydroretinol and 9-cis-13,14-dihydroretinyl acetate via ethyl 9-cis-13,14-dihydroretinoate. Other esters of 9-cis-13,14-dihydroretinoic acid and 9-cis-13,14-dihydroretinol (such as palmitate and others) can be easily prepared using basically the same method.

New synthesis methods for 9-cis-13,14-dihydro-$\beta,\beta$-carotene and synthesized 9-cis-3,3-carotene have also been developed.

Alternatively, chemoenzymatic synthesis of long-chain retinyl esters is also an option. A part of these syntheses utilize retinol as the starting material (O'Connor et. al. 1992; Maugard et. al. 2002). Certain authors have utilized retinyl esters such as retinyl acetate as the starting material for a biocatalytic preparation of long-chain retinyl esters (see e.g. unexamined Japanese Patent Application JP 62-248495, 1987). U.S. Pat. No. 7,566,795B2 describes an improved method for the preparation of long-chain esters of retinol via chemoenzymatic processing from short-chain retinyl esters and an appropriate long-chain acid or ester in the presence of an enzyme and organic solvent and optionally in the presence of at least one molecular sieve and/or at least one ion exchange resin to form the retinyl ester.

Several patent applications have been directed to various vitamin A form precursors and variants thereof.

As to esters of acid forms, WO 95/04018 A1 relates to the preparation of 9-cis-retinoic acid esters. The compounds comprise double bonds between carbon atoms C11 and C12, as well as between carbon atoms C13 and C14 and can have either cis or trans configurations. While methods can be utilized herein, the compounds necessarily cannot be 13,14-dihydro derivatives. WO 95/32946 A1 also relates to the preparation of 9-cis-retinoic acid esters. The compounds must comprise double bonds between carbon atoms C11 and C12 and C13 and C14, which may be both cis and trans isomers.

As to esters of retinol, WO2013134867 A1 describes the treatment of retinitis pigmentosa using 9-cis- or 11-cis-retinyl esters (see claim 17). The description mentions 9-cis-13,14-dihydroretinoic acid as a metabolite, but there is no suggestion to 9-cis-13,14-dihydroretinol derivatives. ("Pharmacokinetic analyses showed the predominant metabolites to be either 9-cis-retinyl oleate or 9-cis-retinyl palmitate and 13,14-dihydro-9-cis-retinoic acid. At 4 hours after dosing, the concentration of these compounds was higher than that of 9-cis-retinyl acetate and 9-cis-retinol." See page 70, penultimate paragraph.)

WO 2011/034551 A2 describes pharmaceutical formulations comprising one or more 9-cis-retinyl esters (acetate, palmitate, etc.) in a lipid vehicle and their uses for ophthalmic purposes. The description does not mention the use of 9-cis-13,14-dihydroretinol derivatives.

Thus, apparently no documents appears to describe the medical use or, in particular, the nutritional use of 9-cis-13, 14-dihydroretinol or its ester derivatives. Moreover, we have not found data relating to the ester derivatives of 9-cis-13, 14-dihydroretinol.

RXR-ligand binding is a highly important mechanism responsible for vitamin A-mediated effects.

The RXR ligand precursor pathway is different from the RAR ligand precursor pathway, the latter including all-trans-retinol (ATROL), its metabolite ATRA and selective RAR-mediated signaling. Alternatively pro-vitamin A1 carotenoids like proven for ATBC cannot be converted in the human organism to 9-cis-derivatives and are thereby no precursors for RXR-selective ligands. Vitamin A1, i.e. all-trans-retinol is only weakly and non-isomer-selectively converted to 9CDHROL or 9CDHRA and is thereby a weak and non-selective precursor for RXR-selective ligands. Importantly, 9CDHROL is an efficient and preferential precursor of 9CDHRA, an active form of vitamin A5. Thus we suggest that ATROL serves as the major precursor for formation of retinyl-ester stores. Such stores play role in homeostasis of retinoid signaling by maintain stable concentrations and bioavailability of ATRA as RAR ligand in the blood, but with little potency of generating 9CDHRA as RXR ligand. In contrast, 9CDHROL, may play role in homeostasis of 9CDHRA, by acting as their immediate, phasic precursor, and storing capacity of 9CDHROL to act as tonic reservoir of 9CDHROL may be supposed It is contemplated herein that 9-cis-13,14-dihydroretinoids can be considered as specific and/or selective precursors of RXR ligands. Based on the information outlined above, potential RXR-ligands originating from vitamin A1 and A2 pathways seem to have no or very limited endogenous relevance. The present inventors have shown, however, that this new signaling pathway, which is relevant for RXR-activation, should also be included as a crucial criterion for general vitamin A functions (FIG. 7). In the figure the presence of 9CDHRAL and ATDHRAL are not yet identified. In summary, because the non-endogenously relevant 9CRA originating from vitamin A1 pathway should be excluded as an endogenous relevant RXR-activator, then 9-cis-13,14-dihydroretinoids and their nutritional precursors represent a novel vitamin A signaling pathway which is called the vitamin A5 pathway.

The present inventors have elucidated the metabolic conversion of different components of this vitamin A5 pathway in supplementation experiments in the mammalian organism and in in vitro cellular systems, identify them in mouse and human organism as endogenous derivatives and identify these derivatives directly or indirectly within the human food chain. In addition, it has been found that: (1) 9CDHROL displays promnemonic activities similarly to 9CDHRA or BMS649, and (2) synthetic RXR ligand and 9CDHROL as well as 9CDHBC display antidepressant activities in social stress defeat protocol as an RXR-mediated process. Therefore the invention relates to novel treatment methods of memory deficits or depression by administration of RXR-ligands or vitamin A5 (9CDHROL) or RXR-ligand precursors or vitamin A5 precursors like pro-vitamin A5 derivatives like 9CDHBC.

As an example to show RXR signaling effect, among RXR-signaling dysregulated diseases, depression has been chosen as a heterogeneous group of psychiatric disorder with non-clearly identified aetiology. It is characterized by a number of core, affective symptoms including anhedonia and feelings of despair as well as less specific, cognitive symptoms such as deficits of working memory. It has been shown that reduced bioavailability of 9CDHRA in mice carrying null mutation for cellular retinol binding protein 1 (Rbp1) leads to depressive-like behaviors, whereas pharmacological treatment with 9CDHRA restores normal behavior in these mice. For depression the administration of selective RAR-ligands does not lead to any improvement and this dysfunction and it seems to be a selective RXR-signaling related dysfunction. The treatments with 9CDHRA precursors as disclosed herein are of direct relevance for research into depression as 9CDHRA and 9CDHRA-precursors, similarly to synthetic RXR ligands was effective in preventing depressive-like behaviors in chronic stress animal model of depressive behaviors.

Specifically the present inventors have determined that 9CDHROL, the precursor of 9CDHRA, when given orally to mice can also induce positive effects on memory performance in mice. Moreover they have determined that 9CDHROL is a precursor of 9CDHRA when given orally to mice (FIG. 1).

These data support the presence of the novel vitamin A pathway by showing that 9CDHROL precursor of 9CDHRA as well as esters thereof are special precursors of selective RXR ligands.

The present results allow the conclusion that 9CDHROL is a novel endogenous retinoid in mice and derivatives, which once administered, result in efficient formation of 9CDHRA in the animal or human body and can be considered as a new type vitamin A5.

The present inventors have also determined that 9CDHROL-ester (9CDHROL-ES) and 9CDHRA-ester (9CDHRA-ES) are alternative to 9CDHROL as precursors for 9CDHRA.

Thus, 9CDHROL and 9CDHROL-ester and 9CDHRA-ester are physiological and nutritional precursors for 9CDHRA and can be used as alternative treatments to reach higher 9CDHRA levels in (specific) tissues.

In additional animal studies in a set of models of mental diseases further evidence has been provided that (R)-9CDHRA displays RXR agonist-like activities in vivo and reverses behavioral deficits in mice.

Together with: (1) evidence that 9CDHRA-esters and 9CDHROL as well as its esters increase the 9CDHRA-levels particularly efficiently in the brain and in oligodendrocytes, that (2) 9CDHRA can reverse behavioral deficits in Rbp1−/− mice, (3) 9CDHROL and 9CDHRA improve cognitive performance in wild type mice and (4) revers/prevent antidepressant effects in chronic social defeat stress model similarly to 9CDHRA, further supports the utility of the compounds of the invention in a broad range of diseases of the central and peripheral nervous system. Note that Rbp1−/− mice were used because they show the same type of deficits as RXRγ−/−, but without loss of RXRγ expression. Since RXR synthetic ligands or 9CDHRA can rescue memory deficits in Rbp1−/− but not in RXRγ−/− mice it can be concluded that RXR ligand bioavailability is compromised in Rbp1−/− brains. This hypothesis was confirmed by direct measurements of 9CDHRA in Rbp1−/− biological material (see the Examples).

RXR-binding and RXR-mediated signaling pathway activation by 9CDHRA results in selective RXR-activation pathways and RXR-LXR, RXR-NR4A, RXR-VDR, RXR-FXR and RXR-PPAR mediated signaling. These RXR-mediated signaling pathways can be modified by an RXR-ligand only and not by an RAR-ligand.

The present inventors have found effective precursors of the endogenous RXR ligand 9CDHRA, e.g. 9CDHROL (vitamin A5) as well as further upstream precursors which are useful to provide 9CDHRA in a subject and thereby improve, maintain or repair RXR-mediated signaling pathways, alternatively called Vitamin A5/provitamin A5 pathway or vitamin A5 pathway in short.

This Vitamin A5/pro-vitamin A5 pathway involves pharmaceutical or nutritional or derma-topical applications of our claimed selective RXR-precursors.

Prevention and usage of these vitamin A5/pro-vitamin A5 compounds for diseases where RXR-mediated signaling is augmented like for various neurodegenerative diseases and further diseases of the skin and cardio-vascular system involving RXR-mediated signaling altered lipid homeostasis and immune-regulation like atherosclerosis, obesity and diabetes. These diseases with a dysfunctional RXR-mediated signaling can be prevented and/or treated by our RXR-selective precursors.

As an example used in this study, depression was treated as an RXR-mediated signaling dysfunction and 9CDHRA as well as 9CDHROL and 9CDHBC as 9CDHRA precursors as an active treatment/prevention strategy. Many other diseases were reported, however, in the art where an RXR-KO phenotype exists ranging mainly from neurodegenerative diseases and dysfunctions in the cardio-vascular system like obesity, diabetes, and atherosclerosis and appetite regulation.

We claim that we have found an important physiological switch-mechanism in the human organisms which can be selectively switched on by a) a selective physiological ligand (9CDHRA) and its esters 9CDHRA-ES or b) selectively by nutritional precursors present in food, which can also be given as supplements/pharmaceuticals, 9CDHROL, 9CDHROL-ES and 9CDHBC. This switch can enable RXR-mediated signaling and thereby prevent RXR-mediated signalling dependent dysfunctions and diseases.

It has been also surprisingly found that the selective 9CDHRA-precursor 9CDHBC is a pro-vitamin A5 carotenoid for enabling RXR-mediated signaling.

As shown here just 9CDHBC and not 9CBC is an excellent precursor of 9CDHROL (vitamin A5). The carotenoid 9CDHBC is a good precursor for 9CDHRA in mouse serum, liver and brain, when given orally to mouse in in vivo supplementation trials. In humans (while not in mice) carotenoids are transported and stored within the body. It has been shown that 9CDHBC, and not 9CBC (and especially not ATBC), is a good precursor of 9CDHROL and also 9CDHRA.

9CBC (already known) and 9CDHBC are both present in the human food chain (shown for 9CDHBC in peach).

According to the present invention functional food is claimed which comprises added isolated vitamin A5 or any precursor thereof like 9CDHBC or other compounds, or compounds for use according to the invention. Preferably the functional food according to the invention is a processed food and preferably a preserved food.

The selective RXR precursor ligands of the invention are surprisingly more effective than non-selective compounds. For example, the known endogenous retinoid vitamin A1 alcohol, ATROL, is just a weak and non-isomer selective precursor of 9CDHROL and no precursor of 9CDHRA in mouse oligodendrocytes cell culture in vitro. In supplemented mice it is just weakly and partly not significantly converted to 9CDHRA. For comparison 9CDHROL, as our novel claimed Vitamin A5 alcohol, is converted to 9CDHRA in mouse oligodendrocytes cell culture in vitro highly efficiently, when given the same amount of these retinoids supplemented to mice. As shown here, 9CDHROL has been confirmed to be present in human serum as well as in the human food chain examined in commercially available beef liver.

9CDHROL is thereby an excellent physiological and nutritional precursor for 9CDHRA and can be used as alternative treatments to selectively reach higher 9CDHRA-levels and selective RXR-mediated signaling proven in mice behavioral studies. 9CDHROL is very efficiently converted to 9CDHRA, as shown in in vitro as well as in vivo supplementation trials. Esters of 9CDHROL (9CDHROL-ester, 9CDHROL-ES) and 9CDHRA (9CDHRA-ester, 9CDHRA-ES) are also excellent and even more stable derivatives and can be given alternatively yielding even higher conversion to 9CDHRA. We claim that 9CDHROL belongs to a novel selective vitamin A family functioning as selective RXR-ligand precursors, named as the vitamin A5 family.

9CDHBC is a novel endogenous derivative identified in high amounts in the human food chain at various levels. We claim therefore that 9CDHBC is a novel selective pro-vitamin, named pro-vitamin A5 as a selective precursor for the selective RXR-ligand 9CDHRA.

We also claim that 9CBC is a precursor of a RXR ligand and a direct precursor of pro-vitamin A5/9CDHBC. 9CBC can be used alternatively as a food ingredient or nutraceutical derivative with a weak and non-selective derivative for preventing VA5-deficiency and for general VA5-supplementation to prevent RXR-dependent dysfunctions of our organisms, here shown representatively by depression, as a selective RXR-ligand/RXR-mediated neurodegenerative disease.

13,14-Dihydrocarotenoids have not been reported to date except for the case of acyclic carotenoids such as lycopene, phytoene and phytofluene. The C13=C14 double bond formal hydrogenation might result from the action of retinol saturase (RETSAT) on the unsaturated precursor retinol or from an alternative metabolism of classical known retinoids (Moise et al., 2004). All-trans-13,14-dihydroretinoic acid has been identified by research groups of the present invention in high concentration in serum, liver and brain of young wild-type non-vitamin A supplemented mice (respectively, 96 ng/ml; 352 ng/mg; 38 ng/g).

In summary, the pathway from 9-cis-dihydrocarotenoids, preferably 9-cis-13,14-dihydrocarotenoids has a physiological relevance for endogenous 9CDHRA synthesis starting from dietary carotenoids. Thus, it is contemplated that 9CDHROL and 9CDHBC are nutritional and endogenous relevant precursors of the endogenous RXR ligand 9CDHRA.

Thus, the invention also relates to the use of 9-cis-dihydrocarotenoids and preferably 9CDHBC for the purposes as disclosed herein.

The experiments show that the compounds of the invention are capable of providing 9CDHRA and could work to maintain health, in particular health of the central or peripheral nervous system and/or maintain health against the diseases mentioned herein or prevent or treat said diseases practically in anybody. In particular the disease is a central or peripheral nervous system disease as listed herein.

Certain aspects and embodiment of the invention are detailed below, then the invention is illustrated by Examples which are part of the invention; however, the skilled person will understand that based on the specific and general teaching provided herein other variants and embodiments are at hand and can be carried out.

Preparation of the Compounds of the Invention

The starting compounds may be obtained commercially or may be synthesized according to standard methods.

Preparation of 9-cis-13,14-dihydroretinoic acid and its esters

In the embodiment presented in the Examples the preparation of the ethyl ester of (R)-9-cis-13,14-dihydroretinoic acid [(R)-1], or (R)-4 was based on the Suzuki coupling of enantiopure trienyliodide 3 and boronic acid 2 (See Scheme 1 in Example 1). The synthesis of 3 started with (Z)-stannyldienol 5 which was transformed into the benzothiazolyl allyl sulfide 6 by Mitsunobu reaction with the corresponding thiol and subsequently oxidized to sulfone 7 with $H_2O_2$ and a peroxymolybdate (VI) reagent. The Julia-Kocienski olefination was performed using slight excess of base and excess of enantiopure aldehyde (R)-8 which is an ethyl ester. As anticipated from previous findings on the stereochemical outcome of the reactions of allylsulfones and aldehydes, the newly formed olefin of trienyl ester (R)-9 is of Z-geometry. Treatment of the precursor stannane with a solution of iodine in $CH_2Cl_2$ produced the iodide (R)-3 via Sn-1 exchange and iodine-promoted isomerization of the (9Z,11Z) diene to the desired (9Z,11E) geometric isomer. Geometric isomers can be confirmed by NOE experiments.

The Suzuki reaction of freshly prepared boronic acid 2 and dienyl iodide (R)-3, followed by immediate work-up resulted in ethyl (R)-9-cis-13,14-dihydroretinoate (R)-4. Saponification of (R)-4 provided the desired carboxylic acid (R)-1 without detectable loss of stereochemical integrity. (See reaction Scheme 1)

Following the general scheme, enantiomer (S)-1 was also prepared with similar efficiency.

The preparation of the compounds of the invention is described in more detail in Example 1.

Alternative esters of 9-cis-13,14-dihydroretinoic acid can be prepared with the corresponding ester variants of compound (R)-8.

In addition, the carboxylic acid 9-cis-13,14-dihydroretinoic acid can be esterified with other alkyl or alkenyl-containing alcohols using standard procedures, such as the treatment of a mixture of both compound with dicyclohexylcarbodiimide (DCC) and dimethylaminopyridine (DMAP).

Moreover further esters could be prepared starting from the corresponding aldehyde (R)-8 with a different ester than ethyl.

Preparation of 9-cis-13,14-dihydroretinol and its 9-cis-13,14-dihydroretinyl esters 9-cis-13,14-Dihydroretinol has been prepared as described herein by DIBAL-H (diisobutylaluminium hydride) reduction of ethyl 13,14-dihydroretinoate.

Ester reduction can also be accomplished with lithium aluminum hydride ($LiAlH_4$) in tetrahydrofuran (THF) or diethyl ether, or with lithium borohydride and an alcohol (EtOH, MeOH) in THF/diethyl ether as solvent.

9-cis-13,14-Dihydroretinyl acetate was prepared from 9-cis-13,14-dihydroretinol by adding excess $Ac_2O$ and pyridine in the presence of DMAP. The obtained ester was isolated and purified.

The synthesis method maintained the configuration and the optical purity of the enantiomers.

By this method alternative esters can be prepared with a carboxylic acid anhydride reagent $R_2O$, being R a carboxylic acid, or using the corresponding chlorides derived from the carboxylic acids, or using the activated carboxylic acid prepared, for example, with DCC and DMAP.

Esters of 9-cis-13,14-dihydroretinol can be prepared by trans-esterification reactions of esters thereby the acyl group can be replaced.

Alternatively, the retinyl esters can be prepared from 9-cis-13,14-dihydroretinol using appropriate esterifying agents.

A further method may be selective enzymatic reactions. For example lecithin:retinol acyltransferase (LRAT) catalyzes a trans-esterification, transferring long chain fatty acyl moieties (primarily palmitic, stearic, oleic and linoleic acids) present at the sn-1 position of membrane bilayer phosphatidylcholine to retinol, forming retinyl esters (O'Byrne, Sheila M. et al. 2013). Lipases form a further group of enzymes suitable for synthesis of esters, like fatty acid ester (Kai Z J 2011, Yin Chunhua 2006). Alternatively, a combined chemo-enzymatic method can be used (Liu ZQ 2015).

Such enzymes may be prepared by recombinant techniques and used to selectively prepare the desired ester. Alternatively the enzyme can be cloned into appropriate host cell, overexpressed in active form and this recombinant cell can be used to prepare the desired ester.

Certain Preferred Esters of the Invention

Preferred 9-cis-13,14-dihydroretinoic Acid Esters

Preferred 9-cis-13,14-dihydroretinoic acid esters are typically lower alkyl esters like methyl, ethyl or propyl esters of 9-cis-13,14-dihydroretinoic acid. Esters of 9-cis-13,14-dihydroretinoic acid with long chain fatty alcohols are less preferred than esters of long chain fatty acids of 9-cis-13,14-dihydroretinol.

Further Preferred 9-cis-13,14-dihydroretinyl Ester Compounds

Further preferred 9-cis-13,14-dihydroretinyl ester compounds include formate (methanoate), ethanoate and propionate esters, as well as, though less preferred, butyrate and valerate esters.

Long chain fatty acids may also form esters with 9-cis-13,14-dihydroretinol.

Long chain fatty acids (LCFA) include fatty acids with aliphatic tails from 13 to 21 carbons.

Long chain fatty acids can be selected from saturated and unsaturated fatty acids the latter including monounsaturated and polyunsaturated fatty acids.

Saturated Fatty Acids

Typical esters with saturated fatty acids can be formed e.g. with the following long chain fatty acids:

| | | |
|---|---|---|
| Myristic acid | $CH_3(CH_2)_{12}COOH$ | 14:0 |
| Palmitic acid | $CH_3(CH_2)_{14}COOH$ | 16:0 |
| Stearic acid | $CH_3(CH_2)_{16}COOH$ | 18:0 |
| Arachidic acid | $CH_3(CH_2)_{18}COOH$ | 20:0 |

While saturated fatty acids are often stated to be non-advantageous in diet, they still may be useful components of the esters of the invention as precursors of 9CDHROL in the human tissues.

Monounsaturated Fatty Acids (MUFAs)

Monounsaturated fatty acids have one carbon-carbon double bond, which can occur in different positions. The most common monoenes have a chain length of 16-22 atoms and a double bond with the cis geometry which is preferred.

Preferred MUFAs which are applicable in the present invention are oleic acid $CH_3(CH_2)_7(HC=CH)(CH_2)_7COOH$ and palmitoleic acid $CH_3(CH_2)_5(HC=CH)(CH_2)_7COOH$.

Polyunsaturated Fatty Acids (PUFAs)

In polyunsaturated fatty acids (PUFAs) the first double bond may be found between the third and the fourth carbon atom from the first carboxylic acid carbon; these are called 0-3 fatty acids. If the first double bond is between the sixth and seventh carbon atom, then they are called 0-6 fatty acids.

Preferred PUFAs which are applicable in the present invention are, for example, ω-3 and ω-6 fatty acids.

Among PUFAs arachidonic acid (ARA) and docohexanoic acid (DHA) are useful in the treatment of Alzheimer's disease (see e.g. EP1419780B1).

In this case, PUFAs, once hydrolysed, also can exert their advantageous effect in the organ in question.

In an embodiment, essential fatty acid esters are preferred. Two essential fatty acids are linoleic acid (LA) and alpha-linolenic acid (ALA). The human body has a limited ability to convert ALA into the longer-chain omega-3 fatty acids-eicosapentaenoic acid (EPA) and docosahexaenoic acid (DHA), which are also preferred.

Branched Chain Fatty Acids (BCFA)

Branched-chain fatty acids (BCFA) are bioactive food components [Ran-Ressler R R et al. 2014], which are present in milk and soy and in some cases (like phytanic acid) in ruminant animal fats, and certain fish. Naturally occurring branched chain fatty acids demonstrate potential health properties and are preferred components of the esters of the invention.

Such preferred BCFAs are e.g. the naturally occurring 13-methyltetradecanoic acid, 15-methylpalmitic acid and phytanic acid (3,7,11,15-tetramethylhexadecanoic acid).

Fatty acids and their role in biology can be found e.g. in the following books:

(Ching Kuang Chow 2007; Arild C et al. 2005)

The compounds and/or the pharmaceutical compositions according to the invention may be used in a therapeutic method. A preferred therapy relates to diseases of the nervous system.

Forms of the Compounds of the Invention

The compounds according to the invention relate to enantiomers (pure enantiomers or mixtures provided that they are obtainable by the method of the invention), geometric isomers of same, salts, hydrates and solvates of same, solid forms of same, as well as mixtures of said forms.

The compounds may be enantiopure or enantiomerically pure compound, e.g. optically pure, more preferably having at least 90%, preferably at least 95%, more preferably at least 98% or 99% optical purity or the compounds may have the same chirality within limits of detection.

When the compounds according to the invention are in the form of salts, they are preferably pharmaceutically acceptable salts of the acid form. Such salts include for example pharmaceutically acceptable base addition salts, pharmaceutically acceptable metal salts, ammonium and alkylated ammonium salts.

Further examples of pharmaceutically acceptable inorganic or organic salts include the pharmaceutically acceptable salts listed in Berge, S M et al. (Berge, S M, 1977).

The Compounds of the Invention in the Nervous System and Nervous Tissue

The compounds of the invention can be converted into their active form in nervous tissue or in the nervous system. Preferably if the compounds are administered to an animal or human subject this conversion in the nervous system or in nervous tissue (in a preferred embodiment in the brain) is preferential.

In the preferred embodiment of the invention the compounds are converted by hydrolysis into 9CDHROL. Alternatively, the compound is 9CDHROL. In the nervous system 9CDHROL is further converted into 9CDHRA, which exerts its RXR agonist effect.

The nervous system as used herein consists of the central nervous system (CNS) and the peripheral nervous system (PNS). The central nervous system (CNS) is comprised of the brain and spinal cord.

The peripheral nervous system (PNS) includes all (branching) peripheral nerves, and regulates and controls bodily functions and activity.

According to the invention 9CDHRA formed in situ exerts its RXR agonist effect in the nervous tissue to prevent or treat diseases of the CNS or PNS (as detailed herein wherein such diseases are discussed).

Nervous tissue (or nerve tissue) is the main tissue component of the above-mentioned two parts of the nervous system: the CNS and the PNS. It is composed of neurons, or nerve cells, which receive and transmit impulses, and neuroglia, also known as (neuro)-glial cells (glia), which assist the propagation of the nerve impulse as well as providing nutrients to the neuron.

Neuroglial cells are e.g. the following cells:

Microglial cells, astrocytes, oligodendrocytes, NG2 glia, Schwann cells, satellite glial cell, enteric glia.

To mention a few in somewhat more detail, oligodendrocytes are central nervous system structures that form myelin sheaths on the axons of a neuron, which are lipid-based insulation that promotes an efficient conduction of nerve impulses down the axon. NG2 glia are CNS cells that serve as the developmental precursors of oligodendrocytes. The Schwann cells are the PNS equivalent of oligodendrocytes, they help maintain axons and form myelin sheaths in the PNS.

Experiments with oligodendrocyte cells together with data reporting role of synthetic RXR agonists in control of remyelination support role and utility of compounds described in the patent for control of oligodendrogenesis and myelin sheath function in the CNs and PNS as well as to NG2 glia.

Thus, the diseases of the CNS and PNS which can be treated, prevented or alleviated by an RXR agonist, can be treated with the esters of 9CDHRA, 9CDHROL and esters of the latter.

RAR/RXR, RXR/PPAR or RXR/LXR signaling in the brain is reviewed or evoked for example in the following publications: (van Neerven 2008; Shudo K et al. 2009; Skerrett R et al. 2015) There are three retinoic X receptors (RXR): RXRα, RXRβ, and RXRγ, encoded by the RXRα, RXRβ, RXRγ genes, respectively. RXR-ligand binding is a highly important mechanism responsible for vitamin A-mediated effects. RXR also occupy a central position in nuclear receptor (NR) signaling, because it serves as the common heterodimerization partner of multiple NRs. These heterodimers are called permissive or non-permissive depending on whether the role of the RXR is as an active or a silent transcription partner, respectively. Permissive RXR-NR heterodimers are activated by the RXR ligand or by the partner's ligand, and synergistic effects are usually observed if both partners of the heterodimer are bound to their ligands. One of the heterodimers is the RXR-RAR heterodimer irrespective of the RXR isotype as RXRα, RXRβ and RXRγ share highly conserved, the same type of ligand binding pocket.

The compounds of the invention are particularly useful as RXR agonist and in conditions wherein agonists of RXR, in particular via RXR-RAR, but also RXR-PPAR or RXR-LXR, are useful to maintain or restore health.

In a preferred embodiment the compounds can be used for the treatment of impaired cognitive functions and/or impaired learning.

The compounds and/or the pharmaceutical compositions according to the invention may be used in a therapeutic method, in particular for the treatment of memory impairment (memory loss), in particular working memory impairment, e.g. defects and loss, or short term memory impairment, e.g. defects and loss, like amnesia, etc. Memory impairment, impaired learning abilities and impaired cognitive functions may be associated with a mental disorder, such as mild cognitive disorder, amnestic syndrome, memory and cognitive deficiencies in schizophrenia and mood disorders, such as bipolar affective disorder and depression, stress related and anxiety disorders, such as partial and complete amnesia, dissociative amnesia.

Several psychoactive substances and medications are known to cause memory loss, impaired learning abilities and impaired cognitive functions, such as tricyclic antidepressants, dopamine agonists, antihistamines, benzodiazepines, statins, beta blockers, barbiturates, opioids, THC, alcohol, etc.

The compounds and/or the pharmaceutical compositions according to the invention are especially useful in reversing such memory impairment effected by a disease or a medication mentioned above.

The compounds and/or the pharmaceutical compositions according to the invention are especially useful in the prevention and/or treatment of short term memory impairment. The compounds and/or the pharmaceutical compositions according to the invention are particularly useful in improving working memory performance or reducing working memory loss.

The compounds and/or the pharmaceutical compositions according to the invention are useful in the treatment of depression, such as mild, moderate and severe depressive episodes as well as the depressive phase of bipolar disease, cyclothymia or dysthymia, mixed anxiety-depression disorder, depression or depressive episode associated with other diseases, such as schizophrenia, cancer, metabolic diseases, etc.

The compounds and/or the pharmaceutical compositions according to the invention are useful in preventing and/or treating neurodegenerative disorders. Preferably a neurodegenerative disorder is selected from Alzheimer's disease, Parkinson's disease, Mild Cognitive Impairment (MCI), Parkinson's disease with MCI, Alzheimer's disease, Huntington's disease, Dementia with Lewy Bodies (DLB), Amyotrophic Lateral Sclerosis (ALS), and other neurodegenerative related dementias due to changes in the brain caused by ageing, disease or trauma; or spinal cord injury and ataxias, disseminated sclerosis and multiple sclerosis or other neurological conditions.

According to a specific embodiment, the invention also relates to a kit that is suitable for the treatment by the methods described above.

In an embodiment these kits comprise a composition containing the compound of the invention in appropriate dosages and a second composition containing a mood stabilizer, an antidepressant an anxiolytic etc.

In a further embodiment the kit comprises a composition containing the compound of the invention in appropriate dosages and a second composition containing an active agent against a neurodegenerative disorder as defined or listed herein.

The invention also relates to a combination comprising components of the kits as listed above.

Testing the compounds of the invention is possible in animal models (and non-animal models), e.g. chronic social defeat stress model of depressive behaviors, animal models of amyloidosis or Alzheimer disease and Parkinson's disease.

Nutritional Uses

The compounds of the invention might be used as a nutritional or dietary supplement, in a functional food composition, in a dietary supplement composition or in a nutraceutical composition. Such nutritional or dietary supplement, functional food composition, dietary supplement compositions or nutraceutical compositions have the benefit of preventing, reversing and/or alleviating a condition as disclosed herein. In a preferred embodiment the condition is memory loss, in particular working or short term memory impairment, particularly memory loss without the administration of a pharmaceutical, i.e. in a non-medical way and/or have the benefit of preventing, reversing and/or alleviating learning impairment and/or decline of cognitive functions. By non-medical a treatment is meant for the purposes of the application wherein the normal body functions are to be maintained wherein the condition is defined herein is non-pathological or has not reached a pathological level. Preferably, in non-medical treatment a nutritional or dietary supplement, a functional food composition, a dietary supplement composition or a nutraceutical composition is used to prevent, reverse and/or alleviate memory loss, learning impairment and/or decline of cognitive functions in a condition which is still not or cannot be considered as an illness.

Nutraceutical compositions may comprise a "nutraceutically acceptable carrier" means that the carrier is acceptable for human consumption and retain or improve the biological properties of the active agent.

In analogy to other dietary vitamin A compositions based on the invention amounts of retinoids of the vitamin A5 pathway can be measured in 9CDROL equivalents.

The compositions of the invention are suitable for use in nutraceutical compositions, e.g. dietary supplement, a functional food, a medical food or a food with a health claim.

As shown herein fat soluble forms would be stored in the liver and supply of the body could be fulfilled therefrom.

Formulations

Compositions comprise, besides the active agent at least one carrier.

The carrier may be e.g. a diluent, adjuvant, excipient, stabilizer, or vehicle with which the agent is formulated for administration. Pharmaceutical carriers can be sterile liquids, such as water and oils, including those of petroleum, animal, vegetable or synthetic origin, such as peanut oil, soybean oil, mineral oil, sesame oil, and the like. Water is a typical carrier when the pharmaceutical composition is administered intravenously. Saline solutions and aqueous dextrose and glycerol solutions can also be employed as liquid carriers, particularly for injectable solutions.

In one embodiment, the agent is formulated in accordance with routine procedures as a pharmaceutical composition adapted for intravenous administration to mammalian or human beings. Typically, compositions for intravenous administration are solutions in sterile isotonic aqueous buffer. Where necessary, the composition can also include a solubilizing agent.

In solid formulations suitable pharmaceutical excipients include starch, glucose, lactose, sucrose, gelatin, malt, rice, flour, chalk, silica gel, sodium stearate, glycerol monostearate, talc, sodium chloride; dried skim milk, glycerol, propylene, glycol, water, ethanol, and the like. The composition, if desired, can also contain wetting or emulsifying agents, like lipids.

Pharmaceutical or nutraceutical compositions can take the form of solutions, suspensions, emulsion, tablets, pills, capsules, powders, sustained-release formulations, and the like.

In particular in case of longer alkyl chain esters a lipid vehicle is advantageous as esters are more stable than the acid form and acid esters may be more stable than the free alcohol.

The compounds of the invention are light sensitive (photosensitive) and oxygen sensitive (easily attacked by oxidants) and are thermolabile. This is mainly due to the electron-rich polyene chain. Light below $\lambda_{max}$ 500 nm, or even in daylight may cause extensive isomerization within a short time. Oxygen, trace metals such as iron and copper, strong acids and excessive heat also deteriorate the molecules. Therefore selection of an appropriate vehicle may depend on its ability to stabilize the compound of the invention.

As stability of Vitamin A compositions is affected by heat, light, and air the composition should be prevented from such effects. In particular, ultraviolet light is harmful. In inert atmosphere and in the dark a moderate increase of temperature is acceptable.

Oxidation may be inhibited by the addition of antioxidants, examples for which are alpha-tocopherol, hydroquinone, propyl gallate, ascorbic acid etc. and their combinations. Preferably the usual concentrations are applied.

In liquid formulations an oil, preferably with low peroxide content, is acceptable. Preferably the composition is to be stored in a vial which protects against light, in particular ultraviolet light. In a preferred embodiment a solvent and an oil is applied together.

Further preferred excipients for stabilizing liquid oral formulations are eg. casein hydrolysate alone or in combination with cysteine hydrochloride gives good protection to Vitamin A. Further information on stability can be found e.g. in Kondepudi, N. (2016).

The oils used as auxiliaries in vitamin products are usually stable vegetable oils (fatty acid glycerides), e.g. peanut oil or soybean oil. Oil containing compositions are sensitive to oxidation and should be stabilized e.g. with an antioxidant combination. Ascorbyl esters and tocopherol may be useful additives (Volker Bühler 2002).

Added food concentrate or extract may also be considered as a stabilizer and/or emulsifier.

Alkaline pH is preferred.

As examples, for solution forms parenteral intramuscular injection can be formulated e.g. as a long chain fatty acid ester, e.g. palmitate ester of the alcohol form with an emulsifier e.g. polysorbate.

As nutraceuticals for example soft gel capsules can be applied. Here the oil can be an edible oil, like vegetable oil, fish oil or other stable oils. Esters of alcohol or the acid form are suitable forms here, too. Palmitate esters of the alcohol are preferred. Further exemplary ingredients are e.g. gelatine or equivalent gel forming agent, glycerin, purified water.

Further possible ingredients e.g. in edible formulations are sugars and sugar derivatives like sucrose ester, sorbitan fatty acid ester as emulsifier, sugar alcohols, etc.

Edible formulations are described e.g. in U.S. Pat. No. 4,966,779A, US20050238675A1, U.S. Pat. No. 8,318,196B2.

The compounds can be formulated together with other fat soluble vitamins like vitamin D U.S. Pat. No. 9,439,913B1.

Liquid forms are typically protected from light by the packaging, e.g. by light protective material, e.g. glass or plastic.

Dry forms can be powders, tablets etc. Such forms are described e.g. in U.S. Pat. Nos. 5,356,636A, 4,254,100A, 3,133,862A, WO2017097974A1.

Tablet formulations or dry formulations typically contain a solubilizer or emulsifier like microcrystalline cellulose. Antioxidants like ascorbic acid are preferred. Further preferred ingredients in tablets are fatty acids or salt (e.g. stearic acid or magnesium stearate), filler material (e.g. silica) or other type of cellulose.

Another possible form for stabilization and solubilization is micelles, vesicles or lyposomes (see e.g. U.S. Pat. No. 6,183,774B1. Preferably micellar formulations comprise antioxidants like tocopherol. Further ingredients are again oils like vegetable oils. Preferred formulae comprise long chain fatty acid esters (e.g. palmitate).

Such formulations may be useful also as topical formulations or drops, like eye drops.

Further emulsifiers may be polyethylene glycol, polyethoxylated oils, sugars like sorbate.

Further formulations are described e.g. in WO2011034551A2 (Boch et al., Pharmaceutical formulations comprising 9-cis-retinyl esters in a lipid vehicle). Exemplary formulations and dosages are described in WO2011034551A2 and in WO2013134867A1.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., Remington "Pharmaceutical Sciences", 17 Ed., Gennaro (ed.), Mack Publishing Co., Easton, Pennsylvania, 1985).

Methods of introduction include but are not limited to intradermal, intramuscular, intraperitoneal, intravenous, subcutaneous, intranasal, intraocular, epidural and oral routes. The agents can be administered by any convenient route such as, for example, by infusion or bolus injection, by absorption through epithelial or mucocutaneous linings (e.g., oral mucosa, rectal and intestinal mucosa), and the like, and can be administered together with other functionally active agents.

Dosages

The doses of the agents can be carefully selected depending on the clinical status, condition and age of the subject, dosage form and the like.

For example the human effective dose can be calculated from the animal dose as described for example in Chapter V. (STEP 2: Human equivalent dose calculation) and in Table 1 of a 2005 July US FDA Guidelines. This indicates that, to give a value of a dose to start with in humans, animal doses shall be divided by a factor calculated based on body surface area, e.g. by a factor of 6.2 in body weight kilogram doses between rats and humans, and a factor of 12.3 in body weight kilogram doses between mice and humans.

Thus, taking into account e.g. 5 mg/kg in mice, this would mean a 0.4 mg/kg starting dose in humans which would result in case of an 80 kg human subject a 30 mg starting dose for 9CDHRA or 9CDRHOL.

Thus, at least an upper limit for a starting dose can be safely given based on animal models depending species.

Side effects depend on dosages and the compounds of the invention are contemplated to be favorable in this regard.

Just to give an illustrative example, and subject to trials, in the case of eye drops, an agent can be administered, for example, from about 0.01 mg, about 0.1 mg, or about 1 mg, to about 25 mg, to about 50 mg, to about 90 mg per single dose. Eye drops or nasal spray can be administered one or more times per day, as needed. In the case of injections, suitable doses can be, for example, about 0.0001 mg, about 0.001 mg, about 0.01 mg, or about 0.1 mg to about 10 mg, to about 25 mg, to about 50 mg, or to about 90 mg of the agent, one to four times per week. In other embodiments, about 1.0 to about 30 mg of agent can be administered one to three times per week or more in case of need more often, e.g. daily. Oral dosages or food complement may fall into the same order of magnitude, e.g. from about 1 mg or 5 mg to about 10 mg, to about 25 mg, to about 50 mg or to about 70 mg, or to about 80 mg or to about 100 mg of the agent in a subject, taking into account, daily or one to 6 or 7 times per week. Typically the dosages are calculated for 9CDHRA or 9CDRHOL. Precursors are considered in amounts equivalent to these doses, e.g. in doses providing an equivalent amount or effect.

Summary of the Results

We claim that we have found an important physiological switch-mechanism in the human organism which can be selectively switched on by a) a selective physiological ligand (9CDHRA) or b) selectively by nutritional precursors present in food, which can also be given as supplements/pharmaceuticals, 9CDHROL and 9CDHBC. This switch can enable RXR-mediated signaling and thereby prevent RXR-dependent dysfunctions and diseases. We have developed a new chemical synthesis of 9-cis-13,14-dihydroretinol and 9-cis-13,14-dihydroretinyl acetate starting from ethyl 9-cis-13,14-dihydroretinoate. Other esters of 9-cis-13,14-dihydroretinoic acid or 9-cis-13,14-dihydroretinol (such as palmitate and others) can be easily prepared using the same sequence.

We have also developed a new synthesis for 9-cis-13,14-dihydro-β,β-carotene and synthesized 9-cis-β,β-carotene based on an already established method.

We determined that 9CDHROL is a novel endogenous retinoid in mice and humans as well as it is present in a representative human food matrix (beef liver).

We determined that 9CDHBC is present in large amounts in the human food matrix (peach as examples for fruits and vegetables, other vegetables were also containing 9CDHBC as analyzed but not shown here).

We determined that 9CDHROL-ester and 9CDHRA-ester are alternative like 9CDHROL excellent precursors for 9CDHRA determined in human oligodendrocytes cell system. In addition, ATBC is not converted to any metabolite in human cellular system experiments, while it is taken up in high amounts by the cells. We determined that ATROL, 9CDHBC and 9CBC are not converted directly to 9CDHRA in human cell system experiments, while like previously mentioned 9CDHBC is an excellent precursor, while 9CBC/ATROL are just weak and non-selective precursors of 9CDHROL in the human oligodendrocytes cell system.

We determined that 9CDHROL is an excellent while 9CDHBC are just good precursor of 9CDHRA (detected in the serum, liver and brain), when given orally supplemented to mice. We determined also that all-trans-retinol (ATROL) is also a weak and non-isomer selective precursor of 9CDHRA but just in mouse brain and liver, when given orally to mice.

We determined that 9CDHBC is the intermediate metabolite of 9CBC determined in human cell cultures after 9CBC administration, but not a metabolite of all-trans-β,β-carotene (ATBC). 9CDHBC, while not 9CBC and ATBC, is an excellent precursor substrate of 9CDHROL in human oligodendrocytes cell culture in vitro.

We determined that selective precursors of the endogenous RXR-ligand (9CDHROL, 9CDHROL-esters, 9CDHRA-esters, 9CDHBC) are claimed selective RXR-ligand precursors with a highly selective RXR-ligand and further RXR-mediated vitamin A activity, named Vitamin A5 activity. 9CDHBC and 9CDHROL belong to a new category of substances called vitamin A5/pro-vitamin A5, serving as selective RXR-ligand precursors and thereby enabling RXR-mediated signaling, starting from food.

We determine that besides 9CDHRA, the selective RXR-ligand precursors 9CDHROL and 9CDHBC are also transmitting indirectly as precursors of 9CDHRA RXR-mediated signaling shown as an example for reduction of depression in a mouse animal model.

The invention is further illustrated by way of examples; is will be understood that these examples are not for defining or limiting the scope of the invention.

EXAMPLES

Example 1: Chemical Synthesis—Synthesis of Dihydroretinoids

Preparation and Characterization of Compounds—General Procedures

Solvents were dried according to published methods and distilled before use. All other reagents were commercial compounds of the highest purity available. Unless otherwise indicated all reactions were carried out under argon atmosphere, and those not involving aqueous reagents were carried out in oven-dried glassware. Analytical thin layer chromatography (TLC) was performed on aluminum plates with Merck Kieselgel 60F254 and visualized by UV irradiation (254 nm) or by staining with an ethanolic solution of phosphomolibdic acid. Flash column chromatography was carried out using Merck Kieselgel 60 (230-400 mesh) under pressure. Electron impact (EI) mass spectra were obtained on a Hewlett-Packard HP59970 instrument operating at 70 eV. Alternatively an APEX III FT-ICR MS (Bruker Daltonics), equipped with a 7T actively shielded magnet was used and ions were generated using an Apollo API electrospray ionization (ESI) source, with a voltage between 1800 and 2200 V (to optimize ionization efficiency) applied to the needle, and a counter voltage of 450 V applied to the capillary. For ESI spectra samples were prepared by adding a spray solution of 70:29.9:0.1 (v/v/v) $CH_3OH$/water/formic acid to a solution of the sample at a v/v ratio of 1 to 5% to give the best signal-to-noise ratio. High Resolution mass spectra were taken on a VG Autospec instrument. $^1H$ NMR spectra were recorded in $C_6D_6$ and acetone-$d_6$ at ambient temperature on a Bruker AMX-400 spectrometer at 400 MHz with residual protic solvent as the internal reference.

Synthesis of (R)-9-cis-13,14-Dihydroretinoic Acid, (R)-17, and Its (S) Enantiomer, (S)-17, and synthesis of (R)-9-cis-13,14-Dihydroretinol Acetate, (R)-28 (Scheme 1)

To confirm whether relative MS-MS signal detected at 303>207 m/z corresponds to 9CDHRA, the stereoselective synthesis of both enantiomers of 9-cis-13,14-dihydroretinoic acid was carried out following the previously described strategy based on a palladium-catalyzed $C_{sp2}$-$C_{sp2}$ Suzuki coupling (Pazos Y et al. 2001). Details of the stereocontrolled synthesis, purification and characterization of the (R)- and (S)-enantiomers of 9-cis-13,14-dihydroretinoic acid are provided below.

The preparation of the ethyl ester of (R)-9-cis-13,14-dihydroretinoic acid (R)-17 was based on the Suzuki coupling of enantiopure trienyliodide 24 and boronic acid 25 (Scheme 1). The synthesis of 24 started with (Z)stannyldienol 19 (Domínguez B. et al. 2000, Pazos Y et al. 1999) which was transformed into the benzothiazolyl allyl sulfide 20 by Mitsunobu reaction with the corresponding thiol and subsequently oxidized to sulfone 21 with $H_2O_2$ and a peroxymolybdate (VI) reagent (Schultz H S et al. 1963) at −10° C. The Julia-Kocienski olefination (Blakemore PR. 2002; Aïssa C 2009) was performed using a slight excess of base (NaHMDS, 1.15 equiv.) and 1.7 equivalents of enantiopure aldehyde (R)-22. (Moise A R et al. 2008, Leonard J. et al. 1995) As anticipated from previous findings on the stereochemical outcome of the reactions of allylsulfones and aldehydes (Sorg A et al. 2005, Vaz B et al., 2005), the newly formed olefin of trienyl ester (R)-23 is of Z-geometry (which was confirmed by NOE experiments). Treatment of the precursor stannane with a solution of iodine in $CH_2Cl_2$ produced the iodide (R)-24 via Sn—I exchange and iodine-promoted isomerization of the 9Z,11Z-diene to the desired 9Z,11E-geometric isomer (as confirmed by NOE experiments).

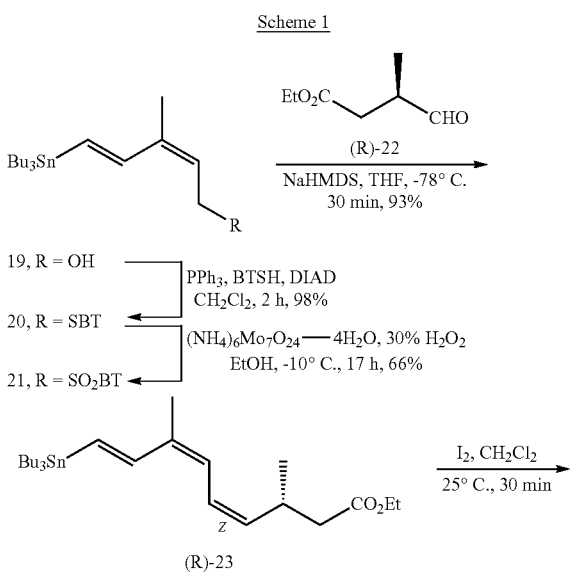

Scheme 1

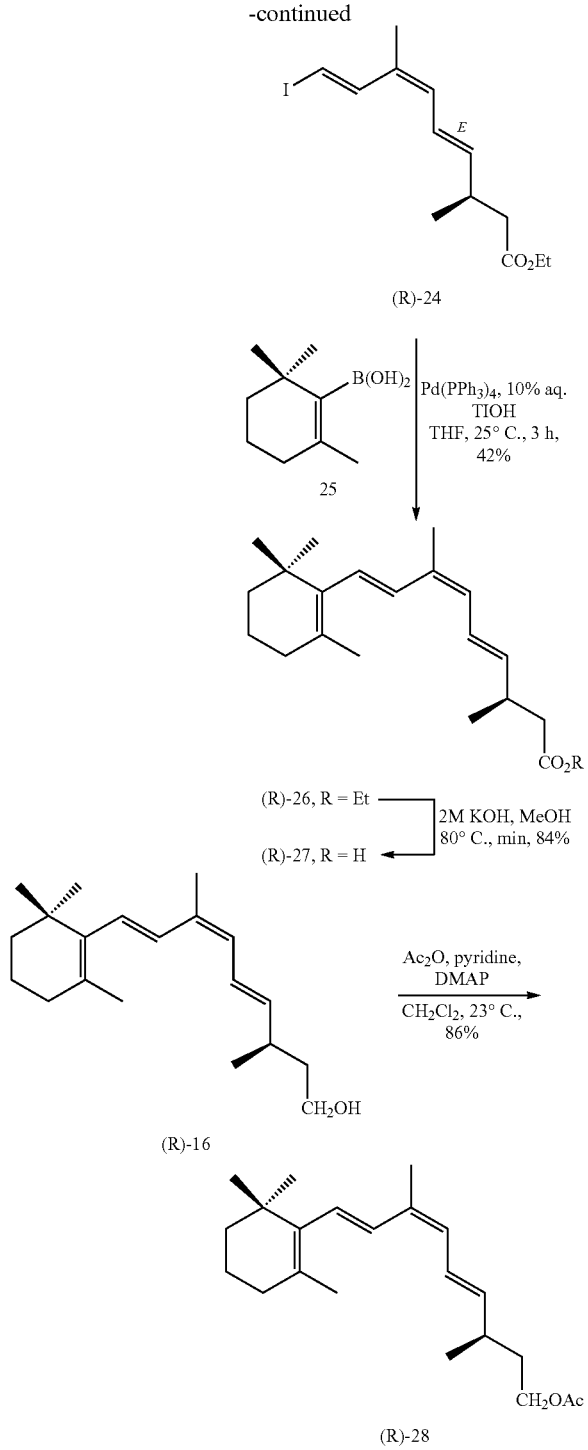

The Suzuki reaction of freshly prepared boronic acid 25 and trienyl iodide (R)-25 using Pd(PPh$_3$)$_4$ as catalyst and 10% aq. TlOH as base in THF at ambient temperature, followed by immediate work-up afforded ethyl (R)-9-cis-13,14-dihydroretinoate (R)-26 in 78% yield. From (R)-4 the corresponding carboxylic acid (R)-17 can be provided in 84% yield without detectable loss of stereochemical integrity. Following the general scheme, enantiomer (S)-17 can also be prepared with similar efficiency.

(R)-9-cis-13,14-dihydroretinyl acetate (R)-28 was prepared in 86% yield by acetylation of (R)-9-cis-13,14-dihydroretinol ((R)-17) with acetic anhydride and pyridine in the presence of dimethylaminopyridine (DMAP).

The starting compounds may be obtained commercially or may be synthesized according to standard methods.

Following the general scheme, enantiomer (S)-4 can also be prepared with similar efficiency.

(2Z,4E)-1-(Benzothiazol-2-yl)sulfanyl-5-(tri-n-butylstannyl)-3-methylpenta-2,4-diene (20)

A solution of (2Z,4E)-3-methyl-5-(tributylstannyl)penta-2,4-dien-1-ol 19 (1.0 g, 2.58 mmol), 2-mercaptobenzothiazol (0.65 g, 3.87 mmol) and PPh$_3$ (1.10 g, 4.21 mmol) in THF (14 mL) was stirred for 5 min at 0° C. A solution of DIAD (0.77 mL, 3.87 mmol) in THF (5 mL) was added dropwise and the mixture was stirred for 30 min at 25° C. The solvent was removed and the residue was purified by column chromatography (C18-silicagel, CH$_3$CN) to afford 1.11 g (78%) of a colorless oil identified as (2Z,4E)-1-(benzothiazol-2-yl)sulfanyl-5-(tri-n-butylstannyl)-3-methylpenta-2,4-diene 17. $^1$H NMR (400 MHz, C$_6$D$_6$): δ 8.04 (d, J=8.2 Hz, 1H, CH), 7.46 (d, J=19.2 Hz, $^3J_{SnH}$=71.2 Hz, 1H, CH), 7.34 (d, J=8.0 Hz, 1H, CH), 7.21 (ddd, J=8.3, 7.3, 1.2 Hz, 1H, CH), 7.01 (ddd, J=8.3, 7.4, 1.1 Hz, 1H, CH), 6.66 (d, J=19.2 Hz, $^2J_{SnH}$=71.2 Hz, 1H, CH), 5.65 (t, J=8.1 Hz, 1H, CH), 4.37 (d, J=8.2 Hz, 2H, CH$_2$), 1.86 (s, 3H, CH$_3$), 1.8-1.6 (m, 6H, CH$_2$), 1.5-1.4 (m, 6H, CH$_2$), 1.1-1.0 (m, 15H, CH$_3$+CH$_2$) ppm. $^{13}$C NMR (100 MHz, C$_6$D$_6$): δ 166.4 (s), 153.7 (s), 142.6 (d), 138.6 (s), 135.7 (s), 132.0 (d), 125.9 (d), 124.1 (d), 122.1 (d), 121.7 (d), 121.0 (d), 30.2 (t), 29.3 (t, 3×), 27.6 (t, 3×), 19.8 (q), 13.8 (q, 3×), 9.7 (t, 3×) ppm; IR (NaCl): ν 2955 (s, C—H), 2923 (s, C—H), 2870 (m, C—H), 2850 (m, C—H), 1460 (s), 1427 (s) cm$^{-1}$. HRMS (ESI$^+$): m/z calcd for C$_{25}$H$_{40}$NS$_2$$^{120}$Sn: 538.1620; found: 538.1621.

(2Z,4E)-1-(Benzothiazol-2-yl)sulfonyl-5-(tri-n-butylstannyl)-3-methylpenta-2,4-diene (21)

To a solution of (2Z,4E)-1-(benzothiazol-2-yl)sulfanyl-5-(tri-n-butylstannyl)-3-methylpenta-2,4-diene 20 (0.48 g, 0.89 mmol) in EtOH (9 mL), at −10° C., was added a solution of (NH$_4$)$_6$Mo$_7$O$_{24}$·4H$_2$O, (0.44 g, 0.36 mmol) in aqueous hydrogen peroxide (35%, 7.7 mL, 89.1 mmol). After stirring for 17 h at −10° C., the mixture was quenched with H$_2$O and extracted with Et$_2$O (3×). The combined organic layers were washed with brine (3×) and dried (Na$_2$SO$_4$), and the solvent was removed. The residue was purified by chromatography (C18-silicagel, MeOH) to afford 0.33 g (66%) of a colorless oil identified as (2Z,4E)-1-(benzothiazol-2-yl)sulfonyl-5-(tri-n-butylstannyl)-3-methylpenta-2,4-diene 21. $^1$H NMR (400 MHz, C$_6$D$_6$): δ 8.10 (d, J=8.2 Hz, 1H, CH), 7.18 (d, J=19.2 Hz, 1H, CH), 7.16 (t, J=7.5 Hz, 1H, CH), 7.12 (t, J=8.1 Hz, 1H, CH), 6.98 (t, J=7.7 Hz, 1H, CH), 6.59 (d, J=19.2 Hz, $^2J_{SnH}$=68.2 Hz, 1H, CH), 5.43 (t, J=8.0 Hz, 1H, CH), 4.32 (d, J=8.1 Hz, 2H, CH$_2$), 1.8-1.6 (m, 9H, CH$_3$+CH$_2$), 1.6-1.4 (m, 6H, CH$_2$), 1.1-1.0 (m, 15H, CH$_3$+CH$_2$) ppm. $^{13}$C NMR (100 MHz, C$_6$D$_6$): δ 167.1 (s), 152.9 (s), 143.1 (s), 141.7 (d), 136.9 (s), 134.4 (d), 127.3 (d), 127.1 (d), 125.0 (d), 122.1 (d), 112.0 (d), 53.3 (t), 29.3 (t, 3×), 27.5 (t, 3×), 20.0 (q), 13.8 (q, 3×), 9.6 (t, 3×) ppm; IR (NaCl): ν 2955 (s, C—H), 2923 (s, C—H), 2850 (m, C—H), 1467 (m), 1333 (s), 1151 (s) cm$^{-1}$. HRMS (ESI$^+$): m/z calcd for C$_{25}$H$_{39}$NNaO$_2$S$_2$$^{120}$Sn: 592.1338; found: 592.1334. UV (MeOH): λ$_{max}$ 239 nm.

Ethyl (3R,4Z,6Z,8E)-3,7-Dimethyl-9-(tri-n-butylstannyl)nona-4,6,8-trienoate ((R)-23)

A cooled (−78° C.) solution of (2Z,4E)-1-(benzothiazol-2-yl)sulfonyl-5-(tri-n-butylstannyl)-3-methylpenta-2,4-diene (0.115 g, 0.20 mmol) in THF (9 mL) was treated with NaHMDS (0.23 mL, 1M in THF, 0.23 mmol). After stirring for 30 min at this temperature, a solution of ethyl (S)-3-methyl-4-oxobutanoate (0.044 g, 0.30 mmol) in THF (4.5 mL) was added and the resulting mixture was stirred for 1 h at −78° C. and 3 h letting the temperature reach to rt. Et$_2$O and water were added at low temperature and the mixture was warmed up to room temperature. It was then diluted with Et$_2$O and the layers were separated. The aqueous layer was extracted with Et$_2$O (3×), the combined organic layers were dried (Na$_2$SO$_4$) and the solvent was removed. The residue was purified by column chromatography (C-18 silica gel, MeOH) to afford 0.94 g (93%) of a pale yellow oil identified as ethyl (3S,4Z,6Z,8E)-3,7-dimethyl-9-(tri-n-butylstannyl)nona-4,6,8-trienoate (R)-23. $[\alpha]^{28}_D$+11.5° (c 1.22, MeOH). $^1$H NMR (400 MHz, C$_6$D$_6$): δ 7.60 (d, J=19.1 Hz, $^3J_{SnH}$=65.1 Hz, 1H, CH), 6.85 (t, J=11.4 Hz, 1H, CH), 6.64 (d, J=19.2 Hz, $^2J_{SnH}$=71.9 Hz 1H, CH), 6.58 (d, J=11.9 Hz, 1H, CH), 5.31 (t, J=10.4 Hz, 1H, CH), 4.03 (q, J=7.1 Hz, 2H, CH$_2$), 3.5-3.3 (m, 1H, CH), 2.4-2.2 (m, 2H, CH$_2$), 2.02 (s, 3H, CH$_3$), 1.8-1.6 (m, 6H, CH$_2$), 1.6-1.4 (m, 6H, CH$_2$), 1.2-0.9 (m, 18H, CH$_3$+CH$_2$) ppm. $^{13}$C NMR (100 MHz, C$_6$D$_6$): δ 171.3 (s), 143.2 (d), 135.8 (d), 135.4 (s), 130.7 (d), 123.8 (d), 122.9 (d), 59.8 (t), 41.8 (t), 29.3 (t, 3×), 29.2 (t), 27.5 (t, 3×), 20.7 (q), 20.3 (q), 14.0 (q), 13.7 (q, 3×), 9.6 (t, 3×) ppm. IR (NaCl): ν 2957 (s, C—H), 2924 (s, C—H), 2871 (m, C—H), 2851 (m, C—H), 1737 (s, C=O), 1459 (m), 1160 (m) cm$^{-1}$. HRMS (ESI$^+$): m/z calcd for C$_{25}$H$_{46}$NaO$_2$$^{120}$Sn: 521.2416; found: 521.2408. UV (MeOH): λ$_{max}$ 285 nm.

Ethyl (3R,4Z,6Z,8E)-3,7-Dimethyl-9-(tri-n-butylstannyl)nona-4,6,8-trienoate ((S)-9)

$[\alpha]^{29}_D$+11.5°−10.3° (c 1.25, MeOH).

Ethyl (3R,4E,6Z,8E)-9-Iodo-3,7-dimethylnona-4,6,8-trienoate ((R)-24)

To a solution of ethyl (3R,4Z,6Z,8E)-3,7-dimethyl-9-(tri-n-butylstannyl)nona-4,6,8-trienoate (R)-23 (0.060 g, 0.121 mmol) in CH$_2$Cl$_2$ (5.3 mL) was added dropwise iodine (0.046 g, 0.182 mmol) in CH$_2$Cl$_2$ (2.8 mL) and the resulting mixture was stirred for 30 min at 25° C. A saturated Na$_2$S$_2$O$_3$ solution was added and the reaction mixture was extracted with Et$_2$O (3×), the combined organic layers were dried (Na$_2$SO$_4$) and the solvent was removed. The residue was purified by column chromatography (silica gel, 97:3 hexane/Et$_3$N) to afford 0.037 g (92%) of a pale yellow oil identified as ethyl (3R,4E,6Z,8E)-9-iodo-3,7-dimethylnona-4,6,8-trienoate (R)-24. $[\alpha]^{24}_D$+14.8° (c 0.74, MeOH). $^1$H NMR (400 MHz, C$_6$D$_6$): δ 7.65 (d, J=14.5 Hz, 1H, CH), 6.28 (dd, J=14.9, 11.3 Hz, 1H, CH), 6.05 (d, J=14.5 Hz, 1H, CH), 5.64 (d, J=11.1 Hz, 1H, CH), 5.44 (dd, J=15.0, 7.8 Hz, 1H, CH), 3.95 (q, J=7.1 Hz, 2H, CH$_2$), 2.64 (dt, J=14.1, 7.0 Hz, 1H, CH), 2.15 (dd, J=14.9, 7.1 Hz, 1H, CH), 2.06 (dd, J=14.9, 7.3 Hz, 1H, CH), 0.97 (t, J=7.2 Hz, 3H, CH$_3$), 0.88 (d, J=6.8 Hz, 3H, CH$_3$) ppm. $^{13}$C NMR (100 MHz, C$_6$D$_6$): δ 171.9 (s), 142.7 (d), 140.4 (d), 132.7 (s), 130.9 (d), 124.6 (d), 78.5 (d), 60.5 (t), 41.8 (t), 34.4 (d), 20.4 (q), 19.9 (q), 14.7 (q) ppm. IR (NaCl): ν 2972 (m, C—H), 2932 (m, C—H), 1731 (s, C=O), 1666 (m), 1180 (m) cm$^{-1}$. HRMS (ESI$^+$): m/z calcd for C$_{13}$H$_{19}$INaO$_2$: 357.0322; found: 357.0316. UV (MeOH): λ$_{max}$ 275 nm.

Ethyl (3S,4E,6Z,8E)-9-Iodo-3,7-dimethylnona-4,6,8-trienoate ((S)-24)

$[\alpha]^{23}_D$−16.7° (c 0.72, MeOH).

Ethyl (9Z,13R)-13,14-Dihydroretinoate ((R)-26)

To a solution of ethyl (3R,4E,6Z,8E)-9-iodo-3,7-dimethylnona-4,6,8-trienoate (R)-24 (0.036 g, 0.107 mmol) in THF (2.3 mL) was added Pd(PPh$_3$)$_4$(0.013 g, 0.011 mmol). After 5 min at room temperature, 2,6,6-trimethylcyclohex-1-enyl-boronic acid 25 (0.027 g, 0.161 mmol) was added in one portion followed by TlOH (10% aqueous solution, 0.75 mL, 0.407 mmol). After stirring for 3 h at 25° C., Et$_2$O was added and the reaction mixture was filtered through a short pad of Celite®. The filtrate was washed with NaHCO$_3$ (sat) and the organic layer was dried (Na$_2$SO$_4$) and the solvent was removed. The residue was purified by column chromatography (silica gel, 97:3 hexane/Et$_3$N) to afford 0.028 g (78%) of a pale yellow oil identified as ethyl (9Z,13R)-13,14-dihydroretinoate (R)-26. $[\alpha]^{23}_D$+14.2° (c 0.48, MeOH). $^1$H NMR (400 MHz, C$_6$D$_6$): δ 6.90 (d, J=16.0 Hz, 1H, CH), 6.71 (dd, J=14.9, 11.2 Hz, 1H, CH), 6.28 (d, J=16.0 Hz, 1H, CH), 5.96 (d, J=11.1 Hz, 1H, CH), 5.51 (dd, J=15.0, 7.8 Hz, 1H, CH), 3.94 (q, J=7.2 Hz, 2H, CH$_2$), 2.77 (dt, J=14.1, 7.1 Hz, 1H, CH), 2.21 (dd, J=14.8, 7.3 Hz, 1H, CH), 2.11 (dd, J=14.8, 7.2 Hz, 1H, CH), 1.95 (t, J=6.1 Hz, 2H, CH$_2$), 1.90 (s, 3H), 1.79 (s, 3H), 1.66-1.52 (m, 2H), 1.52-1.41 (m, 2H), 1.11 (s, 6H), 0.95 (t, J=7.1 Hz, 3H, CH$_3$), 0.94 (d, J=6.8 Hz, 3H, CH$_3$) ppm. $^{13}$C NMR (100 MHz, C$_6$D$_6$): δ 171.4 (s), 138.3 (s), 137.6 (d), 132.7 (s), 130.6 (d), 129.1 (d), 129.0 (s), 127.9 (d), 124.8 (d), 59.8 (t), 41.6 (t), 39.6 (t), 34.2 (s), 34.1 (d), 33.0 (t), 28.9 (q, 2×), 21.8 (q), 20.4 (q), 20.1 (q), 19.5 (t), 14.1 (q) ppm. IR (NaCl): ν 2961 (s, C—H), 2929 (s, C—H), 2866 (m, C—H), 1737 (s, C=O), 1455 (m), 1372 (m), 1167 (m) cm$^{-1}$. HRMS (ESI$^+$): m/z calcd for C$_{22}$H$_{35}$O$_2$: 331.2632; found: 331.2625. UV (MeOH): λ$_{max}$ 287 nm (ε=20000 L·mol$^{-1}$·cm$^{-1}$).

Ethyl (9Z,13S)-13,14-Dihydroretinoate ((S)-26)

$[\alpha]^{22}_D$−15.5° (c 0.51, MeOH).

(9Z,13R)-13,14-Dihydroretinoic Acid ((R)-17)

To a solution of ethyl (9Z,13R)-13,14-dihydroretinoate (R)-26 (0.023 g, 0.069 mmol) in MeOH (4.7 mL) was added KOH (2M aqueous solution, 1.1 mL, 2.27 mmol) and the reaction mixture was stirred for 45 min at 80° C. After letting the reaction cool down to room temperature, CH$_2$Cl$_2$ and brine were added and the layers were separated. The aqueous layer was washed with H$_2$O (3×). The combined aqueous layers were acidified with HCl 10% and extracted with CH$_2$Cl$_2$ (3×). The combined organic layers were dried (Na$_2$SO$_4$) and the solvent was removed. The residue was purified by column chromatography (silica gel, gradient from 95:5 to 90:10 CH$_2$Cl$_2$/MeOH) to afford 0.017 g (84%) of a pale yellow oil identified as (9Z,13R)-13,14-dihydroretinoic acid (R)-17. $[\alpha]^{22}_D$+7.1° (c 0.67, MeOH). $^1$H NMR (400 MHz, acetone-d$_6$): δ 6.66 (d, J=16.0 Hz, 1H), 6.60 (dd, J=15.0, 11.2 Hz, 1H), 6.18 (d, J=16.0 Hz, 1H), 5.93 (d, J=11.1 Hz, 1H), 5.65 (dd, J=15.0, 7.5 Hz, 1H), 2.73 (dt, J=13.9, 7.0 Hz, 1H), 2.4-2.2 (m, 2H), 2.1-2.0 (m, 1H), 1.91 (s, 3H), 1.72 (s, 3H), 1.7-1.6 (m, 2H), 1.5-1.4 (m, 2H), 1.08

(d, J=6.8 Hz, 3H), 1.03 (s, 6H) ppm. $^{13}$C NMR (100 MHz, acetone-$d_6$): δ 173.5 (s), 138.9 (s), 138.8 (d), 133.4 (s), 131.1 (d), 129.8 (s), 129.7 (d), 128.5 (d), 125.4 (d), 41.8 (t), 40.3 (t), 34.9 (s), 34.6 (d), 33.6 (t), 29.4 (q), 22.1 (q), 20.7 (q), 20.6 (q), 20.0 (t) ppm. IR (NaCl): ν 2957 (s, C—H), 2923 (s, C—H), 2855 (m, C—H), 1709 (s, C=O), 1446 (m), 1290 (m) cm$^{-1}$. HRMS (ESI$^+$): m/z calcd for $C_{20}H_{31}O_2$: 303.2319; found: 303.2313. UV (MeOH): $\lambda_{max}$ 289 nm (ε=17600 L·mol$^{-1}$·cm$^{-1}$).

(9Z,13S)-13,14-Dihydroretinoic Acid ((S)-17)

[α]$^{24}$D –6.9° (c 0.26, MeOH).

Example 2.1: Synthesis of (R)-9-cis-13,14-dihydroretinol and (R)-9-cis-13,14-dihydroretinol acetate (R)-9-cis-13,14-dihydroretinol was synthesized by DIBAL-H reduction of ethyl (9Z,13R)-13,14-dihydroretinoate ((R)-4) in THF at –78° C. in 95% yield (Scheme 1).

(R)-9-cis-13,14-Dihydroretinyl acetate was prepared in 86% yield by acetylation of (R)-9-cis-13,14-dihydro-retinol with acetic anhydride and pyridine in the presence of dimethylaminopyridine (DMAP).

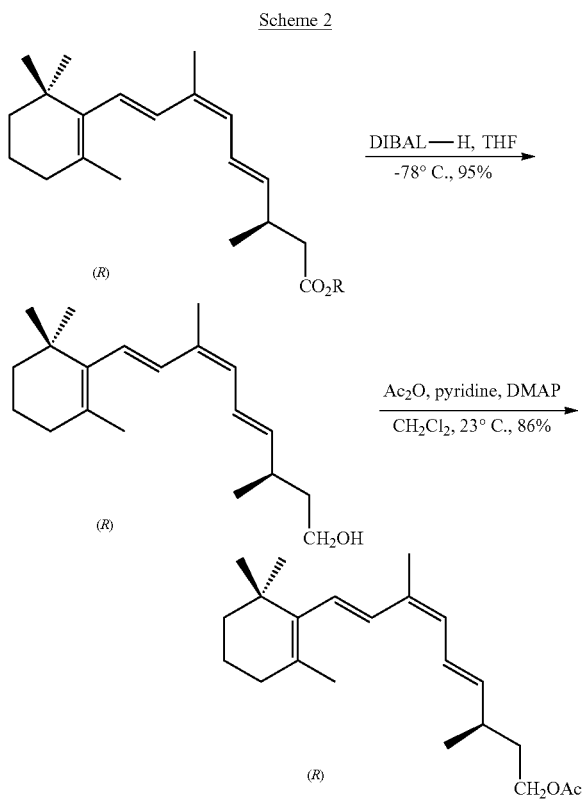

Scheme 2

(3R,4E,6Z,8E)-3,7-Dimethyl-9-(2,6,6-trimethylcyclohex-1-en-1-yl)nona-4,6,8-trien-1-ol ((R)-10)

To a cooled (–78° C.) solution of ethyl (3R,4E,6Z,8E)-3,7-dimethyl-9-(2,6,6-trimethylcyclohex-1-en-1-yl)nona-4,6,8-trienoate [ethyl (R)-9-cis-13,14-dihydroretinoate, (R)-4] (32.0 mg, 0.097 mmol) in THF (1.0 mL), DIBAL-H (0.242 mL, 0.242 mmol, 1.0 M in hexanes) was added and the resulting mixture was stirred for 30 min at –78° C. The mixture was allowed to warm up to –20° C. in 2.5 h. $H_2O$ was added and the mixture was extracted with $Et_2O$ (3×). The combined organic layers were dried ($Na_2SO_4$) and the solvent removed. Flash chromatography of the residue (silica gel, first neutralized with 98:2 hexane/$Et_3N$, then gradient from 95:5 hexane/EtOAc to EtOAc) afforded (3R,4E,6Z,8E)-3,7-dimethyl-9-(2,6,6-trimethylcyclohex-1-en-1-yl)nona-4,6,8-trien-1-ol (26.5 mg, 95%) as a colorless oil. $^1$H-NMR (400.13 MHz, $C_6D_6$): δ 6.93 (d, J=16.0 Hz, 1H), 6.69 (dd, J=14.9, 11.1 Hz, 1H), 6.29 (d, J=16.0 Hz, 1H), 6.01 (d, J=11.1 Hz, 1H), 5.46 (dd, J=15.0, 8.3 Hz, 1H), 3.35 (t, J=6.6 Hz, 2H), 2.27 (dt, J=14.0, 6.7 Hz, 1H), 1.98-1.92 (m, 2H), 1.93 (s, 3H), 1.79 (s, 3H), 1.63-1.52 (m, 2H), 1.51-1.43 (m, 2H), 1.36 (q, J=6.7 Hz, 2H), 1.11 (s, 6H), 0.91 (d, J=6.7 Hz, 3H) ppm. $^{13}$C-NMR (100.62 MHz, $C_6D_6$): δ 140.0 (d), 138.6 (s), 132.5 (s), 130.9 (d), 129.6 (d), 129.2 (s), 128.1 (d), 124.9 (d), 60.9 (t), 40.2 (t), 39.9 (t), 34.5 (s), 34.3 (d), 33.2 (t), 29.21 (q), 29.18 (q), 22.0 (q), 20.9 (q), 20.7 (q), 19.7 (t) ppm HRMS (ESI$^+$): Calcd. for $C_{20}H_{33}O$ ([M+H]$^+$), 289.2526; found, 289.2526. IR (NaCl): ν 3338 (m, O—H), 2957 (s, C—H), 2926 (s, C—H), 2861 (m, C—H), 1454 (m), 1375 (m), 965 (m) cm$^{-1}$.

(3R,4E,6Z,8E)-3,7-Dimethyl-9-(2,6,6-trimethylcyclohex-1-en-1-yl)nona-4,6,8-trien-1-yl Acetate ((R)-11)

To a solution of (3R,4E,6Z,8E)-3,7-dimethyl-9-(2,6,6-trimethylcyclohex-1-en-1-yl)nona-4,6,8-trien-1-ol (5.7 mg, 0.020 mmol) in $CH_2Cl_2$ (0.5 mL) were sequentially added $Ac_2O$ (0.009 mL, 0.099 mmol), pyridine (0.008 mL, 0.099 mmol) and DMAP (0.5 mg, 0.004 mmol). The resulting mixture was stirred for 1 h at 25° C. Then, $Et_2O$ was added and the resulting solution was washed with a saturated aqueous solution of $CuSO_4$ (2×). The organic layer was dried ($Na_2SO_4$) and evaporated. Flash chromatography of the residue (silica gel, gradient from hexane to 85:15 hexane/EtOAc) afforded (3R,4E,6Z,8E)-3,7-dimethyl-9-(2,6,6-trimethylcyclohex-1-en-1-yl)nona-4,6,8-trien-1-yl acetate (5.6 mg, 86%) as a colorless oil. $^1$H-NMR (400.13 MHz, $C_6D_6$): δ 6.92 (d, J=16.0 Hz, 1H), 6.67 (dd, J=15.0, 10.8 Hz, 1H), 6.29 (d, J=16.0 Hz, 1H), 5.98 (d, J=11.1 Hz, 1H), 5.39 (dd, J=15.0, 8.2 Hz, 1H), 4.11-3.92 (m, 2H), 2.16 (dq, J=14.4, 7.2 Hz, 1H), 1.99-1.90 (m, 2H), 1.93 (s, 3H), 1.79 (d, J=1.0 Hz, 3H), 1.67 (s, 3H), 1.62-1.53 (m, 2H), 1.50-1.41 (m, 4H), 1.11 (s, 6H), 0.86 (d, J=6.8 Hz, 3H) ppm. $^{13}$C-NMR (100.62 MHz, $C_6D_6$): δ 170.0 (s), 138.9 (d), 138.6 (s), 132.8 (s), 130.9 (d), 129.4 (d), 129.3 (s), 128.2 (d), 125.2 (d), 62.7 (t), 39.9 (t), 36.0 (t), 34.5 (s), 34.4 (d), 33.2 (t), 29.19 (q), 29.18 (q), 22.0 (q), 20.74 (q), 20.70 (q), 20.6 (q), 19.7 (t) ppm. HRMS (ESI$^+$): Calcd. for $C_{22}H_{35}O_2$ ([M+H]$^+$), 331.2632; found, 331.2621. IR (NaCl): ν 2957 (s, C—H), 2926 (s, C—H), 2860 (m, C—H), 1741 (s, C=O), 1455 (m), 1365 (m), 1238 (s), 966 (m) cm$^{-1}$.

Example 2.2: Synthesis of 9-cis-ß,ß-carotene (Scheme 3, Including Added Numeration)

Ethyl 9-cis-Retinoate 3

To a cooled (0° C.) solution of ethyl (E)-4-(diethoxyphosphoryl)-3-methylbut-2-enoate 1 (0.227 g, 1.10 mmol) in THF (2.0 mL) was added nBuLi (0.63 mL, 1.00 mmol, 1.6 M in hexane) and DMPU (0.15 mL, 1.24 mmol). After stirring for 1 h, the reaction was cooled down to –78° C. and a solution of (2Z,4E)-3-methyl-5-(2,6,6-trimethylcyclohex-1-en-1-yl)penta-2,4-dienal 2 (0.1 g, 0.46 mmol) in THF (2.5 mL) was added and the mixture was stirred for 2 h. Water was added and the mixture was extracted with Et$_2$O (3×). The combined organic layers were dried (Na$_2$SO$_4$) and the solvent was evaporated. The residue was purified by column chromatography (silica gel, 95:5 hexane/EtOAc) to afford 0.144 g (96%) of a yellow solid identified as ethyl 9-cis-retinoate 3. The spectroscopic data are identical to those previously published [Okitsu, T. (2008)].

9-cis-Retinol 4

To a cooled (−78° C.) solution of ethyl 9-cis-retinoate 3 (0.154 g, 0.47 mmol) in THF (2.3 mL) was added DIBAL-H (1.08 mL, 1.08 mmol, 1.0 M in toluene) and the reaction was stirred for 2 h. Water was added and the mixture was extracted with EtOAc (3×). The combined organic layers were dried (Na$_2$SO$_4$) and the solvent was evaporated. The residue was purified by column chromatography (silica gel, gradient from 95:5 to 80:20 hexane/EtOAc) to afford 0.08 g (60%) of a yellow oil identified as 9-cis-retinol 4. The spectroscopic data are identical to those previously published [Englert, G. 1975].

9-cis-Retinal 5

To a solution of 9-cis-retinol 4 (65 mg, 0.23 mmol) in CH$_2$Cl$_2$ (9.1 mL) were added MnO$_2$ (197 mg, 2.27 mmol) and Na$_2$CO$_3$ (240 mg, 2.27 mmol) and the reaction mixture was stirred for 1.5 h at 25° C. The mixture was filtered through a pad of Celite® washing with CH$_2$Cl$_2$. The solvent was evaporated affording 38 mg (58%) of a yellow oil identified as 9-cis-retinal 5. The spectroscopic data are identical to those previously published [Zanoun, A. (2006)].

(2E,4E,6E,8E)-(3,7-Dimethyl-9-(2,6,6-trimethylcyclohex-1-en-1-yl)nona-2,4,6,8-tetraen-1-yl)triphenylphosphonium Chloride 7

To a solution of all-trans-retinol (vitamin A) 6 (1.37 g, 4.78 mmol) in MeOH (2.7 mL) was added PPh$_3$ (1.44 g, 5.5 mmol) and a solution of 4 M HCl in dioxane (1.4 mL) and the reaction mixture was stirred for 2 h at 25° C. Then, the mixture was poured into water and extracted with Et$_2$O (2×). The aqueous layer was extracted with EtOAc (3×), the combined organic layers were dried (Na$_2$SO$_4$) and the solvent was evaporated. The light orange residue was triturated three times with EtOAc to afford 1.39 g (52%) of a yellow solid identified as (2E,4E,6E,8E)-(3,7-dimethyl-9-(2,6,6-trimethylcyclohex-1-en-1-yl)nona-2,4,6,8-tetraen-1-yl) triphenyl-phosphonium chloride 7. $^1$H NMR (400.16 MHz, CDCl$_3$): δ 7.94-7.83 (m, 6H), 7.82-7.74 (m, 3H), 7.73-7.63 (m, 6H), 6.49 (m, 1H), 6.26-5.88 (m, 4H), 5.39 (m, 1H), 5.09-4.97 (m, 2H), 2.01 (d, J=6.1 Hz, 2H, CH$_2$), 1.91 (s, 3H, CH$_3$), 1.69 (s, 3H, CH$_3$), 1.63 (s, 6H, 2×CH$_3$), 1.48 (m, 4H, 2×CH$_2$), 1.01 (s, 3H, CH$_3$) ppm. $^{13}$C NMR (101.63 MHz, CDCl$_3$): δ 143.8 (s, J$_{C-P}$=2.9 Hz, 3×), 137.7 (s), 137.5 (s), 135.0 (d, J$_{C-P}$=2.9 Hz, 3×), 133.9 (d, J$_{C-P}$=9.7 Hz, 6×), 132.0 (d, J$_{-P}$=12.4 Hz), 130.3 (d, J$_{C-P}$=12.4 Hz, 6×), 129.5 (d, J$_{C-P}$=2.9 Hz), 128.5 (d, J$_{C-P}$=12.2 Hz), 127.5 (d), 126.4 (d, J$_{C-P}$=5.2 Hz), 118.7 (s), 117.8 (s), 114.2 (d, J$_{C-P}$=12.1 Hz), 39.6 (t), 34.2 (s), 33.0 (t), 28.9 (q, 2×), 25.4 (t), 24.9 (t), 19.2 (q), 13.1 (q), 12.8 (q) ppm. HRMS (ESI$^+$): Calcd. for C$_{38}$H$_{44}$P$^+$ ([M-Cl]+), 531.3175; found, 531.3166.

9-cis-β,β-Carotene 8

To a solution of phosphonium salt 7 (24.9 mg, 0.044 mmol) in THF (0.20 mL) at −78° C. was added nBuLi (0.027 mL, 1.6 M in hexane, 0.044 mmol) and the resulting mixture was stirred for 30 min. Then a solution of 9-cis-retinal 5 (9.0 mg, 0.031 mmol) in THF (0.13 mL) was added and the mixture was stirred for 1 h at −78° C. and for 30 min at 25° C. Water was added and the mixture was extracted with Et$_2$O (3×). The combined organic layers were washed with brine (2×) and dried (Na$_2$SO$_4$) and the solvent was evaporated. The residue was purified by column chromatography (C18-silica gel, CH$_3$CN) to afford 11.3 mg (67%) of a red foam identified as 9-cis-β-β-carotene 8. $^1$H NMR (400.16 MHz, CDCl$_3$): δ 6.74 (dd, J=14.8, 11.6 Hz, 12H), 6.68 (d, J=7.9 Hz, 1H), 6.66-6.54 (m, 3H), 6.28 (d, J=14.9 Hz, 1H), 6.26-6.19 (m, 2H), 6.19-6.08 (m, 4H), 6.05 (d, J=11.5 Hz, 1H), 2.08-1.99 (m, 4H), 1.97 (s, 3H), 1.95 (s, 6H), 1.76 (s, 3H), 1.71 (s, 3H), 1.66-1.59 (m, 4H), 1.51-1.39 (m, 4H), 1.04 (s, 6H), 1.03 (s, 6H) ppm. $^{13}$C NMR (101.63 MHz, CDCl$_3$): δ 138.4 (s), 138.1 (s), 137.8 (d), 136.7 (d), 136.4 (s, 2×), 136.1 (s), 134.6 (d), 130.9 (d), 132.4 (d), 130.2 (d, 3×), 130.0 (d), 129.6 (s, 2×), 129.5 (d, 2×), 128.5 (d), 127.1 (s), 127.0 (d), 123.8 (d), 39.7 (t, 2×), 34.4 (s, 2×), 33.3 (t, 2×), 29.1 (q), 28.6 (q, 2×), 22.0 (q), 21.9 (q), 20.9 (q), 19.4 (t, 2×), 13.0 (q), 12.9 (q) ppm. UV (MeOH): max. 397 nm. HRMS (ESI$^+$): Calcd. for C$_{40}$H$_{56}$ ([M]+), 536.4375; found, 536.4376.

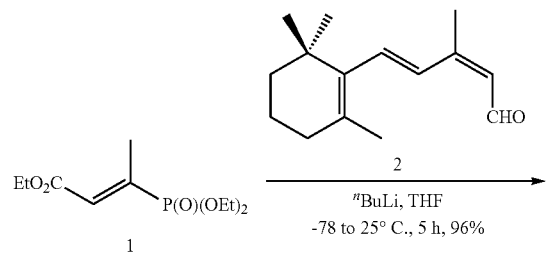

Scheme 3

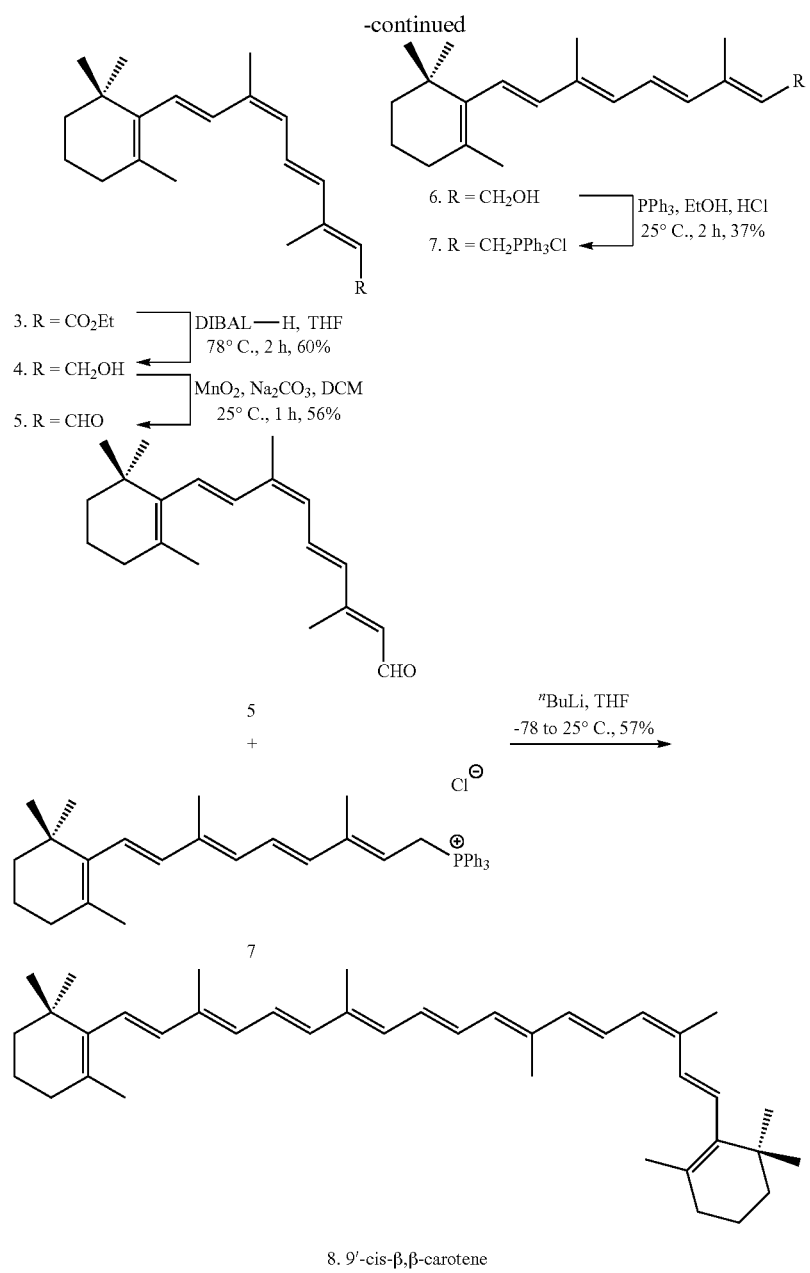

8. 9′-cis-β,β-carotene

Example 2.3: Synthesis of (R)-9-cis-13,14-dihydro-ß,ß-carotene (Scheme 4 Including Numeration) (Z)-3-Iodo-3-methylprop-2-en-1-ol 10

CuI (0.34 g, 1.78 mmol) was added to a solution of prop-2-yn-1-ol 9 (1 g, 11.84 mmol) in $Et_2O$ (13.2 mL). A solution of MeMgBr (17.8 mL, 3 M in $Et_2O$, 53.51 mmol) was added at −20° C. After stirring at this temperature for 2 h, the solution was allowed to reach 25° C. and further stirred for 12 h. A solution of $I_2$ (9.1 g, 35.67 mmol) in $Et_2O$ (40 mL) was added at 0° C. and the cooling bath was removed. After stirring at 25° C. for 24 h, the resulting mixture was cooled down to 0° C. and ice-water was added. The organic layer was washed with a saturated aqueous solution of $Na_2S_2O_4$ (3×) and then filtered through a pad of Celite®. The residue was purified by distillation (0.2 mm Hg, 60° C.) to afford 2.1 g (60%) of a yellow oil identified as (Z)-3-iodo-3-methylprop-2-en-1-ol 10. $^1$H NMR (400.16 MHz, $C_6D_6$): δ 5.49 (s, 1H), 3.90 (s, 2H), 1.55 (s, 3H) ppm. $^{13}$C NMR (101.63 MHz, $C_6D_6$): δ 146.6 (s), 74.1 (d), 67.5 (t), 20.9 (q) ppm. HRMS (ESP): Calcd. for $C_4H_8IO$ ([M+H]$^+$), 198.9609; found, 198.9614.

(Z)-3-Iodo-2-methylacrylaldehyde 11

To a solution of (Z)-3-iodo-3-methylprop-2-en-1-ol 10 (0.21 g, 1.06 mmol) in $CH_2Cl_2$ (53 mL) were sequentially added $MnO_2$ (0.93 g, 10.65 mmol) and $Na_2CO_3$ (1.13 g, 10.65 mmol) and the reaction mixture was stirred for 1 h at 25° C. Then, the mixture was filtered through a pad of Celite® washing with $CH_2Cl_2$. The solvent was evaporated to afford 0.15 g (73%) of a yellow oil identified as (Z)-3- iodo-2-methylacrylaldehyde 11. The spectroscopic data are identical to those previously published (Koukal, P et al. 2016).

2-(1E,3Z)-4-Iodo-3-methylbuta-1,3-dien-1-yl)-1,3,3-trimethylcyclohex-1-ene 13

To a cold (−30° C.) solution of phosphonium salt 12 [(a) Isler, O. et al. (1956) (b) Broek, A. D. et al. (1983)] (0.15 g, 0.31 mmol) in THF (2.5 mL), nBuLi (0.9 mL, 2.36 M in hexanes, 0.36 mmol) was added and the mixture was stirred at 0° C. for 45 min. After cooling down to −30° C., a solution of (Z)-3-iodo-2-methylacrylaldehyde 11 (0.07 g, 0.36 mmol) in THF (2.5 mL) was added and the reaction mixture was stirred for 1.5 h. Water (5 mL) was added and the mixture was extracted with hexane (3×). The organic extracts were dried ($Na_2SO_4$) and the solvent was evaporated. The residue was purified by column chromatography (C18-silica gel, $CH_3CN$) to afford 65 mg (64%) of a yellow oil identified as 2-(1E,3Z)-4-iodo-3-methylbuta-1,3-dien-1-yl)-1,3,3-trimethylcyclohex-1-ene 13. $^1H$ NMR (400.16 MHz, $C_6D_6$): δ 6.80 (d, J=16.1 Hz, 1H), 6.32 (d, J=16.1 Hz, 1H), 5.80 (s, 1H), 1.90-1.86 (m, 2H), 1.78 (s, 3H, $CH_3$), 1.66 (s, 3H, $CH_3$), 1.57-1.48 (m, 2H), 1.44-1.39 (m, 2H), 1.07 (s, 6H, 2×$CH_3$) ppm. $^{13}C$ NMR (101.63 MHz, $C_6D_6$): δ 142.3 (s), 137.5 (s), 135.1 (d), 132.1 (d), 130.8 (s), 78.6 (d), 39.7 (t) 34.0 (s), 33.1 (t), 29.1 (q, 2×), 22.0 (q), 20.9 (q), 19.3 (t) ppm. UV (MeOH): $\lambda_{max}$ 266 nm. IR (NaCl): ν 2925 (s, C—H), 2861 (m, C—H), 1441 (m), 741 (s) $cm^{-1}$. HRMS ($ESI^+$): Calcd. for $C_{14}H_{21}I$ ($[M+H]^+$), 316.0688; found, 316.0684.

Silylether 15

To a solution of 2-(1E,3Z)-4-iodo-3-methylbuta-1,3-dien-1-yl)-1,3,3-trimethylcyclohex-1-ene 13 (0.16 g, 0.51 mmol) in THF (0.2 mL) was added Pd(PPh$_3$)$_4$ (45 mg, 0.039 mmol). After stirring for 5 min at 25° C., a solution of (R)-borolane 14 (150 mg, 0.392 mmol) in THF (1.0 mL) and a 10% aqueous solution of TlOH (4.26 mL) were added and the reaction mixture was stirred for 2 h. The mixture was extracted with $Et_2O$ (3×) and the combined organic layers were washed with brine (3×) and dried ($Na_2SO_4$) and the solvent was evaporated. The residue was purified by column chromatography (silica gel, 95:5 hexane/EtOAc) to afford 0.12 g (71%) of a colorless oil identified as a mixture of (3R,4E,6Z,8E)-{[3,7-dimethyl-9-(2,6,6-trimethylcyclohex-1-en-1-yl)nona-4,6,8-trien-1-yl]oxy}triisopropylsilane 15 and an unidentified product in a 60:40 ratio and used in the next step without further purification.

(R)-9-cis-13,14-Dihydroretinol 16

To a cooled (0° C.) solution of silylether 15 (91.2 mg, 0.212 mmol) in THF (3.5 mL) was added nBu$_4$NF (0.32 mL, 1M in THF, 0.32 mmol) and the mixture was stirred for 0.5 h at 25° C. A saturated aqueous solution of $NaHCO_3$ was added and the mixture was extracted with $Et_2O$ (3×). The combined organic layers were washed with brine (3×) and dried ($Na_2SO_4$) and the solvent was evaporated. The residue was purified by column chromatography (gradient from 95:5 to 70:30 hexane/EtOAc) to afford 41 mg (67%) of a colorless oil identified as (R)-9-cis-13,14-dihydroretinol 16. $^1H$ NMR (400 MHz, $C_6D_6$): δ 6.93 (d, J=16.0 Hz, 1H), 6.69 (dd, J=14.9, 11.1 Hz, 1H), 6.29 (d, J=16.0 Hz, 1H), 6.01 (d, J=11.1 Hz, 1H), 5.46 (dd, J=15.0, 8.3 Hz, 1H), 3.35 (t, J=6.6 Hz, 2H), 2.34-2.19 (m, 1H), 1.99-1.89 (m, 2H), 1.93 (s, 3H, $CH_3$), 1.79 (s, 3H, $CH_3$), 1.62-1.53 (m, 2H), 1.50-1.44 (m, 2H), 1.36 (q, J=6.7 Hz, 2H), 1.11 (s, 6H, 2×$CH_3$), 0.91 (d, J=6.7 Hz, 3H, $CH_3$) ppm. $^{13}C$ NMR (101 MHz, $C_6D_6$): δ 140.0 (d), 138.6 (s), 132.5 (s), 130.9 (d), 129.6 (d), 129.2 (s), 128.0 (d), 124.9 (d), 60.9 (t), 40.2 (t), 39.9 (t), 34.5 (s), 34.3 (d), 33.2 (t), 29.21 (q), 29.19 (q), 22.0 (q), 20.9 (q), 20.7 (q), 19.7 (t) ppm. IR (NaCl): ν 3500-3300 (br, O—H), 2926 (s, C—H), 1451 (m, C—H), 965 (s) $cm^{-1}$. HRMS ($ESI^+$): Calcd. for $C_{20}H_{33}O$ ($[M+H]^+$), 289.2584; found, 289.2525.

(R)-9-cis-13,14-Dihydroretinal 17

To a solution of (R)-9-cis-13,14-dihydroretinol 16 (25 mg, 0.087 mmol) in $CH_2Cl_2$ (3.7 mL) at 0° C. were added Dess-Martin periodinane (73.5 mg, 0.173 mmol) and pyridine (0.014 mL, 0.173 mmol) and the reaction mixture was stirred for 30 min at 0° C. and for 1 h at 25° C. Then, $Et_2O$ (5 mL), a saturated aqueous solution of $NaHCO_3$ (3 mL) and a saturated aqueous solution of $Na_2S_2O_3$ (3 mL) were added. The layers were separated, the aqueous layer was extracted with $Et_2O$ (3×), the combined organic layers were washed with a saturated aqueous solution of $NaHCO_3$ (2×) and brine (2×), dried ($Na_2SO_4$) and the solvent was evaporated. The residue was purified by column chromatography (silica gel, gradient from 95:5 to 70:30 hexane/EtOAc) to afford 14 mg (57%) of a colorless oil identified as (R)-9-cis-13,14-dihydroretinal 17. $^1H$ NMR (400.63 MHz, $C_6D_6$): δ 9.27 (t, J=2.0 Hz, 1H, CHO), 6.91 (d, J=16.0 Hz, 1H, $H_7$), 6.60 (dd, J=14.8, 11.0 Hz, 1H, $H_1$), 6.30 (d, J=16.0 Hz, 1H, $H_8$), 5.93 (d, J=11.0 Hz, 1H, $H_{10}$), 5.36 (dd, J=15.1, 7.5 Hz, 1H, $H_{12}$), 2.53-2.43 (m, 1H, $H_{13}$), 1.98-1.93 (m, 2H$_3$), 1.91 (s, 3H, $CH_3$), 1.88 (dd, J=6.7, 1.9 Hz, 1H, $H_{14A}$), 1.81 (s, 3H, $CH_3$), 1.81-1.77 (d, J=2.1 Hz, 1H, $H_{14B}$), 1.63-1.53 (m, 2H, 2H$_2$), 1.50-1.44 (m, 2H, 2H$_4$), 1.38 (s, 3H, $CH_3$), 1.12 (s, 6H, 2×$CH_3$) ppm. $^{13}C$ NMR (101.63 MHz, $C_6D_6$): δ 200.1 (s), 138.6 (s), 137.7 (d), 133.2 (s), 130.8 (d), 129.4 (d), 129.1 (s), 128.7 (d), 125.1 (d), 50.4 (t), 39.7 (t), 34.5 (s), 33.3 (q), 31.9 (d), 30.3 (t), 29.2 (d), 22.1 (q), 20.7 (q), 20.4 (q), 19.7 (t), 14.4 (q) ppm. IR (NaCl): ν 2920 (s, C—H), 2854 (s, C—H), 1458 (w), 965 (w) $cm^{-1}$. HRMS ($ESI^+$): Calcd. for $C_{20}H_{31}O$ ($[M+H]^+$), 287.2362; found, 287.2369.

(R)-9-cis-13,14-Dihydro-β,β-carotene 18

To a cooled (−78° C.) solution of phosphonium chloride 7 (24.9 mg, 0.044 mmol) in THF (0.2 mL) was added nBuLi (0.027 mL, 1.6 M in hexanes, 0.044 mmol) and the reaction mixture was stirred for 30 min. Then a solution of (R)-9-cis-13,14-dihydroretinal 17 (9.0 mg, 0.031 mmol) in THF (0.13 mL) was added and the mixture was stirred for 1 h at −78° C. and for 30 min at 25° C. Water was added and the mixture was extracted with $Et_2O$ (3×). The combined organic layers were washed with a saturated aqueous solution of NaCl (2×) and dried ($Na_2SO_4$). The solvent was evaporated and the residue was purified by column chromatography (C18-silica gel, $CH_3CN$) to afford 11.3 mg (67%) of a red foam identified as (R)-9-cis-13,14-dihydro-β,β-carotene 18. It was observed that this product was very unstable and easily degraded. $^1H$ NMR (400.16 MHz, acetone-d$_6$): δ 6.69-6.60 (m, 2H), 6.56 (dd, J=14.4, 11.2 Hz, 1H, $H_{11'}$), 6.48 (dd, J=14.9, 11.1 Hz, 1H, $H_{15'}$), 6.34 (d, J=15.1 Hz, 1H), 6.21-6.13 (m, 4H), 6.12 (dd, J=11.5, 7.8 Hz, 1H), 5.94 (d, J=11.7 Hz, 1H, $H_{10'}$), 5.81-5.71 (m, 1H, $H_{15'}$), 5.62 (dd, J=15.0, 8.2 Hz, 1H, $H_{12}$), 2.44-2.33 (m, 1H, $H_{13'}$), 2.25-2.19 (m, 2H, 2H$_{14'}$), 2.05-2.00 (m, 4H), 1.96 (s, 3H, $CH_3$), 1.92 (s, 3H, $CH_3$), 1.91 (s, 3H, $CH_3$), 1.72 (s, 3H, $CH_3$), 1.70 (s, 3H, $CH_3$), 1.67-1.56 (m, 4H), 1.50-1.45 (m, 4H), 1.04 (s, 3H, CH$_3$), 1.03 (s, 12H, 4×CH$_3$) ppm. $^{13}$C NMR (101.63 MHz, acetone-d$_6$): δ 140.3 (d), 139.1 (d), 139.0 (s), 138.9 (s), 138.7 (d), 134.9 (d), 134.8 (s), 133.1 (s), 132.8 (d), 132.2 (d), 131.3 (d), 130.0 (d, 2×), 129.8 (s), 129.7 (s), 129.6 (d), 128.5 (d), 127.1 (d), 126.2 (s), 125.4 (d), 41.6 (t, 2×), 40.6 (t), 40.7 (t), 38.3 (d), 35.1 (s), 35.0 (s), 30.9 (t, 2×), 30.8 (q), 29.5 (q, 4×), 22.2 (q), 22.1 (q), 20.8 (q), 20.7 (q), 20.1 (t), 12.9 (q) ppm. UV (MeOH): λ$_{max}$ 324 nm. HRMS (ESI$^+$): Calcd. for C$_{40}$H$_{59}$ ([M+H]$^+$), 539.4604; found, 539.4611.
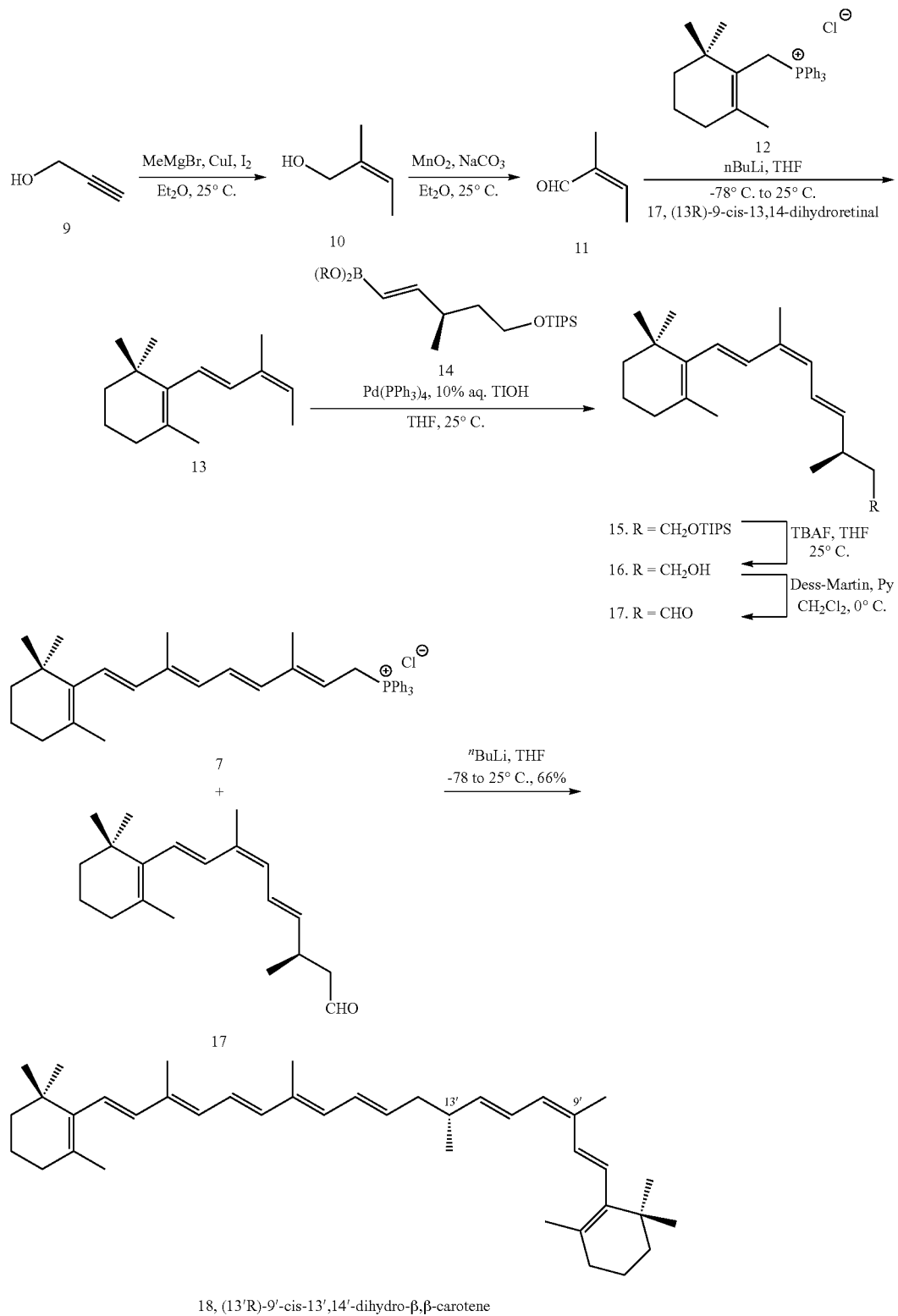

Example 3: Animal Experiments

Example 3.1: Animals

Male mice (Charles River, France) were housed in groups of 3 mice per cage in a 7 am-7 pm light/dark cycle in individually ventilated cages (Techniplast, Italy). Food (standard chow diet, D04 from SAFE, France) and water were freely available. All experiments were carried out in accordance with the European Community Council Directives of 24 Nov. 1986 (86/609/EEC) and in compliance with the guidelines of CNRS and the French Agricultural and Forestry Ministry (decree 87848).

For social defeat stress protocol we used C57BL/6N mice (Charles River, France) at the age of 6-7 weeks. All mice were housed in groups of 4-5 mice per cage in a 7 am-7 pm light/dark cycle in individually ventilated cages (Techniplast, Italy) until stress protocol which was carried out in MICE cages adapted for social defeat stress (see below). CD1 males mice purchased from Charles River (France) were used as aggressors in this test (see below).

Rbp1−/− and Rxrγ−/− mutants as well as wild type (WT) control mice were raised on a mixed genetic background (50% C57BL/6J and 50% 129SvEms/j; bred for more than 10 generations) from heterozygous crosses as described [24,33] (Krezel W et al. 2006), and tested at the age of 3-6 months.

Food and water were freely available. All experiments were carried out in accordance with the European Community Council Directives of 24 Nov. 1986 (86/609/EEC) and in compliance with the guidelines of CNRS and the French Agricultural and Forestry Ministry (decree 87848) and authorisation of French Ministry of Research.

Example 3.2: Behavioral Procedures and Tissue Sample Collection

Behavioral tests were carried out in the Institute Clinique de la Souris (http://www.ics-mci.fr/) according to standard operating procedures.

Behaviorally naïve groups of mice were tested in the DNMTP (delayed non-match to place) procedure in the T-maze according to a protocol previously described (Wietrzych et al., 2005), with modifications to facilitate pharmacological tests (Wietrzych-Schindler et al., 2011). Spontaneous alternation was evaluated in the Ymaze apparatus according to protocol described in detail below.

DNMTP Procedure with 9CDHROL

Specifically, in the present protocol, animals were first trained for 10 consecutive days with minimal inter-trial intervals (ITI) of about 15 sec, which was necessary to attain the criterion of 90% or more of correct choices during four consecutive days (days 9-10). After this period ITI was increased semi-randomly by blocks of 3-6 min during 5 consecutive days (days 11-15 indicated) to determine "test ITI" for each animal, which was defined as the shortest ITI at which mice perform at chance level. From day 16 mice were tested using corresponding "test ITI" delays following vehicle injection on the day 16 (to test for the effect of vehicle alone) and following 9CDHROL (40 mg/kg) injection on day 17. Three mice were excluded from testing since their latency to choose the arm during the retention phase exceeded 3 min in more than one trial/day on three consecutive days (exclusion criterion). On the day 18 mice were again injected (IP) with 9CDHROL (40 mg/kg) and 9 hours later sacrificed for chemical analyses. Mice which received vehicle injections on three consecutive days were used as vehicle-treated controls for analyses of 9CDHROL metabolism. An additional group of 3 naïve mice was also injected with 9CDHROL (40 mg/kg) to test for 9CDHROL metabolism following acute treatment.

DNMTP Procedure with 9CDHRA

In this variant, animals were first trained for 9 consecutive days of with minimal inter-trial intervals (ITI) of about 15 sec, which was necessary to attain the criterion of 90% or more of correct choices during three consecutive days (days 7-9). After this period ITI was increased semi-randomly to 180, 360, 720 and for some WT mice also 1080 seconds so that each animal was tested 6 times with each interval during four consecutive days (days 10-13 indicated). From day 13 mice were tested only twice per week beginning with training session on day one (with minimal, 15 sec ITIs) and testing pharmacological treatments on the second day. Only one pharmacological treatment was tested every 7 days. To test pro-mnemonic activities of UVI2108 and (R)-9CDHRA inventors used a minimal ITI, at which mice performed at chance level (50%) and which was 6 min for the Rbp1−/− or Rxrγ−/− groups and 12 min for most WT mice with exception of two mice tested at 18 min. Four mice (two wild types and one of each knockout line), were excluded from testing since their latency to choose the arm during the retention phase exceeded 3 min in more than one trial/day on three consecutive days (exclusion criterion).

Y-Maze Spontaneous Alternation

The Y-maze apparatus and the procedure were as previously described (Wietrzych et al., 2005). Briefly, each mouse was placed at the end of one arm and allowed to explore freely the apparatus for 5 min, with the experimenter out of the animal's sight. Spontaneous alternation performance (SAP) was assessed visually by scoring the pattern of entries into each arm and expressed as a percentage of total number of entries, discounting the first two visits. Total entries were scored as an index of ambulatory activity in the Y-maze, but none of tested mice had to be excluded due to low locomotor performance (score below 9 entries).

Forced Swim Test:

The forced swim paradigm was carried out between 1 pm and 4 pm in a 3-litre glass beaker half-filled with water at 22-23° C. (the water depth was 17 cm). All mice were tested only once in this task. To this end, each mouse was lowered gently into the water and the time of immobility was scored during a 6-minute testing period. The mouse was judged immobile when it floated in an upright position and made only small movements to keep its head above the water. After 6 min, the mouse was taken out of the water, left to dry under a red light lamp and returned to its home cage. The immobility scores of each animal were used as an index of despair behavior.

Sucrose Preference Test:

This task, designed to measure hedonic behaviors in mice is based on the palatable nature of sucrose observed in a number of mouse strains. On the first day of the test, sucrose-naive mice were placed in individual cages at 11 am and left there with water and food for habituation period. At 5 pm one water bottle was replaced with two bottles: one containing water and another 0.8% sucrose solution. Three hours later (8 pm) the bottles were weighed to measure liquid consumption and were replaced in cages until morning. The measures of an overnight consumption were then carried out for additional day to evaluate sucrose preference. Mice were not water deprived at any moment, in order to measure spontaneous sucrose preference and exclude any potential emotional confounds induced by stress of water deprivation. The sucrose preference was expressed as the percent of sucrose solution consumed with respect to total liquid consumption.

Social Defeat Stress:

Social defeat stress procedure was a modified version of the protocol previously described (Berton, McClung et al. 2006). C57BL/6N mice were defeated chronically for 10 consecutive days. Every day they were exposed to the physical contact with an unfamiliar CD1 aggressor in its home cage for maximal interaction time of 5 minutes. After each session of physical stress, C57BL/6N and CD1 mice were separated by a perforated wall and maintained in sensory contact for 24 h. After the last session of stress, mice were transferred into new cages and housed separately throughout the behavioral tests period. C57BL/6N control mice, similarly to the experimental animals, were housed two per cage separated by a metal perforated wall. Every day, they were exposed to the physical contact for 5 minutes.

Animals were then tested in the forced swim and sucrose tests.

Animal Treatments

For behavioral analysis, 9CDHROL and 9CDHBC were dissolved in ethanol, and then mixed with sunflower oil, so that the final solution contained 3% ethanol. Vehicle treatments consisted of 3% ethanol solution in sunflower oil. For memory studies treatments with 9CDHRA were administered by intraperitoneal injections at volume/weight ratio 3 ml/kg at 7 am and 7 hours before the beginning of testing. For tests with animal model of chronic social defeat, different treatments were administered by intraperitoneal injections at volume/weight ratio 3 ml/kg at 10 mg/kg for each substance between 5-6 pm every second day of stress protocol immediately after the stress session starting from day 1 of the stress protocol.

For metabolic analyses ATROL, 9CDHROL, 9CDHBC and control solutions were prepared as described above. Single per os application of the dose of 40 mg/kg of each substance was used to treat mice in the evening and samples were collected 11 h later in the light protected conditions, weighted, frozen in liquid nitrogen and stored at −80° C. until analyses. Serum was prepared and immediately stored in brown vials at −80° C., till further analysis.

For other treatments, (R)-9CDHRA, UVI2108, ATRA (Sigma), DHA (Sigma), MA (Sigma) and TTNPB (Sigma), were dissolved in ethanol and DMSO, and then mixed with sunflower oil, so that the final solution contained 3% ethanol and 3% DMSO. Vehicle treatments consisted of 3% ethanol and 3% DMSO solution in sunflower oil. Treatments were administered by intraperitoneal injections at volume/weight ratio 3 ml/kg between 8-10 am and 5-6 h before the test as previously validated (Wietrzych-Schindler M, 2011).

Statistical Analysis

The comparisons of behavioral performance in Rbp1−/− and Rxrγ−/− mice were carried out using the protected least significant difference (PLSD) Fischer test. The pharmacological data for the treatments in WT and Rbp1−/− or Rxrγ−/− mice were analysed using 2-way analysis of variance (ANOVA)—with treatment and genotype as two independent factors and behavioral responses as dependent variables. The evolution of learning curves in WT, Rbp1−/− and Rxrγ−/− mice were done using ANOVA on repeated measures. Global and post-hoc statistical analyses were performed using student t-test for two-group comparisons or for three-group comparisons the PLSD Fischer test was used. Significant differences are indicated in the corresponding figures.

The comparisons of behavioral performance during learning phase was carried out using one-way ANOVA on repeated measures with time as dependent parameter and percent of correct choices as an independent parameter. The pharmacological data were analyzed by comparing animal performance after vehicle and 9CDHROL treatment using one-way ANOVA on repeated measures. Post-hoc statistical analyses were performed to compare animal performance to 50% chance level using one-group student t-test. Significant differences are indicated in the corresponding figure.

Example 4 Analytical Procedures

Example 4.1: LC-MS Analysis of Tissue Samples

A. Just Retinoid Analysis:

Analytical procedures: High performance liquid chromatography mass spectrometry (HPLC-MS-MS) (Agilent 1260 Infinity LC system; Madrid, Spain)—(mass spectrometry: SCIEX Triple Quad 3500 System; Sciex, Madrid, Spain) analyses were performed under dark yellow/amber light using previously validated protocol (Rühl, 2006; Rühl et al., 2015). For the detection of 13,14-dihydroretinoic acid MS-MS setting were 303→207 m/z and for the detection of 13,14-dihydroretinol MS-MS settings were 290→69 m/z using the same dwell time and collision energy comparable to MS-MS specific settings of retinoic acids.

Quantification was performed as previously described (Rühl, R. 2006). For details of sample preparation see below. High performance liquid chromatography mass spectrometry (2695XE separation module; Waters)—mass spectrometry (Micromass Quattro Ultima PT; Waters) analyses were performed under dark yellow/amber light using previously validated protocol (Rühl, R. 2006).

Accordingly, for sample preparation 100 mg of the material (if samples were under 100 mg, water was added up to the used standard weight: 100 mg) or 100 l serum was diluted with a threefold volume of isopropanol, the tissues were minced by scissors, vortexed for 10 seconds, put in a ultra sonic bath for 5 minutes, shaken for 6 minutes and centrifuged at 13000 rpm in a Heraeus BIOFUGE Fresco at +4° C. After centrifugation, the supernatants were dried in an Eppendorf concentrator 5301 (Eppendorf, Germany) at 30° C. The dried extracts were resuspended with 60 µl of methanol, diluted with 40 l of 60 mM aqueous ammonium acetate solution and transferred into the autosampler and subsequently analyzed.

B. Combined Retinoid and Carotenoid Analysis:

Analytical procedures: High performance liquid chromatography mass spectrometry (Agilent 1260 Infinity LC system; Madrid, Spain)-mass spectrometry (SCIEX Triple Quad 3500 System; Sciex, Madrid, Spain) plus and additional online diode array detector (Waters 966 DAD, Waters, Santiago de Compostella, ES) analyses were performed under dark yellow/amber light using previously validated protocol (LIT) plus adding a third and 4th eluent after 20 min elution time. Linear gradient from 20 min 20% (isopropanol:methanol:methyl-tert-butyl-ether (MTBE)/30:30:40)—80% (isopropanol:methanol/50:50), 25 min 40% (isopropanol:methanol:methyl-tert-butyl ether (MTBE)/30:30:40)—60% (isopropanol:methanol/50:50), 29 min 70% (isopropanol:methanol:methyl-tert-butyl ether (MTBE)/30:30:40)—30% (isopropanol:methanol/50:50), 30 min 0% (isopropanol:methanol:methyl-tert-butyl ether (MTBE)/30:30:40)—100% (isopropanol:methanol/50:50), 30.1 min 20% (isopropanol:methanol:methyl-tert-butyl ether (MTBE)/30:30:40)—80% (isopropanol:methanol/50:50).

For the detection of 13,14-dihydroretinoic acid MS-MS setting were 303→207 m/z, for the detection of 13,14-dihydroretinol MS-MS settings were 290→69 m/z and for the detection of 9CDHBC 405→405/405→95 m/z. Accordingly, for sample preparation 100 mg of the material (if samples were under 100 mg, water was added up to the used standard weight: 100 mg) or 100 μl serum was diluted with a threefold volume of isopropanol, the tissues were minced by scissors, vortexed for 10 seconds, put in a ultrasonic bath for 5 minutes, shaken for 6 minutes and centrifuged at 13000 rpm in a Heraeus BIOFUGE Fresco at +4° C. After centrifugation, the supernatants were dried dried in a GYROZEN centrifugal vacuum concentrator equipped with a ILMAC MPC 301-Z vacuum pump (CONTROLTECNICA, Madrid, ES) at 30° C. The dried extracts were resuspended with 30 μl of methanol—MTBE (50-50) and transferred into the autosampler and 10 μl subsequently analysed.

Statistical Analysis

Statistical analyses for behavioral analysis and retinoid/carotenoid analysis were performed using student t-test for each of the two-group comparisons. Significant differences are indicated in the corresponding figures.

Identification of Endogenous 9CDHROL in Mouse, Human and the Human Food Matrix:

Mouse brain samples were prepared according to the procedure described above. Briefly, after single per os application of the dose of 40 mg/kg of 9CDHROL (or other cited substances) in the evening mice were sacrificed after 11 hours and tissues samples including brain were dissected under light-protection conditions, weighted, frozen in liquid nitrogen and stored at −80° C. until analyses. Serum was prepared and immediately stored in brown vials at −80° C., till further analysis.

Human serum samples were obtained from the blood of healthy volunteers with all the subjects' written informed consent.

Food samples: Beef liver was bought at a local butcher in Vigo, Spain. Conserves of peaches in can (Metades, Pessago em calda, Auchan/Alcampo-home-brand/420 g can) were purchased at Alcampo, Vigo, Spain.

Example 4.2: Reporter Cell Lines

COS1 cells were maintained in DMEM medium with 10% FBS, 5% L-glutamine, 1% penicillin streptomycin in 24-well plates and transfections were carried out in triplicates. Cells were transfected with equal amounts of relevant plasmids including Gal-RXRα-LBD for RXR-reporter line or Gal-RARα-LBD and Gal-RXRα-LBD for RAR-RXR reporter line, a reporter plasmid (luciferase MH100-TKLuc reporter construct with GAL-binding site [Nagy L. et al. 1999] and beta-galactosidase (for transfection efficiency calculation). For details of transfection and measurements see below.

Transfection was carried out using PEI (Sigma) as transfection reagent. DMSO solution of each ligand was added 6 h later and cells were incubated for 48 h at 37° C. Luciferase activity was determined in the lysates of the cells using the Luciferase Assay Kit (Promega). Measurements were made with a Wallac Victor2 multilabel counter. The signal of each sample was normalized to 3-gal activity to take the transfection efficiency and cell viability into account.

Example 4.3: Binding Assays cDNAs encoding hRXRα LBD (223-462), hRARα LBD (153-421), hRARβ LBD (169-414) and hRARγ LBD (178-423) were cloned into pET28b vector to generate N-terminal Histag fusion proteins. Purification was carried out as previously described [Lippert W P et al. 2009, Osz J, et al. 2012], including a metal affinity chromatography and a gel filtration. For details of sample preparation and ESI-MS analyses see below.

cDNAs encoding hRXRαLBD (223-462), hRARαLBD (153-421), hRARβLBD (169-414) and hRARγ LBD (178-423) were cloned into pET28b vector to generate N-terminal His-tag fusion proteins. Purification was carried out as previously described [Lippert W P et al. 2009, Osz J, et al. 2012], including a metal affinity chromatography and a gel filtration. Prior to ESI-MS analysis, samples were desalted on Zeba Spin desalting columns (Pierce) in 150 mM ammonium acetate (pH 8.0). ESI-MS measurements were performed on an electrospray time-of-flight mass spectrometer (MicrOTOF, Bruker Daltonics). Purity and homogeneity of the proteins were verified by mass spectrometry in denaturing conditions (samples were diluted at 2 pmol/μl in a 1:1 water-acetonitrile mixture (v/v) acidified with 1% formic acid). The mass measurements of the noncovalent complexes were performed in ammonium acetate (200 mM; pH 8.0). Samples were diluted to 8 pmol/ml in the previous buffer and continuously infused into the ESI ion source at a flow rate of 3 ml/min through a Harvard syringe pump (Harvard Apparatus model 11). A careful optimization of the interface parameters was performed to obtain the best sensitivity and spectrum quality without affecting the noncovalent complexes stability. In particular, the capillary exit (CE) ranged from 60 to 150 V with a vacuum interface pressure of 2.3 mbar and was set to 80 V. For ligand-interaction analysis, ligands were added to the proteins in a 5-fold molar excess.

Fluorescence Quenching Assay:

Fluorescence spectra were measured as previously described [Wietrzych M. et al. 2005, Ghyselinck N B et al. 1999] using a Fluoromax-4 Horiba spectrophotometer. RXRα LBD was prepared as for ESI-MS analyses and incubated with different concentrations of 9CDHRA or 9CRA in Tris 10 mM, NaCl 100 mM buffer. Quenching of tryptophan fluorescence was monitored at 10° C. using 5 nm of excitation and 5 nm of emission slit-width. The excitation wavelength was 295 nm and the emission spectra were measured between 260 and 450 nm. Corrections for inner filter effect were performed and data were analyzed by Cogan plot as described [Chen Z P et al. 1994].

Example 4.4: Structure Analysis of RXR-LBD in Complex with (R)-9CDHRA

Crystals of the complex of hRXRα LBD/(R)-9-cis-13,14-DHRA and TIF-2 peptide were obtained at 17° C. by vapor diffusion in hanging drops by mixing of 0.5 μl of the protein solution and 0.5 μl of reservoir solution which contains 50 mM calcium acetate and 18% PEG3350. The crystals were mounted in fiber loops and flash-cooled in liquid nitrogen after cryoprotection with the reservoir solution plus 5% ethylene glycol. Data collection from the frozen crystal was performed at 100 K on the beamline ID29 at the ESRF (Grenoble, France). The crystal belongs to the tetragonal space group $P4_32_12$, with one monomer per asymmetric unit. The data were integrated and scaled with HKL2000 [Otwinowski Z et al. 1997] (statistics in Table 1). The structure was solved and refined as described [Lippert W P et al. 2009]. Refinement involved iterative cycles of manual building and refinement calculations. Anisotropic scaling, a bulk solvent correction and TLS restraints were used for the refinement. Individual atomic B factors were refined isotropically. Solvent molecules were then placed according to unassigned peaks in the electron density map. For additional information see also FIGS. 3E-H and Table 1.

TABLE 1

Data collection and refinement statistics.
RXRα LBD/(R)-9-cis-13,14-DHRA/NCoA2

| Data processing | |
| --- | --- |
| Resolution (Å) | 25-1.8 (1.86-1.80) |
| Crystal space group | P43212 |
| Cell parameters (Å) | a = b = 64.014; C = 112.066 |
| Unique reflections | 22407 |
| Mean redundancy | 7.9 (3.8) |
| Rsym (%)$^a$ | 5.2 (48.1) |
| Completeness (%) | 99.2 (97.2) |
| Refinement | |
| Resolution (Å) | 24-1.8 |
| Number of non-hydrogen atoms | |
| RXR-LBD | 1680 |
| Coactivator peptide | 98 |
| Ligand | 22 |
| Water molecules | 181 |
| RMSD bond length (Å) | 0.006 |
| RMSD bond angles (°) | 1.065 |
| Rcryst (%)$^b$ | 17.9 |
| Rfree (%)$^c$ | 22.1 |
| Averaged B factor for non-hydrogen atoms (Å$^2$) | |
| RXR-LBD | 37.6 |
| Coactivator peptide | 44.6 |
| R-DHRA | 31.2 |
| Water | 44.5 |

$^a$Rsym = 100 × Shj|Ihj − <Ih>|/Shj Ihj, where ihj is the jth measurement of the intensity of reflection h and <Ih> is its mean value.
$^b$Rcryst = 100 × S||Fo|− |Fc||/S|Fo|, where |Fo| and |Fc| are the observed and calculated structure 10 factor amplitudes, respectively.
$^c$Calculated using a random set containing 10% of observations that were not included throughout refinement [Brünger A. T., (1992) The Free R Value: a Novel Statistical Quantity for Assessing the Accuracy of Crystal Structures, Nature 355, 472-474].

Example 5: Human Dendritic Cell (DC) Generation and DNA Microarray Analysis

The generation and transcriptional analysis of differentiating DCs were performed as described previously [Szeles L et al. 2010]. Microarray data were deposited into the Gene Expression Omnibus database under accession no. GSE48573.

The generation and analysis of differentiating DCs were performed as described previously [Szeles L et al. 2010] with minor modifications. Briefly, human monocytes were isolated from healthy volunteer's buffy coat, obtained with a Regional Ethical Board permit from the Regional Blood Bank and isolated by Ficoll gradient centrifugation followed by immunomagnetic cell separation, and were cultured in the presence of GM-CSF and IL-4. Differentiating DCs were stimulated 18 h after plating by various agonists for 12 h. The ligands were used in the following concentrations: 10 μM (R)-9CDHRA, 10 μM (S)-9CDHRA, 1 μM 9cisRA, 100 nM LG100268, 1 μM GW3965, 1 μM Rosiglitazone (RSG), 1 μM GW1516, 100 nM AM580. Experiments were performed in biological triplicates. Samples were processed and hybridized to Human Genome U133 Plus 2.0 Arrays. Data were analysed using to GeneSpring 12.6.1 software. In detail, normalization was performed using RMA summarization algorithm. Significantly regulated genes were identified using a two-fold change cut-off (only transcripts with FC>2 were included) and moderated t-test with the Benjamini-Hochberg procedure for multiple test correction (FDR<0.05). Microarray data were deposited into the Gene Expression Omnibus database under accession no. GSE48573.

Example 6: Experimental Procedure—Testing Compounds of the Invention for Mnemonic and Antidepressant Effects in Animal Models Example 6.1: Methods Animals:
Rbp1−/− and Rxrγ−/− mutants as well as their wild type (WT) control mice were raised on a mixed genetic background (60% C57BL/6J and 40% 129SvEms/j) from heterozygous crosses as described (Ghyselinck N B 1999; Krezel et al., 1996), and tested at the age of 3-6 months.

In general male mice (Charles River, France) were housed in groups of 3 mice per cage in a 7 am-7 pm light/dark cycle in individually ventilated cages (Techniplast, Italy). Food (standard chow diet, D04 from SAFE, France) and water were freely available.

All mice were housed in groups of 4-5 mice per cage in a 7 am-7 pm light/dark cycle in individually ventilated cages (Techniplast, Italy) until stress protocol which was carried out in MICE cages adapted for social defeat stress (see below). CD1 males mice purchased from Charles River (France) were used as aggressors in this test (see below). Food and water were freely available.

All experiments were carried out in accordance with the European Community Council Directives of 24 Nov. 1986 (86/609/EEC) and in compliance with the guidelines of CNRS and the French Agricultural and Forestry Ministry (decree 87848).

For social defeat stress protocol we used C57BL/6N mice which were transferred from Taconic (France) at the age of 6 weeks and housed in groups of 4 per cage. After 1 week of habituation period they were subjected to the social defeat stress. CD1 purchased from Charles River (France), were used as aggressors in this test.

Behavioral Procedures:
All behavioral tests were carried out in the Institute Clinique de la Souris (http://www.ics-mci.fr/) according to standard operating procedures.

Forced Swim Test:
The forced swim paradigm (Dalvi and Lucki, 1999) was carried out between 1 pm and 4 pm in a 2-litre glass beaker half-filled with water at 22-23° C. (the water depth was 17 cm). All mice were tested only once in this task. To this end, each mouse was lowered gently into the water and the time of immobility was scored during a 6-minute testing period. The mouse was judged immobile when it floated in an upright position and made only small movements to keep its head above the water. After 6 min, the mouse was taken out of the water, left to dry under a red light lamp and returned to its home cage. The immobility scores of each animal were used as an index of despair behavior.

Sucrose Preference Test:
This task, designed to measure hedonic behavior in mice (Moreau, 1997), is based on the palatable nature of sucrose observed in a number of mouse strains. On the first day of the test, sucrose-naive mice were placed in individual cages at 11 am and left there with water and food for habituation period. At 5 pm one water bottle was replaced with two bottles: one containing water and another 0.8% sucrose solution. Three hours later (8 pm) the bottles were weighed to measure liquid consumption and were replaced in cages until morning. The measures of an overnight consumption were then carried out for additional day to evaluate sucrose preference. Mice were not water deprived at any moment, in order to measure spontaneous sucrose preference and exclude any potential emotional confounds induced by stress of water deprivation. The sucrose preference was expressed as the percent of sucrose solution consumed with respect to total liquid consumption.

Social Defeat Stress:

Social defeat stress procedure was a modified version of the protocol previously described (Berton et al. 2006). C57BL/6N mice were defeated chronically for 10 consecutive days. Every day they were exposed to the physical contact with an unfamiliar CD1 aggressor in its home cage for maximal interaction time of 5 minutes. After each session of physical stress, C57BL/6N and CD1 mice were separated by a perforated wall and maintained in sensory contact for 24 h. After the last session of stress, mice were transferred into new cages and housed separately throughout the behavioral tests period. C57BL/6N control mice, similarly to the experimental animals, were housed two per cage separated by a metal perforated wall. Every day, they were exposed to the physical contact for 5 minutes.

Animals were then tested in the forced swim and sucrose tests.

Example 6.2: R-9CDHRA Supplementation Reverses Behavioral Changes in Rbp1−/− Mice In the following experiments it has been established that affective and memory deficits in Rbp1−/− mice are associated with deficient RXR-signaling.

Rbp1−/− mice displayed depressive-like behavioral deficits including increased despair illustrated by long immobility states in the forced swim test (FIG. 8A) and anhedonia on evidence of reduced sucrose preference (FIG. 8C). Such deficits resemble phenotype of mice carrying null mutation for RXRγ (FIGS. 8A and 8C and Krzyzosiak A et al. 2010) suggesting that RXR signaling is compromised in Rbp1−/− mice. To challenge this hypothesis functionally, we took advantage of the sensitivity of the forced swim test to reveal antidepressant activities of acute treatments with RXR-agonists (Wietrzych-Schindler M et al., 2011). All-trans retinoic acid (ATRA), which in vivo can rapidly be transformed to the RXR agonist, 9CRA, similarly to a synthetic RXR agonist, UVI2108 (known also as BMS649) reduced significantly immobility time of Rbp1−/− mice in the forced swim test (FIG. 8B). Distinct RXR agonists of synthetic (methoprene acid) or nutritional origin (DHA) also normalized increased despair of Rbp1−/− mice and such effect was independent of RAR activation since TTNPB, a synthetic RAR agonist did not display such effects (FIG. 8D). RXRγ appeared as the functionally predominant RXR in mediating such activities in the forced swim as Rxrγ−/− mice displayed increased despair behaviors, which were not normalised by RXR agonists (FIG. 8B and FIG. 8D).

In order to address relevance of 9CDHRA in modulation of RXR functions in vivo inventors tested whether (R)-9CDHRA can reverse behavioral deficits in Rbp1−/− mice. Acute treatment with (R)-9CDHRA reduced in dose dependent manner immobility of knockout mice in the forced swim test attaining maximal effect already at 1 mg/kg, which was comparable to antidespair effect of synthetic RXR agonist UVI2108 at the same dose or 5 mg/kg treatment with ATRA (FIG. 9B). Effects of treatments were not evident in WT mice, which may be related to the low baseline immobility in this strain and in consequence floor effect. Such activities were mediated by RXRγ as 2 mg treatment with (R)-9CDHRA did not improve performance of Rxrγ−/− mice, which remained immobile for 120±25 sec as compared to 119±19 sec in vehicle treated Rxrγ−/− animals.

Similarly to antidespair effects in the forced swim test, 1 or 2 mg/kg of (R)-9CDHRA also improved performance of Rbp1−/− mice in memory tests. Such treatments increased the rate of successful choices of Rbp1−/−, which performed significantly better than 50% of chance level when tested at inter-trial interval of 6 min in DNMTP test (FIG. 9A). Treatment with 2 mg/kg of (R)-9CDHRA raised also performance of WT mice to about 70% of correct choices when tested at long inter-trial intervals of 12 or 18 min at which the same WT mice performed at chance level (50% of correct choices) if treated with vehicle. Such treatment did not improve performance of Rxrγ−/− mice which performed at 57±7% of correct choices, providing further evidence that compromised RXRγ function associated with reduced levels of 9CDHRA is at the origin of the deficits observed in Rbp1−/− animals.

Example 6.3: (R)-9CDHRA Displays Antidepressant Effects in Chronic Social Defeat Stress Model The present inventors have found that (R)-9CDHRA supplementation treats depressive behaviors in chronic stress model of depression. Stress is an important environmental factor in the etiology of depression. To test efficiency of 9CDHRA for treatment of depressive behaviors induced by stress, we used social defeat stress animal model (Berton et al., 2006, Hollis and Kabbaj, 2014). Ten days of short daily physical contacts with resident dominant CD1 male followed by subsequent sensory contact efficiently induced despair in the forced swim task (FIG. 10A). Treatment with 1 or 3 mg/kg of 9CDHRA during the stress protocol efficiently normalized immobility time, which was comparable with control non-stressed mice. In contrast to the lower dose, treatment with 3 mg/kg of 9CDHRA displayed anti-despair effects as it was significantly lower than immobility time observed in stressed, nontreated mice indicating thus that 9CDHRA displays dose effect in controlling this behavioral parameter. The effect of 9CDHRA was comparable with activity of synthetic pan-RXR agonist UVI2108, suggesting critical role of RXR activation in attaining anti-despair activity of by 9CDHRA. In addition to despair behaviors chronic stress induced also anhedonia reflected by absence of preference of sweetened drink which was consumed at the level not significantly different from 50% reflecting random choice (FIG. 10B). Anhedonia was abolished in stressed mice treated already with low dose of 9CDHRA (1 mg/kg) as illustrated by sucrose preference significantly exceeding a chance level of 50%, although this preference was even more marked after treatment with higher dose of 3 mg/kg of 9CDHRA. A pan-RXR agonist UVI2108 displayed activities similar to 9CDHRA supporting the involvement of RXR activation by 9CDHRA in antidepressant activities.

As shown above in Example 6.2, use of RXRγ−/− was a negative control to show that 9CDHRA acts at RXRγ to improve memory—in consequence in absence of RXRγ it cannot improve memory. Rbp1−/− mice were used because they show the same type of deficits as RXRγ−/− suggesting that RXRγ signaling is down. By showing that 9CDHRA can normalize their memory was a proof of concept that these mice are missing RXR ligand and not the receptor itself (or receptor functionality). Even in previous experiments we showed that 9CDHRA can also improve memory of WT mice suggesting that it could work as memory enhancer in healthy subjects, but also could be used as memory enhancer in AD.

Example 6.4: Discussion and Summary of Results with 9CDHRA

Discussion:

The inventors first employed behavioral and pharmacological analyses sensitive to RXR signaling as a tool to identify animal models with reduced RXR signaling. In particular, inventors focused on spatial working memory previously reported as dependent on RXR and not RAR functions, including ligand-dependent RXR activities [Wietrzych-Schindler M et al.]. Using delayed non-match to place (DNMTP) task, inventors found that mice carrying a null mutation of cellular retinol binding protein I (RBP1), known for its role in retinoid metabolism [Ghyselinck N B et al. 1999], display memory deficits which phenocopy the effect of the loss of function of Rxrγ, a functionally predominant RXR in control of working memory (FIG. 1C [Wietrzych-Schindler M et al.]). In particular, Rbp1−/− and Rxrγ−/− mice performed significantly worse when compared to wild type (WT) mice at 3 or 6 min inter-trial intervals (ITI) in DNMTP task, attaining chance level (complete forgetting) already at 6 min, whereas WT mice performed at chance level only at 12 or 18 min depending on individual (FIG. 1C, see grey part of the left panel). These data suggest that RXR signaling is compromised in Rbp1−/− mice.

To challenge this hypothesis functionally, inventors took advantage of the sensitivity of working memory performance in delayed task to treatments with RXR agonists [Wietrzych-Schindler M et al.]. Activation of RXR signaling by the synthetic RXR agonist, UVI2108 (also known as SR11217 or BMS649) or by ATRA, which under pharmacological conditions is rapidly transformed in vivo to RXR agonist 9CRA [Heyman R A et al. 1992, Duell E A et al., 1996], reversed memory deficits in Rbp1−/− mice, but remained ineffective in mice lacking RXRγ (FIG. 1D). Working memory deficits were also observed in a distinct, rodent specific memory test of spontaneous alternation in the Y-maze (FIG. 8E). Treatments with ATRA, UVI2108 and other RXR agonists, including DHA and methoprene acid, but not pan-RAR agonist TTNPB led to pro-mnemonic effects in Rbp1−/−, but not Rxrγ−/− mice (FIG. 8E), supporting the possibility of compromised RXR signaling due to reduced availability of RXR ligand(s) in Rbp1−/− mice. Accordingly, reduced expression of RXRγ could not explain behavioral deficits in Rbp1−/− mice. On the contrary, expression of RXRγ was clearly increased in Rbp1−/− striatum attaining level of 3.2±0.6 in Rbp1−/− mice as compared to 1.2±0.3 arbitrary RNA units (qRT-PCR).

To evaluate RXR ligand availability in Rbp1$^{-/-}$ mice, inventors first addressed concentration of 9CRA in mouse brain and serum. Using a sensitive method of retinoic acid detection based on HPLC separation followed by highly specific DAD detection and destructive MS-MS [Rühl R (2006)], inventors clearly identified ATRA in serum (0.3±0.1 ng/ml) and brain (0.6±0.1 ng/g) samples from WT mice, whereas in the range of 9CRA elution no conclusive peak was identified indicating that 9CRA levels were under our detection limit of 0.1 ng/g and thereby too low for RXR-activation in WT (Data not shown) and Rbp1$^{-/-}$ animals. Inventors then focused on dihydroretinoids described as novel endogenous retinoids [Moise A R et al. 2004, Shirley M A et al. 1996]. Using stereo- and enantiocontrolled organic synthesis approaches we obtained a series of dihydroretinoids, including all-trans-13,14-dihydroretinoic acid (ATDHRA) and its stereoisomer 9-cis-13,14-dihydroretinoic acid (9CDHRA), which inventors next used as reference molecules in HPLC-MS-MS analyses. Focusing such analyses on liver, as major site of Rbp1 expression, serum through which retinoids are distributed to target organs and brain, with discrete areas expressing Rbp1 [Lein E S, et al. 2007], inventors identified two major peaks, which co-eluted with standards of ATDHRA and 9CDHRA at UV specific absorption of 290 nm (FIG. 2B, left panel). Such co-elution was also observed at dihydroretinoid-specific MS-MS settings (FIG. 2B, right panel). Concentrations of 9CDHRA were high in serum samples attaining 118±15 ng/ml (corresponding to ~4×10$^{-7}$M), 135±12 ng/g in mouse liver (corresponding to a concentration of ~7×10$^{-7}$ M) and relatively low (7±1 ng/g, corresponding to ~2×10$^{-8}$ M) in brain. A direct comparison of these retinol metabolites in WT and littermate Rbp1$^{-/-}$ mice (FIG. 2C) showed comparable concentration of ATDHRA in contrast to significantly decreased 9CDHRA levels in serum, liver and brain of Rbp1$^{-/-}$ mice. Importantly, whereas such decrease in serum may be at the origin of systemic reduction of RXR signaling, almost complete loss of 9CDHRA availability in Rbp1$^{-/-}$ brain suggest more significant reduction of local RXR signaling in this organ. Furthermore, whole brain measures reflect most probably more dramatic changes of 9CDHRA levels in discrete brain areas expressing Rbp1 [Lein E S, et al. 2007]. Unfortunately it is technically impossible to identify retinoid concentrations in these small areas, which can be only prompted by whole brain measures.

Direct evidence for 9CDHRA binding to RXR was given by electrospray ionisation mass spectrometry (ESI-MS) performed in non-denaturing conditions with purified RXR ligand binding domains (LBD). In order to evaluate relative affinities of R- and S-enantiomers and 9CDHRA for RXR LBD, titration experiments were monitored by ESI-MS. As shown in FIG. 3A and FIG. 3B, all retinoids bind to hRXRα LBD used in these studies as model RXR LBD due to high conservation of LBD structure among all RXRs. Analyses of peak amplitude revealed that (R)-9CDHRA has approximately 30% lower affinity than 9CRA, but about 65% higher affinity than (S)-9CDHRA. Quantitative binding affinities to RXR LBD obtained by fluorescence quenching assay (FIGS. 3C and 3D) are equal to 90±20 nM for (R)-9CDHRA and 20±10 nM for 9CRA, and fall in the range of published Kd [Chen Z P et al. 1994] indicating that 9CDHRA binds RXRs with high affinity at concentrations which are physiologically relevant. Since 9CRA can bind to RARs we also tested affinity of 9CDHRA for all three RAR isotypes. ESI-MS experiments performed with hRARα, β and γ LBDs (FIGS. 3E and 3F) revealed that 9CDHRA (R and S) bind to all RAR LBD isotypes.

To provide structural evidence of the binding of (R)-9CDHRA to RXR, the hRXRα LBD was crystallized in complex with (R)-9CDHRA and a 13-residue peptide comprising the nuclear receptor-binding surface NR2 of NCoA2. Note that the residues lining the ligand-binding pocket are strictly conserved between the RXRα and RXRγ and that the conclusions drawn for RXRα will also be valid for RXRγ. The structure refined at 1.8 Å resolution (Table S1) revealed the canonical active agonist conformation common to all previously reported agonist-bound nuclear receptor LBDs with 12 or 13 α-helices organized in a three-layered sandwich (FIGS. 3G and 3H). (R)-9CDHRA adopts a similar binding mode as 9CRA [Egea P F et al. 2000, Pogenberg V.

et al. 2005] including interactions of carboxyl groups of the ligand with Arg316 (H5), and hydrogen bonds with the amide group of Ala327 in the beta turn (FIGS. 3I and 3J). The number of contacts is similar between the two ligands although some interactions are weaker in the case of (R)-9CDHRA compared to 9CRA as for example the interactions with Leu436 (4.0 Å instead of 3.6 Å for 9CRA), Arg316 (2.7 Å instead of 2.3 Å) or Trp305 (4.3 Å instead of 3.5 Å) that account for the weaker binding of the (R)-9CDHRA compound. In silico comparison of (S)- and (R)-9CDHRA binding mode in RXRα LBP revealed that the opposite configuration at C13 leading to slightly different side chain conformation of (S)-9CDHRA may underlay its lower affinity to RXR (data not shown), further supported by the lower relative binding affinity measured by ESI-MS.

The relevance of (R)-9CDHRA and (S)-9CDHRA receptor binding for transcriptional activities of RXRs was tested in COS1 reporter cell lines transfected with a RXRα expression vector (FIGS. 3K-3M). In agreement with previous reports, 9CRA induced transcription of reporter gene at concentrations starting from $10^{-9}$M, whereas (R)-9CDHRA or (S)-9CDHRA displayed similar activity to 9CRA, although at concentrations higher than $10^{-7}$M. Importantly, the activities of (R)- and (S)-9CDHRA at $10^{-5}$M were prevented by co-treatment with an RXR-antagonist LG101208 at $10^{-6}$M (FIG. 3L). 9CDHRAs also activated RAR-RXR signaling in COS1 model reporter cells (transfected with RARα and RXRα expression vectors) starting at $10^{-6}$M (FIG. 3M). Considering that all RXR isotypes share the same structure of ligand binding pocket, present data obtained with RXRα isotype indicate that 9CDHRA may efficiently bind to all RXRs and induce their transcriptional activities at concentrations found in physiological conditions.

Behavioural analyses revealed that 9CDHRA modulation of RXR functions is also relevant in vivo. Accordingly, acute treatment with (R)-9CDHRA improved memory performance of Rbp1$^{-/-}$ mice as compared to vehicle treatment or chance level of 50% when tested in DNMTP task at ITI of 6 min (FIG. 9A). (R)-9CDHRA treatments also raised performance of WT mice when tested at long ITIs of 12 or 18 min, at which the corresponding WT mice treated with vehicle performed at chance level. Such treatment did not improve performance of Rxrγ$^{-/-}$ mice (57±7% of correct choices) indicating RXR specificity of 9CDHRA effects, which is further supported by similar effects of 9CDHRA and UVI2108 treatments (compare FIG. 9A and FIGS. 1C and 1D).

In order to identify 9CDHRA specificity for induction of RXR-dependent transcriptional activity at the transcriptomic level and its capacity to activate permissive heterodimers inventors took advantage of human differentiating monocyte-derived dendritic cell cultures, a well characterized in vitro model for studies of signaling through RXR and its heterodimers [Szatmari I et al. 2007, Szeles L et al. 2010]. The gene expression changes induced by (R)-9CDHRA, (S)-9CDHRA, other RXR ligands or ligands for RXR partners, revealed that (R)-9CDHRA and 9CRA regulate approximately the same number of transcripts (518 and 450, respectively; FIG. 4). Importantly, 384 transcripts were similarly regulated by both agonists (FIGS. 4A, 4B), which corresponded to 85% of all transcripts regulated by 9CRA. Within this set, a group of 61 transcripts was also regulated by LG268, a synthetic RXR specific ligand used in our analysis as a reference to previous studies of this model [Szatmari I et al. 2007, Szeles L et al. 2010]. Remarkably, none of the transcripts were regulated solely by 9CRA and LG268, and not by 9CDHRA, indicating that 9CDHRA induces similar gene expression changes as 9CRA.

Inventors also investigated the capacity of 9CDHRA for activating permissive heterodimers, e.g. LXRα/β-RXR, PPARγ-RXR, and PPARδ-RXR. As expected, inventors found that (R)-9CDHRA similarly to 9CRA and LG268 could induce the expression of many genes, which are known as direct targets of RXR permissive heterodimers. Accordingly these genes were also regulated by LXR or PPAR specific ligands (FIG. 4C). To address whether 9CDHRA also activates RAR-RXR target genes inventors compared the effect of RXR ligands and AM580, a synthetic RARα selective ligand. Typically genes induced by AM580 were not induced by any other agonist for permissive partners (FIG. 4C), but were also induced by 9CDHRA or 9CRA. Collectively, gene expression profiling indicated that (R)- and (S)-9CDHRAs display RXR agonist activity, but can also activate RARs, acting thus with similar selectivity to 9CRA.

Example 7: Identification of Compounds after Treatment in Mice

Example 7.1: Identification of 9CDHRA after 9CDHROL Treatment in Mice

As shown herein (FIGS. 2B and C) the present inventors have identified that 9CDHRA is an endogenous derivative in mice and in humans. The next step was to identify precursors of 9CDHRA in in vivo and in vitro models.

Animal treatment, administration of 9CDHROL and sample analysis, was carried out as described in Examples 3 and 4.

For mouse supplementation experiments we treated n=6 mice per os with 40 mg/kg bw 9CDHROL and 11 h after the treatment the mice were killed and blood, brain and liver was taken. After centrifugation of the drawn blood, serum was obtained.

Example 7.2: Initial Results from HPLC and LC-MS Analysis

Identification of Endogenous 9CDHROL and Identification of 9CDHROL after Treatment of 9CDHROL to Mice Initially we analyzed a mixed standard of 9-cis-13,14-dihydroretinol (9CDHROL) and all-trans-dihydroretinol (ATDHROL) for comparison using our LC-MS analytics (top Figure of FIG. 2A) and after we analyzed a liver sample from vehicle treated mice (bottom figure of FIG. 2A). The 9CDHROL peak from the standard 9CDHROL co-eluted with the peak identified in the liver samples using the same MS-MS fragmentation channels in our LC-MS system. Based on the co-elution and using the same LC-MS parameters and the same fragmentation pattern channels (290→69 m/z) used, we claim and identify 9CDHROL as an endogenous retinoid in the mammalian organism. In addition, this co-eluting peak can also be observed in lower levels in serum and brain of mice and 9CDHROL is strongly increased after 9CDHROL-treatment (FIG. 5A).

In serum, brain and liver 9CDHRA was found endogenously in low levels. In addition after 9CDHROL-treatment a strong increase of 9CDHRA levels were identified in serum, brain and liver analyzed samples (FIG. 5B).

As a comparison we displayed the increase levels of 9CDHRA in liver samples in FIG. 6.

Example 7.3: Identification of 9CDHROL in Mice

9CDHROL is Accumulated in Mice 9CDHROL-Treated Mice and a Metabolite from 9CDHBC In Vitro Oligodendrocyte Cell Culture:

While in vitro cell treatments with 9CBC and ATBC (functioning as pro-vitamin A1) were proven to be mainly inefficiently metabolized to 9CDHROL, we further followed on with treatments of direct 9CDHROL precursors as well as 9CDHROL itself.

Initially we analyzed a standard of 9-cis-13,14-dihydroretinol (9CDHROL, top chromatogram of FIG. 11A) using our LC-MS analytics (see Example 4) and after this we analyzed a control brain sample from control treated mice (middle chromatogram of FIG. 11A). The peak from the 9CDHROL standard is co-eluting with the peak identified in the brain samples using the same MS-MS fragmentation channels in our LC-MS system.

In addition we identified 9CDHROL in human serum (FIG. 11B) as well as in relevant human food/beef liver (FIG. 11C). Based on the co-elution and using the same LC-MS parameters and the same fragmentation pattern channels (290→69 m/z) used, we claim and identify 9CDHROL as a novel endogenous retinoid in the mammalian organism mouse and humans as well as being present in human food represented by beef liver, which is also a mammalian organism.

Thus, treatment with 9CDHROL in orally supplemented mice increases 9CDHROL in mouse brain (FIG. 11A, bottom chromatogram) compared to control-treated brain (middle chromatogram of FIG. 11A). We note herein that administration of 9CDHBC and 9CDHROL increases 9CDHROL levels in mouse oligodendrocytes cell culture, while ATBC did not display any increase. 9CBC (and ATROL) display no or just a weak and non-isomer selective increase of 9CDHROL in oligodendrocytes cell culture (FIGS. 11D and E see below).

Comparative analysis from control, ATROL, 9CDHBC or 9CDHROL-treated animals in serum, brain and liver confirmed that after 9CDHROL-treatments strong and significantly increased levels of 9CDHROL were observed, while ATROL and 9CDHBC did not increase 9CDHROL levels (FIG. 11F).

9CDHROL is Accumulated in 9CDHROL-Treated Mice:

While in vitro cell treatments with 9CBC and ATBC functioning as pro-vitamin A1 were proven to be mainly inefficiently metabolized to 9CDHROL, we further followed on with treatments of direct 9CDHROL precursors as well as 9CDHROL itself. Treatment with 9CDHROL in orally supplemented mice increased 9CDHROL levels in mouse brain as visually displayed in FIG. 11A (bottom chromatogram) compared to control-treated brain (middle chromatogram of FIG. 11A). Comparative analysis from control, ATROL, 9CDHBC or 9CDHROL-treated animals in serum, brain and liver confirmed that just after 9CDHROL-treatments strong and significantly increased levels of 9CDHROL were observed, while ATROL and 9CDHBC did not increase 9CDHROL levels (FIG. 11F).

ATROL Treatment Mainly Results in Increased ATROL Accumulation:

For comparative reason, we also displayed the levels of ATROL and observed that after ATROL treatment to the cells (FIG. 11G) or to mice (FIG. 11H) strongly and significantly increased ATROL levels were observed. No metabolic conversion of ATROL and 9CDHBC to 9CDHROL were observed in mice (FIG. 11H), while only low conversion was observed in mouse oligodendrocytes cells (FIG. 11G). In addition, the conversion of ATROL to 9CDHROL was very unspecific and large unknown and non-identified peaks eluting in front of 9CDHROL were present (data not displayed) which indicates a complex metabolism. Comparable to these non-identified peaks, we observed additionally these endogenous and unknown peaks in human serum and beef liver (marked with a double lined arrow in FIGS. 11B and 11C)

Identification of 9CDHBC in the Human Food Matrix (FIG. 12):

9CDHBC was identified using co-elution and comparable UV/VIS spectra in peaches in a can (conserve).

Example 8: Cell Culture Experiments

Cell Culture Experiments

Normal immortalized oligodendrocytes cell line 158N was cultured as previously reported (Feutz et al., 2001). Expediently, cells were cultured in supplemented with 5% calf serum (Invitrogen, France). When cells attained 70% of confluency they were treated with $10^{-2}$ M ethanol solution of one of the following compounds: 9CDHROL, 9CDHROL-acetate, 9CDHRA-ethyl ester. 9CDHRA and ethanol as controls, vehicle treatment. 18 h after treatment cells were collected in amber Eppendorf tubes and stored at −80° C. until analyses. Treatments and cell collection were carried out in light limited conditions to avoid photolysis of retinoids.

In a slight variant of the method, after reaching confluency of 80% cells were treated with 9CDHROL, 9CDH-retinyl ester (acetate, 9CDHROL-ES), 9CDHRA, 9CDH-retinoyl ester, (ethyl ester, 9CDHRA-ES), ATROL, 9CDHBC, 9CBC and ATBC at a concentration of $10^{-6}$ M or ethanol at corresponding concentration was used as control vehicle treatment. Cells were harvested 18 hours later, centrifuged, weighted, frozen in liquid nitrogen and stored at −80° C. until analyses.

High performance liquid chromatography mass spectrometry (LC-MS) was carried out as described in Example 4.

Administration of 9CDHBC and 9CDHROL increases 9CDHROL levels in mouse oligodendrocytes cell culture (FIG. 11D), while ATBC did not display any increase (data not shown). 9CBC (and ATROL) display no or just a weak increase of 9CDHROL in oligodendrocytes cell culture (FIG. 11D see below). In summary, 9CDHBC is a weak/ moderate precursor substrate of 9CDHROL in mouse oligodendrocytes cell culture in vitro.

9CDHROL is accumulated in 9CDHROL-treated mouse oligodendrocytes and is a metabolite from 9CDHROL-ES and 9CDHBC in in vitro oligodendrocytes cell culture: Administration of 9CDHBC and 9CDHROL increases 9CDHROL levels moderately (after administration of 9CDHBC) to excellent/strongly (9CDHROL and 9CDHROL-ES) in mouse oligodendrocytes cell culture. These data were summarized in comparison to other retinoids/carotenoids used for in vitro cell culture treatments (FIG. 11E). We found that ATBC treatment did not result in any increase in 9CDHROL, while after 9CBC- and ATROL-treatments induced a weak significant increase compared to endogenous levels analyzed in oligodendrocytes cell culture was observed (FIG. 11E). Like visually dis-µlayed in FIG. 11D 9CDHBC and 9CDHROL are excellent precursor substrates of 9CDHROL in human oligodendrocytes cell culture in vitro.

As mentioned in Example 5 regarding ATROL levels, a low conversion or induced increase after 9CBC, 9CDHBC, 9CDHROL and 9CDHRA treatments to ATROL were observed in mouse oligodedrocytes cells (FIG. 11G), while no metabolic conversion of ATROL and 9CDHBC to ATROL were observed in all examined compartments in mice (FIG. 11H).

Figures 13A, 13B:
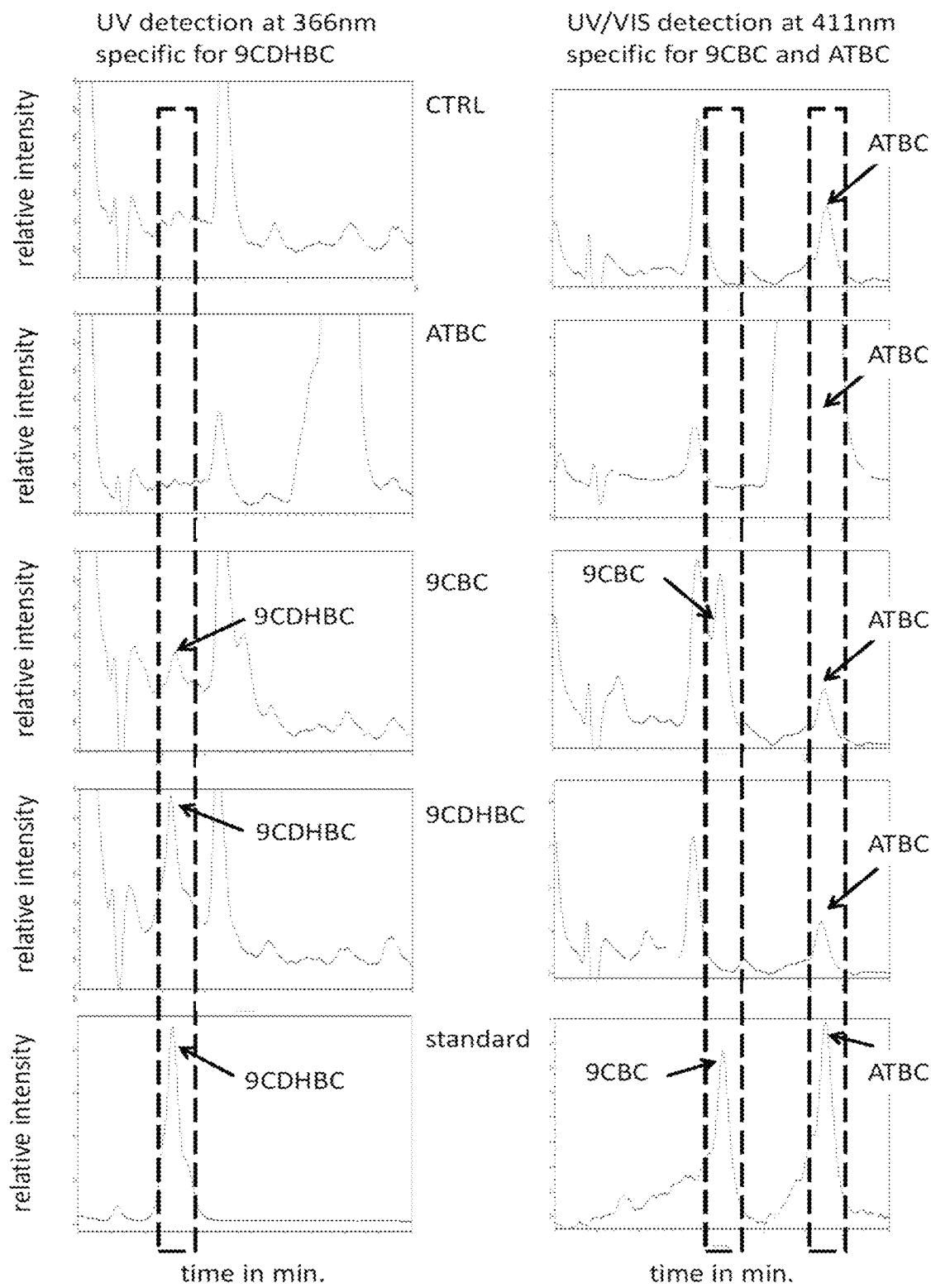

Identification of 9CDHBC after 9CDHBC and 9CBC Administration, but not after ATBC Administration to Oligodendrocytes Cell Culture In Vitro (FIG. 13):

In oligodendrocytes cell culture 9CBC could not be identified to be present endogenously in control treatment oligodendrocytes (top chromatogram, right panel of FIG. 13). ATBC could be easily detected even at detection wavelength not specific for ATBC detection at 411 nm and even better using a specific wavelength for ATBC at 450 nm (data not shown), always compared to standard compound analyzed (bottom chromatograms of FIG. 13). After administration of 9CBC to the cells, we could detect 9CBC with a retention time of 26.1 min at 411 nm detection wavelength in these treated cells (FIG. 13A, 411 nm detection at the right panel), while no 9CBC could be detected in control treatments as well as either after ATBC or 9CDHBC-treatments. The existence of 9CBC was also confirmed by comparing HPLC-MS co-elution with a specific MS-MS detection pattern of organic chemically synthesized 9CBC as well as by comparison of UV/VIS spectra taken by the diode array detector (data not shown here).

Focusing on 9CDHBC with a UV detection wavelength at 366 nm (left panel, FIG. 13A), a small peak is co-eluting endogenously in control treatments in oligodendrocytes (top chromatogram, left panel, FIG. 13A) with a chemical synthesized 9CDHBC standard (bottom chromatogram, left panel of FIG. 13), but due to low potential endogenous levels it could not be conclusively identified when comparing the UV spectra vs. standard. In addition, 9CDHBC could also not be conclusively detected after ATBC treatment (second chromatogram from the top at the left panel, FIG. 13A). However, after 9CBC-treatment a higher peak was observed and an even higher peak was conclusively detected after 9CDHBC-treatment (at 25.1 min retention time) in the carotenoid treated oligodendrocytes. It was confirmed by co-elution in LC-MS as well as comparison with UV spectra taken by the diode array detector (data not shown here) when compared to standard 9CDHBC.

Identification of 9CDHRA after 9CDHROL, 9CDHROL-ES, 9CDHRA and 9CDHRA-ES Administration to Oligodendrocyte Cell Culture (FIG. 14A):

In oligodendrocytes cell lines treated with $10^{-5}$M of 9CDHROL, 9CDH-retinyl acetate (9CDHROL-ester, 9CDHROL-ES), 9CDHRA or 9CDHRA-ethyl ester (9CDHRA-ester, 9CDHRA-ES) for 18 h we observed that after 9CDHROL, 9CDHROL-ES a strong increase of 9CDHRA levels were found (FIG. 14A). In addition, we found that after 9CDHRA-ES (and even 9CDHRA, data not shown) applications a very strong increase of 9CDHRA was identified (bottom chromatogram of FIG. 14A).

While 9CDHROL and 9CDHROL-ES are excellent precursor of 9CDHRA, we also determined that ATROL, 9CDHBC, 9CBC and ATBC are not converted to 9CDHRA in mouse oligodendrocytes cell cultures (data not shown in Figures).

9CDHRA levels including standard deviation in human oligodendrocytes cultures were assessed using HPLC-MS analysis after control treatment using ethanol (CTRL), as well as ATROL treatment (ATROL), 9CBC treatments (9CBC), ATBC treatments (ATBC), 9CDHBC treatment (9CDHBC), 9CDHROL treatments (9CDHROL), 9CDHROL-ester treatments (9CDHROL-ES), 9CDHRA treatments (9CDHRA) or 9CDHRA-ester treatments (9CDHRA-ES), each with $10^{-6}$M concentration and n=3 (FIG. 14D).

On FIG. 14D, accumulation and metabolism can be tracked, as, for example when 9CDHRA is added to the cells and a high level of 9CDHRA is seen it is an evidence for accumulation; when for example 9CDHROL is added and high levels of 9CDHRA can be observed in the cells, then it is indicative of metabolism of 9CDHROL to 9CDHRA. When 9CDHRA-ES is given to the cells and a high level of 9CDHRA is resulted, this is preferably considered as metabolism of the ester form to the acid form.

It can be seen from FIG. 14D that ATROL, 9CDHBC, 9CBC and ATBC, similarly to mouse oligodendrocytes, are not converted to 9CDHRA in human oligodendrocytes cell cultures either.

9CDHROL was moderately but significantly metabolized to 9CDHRA, 9CDHROL-ES even stronger, while for 9CDHRA and 9CDHRA-ES a strong accumulation was observed in treated oligodendrocytes in vitro (FIG. 14D).

Thus, in case of 9-cis-13,14-dihydroretinyl esters (9CDHROL-ES) and 9-cis-13,14-dihydroretinoyl ethyl ester (9CDHRA-ES) we can see that administration of the ester form results in a higher production of both 9CDHRA than in case of administration of 9CDHROL and 9CDHRA, respectively.

Thus, esters are surprisingly a better shuttle to enter the cell, because of better physicochemical properties, and are resulting in higher levels of 9CDHRA in the cells (as shown by oligodendrocytes studies). The esters are better taken up and are protected from phase 2 metabolism. Thus they are the preferred source of 9CDHRA than 9CDHRA itself and have improved potential to use them in therapy/prevention.

In summary, it can be concluded that 9CDHROL and 9CDHROL esters are excellently converted to 9CDHRA, while 9CDHRA and 9CDHRA esters are excellently accumulated/metabolised, to the selective RXR-ligand 9CDHRA in human oligodendrocytes cell culture in vitro.

Example 9: Identification of 9CDHRA, 9CDHROL and 9CDHBC Biological Activity in Mouse Models The experiments were analogous to those described in Example 3.2 and 6.

Example 9.1: Initial Results from Animal Supplementation Studies (with 9CDHROL)

To test the possibility that 9CDHROL can act as substrate for production of 9CDHRA in vivo, we have tested working memory in delayed non-match to place (DNMTP) as a behavioral paradigm sensitive to detect activity of 9CDHRA (Rühl et al., 2015). To this end we have trained a cohort of C57BL6J male mice in DNMTP task to attain the criterion of maximal performance (above 90%) over 4 consecutive days (FIG. 1A). Wild type C57BL6N male mice acquired working memory task as indicated by significant effect of the day of training (F[9,39]=8.28; p<0.001, one-way ANOVA on repeated measures) when trained with 15 sec inter-trial intervals (ITI). Memory performance was decreased when mice were tested at longer ITI of 3 min. However, when ITI reached on average 13 min (the mean for the whole group indicated in the graph as gr13) mice displayed complete memory loss in DNMTP task as their performance was not different from the chance level of 50% (p<0.05, one group t-test). The ITI at which each animal displayed complete forgetting were identified as "test ITI" for each individual animal and was used when testing pro-mnemonic activity of 9CDHROL (FIG. 1B). During such tests vehicle application did not improve memory as percent of correct choices was comparable to chance level of 50% (p=0.2, ns; one group t-test), whereas 9CDHROL treatment significantly enhanced memory performance (F[1,4]16; p<0.05, one-way ANOVA on repeated measures for the effect of treatment). 9CDHROL treated mice performed significantly better than the chance level of 50% (p<0.05; one group t-test).

Example 9.2: Results from Animal Supplementation Studies with 9CDHBC and 9CDHROL In addition to the in vitro experiments we also performed in vivo supplementation experiments with orally supplemented mice with 9CDHBC and 9CDHROL (FIGS. 14B and 14C). A moderate but significant increase of 9CDHRA was observed after 9CDHBC supplementation (FIG. 14B) in comparison with control. Low levels of 9CDHRA and its isomer ATDHRA can also be observed in serum, liver and brain of control-mice (top chromatograms of FIG. 14C) of mice and especially 9CDHRA is strongly increased after 9CDHROL-supplementation (bottom chromatograms of FIG. 14C).

An increase of 9CDHRA was observed after 9CDHBC supplementation in mouse liver (bottom FIG. 14B), when compared to a vehicle/control treatment mouse liver (bottom FIG. 14B). Endogenous levels of 9CDHRA can also be observed in a lower range in serum, liver and brain of control/vehicle-treated mice (top chromatograms of FIG. 14C) in all three examined organs, while after 9CDHROL-supplementation (bottom chromatograms of FIG. 14C) 9CDHRA is strongly increased in all three examined organs. Using HPLC-MS analysis a significant increase of 9CDHRA was observed in 9CDHBC-treated animals in all three analyzed organs after 9CDHBC treatment in mouse serum, in mouse brain and in mouse liver. ATROL treatment to mice just resulted in significantly increased levels in brain and liver. The best conversion to 9CDHRA was observed for 9CDHROL treatments in all three examined organs serum, brain and liver.

Example 9.3: 9CDHROL or 9CDHBC Prevent Depressive Behaviors in Chronic Stress Model of Depression (FIG. 15)

Stress is an important environmental factor in the aetiology of depression. To test efficiency of 9CDHROL and 9CDHBC for treatment of depressive behaviors induced by stress, we used social defeat stress animal model (Berton et al., 2006, Hollis and Kabbaj, 2014). Ten days of short daily physical contacts with resident dominant CD1 male followed by subsequent sensory contact efficiently induced despair in the forced swim task (FIG. 15A). Treatment with 10 mg/kg of 9CDHROL or 10 mg/kg of 9CDHBC during the stress protocol efficiently normalised immobility time, which was comparable with control non-stressed mice. In addition to despair behavior's chronic stress induced also anhedonia reflected by absence of preference of sweetened drink which was consumed at the level not significantly different from 50% reflecting random choice (FIG. 15B). Anhedonia was abolished in stressed mice treated with 10 mg/kg of 9CDHROL or 10 mg/kg of 9CDHBC during the stress protocol as illustrated by sucrose preference significantly exceeding a chance level of 50%.

SUMMARY AND INDUSTRIAL APPLICABILITY

Vitamin A is a cluster of derivatives which can be converted in the body to visual pigments and ligands for nuclear hormone receptors. The vitamin A1 (retinol) is well known to be a precursor for the RAR ligand all-trans retinoic acid (ATRA), while the identity of the precursor of 9-cis-13,14-dihydroretinoic acid (9CDHRA), the recently discovered endogenous ligand of the retinoid X receptor (RXR) was unknown in the prior art.

RXR binding by 9CDHRA results in selective RXR-activation pathways and RXR-LXR, RXR-NR4A, RXR-VDR, RXR-FXR and RXR-PPAR mediated signaling. These RXR-mediated signaling pathways can be modified by an RXR-ligand only and not by an RAR-ligand. Pharmaceutical or nutritional or derma topical application of our claimed selective RXR-precursors were named here as Vitamin A5/pro-vitamin A5.

In the present invention the prevention and treatment of RXR signaling conditions, or vitamin A5 deficiencies by compounds of the invention or Vitamin A5/pro-vitamin A5 compounds, where RXR-mediated signaling is augmented, is disclosed. Such conditions may well arise for various neurodegenerative diseases and further diseases of the skin and cardiovascular system involving RXR-mediated altered lipid homeostasis and immune-regulation like atherosclerosis, obesity and diabetes. These diseases with a dysfunctional RXR-mediated signaling can be prevented and/or treated by the present RXR-selective precursors.

In this study the present inventors have shown that nutritional precursors of 9CDHRA are 9-cis-13,14-dihydroretinol (9CDHROL) and 9-cis-13,14-dihydro-β,β-carotene (9CDHBC), which are respectively novel types of retinoid and carotenoid never described up to date, but present at high levels in food matrix and endogenously in mammalian organisms, including human. Using in vitro and in vivo experiments the present inventors have demonstrated that such precursors might be directly or indirectly metabolized to 9CDHRA. In contrast, well known endogenous retinoids/carotenoids like all-trans-retinol and all-trans-β,β-carotene are only weak and non-selective precursors of 9CDHRA.

Through our metabolic screen we established for the first time that 9CDHRA esters, 9CDHROL, 9CDHROL ester, 9CDHBC are excellent to moderate nutritional and physiologically relevant selective precursors of the endogenous RXR ligand 9CDHRA to induce RXR-mediated signaling. We further described this new class of substances as a new independent and selective new type of vitamin A, named hereafter vitamin A5 for 9CDHROL or pro-vitamin A5 for 9CDHBC.

It is to be noted that the known endogenous retinoid vitamin A1 alcohol, ATROL, is just a weak and non-isomer selective precursor of 9CDHROL and no precursor of 9CDHRA in human oligodendrocytes cell culture in vitro. In supplemented mice it is just weakly and partly non-significantly converted to 9CDHRA examined in mouse after oral supplementation we determine thereby no or just inefficient precursor substrate potential for the usage as a selective RXR-ligand precursor. For comparison 9CDHROL, as our novel claimed Vitamin A5 alcohol, is converted to 9CDHRA in mouse oligodendrocytes cell culture in vitro excellently and highly efficiently, when given the same amount of these retinoids supplemented to mice. As shown here, 9CDHROL has been confirmed to be present in human serum as well as in the human food chain examined in commercially available beef liver.

9CDHROL is thereby an excellent physiological and nutritional precursor for 9CDHRA and can be used as alternative treatments to selectively reach higher 9CDHRA levels and selective RXR-mediated signaling proven in mice behavioral studies. 9CDHROL is very efficiently converted to 9CDHRA, as shown in in vitro as well as in vivo supplementation trials. Esters of 9CDHROL (9CDHROL ester) and 9CDHRA (9CDHRA ester) are also excellent and even more stable derivatives and can be given alternatively and yielding even higher conversion to 9CDHRA. We claim that 9CDHROL belongs to a novel selective vitamin A family functioning as selective RXR-ligand precursors, named to be Vitamin A5.

The selective 9CDHRA precursor 9CDHBC has been found to be a direct pro-vitamin A5 carotenoid for enabling RXR-mediated signaling.

As shown here just 9CDHBC and not 9CBC is an excellent precursor of 9CDHROL. Based on later we focused just on the carotenoid 9CDHBC and we determined that it is a good precursor for 9CDHRA in mouse serum, liver and brain, when given orally to mouse in in vivo supplementation trials. In humans carotenoids are transported (while not in mice) and stored within the body, while this does not happen in mice. Thus, 9CDHBC is an excellent precursor of 9CDHROL and 9CDHRA.

We have demonstrated that compound 9CBC, a well-known carotenoid, is an important physiological and nutritional derivative present in the human food and as a partial component in the dietary food coloring additive E160a(IV) is a low efficient precursor of our novel claimed derivative 9CDHBC and transmitting its biological activity via our novel derivative. Thus, besides 9CDHBC (pro-vitamin A5), also 9CBC also can be used as a weak/moderate pre-precursor for its use as a pro-vitamin A5 precursor derivative and a selective RXR-ligand precursor for the prevention of general VA5-deficiency and general VA5-supplementation to prevent RXR-ligand dependent mediated signaling dysfunctions of the human organisms like shown here for depression as a representative selective RXR-mediated signaling dysfunctional neurodegenerative disease. 9CBC (already known) and 9CDHBC are both present in the human food chain (shown for peaches).

As an example used in this study, we determined depression as an RXR-mediated signaling dysfunction and 9CDHRA as well as 9CDHROL and 9CDHBC as 9CDHRA precursors as an active treatment/prevention strategy. Many other diseases were reported where an RXR-KO phenotype exists ranging mainly from neurodegenerative diseases and dysfunctions in the cardio-vascular system like obesity, diabetes, atherosclerosis and appetite regulation.

The proof of concept for preventive/pharmaceutical usage of those compounds is shown in treatment of depressive-like behaviors in chronic stress animal model of depression. Similar use of these compounds can be envisaged for various diseases where RXR-mediated signaling is affected or was proposed as therapeutic target. Such diseases may include neurodegenerative and metabolic diseases, skin- and immunological-dysfunctions (including inflammation) as well as cardio-vascular diseases, but may also concern life-style applications like memory enhancing effects.

REFERENCES

Allenby G, Bocquel M T, Saunders M, Kazmer S, Speck J, et al. (1993) Retinoic acid receptors and retinoid X receptors: interactions with endogenous retinoic acids. Proc Natl Acad Sci USA 90: 30-34.

Altucci L, Leibowitz M D, Ogilvie K M, de Lera A R, Gronemeyer H (2007) RAR and RXR modulation in cancer and metabolic disease. Nat Rev Drug Discov 6: 793-810.

Aïssa C (2009) Mechanistic Manifold and New Development of the Julia-Kocienski Reaction. Eur J Org Chem: 1831-1844.

Arild C RustaN, and Christian A Drevon, Fatty Acids 2005 Structures and Properties ENCYCLOPEDIA OF LIFE SCIENCES. John Wiley & Sons, doi: 10.1038/npg.els.0003894

Arnold S L, Amory J K, Walsh T J, Isoherranen N (2012) A sensitive and specific method for measurement of multiple retinoids in human serum with UHPLC-MS/MS. J Lipid Res 53: 587-598.

Babino, D., M. Golczak, P. D. Kiser, A. Wyss, K. Palczewski, and J. von Lintig. 2016. The Biochemical basis of vitamin A3 production in athopod vision. ACS Chem. Biol. (in press)

Berge, S M, Bighley L D., Monkhouse D C, (197) "Pharmaceutical Salts" J. Pharm. Sci., 66(1) 1-19

Berton O. et al. 2006 Essential Role of BDNF in the Mesolimbic Dopamine Pathway in Social Defeat Stress. Science 311(5762) 864-868

Blakemore P R (2002) The modified *Julia* olefination: alkene synthesis via the condensation of metallated heteroarylalkylsulfones with carbonyl compounds. J Chem Soc Perkin Trans 1: 2563-2585.

Broek, A. D.; Muradin-Szweykowska, M.; Courtin, J. M. L.; Lugtenburg, J. 1983 Preparation of 11,14-epoxy-bridged and isomeric chain-demethylated retinals. 13-Demethyl-11,14-epoxy-, 9-demethyl-, 13-demethyl- and 9,13-bisdemethyl-retinals. Red. Tray. Chim. Pays-Bas 102, 46

Cama, H. R., P. D. Dalvi, R. A. Morton, and M. K. Salah. 1952. Studies in vitamin A. XXI. Retinene2 and vitamin A2. Biochem J 52:542-7.

Chawla, A., J. J. Repa, R. M. Evans, and D. J. Mangelsdorf. 2001. Nuclear receptors and lipid physiology: opening the X-files. Science 294:1866-70.

Chen Z P, Shemshedini L, Durand B, Noy N, Chambon P, et al. (1994) Pure and functionally homogeneous recombinant retinoid X receptor. J Biol Chem 269: 25770

Ching Kuang Chow 2007 Fatty Acids in Foods and their Health Implications, Third Edition Series: Food Science and Technology by CRC Press ISBN 9780849372612

Dalvi A, Lucki I (1999) Murine models of depression. Psychopharmacology 147:14-16 de Lera A R, Krezel W, Rühl R. 2016. An Endogenous Mammalian Retinoid X Receptor Ligand, At Last! ChemMedChem 11(10):1027-1037.

de Lera, A. R., W. Krezel, and R. Rühl. 2016. An endogenous mammalian RXR ligand, at last ChemMedChem 2016, 11, 1027-1037

Desvergne B. 2007. RXR: from partnership to leadership in metabolic regulations. Vitam Horm 75:1-32.

Diagnostic and Statistical Manual of Mental Disorders, Fourth Edition, (DSM IV) American Psychiatric Association.

Dominguez B, Pazos Y, de Lera A R (2000) Stereocontrolled Synthesis of 6-s-cis and 6-s-trans-Locked 9ZRetinoids by Hydroxyl-Accelerated Stille Coupling of (Z)-Tri-n-Butylstannylbut-2-en-1-ol and Bicyclic Dienyl Triflates. J Org Chem 65: 5917-5925.

Duell E A, Kang S, Voorhees J J (1996) Retinoic acid isomers applied to human skin in vivo each induce a 4-hydroxylase that inactivates only trans retinoic acid. J Invest Dermatol 106: 316-320.

Englert G. 1975 A 13C-NMR. Study of cis-trans Isomeric Vitamins A, Carotenoids and Related Compounds. Helv. Chim. Acta 58(8), 2367-2390.

Edisbury, J. R., M. R. A., and S. G. W. 1937. A possible Vitam A2. Nature 140:234-234.

Egea P F, Mitschler A, Rochel N, Ruff M, Chambon P, et al. (2000) Crystal structure of the human RXRalpha ligand-binding domain bound to its natural ligand: 9-cis-retinoic acid. Embo J 19: 2592 2601.

Evans, R. M. and Mangelsdorf, D. J. 2014 *Cell,* 157, 255.

Evans, R. M., and D. J. Mangelsdorf. 2014. Nuclear Receptors, RXR, and the Big Bang. Cell 157:255-66.

Feutz A C, Pham-Dinh D, Allinquant B, Miehe M, Ghandour M S. 2001. An immortalized jimpy oligodendrocyte cell line: defects in cell cycle and cAMP pathway. Glia 34(4):241-252.

Foster J M, Pennock J F, Marshall I, Rees H H (1993) Biosynthesis of isoprenoid compounds in *Schistosoma mansoni*. Mol Biochem Parasitol 61: 275-284.

Gennaro (ed.) Remington "Pharmaceutical Sciences", 17 Ed., Mack Publishing Co., Easton, Pennsylvania, 1985.

Ghyselinck N B, Bavik C, Sapin V, Mark M, Bonnier D, et al. (1999) Cellular retinol-binding protein I is essential for vitamin A homeostasis. Embo J 18: 4903-4914.

Giguere, V., E. S. Ong, P. Segui, and R. M. Evans. 1987. Identification of a receptor for the morphogen retinoic acid. Nature 330:624-9.

Gillam, A. E., I. M. Heilbron, W. E. Jones, and E. Lederer. 1938. On theoccurrence and constitution of the 693 mu chromogen (Vitamn A2 ?) of fish liver oils. Biochemical Journal 32:405-416.

Goldstein, J. T., A. Dobrzyn, M. Clagett-Dame, J. W. Pike, and H. F. DeLuca. 2003. Isolation and characterization of unsaturated fatty acids as natural ligands for the retinoid-X receptor. Arch Biochem Biophys 420:185-93.

Gouranton E, Aydemir G, Reynaud E, Marcotorchino J, Malezet C, et al. (2011) Apo-10'-lycopenoic acid impacts adipose tissue biology via the retinoic acid receptors. Biochim Biophys Acta 1811: 1105-1114.

Heyman, R. A., D. J. Mangelsdorf, J. A. Dyck, R. B. Stein, G. Eichele, R. M. Evans, and C. Thaller. 1992. 9-cis retinoic acid is a high affinity ligand for the retinoid X receptor. Cell 68:397-406.

Hollis F, Kabbaj M. 2014 Social defeat as an animal model for depression. ILAR J. 55(2) 221-32.

Huang J K, Jarjour A A, Nait Oumesmar B, Kerninon C, Williams A, et al. (2011) Retinoid X receptor gamma signaling accelerates CNS remyelination. Nat Neurosci 14: 45-53.

Isler, O.; Gutmann, H.; Lindlar, H.; Montaron, M.; Riiegg, R.; Ryser, G.; Zeller, P. 1956, Synthesen in der Carotinoid-Reihe. 6. Mitteilung. Synthese von Crocetindialdehyd und Lycopin. Helv. Chim. Acta 39, 463.

Iwema T, Billas I M, Beck Y, Bonneton F, Nierengarten H, et al. (2007) Structural and functional characterization of a novel type of ligand-independent RXR-USP receptor. Embo J 26: 3770-3782.

Kai Z J 2011 Nanosci Nanotechnol. Synthesis of retinyl palmitate catalyzed by *Candida* sp. 99-125 lipase immobilized on fiber-like SBA-15 mesoporous material. 11(9): 7593-602.

Kane M A, Chen N, Sparks S, Napoli J L (2005) Quantification of endogenous retinoic acid in limited biological samples by LC/MS/MS. Biochem J 388: 363-369.

Karrer, P., R. Morf, and K. Schipp. 1931a. Zur Kenntnis des Vitamin A aus Fischtranen I I. Helvetica Chimica Acta 14:1431-1436.

Kastner, P., M. Mark, N. Ghyselinck, W. Krezel, V. Dupe, J. M. Grondona, and P. Chambon. 1997a. Genetic evidence that the retinoid signal is transduced by heterodimeric RXR/RAR functional units during mouse development. Development 124:313-26.

Kastner, P., N. Messaddeq, M. Mark, O. Wendling, J. M. Grondona, S. Ward, N. Ghyselinck, and P. Chambon. 1997b. Vitamin A deficiency and mutations of RXRalpha, RXRbeta and RARalpha lead to early differentiation of embryonic ventricular cardiomyocytes. Development 124:4749-58.

Kitareewan, S., L. T. Burka, K. B. Tomer, C. E. Parker, L. J. Deterding, R. D. Stevens, B. M. Forman, D. E. Mais, R. A. Heyman, T. McMorris, and C. Weinberger. 1996. Phytol metabolites are circulating dietary factors that activate the nuclear receptor RXR. Mol Biol Cell 7:1153-66.

Kliewer, S. A., K. Umesono, D. J. Mangelsdorf, and R. M. Evans. 1992. Retinoid X receptor interacts with nuclear receptors in retinoic acid, thyroid hormone and vitamin D3 signalling. Nature 355:446-9.

Kondepudi, N. (2016). Stability of Vitamin sin Pharmaceutical Preparations—A Review. International Journal for Research in Applied Science & Engineering Technology (IJRASET), 4

Koukal, P.; Ulc, J.; Necas, D.; Kotora, M. 2016 Enantioselective Allylation of β-Haloacrylaldehydes: Formal Total Syntheses of Pteroenone and Antillatoxin. Eur. J. Org. Chem., 2110-2114

Koyama, Y.; Hosomi, M.; Hashimoto, H. Shimamura, 1989, 1H NMR spectra of the all-trans, 7-cis, 9-cis, 13-cis and 15-cis isomers of β-carotene: elongation of the double bond and shortening of the single bond toward the center of the conjugated chain as revealed by vicinal coupling constants. T. J. Mol. Struct. 193, 185-201.

Krezel W, Dupe V, Mark M, Dierich A, Kastner P, et al. (1996) RXR gamma null mice are apparently normal and compound RXR alpha+/−/RXR beta−/−/RXR gamma−/− mutant mice are viable. Proc Natl Acad Sci USA 93: 9010-9014

Krzyzosiak A, Szyszka-Niagolov M, Wietrzych M, Gobaille S, Muramatsu S, et al. 2010 Retinoid x receptor gamma control of affective behaviors involves dopaminergic signaling in mice. Neuron 66: 908-920.

Lein E S, Hawrylycz M J, Ao N, Ayres M, Bensinger A, et al. (2007) Genome-wide atlas of gene expression in the adult mouse brain. Nature 445: 168-176.

Leonard J, Mohialdin S, Reed D, Ryan G, Swain P A (1995) Stereoselective conjugate addition of organolithium and organocopper reagents to [delta]-oxygenated [alpha], [beta]-unsaturated carbonyl systems derived from glyceraldehyde acetonide. Tetrahedron 51: 12843-12858.

Lerner V, Miodownik C, Gibel A, Kovalyonok E, Shleifer T, et al. (2008) Bexarotene as add-on to antipsychotic treatment in schizophrenia patients: a pilot open-label trial. Clin Neuropharmacol 31: 25-33

Lippert W P, Burschka C, Gotz K, Kaupp M, Ivanova D, et al. (2009) Silicon analogues of the RXR-selective retinoid agonist SR11237 (BMS649): chemistry and biology. ChemMedChem 4: 1143-1152

Liu Z Q 2015 Appl Microbiol Biotechnol. Efficient two-step chemo-enzymatic synthesis of all-trans-retinyl palmitate with high substrate concentration and product yield. 99(21):8891-902

Mangelsdorf, D. J., and R. M. Evans. 1995. The RXR heterodimers and orphan receptors. Cell 83:841-50.

Mangelsdorf, D. J., C. Thummel, M. Beato, P. Herrlich, G. Schutz, K. Umesono, B. Blumberg, P. Kastner, M. Mark, P. Chambon, and R. M. Evans. 1995. The nuclear receptor superfamily: the second decade. Cell 83:835-9.

Maugard et. al. Biolechnol. Prog. 2002, 18, 424.

Moise A R, Dominguez M, Alvarez S, Alvarez R, Schupp M, et al. (2008) Stereospecificity of Retinol Saturase: Absolute Configuration, Synthesis, and Biological Evaluation of Dihydroretinoids. J Am Chem Soc 130: 1154-1155.

Moise, A. R., A. Isken, M. Dominguez, A. R. de Lera, J. von Lintig, and K. Palczewski. 2007. Specificity of zebrafish retinol saturase: formation of all-trans-13,14-dihydroretinol and all-trans-7,8-dihydroretinol. Biochemistry 46:1811-20.

Moise, A. R., A. Isken, M. Dominguez, A. R. de Lera, J. von Lintig, and K. Palczewski. 2007. Specificity of zebrafish retinol saturase: formation of all-trans-13,14-dihydroretinol and all-trans-7,8-dihydroretinol. Biochemistry 46:1811-20.

Moise, A. R., S. Alvarez, M. Dominguez, R. Alvarez, M. Golczak, G. P. Lobo, J. von Lintig, A. R. de Lera, and K. Palczewski. 2009. Activation of retinoic acid receptors by dihydroretinoids. Mol Pharmacol 76:1228-37.

Moise, A. R., V. Kuksa, W. S. Blaner, W. Baehr, and K. Palczewski. 2005. Metabolism and transactivation activity of 13,14-dihydroretinoic acid. J Biol Chem 280: 27815-25.

Moise, A. R., V. Kuksa, Y. Imanishi, and K. Palczewski. 2004. Identification of all-trans-retinol:all-trans-13,14-dihydroretinol saturase. J Biol Chem 279:50230-42.

Moreau, J. L. 1997 Validation of an animal model of anhedonia, a core symptom of depression. Encephale, vol. 23, no. 4, pp. 280-289, Nagy L, Kao H Y, Love J D, Li C, Banayo E, et al. (1999) Mechanism of corepressor binding and release from nuclear hormone receptors. Genes Dev 13: 3209

Nowickyj S M, Chithalen J V, Cameron D, Tyshenko M G, Petkovich M, et al. (2008) Locust retinoid X receptors: 9-Cis-retinoic acid in embryos from a primitive insect. Proc Natl Acad Sci USA 105: 9540-9545.

Nunez, V., D. Alameda, D. Rico, R. Mota, P. Gonzalo, M. Cedenilla, T. Fischer, L. Bosca, C. K. Glass, A. G. Arroyo, and M. Ricote. 2010. Retinoid X receptor alpha controls innate inflammatory responses through the up-regulation of chemokine expression. Proc Natl Acad Sci USA 107: 10626-31.

O'Byrne, Sheila M. and Blaner, William S., 2013 The Journal of Lipid Research, Retinol and retinyl esters: biochemistry and physiology Thematic Review Series: Fat-Soluble Vitamins: Vitamin A 54, 1731-1743

O'Connor et. al. Aust. J. Chem. 1992, 45, 641

Okitsu, Takashi; Iwatsukaa K and Wada A, 2008 Caesium fluoride-promoted Stille coupling reaction: an efficient synthesis of 9Z-retinoic acid and its analogues using a practical building block, T. Chem. Comm. 47, 6330-6332.

Osz J, Brelivet Y, Peluso-Iltis C, Cura V, Eiler S, et al. (2012) Structural basis for a molecular allosteric control mechanism of cofactor binding to nuclear receptors. Proc Natl Acad Sci USA 109: E588-594.

Otwinowski Z, Minor W, editors (1997) Processing of X-ray Diffraction Data Collected in Oscillation Mode. Macromolecular Crystallography, part A ed. New York: Academic Press. 307-326 p.

Palli S R, Kapitskaya M Z, Potter D W (2005) The influence of heterodimer partner ultraspiracle/retinoid X receptor on the function of ecdysone receptor. FEBS J 272: 5979-5990.

Pazos Y, de Lera A R (1999) Stereoselective Synthesis of 9-cis-Retinoic Acid Based on Stepwise or Convergent Suzuki Coupling Reactions. Tetrahedron Lett 40: 8287-8290.

Pazos Y, Iglesias B, de Lera A R (2001) The Suzuki coupling reaction in the stereocontrolled synthesis of 9-cis-retinoic acid and its ring-demethylated analogues. J Org Chem 66: 8483-8489.

Perez E, Bourguet W, Gronemeyer H, de Lera A R 2012 Modulation of RXR function through ligand design. Biochim Biophys Acta 1821: 57

Petkovich, M., N. J. Brand, A. Krust, and P. Chambon. 1987. A human retinoic acid receptor which belongs to the family of nuclear receptors. Nature 330:444-50.

Pogenberg V, Guichou J F, Vivat-Hannah V, Kammerer S, Perez E, et al. (2005) Characterization of the interaction between retinoic acid receptor/retinoid X receptor (RAR/RXR) heterodimers and transcriptional coactivators through structural and fluorescence anisotropy studies. J Biol Chem 280: 1625-1633.

Ran-Ressler R R et al. "Branched-chain fatty acid content of foods and estimated intake in the USA." Br J Nutr. 2014 Aug. 28; 112(4):565-72.

Rühl R, Krzyzosiak A, Niewiadomska-Cimicka A, Rochel N, Szeles L, Vaz B, Wietrzych-Schindler M, Alvarez S, Szklenar M, Nagy L, de Lera A R, Krezel W. 2015. 9-cis-13,14-dihydroretinoic acid is an endogenous retinoid acting as RXR ligand in mice. PLoS Genet 11(6): e1005213.

Rühl R. 2006. Method to determine 4-oxo-retinoic acids, retinoic acids and retinol in serum and cell extracts by liquid chromatography/diode-array detection atmospheric pressure chemical ionisation tandem mass spectrometry. Rapid Commun Mass Spectrom 20(16):2497-2504.

Rühl R, Bub A, Watzl B (2008) Modulation of plasma all-trans retinoic acid concentrations by the consumption of carotenoid-rich vegetables. Nutrition 24: 1224-1226.

Schultz H S, Freyermuth H B, Buc S R (1963) New Catalysts for the Oxidation of Sulfides to Sulfones with Hydrogen Peroxide. J Org Chem 28: 1140-1142.

Shirley M A et al. 1996 Oxidative and reductive metabolism of 9-cis-retinoic acid in the rat. Identification of 13,14-dihydro-9-cis-retinoic acid and its taurine conjugate. Drug Metab Dispos. 24(3):293-302

Shudo K et al. 2009 Towards Retinoid Therapy for Alzheimer's Disease Curr Alzheimer Res.6(3): 302-311

Shulman A I, Larson C, Mangelsdorf D J, Ranganathan R 2004 Structural determinants of allosteric ligand activation in RXR heterodimers. Cell 116: 417

Shulman, A. I., and D. J. Mangelsdorf. 2005. Retinoid x receptor heterodimers in the metabolic syndrome. N Engl J Med 353:604-15.

Skerrett R, Pellegrino M P, Casali B T, Taraboanta L, Landreth G E. J Biol Chem. 2015 Combined Liver X Receptor/Peroxisome Proliferator-activated Receptor γ Agonist Treatment Reduces Amyloid β Levels and Improves Behavior in Amyloid Precursor Protein/Presenilin 1 Mice. 290(35) 21591-602

Sorg A, Bruickner R (2005) Unexpected cis-Selectivity in (Sylvestre) Julia Olefinations with Bu3Sn-Containing Allyl Benzothiazolyl Sulfones: Stereoselective Synthesis of 1,3-Butadienyl- and 1,3,5-Hexatrienylstannanes. Synlett 2005: 289,293.

Stephensen, C. B., A. D. Borowsky, and K. C. Lloyd. 2007. Disruption of Rxra gene in thymocytes and T lymphocytes modestly alters lymphocyte frequencies, proliferation, survival and T helper type 1/type 2 balance. Immunology 121:484-98.

Szanto A, Narkar V, Shen Q, Uray I P, Davies P J, Nagy L. 2004. Retinoid X receptors: X-ploring their (patho)physiological functions. Cell Death Differ 11 Suppl 2:S126-143.

Szatmari I, Torocsik D, Agostini M, Nagy T, Gurnell M, et al. (2007) PPARgamma regulates the function of human dendritic cells primarily by altering lipid metabolism. Blood 110: 3271-3280.

Szeles L, Poliska S, Nagy G, Szatmari I, Szanto A, et al. (2010) Research resource: transcriptome profiling of genes regulated by RXR and its permissive and nonpermissive partners in differentiating monocyte Tocchini-Valentini G D, Rochel N, Escriva H, Germain P, Peluso-Iltis C, et al. (2009) Structural and functional insights into the ligand-binding domain of a nonduplicated retinoid X nuclear receptor from the invertebrate chordate amphioxus. J Biol Chem 284: 1938-1948

Ulven, S. M., T. E. Gundersen, A. K. Sakhi, J. C. Glover, and R. Blomhoff. 2001. Quantitative axial profiles of retinoic acid in the embryonic mouse spinal cord: 9-cis retinoic acid only detected after all-trans-retinoic acid levels are super-elevated experimentally. Dev Dyn 222:341-53.

Vahlquist, A., J. B. Lee, G. Michaelsson, and O. Rollman. 1982. Vitamin A in human skin: II Concentrations of carotene, retinol and dehydroretinol in various components of normal skin. J Invest Dermatol 79:94-7.

van Neerven S. 2008 RAR/RXR and PPAR/RXR signaling in neurological and psychiatric diseases. Prog Neurobiol. 85(4):433-51.

Vaz B, Alvarez R, Souto J A, de Lera A R (2005) γ-Allenyl Allyl Benzothiazole Sulfonyl Anions Undergo cisSelective (Sylvestre) Julia Olefinations. Synlett 2005: 294, 298.

Volker Btihler: Vademecum for Vitamin Formulations Published by CRC Press, 2002

Wan, Y. J., G. Han, Y. Cai, T. Dai, T. Konishi, and A. S. Leng. 2003. Hepatocyte retinoid X receptor-alphadeficient mice have reduced food intake, increased body weight, and improved glucose tolerance. Endocrinology 144:605-11.

Wietrzych M, Meziane H, Sutter A, Ghyselinck N, Chapman P F, Chambon P, Krezel W. 2005. Working memory deficits in retinoid X receptor gamma-deficient mice. Learn Mem 12(3):318-326.

Wietrzych-Schindler M, Szyszka-Niagolov M, Ohta K, Endo Y, Perez E, de Lera A R, Chambon P, Krezel W. 2011. Retinoid x receptor gamma is implicated in docosahexaenoic acid modulation of despair behaviors and working memory in mice. Biol Psychiatry 69(8):788-794.

Yin Chunhua 2006 Chinese J. Chem. Eng. Synthesis of Vitamin A Esters by Immobilized *Candida* sp. Lipase in Organic Media 14(1) 81-86

Zanoun A., S. Bouaziz, A. Belaidi, G. Vergoten 2006 The SPASIBA force field for some retinal conformers. J. Mol. Struct.: THEOCHEM 777(1-3), 113-120

EP1419780B1
JP 62-248495
US20050238675A1
U.S. Pat. No. 3,133,862A
U.S. Pat. No. 4,254,100A
U.S. Pat. No. 4,966,779A
U.S. Pat. No. 5,356,636A
U.S. Pat. No. 6,183,774B1
U.S. Pat. No. 7,566,795B2
U.S. Pat. No. 8,318,196B2
U.S. Pat. No. 9,439,913B1
WO 95/04018 A1
WO 95/32946 A1
WO2011/034551 A2
WO2013/134867 A1
WO2017097974A1

The invention claimed is:

1. A method for the treatment or reducing the risk of a retinoid X receptor (RXR)-mediated signaling dysfunction by providing (R)-9-cis-13,14-dihydroretinoic acid (9CDHRA) as an RXR ligand in a subject, said method selected from the group consisting of
ameliorating or reducing the development of, ameliorating at least one physical parameter of, or inhibiting cancer or depression,
ameliorating or reducing the risk of vitamin A5 deficiency, and
ameliorating or reducing memory impairment,
said method comprising administration of a compound of general formula (I) to a mammalian subject suffering from or being endangered by a retinoid X receptor-mediated signaling dysfunction in the nervous system,

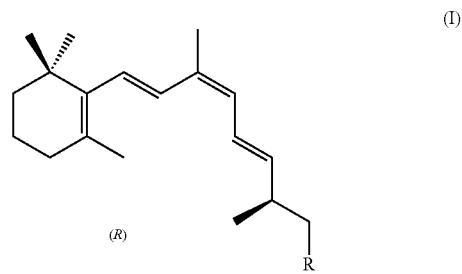

wherein
R is a group of general formula (A)

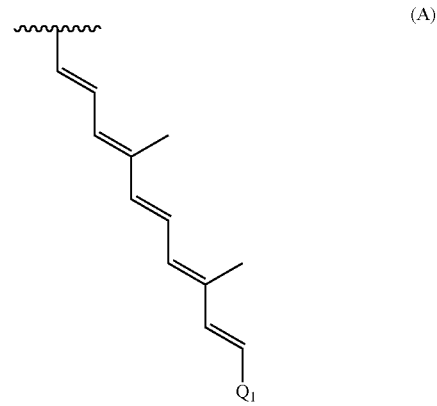

wherein $Q_1$ is an unsubstituted trimethylcyclohexenyl group so that the compound of general formula (I) is 9-cis-13,14-dihydro-β,β-carotene or a 9-cis-13,14-dihydro-β,α-carotene, or R is —CH$_2$OR$_2$, wherein R$_2$ is H or an acyl group —C(O)R$_3$ wherein —C(O)R$_3$ is a group which is removed by hydrolysis in a mammalian tissue or organ to result in (R)-9-cis-13,14-dihydroretinol and a biologically acceptable tolerable compound, wherein $R_3$ is a $C_{1-25}$ alkyl or a $C_{2-25}$ alkenyl, or R is —COOH, said compound of general formula (I) being converted into (R)-9-cis-13,14-dihydroretinoic acid in a tissue or organ or cells of the mammalian subject.

2. A method for the treatment or reducing the risk of a retinoid X receptor (RXR)-mediated signaling dysfunction in a disease of the central or peripheral nervous system by providing 9-cis-13,14-dihydroretinoic acid as an RXR ligand in a subject, said method selected from the group consisting of ameliorating or reducing the development of, ameliorating at least one physical parameter of, or inhibiting depression, reducing the risk of vitamin A5 deficiency in a disease of the nervous system, and ameliorating or reducing memory impairment, said method comprising the administration of a compound of general formula (V) to a mammalian subject suffering from or being endangered by a retinoid X receptor-mediated signaling dysfunction,

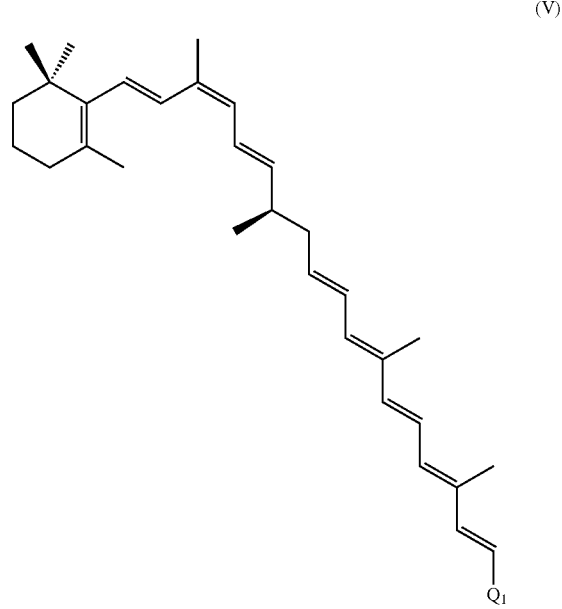

(V)

wherein $Q_1$ is a substituted or unsubstituted trimethylcycloalkenyl, wherein if the trimethylcyclohexenyl group is substituted, it is hydroxyl-substituted or oxo-substituted; or a 9-cis-carotenoid which is a 9-cis-β,β-carotene (9CBC) or a 9-cis-β,α-carotene, said compound being converted into a 9-cis-13,14-dihydro-β,β-carotene or a 9-cis-13,14-dihydro-β,α-carotene, once administered to the subject, wherein said compound is converted into 9-cis-13,14-dihydroretinol and in turn into (R)-9-cis-13,14-dihydroretinoic acid in mammalian tissue or organ or cells, once administered.

3. The method according to claim 1 wherein in said compound of general formula (I)

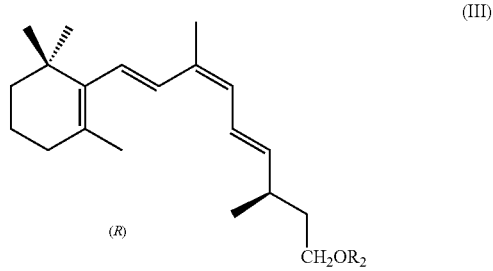

(III)

R is COOH or

R is $CH_2OR_2$, wherein $R_2$ is H or an acyl group $C(O)R_3$ wherein $R_3$ is a $C_{1-25}$ alkyl or a $C_{2-25}$ alkenyl, wherein said compound of general formula (I) is converted into (R)-9-cis-13,14-dihydroretinol in the mammalian tissue or organ or cells, once administered.

4. The method according to claim 3 wherein said compound of general formula (I) is a compound of general formula (III)

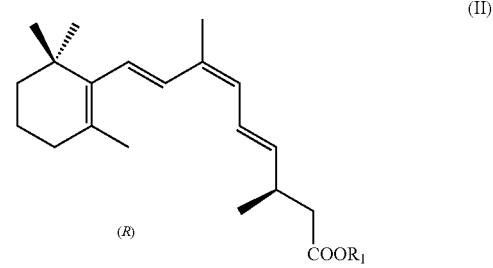

(II)

wherein $R_2$ is H or an acyl group $C(O)R_3$ wherein $R_3$ is selected from a $C_{1-23}$ alkyl, and a $C_{2-25}$ alkenyl, wherein said compound of general formula (III) is converted into (R)-9-cis-13,14-dihydroretinol in mammalian tissue or organ or cells, once administered.

5. The method according to claim 4, wherein said compound of general formula (I) is of general formula (IV)

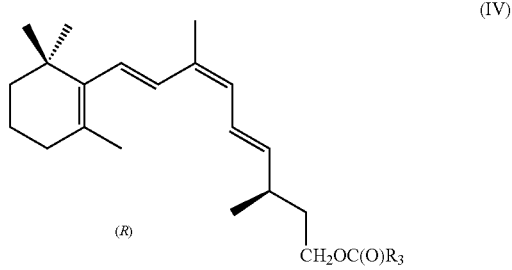

(IV)

wherein $R_3$ is selected from
a $C_{1-4}$ alkyl,
a $C_{11-21}$ alkyl, or
a $C_{11-23}$ alkenyl.

6. The method according to claim 4 wherein said compound of general formula (III) is a 9-cis-carotenoid,
which is a 9-cis-13,14-dihydro-β,β-carotene or a 9-cis-13,14-dihydro-β,α-carotene wherein said compound of general formula (III) is converted into (R)-9-cis-13,14-dihydroretinoic acid in the mammalian tissue or organ or cells, once administered to the subject.

7. The method according to claim 2 for using a compound which is a 9-cis-β,β-carotene (9CBC) or a 9-cis-β,α-carotene as a pro-vitamin A5, wherein said compound is in the form of a composition,
wherein said composition is a nutraceutical composition, or said composition is a food extract.

8. The method according to claim 1 wherein the vitamin A5 deficiency is ameliorated or the risk thereof is reduced in a neuropsychiatric disorder.

9. The method according to claim 1 wherein the retinoid X receptor-mediated signaling dysfunction is memory impairment.

10. The method according to claim 1 wherein the compound of general formula (I) is administered to said mammalian subject to reduce the risk of an RXR-mediated signaling dysfunction in a disease of the nervous system, wherein said compound of general formula (I) is administered to said mammalian subject in the form of a nutraceutical composition or as a dietary supplement.

11. The method according to claim 10 wherein
R is $CH_2OR_2$, wherein $R_2$ is H or an acyl group $C(O)R_3$ wherein $R_3$ is a $C_{1-25}$ alkyl or a $C_{2-25}$ alkenyl, wherein said compound of general formula (I) is converted into 9-cis-13,14-dihydroretinol in the mammalian tissue or organ or cells, once administered
or
R is COOH.

12. The method according to claim 2 wherein a 9-cis-carotenoid compound is administered to said mammalian subject,
which is a 9-cis-13,14-dihydro-β, β-carotene or a 9-cis-13,14-dihydro-β,α-carotene, wherein said compound is converted into 9-cis-13,14-dihydroretinoic acid in the mammalian tissue or organ or cells, once administered to the subject;
or wherein said compound is a 9-cis-carotenoid which is a 9-cis-β,β-carotene (9CBC) or a 9-cis-β,α-carotene, said compound being converted into a 9-cis-13,14-dihydro-β,β-carotene or a 9-cis-13,14-dihydro-(3,a-carotene, once administered to the subject.

13. The method according to claim 1 wherein said compound of general formula (I) is in the form of a pharmaceutical or nutraceutical composition being formulated to protect said compound of general formula (I) against light,
said composition also comprising at least one pharmaceutically or nutraceutically acceptable excipient for stabilizing the 9-cis-13,14-dihydroretinoid compound, i.e. a stabilizer, or for solubilizing or emulsifying the 9-cis-13,14-dihydroretinoid compound, i.e. a solubilizer or an emulsifier.

14. The method according to claim 1 wherein the vitamin A5 deficiency is ameliorated or the risk thereof is reduced in a subject suffering from impaired cognitive functions or impaired learning.

15. The method according to claim 1 wherein said compound of general formula (I) is synthetic and is administered in a composition which is enriched in the (R) enantiomer of the compound of general formula (I).

16. A method for improving or increasing the activation of RXR signaling in a subject, said method comprising administering (R)-9-cis-13,14-dihydroretinoic acid to a mammalian subject.

17. The method according to claim 2 wherein in the compound of general formula (V) the substituted or unsubstituted trimethylcycloalkenyl is a substituted or unsubstituted 2,6,6-trimethylcyclohexenyl, wherein said 2,6,6-trimethylcyclohexenyl is hydroxyl-substituted or oxo-substituted;
wherein said compound of general formula (V) is converted into 9-cis-13,14-dihydroretinol and in turn into (R)-9-cis-13,14-dihydroretinoic acid in mammalian tissue or organ or cells, once administered.

* * * * *

UNITED STATES PATENT AND TRADEMARK OFFICE
CERTIFICATE OF CORRECTION

PATENT NO. : 12,029,715 B2
APPLICATION NO. : 16/102137
DATED : July 9, 2024
INVENTOR(S) : Krezel et al.

Page 1 of 1

It is certified that error appears in the above-identified patent and that said Letters Patent is hereby corrected as shown below:

In the Claims

The formula in Claim 3, Lines 4-15 (Column 96, Lines 4-15), should read:

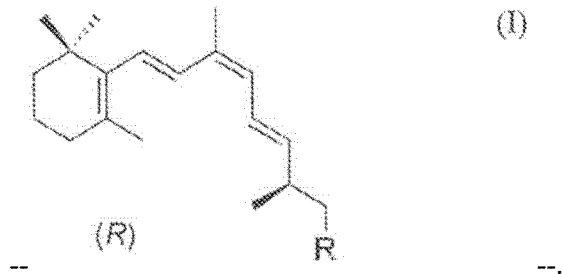

The formula in Claim 4, Lines 5-16 (Column 96, Lines 27-38), should read:

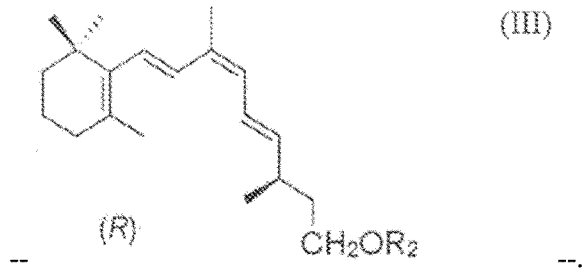

In Claim 12, Lines 12-13 (Column 98, Lines 7-8), "9-cis-13,14-dihydro-(3,a-carotene" should read -- 9-cis-13,14-dihydro-β,α-carotene --.

Signed and Sealed this
Twentieth Day of August, 2024

Katherine Kelly Vidal
*Director of the United States Patent and Trademark Office*